US011033671B2

(12) United States Patent
van der Merwe et al.

(10) Patent No.: US 11,033,671 B2
(45) Date of Patent: Jun. 15, 2021

(54) SYSTEMS AND METHODS FOR DETECTING VASCULAR ACCESS DISCONNECTION

(71) Applicant: DEKA Products Limited Partnership, Manchester, NH (US)

(72) Inventors: Dirk A. van der Merwe, Canterbury, NH (US); Michael G. Norris, Manchester, NH (US); Michael A. Baker, Manchester, NH (US); Todd A. Ballantyne, Amherst, NH (US); Michael J. Wilt, Windham, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 245 days.

(21) Appl. No.: 16/011,294

(22) Filed: Jun. 18, 2018

(65) Prior Publication Data

US 2018/0296746 A1    Oct. 18, 2018

Related U.S. Application Data

(60) Division of application No. 14/723,221, filed on May 27, 2015, now Pat. No. 9,999,717, which is a
(Continued)

(51) Int. Cl.
*A61M 1/36*    (2006.01)

(52) U.S. Cl.
CPC ..... *A61M 1/3656* (2014.02); *A61M 2205/128* (2013.01); *A61M 2205/14* (2013.01); *A61M 2205/33* (2013.01); *A61M 2205/3317* (2013.01)

(58) Field of Classification Search
CPC .............. A61M 1/3656; A61M 1/3661; A61M 2205/128; A61M 2205/14; A61M 2205/33; A61M 2205/3317
See application file for complete search history.

(56) References Cited

U.S. PATENT DOCUMENTS 2,339,876 A    1/1944  Phillips
3,083,943 A    4/1963  Stewart et al.
(Continued)

FOREIGN PATENT DOCUMENTS

CA    1119971 A    3/1982
CA    1323312 C    10/1993
(Continued)

OTHER PUBLICATIONS

Search Report and Written Opinion for SG Application No. 11201609765V filed May 27, 2015, which Report is dated Nov. 3, 2017, and claims as pending for SG Application No. 11201609765V as of Nov. 3, 2017.
(Continued)

*Primary Examiner* — Benjamin J Klein
(74) *Attorney, Agent, or Firm* — Wolf, Greenfield & Sacks, P.C.

(57) ABSTRACT

A system for detecting whether a vascular access has been interrupted in an arrangement in which two catheters or needles are present in a blood vessel, fistula or graft. A fluid line leading to a pump is connected via a first connector to a first indwelling catheter, and a fluid line leading from a pump is connected via a second connector to a second indwelling catheter. Each connector is equipped with an electrode in contact with the lumen of the connector, the electrodes electrically connected to an electronic circuit that measures the impedance or conductivity of fluid between the first connector and second connectors via a fluid path through the blood vessel, fistula or graft. An electronic controller receives the impedance or conductivity data and processes the data to determine whether a vascular access disconnection has occurred. The processing may involve filtering the signal received by the controller, and/or setting provisional flags for a disconnection event that may be
(Continued)

cleared if the signal changes before the expiration of a counter.

11 Claims, 81 Drawing Sheets

Related U.S. Application Data continuation-in-part of application No. 14/122,166, filed as application No. PCT/US2012/039369 on May 24, 2012, now Pat. No. 9,724,458.

(60) Provisional application No. 62/121,980, filed on Feb. 27, 2015, provisional application No. 62/003,346, filed on May 27, 2014, provisional application No. 61/489,464, filed on May 24, 2011.

(56) References Cited

U.S. PATENT DOCUMENTS

| | | |
|---|---|---|
| 3,847,809 A | 11/1974 | Kopf |
| 3,882,861 A | 5/1975 | Kettering et al. |
| 3,900,396 A | 8/1975 | Lamadrid |
| 3,908,441 A | 9/1975 | Virloget |
| 3,946,731 A * | 3/1976 | Lichtenstein .......... A61M 1/16 604/66 |
| 4,085,047 A | 4/1978 | Thompson |
| 4,114,144 A | 9/1978 | Hyman |
| 4,155,852 A | 5/1979 | Fischel et al. |
| 4,181,610 A | 1/1980 | Shintani et al. |
| 4,222,127 A | 9/1980 | Donachy et al. |
| 4,227,814 A | 10/1980 | Soodak et al. |
| 4,267,040 A | 5/1981 | Schal |
| 4,381,545 A | 4/1983 | Biddle, III et al. |
| 4,441,357 A | 4/1984 | Kahn et al. |
| 4,479,762 A | 10/1984 | Bilstad et al. |
| 4,492,258 A | 1/1985 | Lichtenstein et al. |
| 4,517,081 A | 5/1985 | Amiot et al. |
| 4,656,427 A | 4/1987 | Dauphinee |
| 4,661,246 A | 4/1987 | Ash |
| 4,666,598 A | 5/1987 | Heath et al. |
| 4,668,400 A | 5/1987 | Veech |
| 4,695,385 A | 9/1987 | Boag |
| 4,718,022 A | 1/1988 | Cochran |
| 4,745,279 A | 5/1988 | Karkar et al. |
| 4,767,526 A | 8/1988 | Vantard |
| 4,781,535 A | 11/1988 | Frawley et al. |
| 4,797,655 A | 1/1989 | Orndal et al. |
| 4,828,543 A | 5/1989 | Weiss et al. |
| 4,829,448 A | 5/1989 | Balding et al. |
| 4,844,072 A | 7/1989 | French et al. |
| 4,884,065 A | 11/1989 | Crouse et al. |
| 4,927,411 A | 5/1990 | Pastrone et al. |
| 4,950,235 A | 8/1990 | Slate et al. |
| 4,971,700 A | 11/1990 | Tsuji et al. |
| 4,997,570 A | 3/1991 | Polaschegg |
| 5,024,756 A | 6/1991 | Sternby |
| 5,098,262 A | 3/1992 | Wecker et al. |
| 5,209,903 A | 5/1993 | Kanamori et al. |
| 5,247,434 A | 9/1993 | Peterson et al. |
| 5,324,422 A | 6/1994 | Colleran et al. |
| 5,350,357 A | 9/1994 | Kamen et al. |
| 5,351,686 A | 10/1994 | Steuer et al. |
| 5,411,472 A | 5/1995 | Steg, Jr. et al. |
| 5,421,823 A | 6/1995 | Kamen et al. |
| 5,438,510 A | 8/1995 | Bryant et al. |
| 5,469,070 A | 11/1995 | Koluvek |
| 5,472,614 A | 12/1995 | Rossi |
| 5,486,286 A | 1/1996 | Peterson et al. |
| 5,487,827 A | 1/1996 | Peterson et al. |
| 5,496,273 A | 3/1996 | Pastrone et al. |
| 5,580,460 A | 12/1996 | Polaschegg |
| 5,591,344 A | 1/1997 | Kenley et al. |
| 5,601,080 A | 2/1997 | Oppenheimer |
| 5,609,572 A | 3/1997 | Lang |
| 5,616,248 A | 4/1997 | Schal |
| 5,628,908 A | 5/1997 | Kamen et al. |
| 5,676,644 A | 10/1997 | Toays et al. |
| 5,676,645 A | 10/1997 | Van Waeg et al. |
| 5,680,111 A | 10/1997 | Danby et al. |
| 5,690,831 A | 11/1997 | Kenley et al. |
| 5,702,597 A | 12/1997 | Chevallet et al. |
| 5,734,464 A | 3/1998 | Gibbs |
| 5,744,027 A | 4/1998 | Connell et al. |
| 5,769,811 A | 6/1998 | Stacey et al. |
| 5,788,851 A | 8/1998 | Kenley et al. |
| 5,795,317 A | 8/1998 | Brierton et al. |
| 5,797,897 A | 8/1998 | Jepson et al. |
| 5,857,379 A | 1/1999 | Lulofs et al. |
| 5,906,978 A | 5/1999 | Ash |
| 5,925,011 A | 7/1999 | Faict et al. |
| 5,932,103 A | 8/1999 | Kenley et al. |
| 5,948,251 A | 9/1999 | Brugger |
| 6,039,877 A | 3/2000 | Chevallet et al. |
| 6,041,801 A | 3/2000 | Gray et al. |
| 6,044,691 A | 4/2000 | Kenley et al. |
| 6,089,105 A | 7/2000 | Ricciardelli |
| 6,139,534 A | 10/2000 | Niedospial, Jr. et al. |
| 6,195,887 B1 | 3/2001 | Danby et al. |
| 6,223,130 B1 | 4/2001 | Gray et al. |
| 6,228,047 B1 | 5/2001 | Dadson |
| 6,261,065 B1 | 7/2001 | Nayak et al. |
| 6,264,680 B1 | 7/2001 | Ash |
| 6,270,673 B1 | 8/2001 | Belt et al. |
| 6,277,272 B1 | 8/2001 | Nikaido et al. |
| 6,284,131 B1 | 9/2001 | Hogard et al. |
| 6,295,918 B1 | 10/2001 | Simmons et al. |
| 6,327,895 B1 | 12/2001 | Jeppsson et al. |
| 6,331,252 B1 | 12/2001 | El Sayyid et al. |
| 6,406,426 B1 | 6/2002 | Reuss et al. |
| 6,481,980 B1 | 11/2002 | Vandlik et al. |
| 6,491,656 B1 | 12/2002 | Morris |
| 6,497,676 B1 | 12/2002 | Childers et al. |
| 6,510,330 B1 | 1/2003 | Enejder |
| 6,579,253 B1 | 6/2003 | Burbank et al. |
| 6,635,491 B1 | 10/2003 | Khalil et al. |
| 6,638,478 B1 | 10/2003 | Treu et al. |
| 6,649,063 B2 | 11/2003 | Brugger et al. |
| 6,663,585 B1 | 12/2003 | Ender |
| 6,687,004 B1 | 2/2004 | Shana et al. |
| 6,692,457 B2 | 2/2004 | Flaherty |
| 6,743,201 B1 | 6/2004 | Donig et al. |
| 6,758,975 B2 | 7/2004 | Peabody et al. |
| 6,811,707 B2 | 11/2004 | Rovatti et al. |
| 6,814,547 B2 | 11/2004 | Childers et al. |
| 6,821,441 B2 | 11/2004 | Pedrini et al. |
| 6,852,090 B2 | 2/2005 | Burbank et al. |
| 6,877,419 B2 | 4/2005 | Ohrle et al. |
| 6,946,299 B2 | 9/2005 | Neel et al. |
| 6,947,131 B2 | 9/2005 | O'Mahony et al. |
| 6,949,079 B1 | 9/2005 | Westberg et al. |
| 7,029,245 B2 | 4/2006 | Maianti et al. |
| 7,041,076 B1 | 5/2006 | Westberg et al. |
| 7,060,047 B2 | 6/2006 | Lodi et al. |
| 7,138,088 B2 | 11/2006 | Wariar et al. |
| 7,147,616 B2 | 12/2006 | Pedrazzi et al. |
| 7,153,286 B2 | 12/2006 | Busby et al. |
| 7,175,606 B2 | 2/2007 | Bowman, Jr. et al. |
| 7,230,687 B2 | 6/2007 | O'Mahony et al. |
| 7,238,164 B2 | 7/2007 | Childers et al. |
| 7,273,465 B2 | 9/2007 | Ash |
| 7,300,413 B2 | 11/2007 | Burbank et al. |
| 7,387,734 B2 | 6/2008 | Felding |
| 7,473,238 B2 | 1/2009 | Brugger et al. |
| 7,476,209 B2 | 1/2009 | Gara et al. |
| 7,524,417 B2 | 4/2009 | Sunohara et al. |
| 7,530,962 B2 | 5/2009 | Ross et al. |
| 7,544,179 B2 | 6/2009 | Distler et al. |
| 7,544,301 B2 | 6/2009 | Shah et al. |
| 7,559,524 B2 | 7/2009 | Gray et al. |
| 7,563,240 B2 | 7/2009 | Gross et al. |
| 7,575,564 B2 | 8/2009 | Childers |
| 7,615,028 B2 | 11/2009 | O'Mahony |

(56) References Cited

U.S. PATENT DOCUMENTS

| | | |
|---|---|---|
| 7,644,889 B2 | 1/2010 | Johnson |
| 7,648,627 B2 | 1/2010 | Beden et al. |
| 7,699,806 B2 | 4/2010 | Ware et al. |
| 7,741,756 B2 | 6/2010 | Sudol |
| 7,758,532 B2 | 7/2010 | Mori et al. |
| 7,776,006 B2 | 8/2010 | Childers et al. |
| 7,794,141 B2 | 9/2010 | Perry et al. |
| 7,867,214 B2 | 1/2011 | Childers et al. |
| 7,892,197 B2 | 2/2011 | Folden et al. |
| 7,899,508 B2 | 3/2011 | Dearmond |
| 7,909,795 B2 | 3/2011 | Childers et al. |
| 7,938,792 B2 | 5/2011 | Roger et al. |
| 7,959,593 B2 | 6/2011 | Ueda et al. |
| 7,967,022 B2 | 6/2011 | Grant et al. |
| 8,029,454 B2 | 10/2011 | Kelly et al. |
| 8,042,563 B2 | 10/2011 | Wilt et al. |
| 8,049,979 B2 | 11/2011 | Yumiki et al. |
| 8,105,265 B2 | 1/2012 | Demers et al. |
| 8,113,244 B2 | 2/2012 | Kamen et al. |
| 8,137,553 B2 | 3/2012 | Fulkerson et al. |
| 8,180,443 B1 | 5/2012 | Kleinekofort et al. |
| 8,211,048 B2 | 7/2012 | Szamosfalvi et al. |
| 8,246,826 B2 | 8/2012 | Wilt et al. |
| 8,248,087 B2 | 8/2012 | Ishino et al. |
| 8,266,967 B2 | 9/2012 | Kitani et al. |
| 8,273,049 B2 | 9/2012 | Demers et al. |
| 8,287,480 B2 | 10/2012 | Sasaki et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,444,587 B2 | 5/2013 | Kelly et al. |
| 8,459,292 B2 | 6/2013 | Wilt et al. |
| 8,469,331 B2 | 6/2013 | Burbank et al. |
| 8,491,184 B2 | 7/2013 | Kamen et al. |
| 8,499,780 B2 | 8/2013 | Wilt et al. |
| 8,512,553 B2 | 8/2013 | Cicchello et al. |
| 8,545,698 B2 | 10/2013 | Wilt et al. |
| 8,562,834 B2 | 10/2013 | Kamen et al. |
| 8,597,229 B2 | 12/2013 | Pan |
| 8,597,505 B2 | 12/2013 | Fulkerson et al. |
| 8,612,055 B2 | 12/2013 | Ali et al. |
| 8,708,950 B2 | 4/2014 | Scarpaci et al. |
| 8,721,879 B2 | 5/2014 | van der Merwe et al. |
| 8,721,884 B2 | 5/2014 | Wilt et al. |
| 8,764,702 B2 | 7/2014 | Childers et al. |
| 8,771,508 B2 | 7/2014 | Grant et al. |
| 8,821,475 B2 | 9/2014 | Distler et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,881,600 B2 | 11/2014 | Puppini et al. |
| 8,882,700 B2 | 11/2014 | Chapman et al. |
| 8,888,470 B2 | 11/2014 | Demers et al. |
| 8,906,240 B2 | 12/2014 | Crnkovich et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,986,252 B2 | 3/2015 | Cummings et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,039,395 B2 | 5/2015 | Gray et al. |
| 9,072,831 B2 | 7/2015 | Kelly et al. |
| 9,089,653 B2 | 7/2015 | O'Mahony |
| 9,115,708 B2 | 8/2015 | van der Merwe et al. |
| 9,212,988 B2 | 12/2015 | Akita et al. |
| 9,272,082 B2 | 3/2016 | Demers et al. |
| 9,302,037 B2 | 4/2016 | Wilt et al. |
| 9,302,039 B2 | 4/2016 | Kelly et al. |
| 9,364,655 B2 | 6/2016 | Grant et al. |
| 9,366,781 B2 | 6/2016 | Scarpaci et al. |
| 9,488,167 B2 | 11/2016 | Gray et al. |
| 9,494,150 B2 | 11/2016 | Gray et al. |
| 9,494,151 B2 | 11/2016 | Gray et al. |
| 9,514,283 B2 | 12/2016 | Childers et al. |
| 9,517,295 B2 | 12/2016 | Wilt et al. |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,561,317 B2 | 2/2017 | Distler et al. |
| 9,561,318 B2 | 2/2017 | Distler et al. |
| 9,593,678 B2 | 3/2017 | Gray et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |
| 9,713,667 B2 | 7/2017 | Distler et al. |
| 9,717,834 B2 | 8/2017 | Wilt et al. |
| 9,724,458 B2 | 8/2017 | Grant et al. |
| 9,750,865 B2 | 9/2017 | Vasta et al. |
| 9,770,546 B2 | 9/2017 | Vasta |
| 9,795,728 B2 | 10/2017 | Grant et al. |
| 9,907,972 B2 | 3/2018 | Kameli |
| 9,951,768 B2 | 4/2018 | Grant et al. |
| 9,987,407 B2 | 6/2018 | Grant et al. |
| 9,999,717 B2 | 6/2018 | van der Merwe et al. |
| 10,060,867 B2 | 8/2018 | Kamen et al. |
| 10,077,766 B2 | 9/2018 | Demers et al. |
| 10,098,998 B2 | 10/2018 | Wilt |
| 10,195,330 B2 | 2/2019 | Coll et al. |
| 10,201,647 B2 | 2/2019 | Norris et al. |
| 10,201,650 B2 | 2/2019 | Wilt et al. |
| 10,302,075 B2 | 5/2019 | Tracey et al. |
| 10,415,559 B2 | 9/2019 | Demers et al. |
| 10,441,697 B2 | 10/2019 | Kamen et al. |
| 10,443,591 B2 | 10/2019 | Wilt et al. |
| 10,449,280 B2 | 10/2019 | Wilt et al. |
| 10,463,774 B2 | 11/2019 | Ballantyne et al. |
| 10,500,327 B2 | 12/2019 | Grant et al. |
| 10,537,671 B2 | 1/2020 | Wilt et al. |
| 10,576,194 B2 | 3/2020 | Distler et al. |
| 10,682,450 B2 | 6/2020 | Wilt et al. |
| 10,697,913 B2 | 6/2020 | Kamen et al. |
| 10,780,210 B2 | 9/2020 | Grant et al. |
| 10,780,213 B2 | 9/2020 | Grant et al. |
| 10,799,628 B2 | 10/2020 | Wilt et al. |
| 10,850,089 B2 | 12/2020 | Grant et al. |
| 10,851,769 B2 | 12/2020 | Demers et al. |
| 10,871,157 B2 | 12/2020 | Tracey et al. |
| 2002/0000871 A1 | 1/2002 | Davies |
| 2003/0036719 A1 | 2/2003 | Giacomelli et al. |
| 2003/0195453 A1 | 10/2003 | Han et al. |
| 2003/0195454 A1 | 10/2003 | Wariar et al. |
| 2003/0220607 A1 | 11/2003 | Busby et al. |
| 2003/0220627 A1 | 11/2003 | Distler et al. |
| 2004/0254513 A1 | 12/2004 | Shang et al. |
| 2005/0045540 A1 | 3/2005 | Connell et al. |
| 2005/0131332 A1 | 6/2005 | Kelly et al. |
| 2005/0195087 A1 | 9/2005 | Thompson et al. |
| 2005/0209563 A1 | 9/2005 | Hopping et al. |
| 2005/0234385 A1 | 10/2005 | Vandlik et al. |
| 2005/0242034 A1 | 11/2005 | Connell et al. |
| 2006/0195064 A1 | 8/2006 | Plahey et al. |
| 2006/0229586 A1 | 10/2006 | Faries |
| 2007/0000847 A1* | 1/2007 | Ross .................. A61M 1/3621 210/781 |
| 2007/0060872 A1 | 3/2007 | Hall et al. |
| 2007/0210047 A1 | 9/2007 | Child |
| 2008/0021377 A1 | 1/2008 | Kienman et al. |
| 2008/0058697 A1 | 3/2008 | Kamen et al. |
| 2008/0065006 A1* | 3/2008 | Roger .................. A61M 1/34 604/65 |
| 2008/0114330 A1 | 5/2008 | Distler et al. |
| 2008/0205481 A1 | 8/2008 | Faries et al. |
| 2008/0253911 A1 | 10/2008 | Demers et al. |
| 2009/0007642 A1 | 1/2009 | Busby et al. |
| 2009/0088683 A1 | 4/2009 | Roger et al. |
| 2009/0107335 A1 | 4/2009 | Wilt et al. |

(56) References Cited

U.S. PATENT DOCUMENTS

| | | |
|---|---|---|
| 2009/0294359 A1 | 12/2009 | Hopping et al. |
| 2009/0306573 A1 | 12/2009 | Gagner et al. |
| 2010/0056975 A1 | 3/2010 | Dale et al. |
| 2010/0185134 A1 | 7/2010 | Houwen et al. |
| 2010/0190204 A1 | 7/2010 | Gazenko |
| 2010/0191181 A1 | 7/2010 | Childers et al. |
| 2010/0204765 A1 | 8/2010 | Hall et al. |
| 2011/0005992 A1 | 1/2011 | Kelly et al. |
| 2011/0009797 A1 | 1/2011 | Kelly et al. |
| 2011/0105877 A1 | 5/2011 | Wilt et al. |
| 2011/0303588 A1 | 12/2011 | Kelly et al. |
| 2011/0303598 A1 | 12/2011 | Lo et al. |
| 2012/0123322 A1 | 5/2012 | Scarpaci et al. |
| 2013/0037485 A1 | 2/2013 | Wilt et al. |
| 2013/0193041 A1 | 8/2013 | Rohde |
| 2013/0204174 A1* | 8/2013 | Olde .............. A61M 1/3656 604/6.11 |
| 2013/0304020 A1 | 11/2013 | Wilt et al. |
| 2013/0343936 A1 | 12/2013 | Gray |
| 2014/0112828 A1 | 4/2014 | Grant et al. |
| 2014/0199193 A1 | 7/2014 | Wilt et al. |
| 2014/0231319 A1* | 8/2014 | Olde .............. A61M 1/34 210/97 |
| 2014/0260551 A1 | 9/2014 | Gray et al. |
| 2014/0260556 A1 | 9/2014 | Gray et al. |
| 2014/0276428 A1 | 9/2014 | Gray et al. |
| 2014/0288488 A1 | 9/2014 | Distler et al. |
| 2014/0288489 A1 | 9/2014 | Distler et al. |
| 2014/0288490 A1 | 9/2014 | Distler et al. |
| 2014/0309611 A1 | 10/2014 | Wilt et al. |
| 2014/0319041 A1 | 10/2014 | Wilt et al. |
| 2014/0323954 A1 | 10/2014 | Scarpaci et al. |
| 2015/0042366 A1 | 2/2015 | Wilt et al. |
| 2015/0196699 A9 | 7/2015 | Wilt et al. |
| 2016/0030657 A1 | 2/2016 | Kelly et al. |
| 2016/0030658 A1 | 2/2016 | van der Merwe et al. |
| 2016/0058933 A1 | 3/2016 | Ballantyne et al. |
| 2016/0101227 A1 | 4/2016 | Norris et al. |
| 2016/0101278 A1 | 4/2016 | Norris et al. |
| 2016/0144093 A1 | 5/2016 | Demers et al. |
| 2016/0175506 A1 | 6/2016 | Wilt et al. |
| 2017/0143886 A1 | 5/2017 | Wilt et al. |
| 2017/0296803 A1 | 10/2017 | Grant et al. |
| 2017/0319765 A1 | 11/2017 | Wilt et al. |
| 2018/0296746 A1 | 10/2018 | van der Merwe et al. |
| 2018/0372084 A1 | 12/2018 | Grant et al. |
| 2019/0099534 A1 | 4/2019 | McGill et al. |
| 2019/0160220 A1 | 5/2019 | Wilt et al. |
| 2019/0186483 A1 | 6/2019 | Demers et al. |
| 2019/0321535 A1 | 10/2019 | Beavers et al. |
| 2019/0323492 A1 | 10/2019 | Tracey et al. |
| 2020/0054809 A1 | 2/2020 | Kamen et al. |
| 2020/0086030 A1 | 3/2020 | Scarpaci et al. |
| 2020/0086035 A1 | 3/2020 | Wilt et al. |
| 2020/0139031 A1 | 5/2020 | Wilt et al. |
| 2020/0171226 A1 | 6/2020 | Wilt et al. |
| 2020/0191132 A1 | 6/2020 | Demers et al. |
| 2020/0215252 A1 | 7/2020 | Distler et al. |
| 2020/0222609 A1 | 7/2020 | Ballantyne et al. |
| 2020/0282124 A1 | 9/2020 | Grant et al. |
| 2020/0376185 A1 | 12/2020 | Wilt et al. |
| 2020/0376186 A1 | 12/2020 | Wilt et al. |
| 2020/0400595 A1 | 12/2020 | Kamen et al. |

FOREIGN PATENT DOCUMENTS

| | | |
|---|---|---|
| CA | 2336478 A1 | 2/2000 |
| CA | 2341993 A1 | 3/2000 |
| CA | 2704411 A1 | 5/2009 |
| CN | 1455262 A | 11/2003 |
| EP | 0 238 809 A2 | 9/1987 |
| EP | 0 406 562 A2 | 1/1991 |
| EP | 0 706 044 A1 | 4/1996 |
| EP | 1 195 171 A2 | 4/2002 |
| EP | 1 356 836 A2 | 10/2003 |
| EP | 1 666 078 A2 | 6/2006 |
| EP | 1 837 046 A1 | 9/2007 |
| GB | 2 423 241 A | 8/2006 |
| JP | S58-169462 | 10/1983 |
| JP | H04-358779 A | 12/1992 |
| JP | H06-77745 | 11/1994 |
| JP | 2001-112863 A | 4/2001 |
| JP | 2003-180825 A | 7/2003 |
| JP | 2003-265599 A | 9/2003 |
| JP | 2006-218068 A | 8/2006 |
| JP | 2007-020961 A | 2/2007 |
| JP | 2008-104737 A | 5/2008 |
| JP | 2008-136673 A | 6/2008 |
| JP | 4233717 B2 | 3/2009 |
| JP | 2010-206946 A | 9/2010 |
| JP | 2011-033760 A | 2/2011 |
| JP | 5031184 B2 | 9/2012 |
| WO | WO 84/02473 A1 | 7/1984 |
| WO | WO 1993/011829 A1 | 6/1993 |
| WO | WO 94/11093 A1 | 5/1994 |
| WO | WO 97/11771 A1 | 4/1997 |
| WO | WO 99/29356 A1 | 6/1999 |
| WO | WO 00/15278 A1 | 3/2000 |
| WO | WO 01/18396 A1 | 3/2001 |
| WO | WO 03/080268 A1 | 10/2003 |
| WO | WO 03/086505 A1 | 10/2003 |
| WO | WO 03/099353 A2 | 12/2003 |
| WO | WO 2004/041081 A1 | 5/2004 |
| WO | WO 2006/013312 A1 | 2/2006 |
| WO | WO 2006/088419 A2 | 8/2006 |
| WO | WO 2006/120415 A1 | 11/2006 |
| WO | WO 2007/113936 A1 | 10/2007 |
| WO | WO 2007/120812 A2 | 10/2007 |
| WO | WO 2008/028653 A2 | 3/2008 |
| WO | WO 2011/053810 A2 | 5/2011 |
| WO | WO 2012/006425 A2 | 1/2012 |
| WO | WO 2015/183976 A2 | 12/2015 |
| WO | WO 2015/183981 A2 | 12/2015 |

OTHER PUBLICATIONS

[No Author Listed] Homechoice Patient At-Home Guide, Jun., 1998. 84 pages.

No Author Listed, Patient At-Home Guide, HomeChoice Automated PD System. Version 2.0 (published May, 1997); Baxter Healthcare Corporation. Copyright 1994. 61 pages.

2008K2 Hemodialysis Machine Operator's Manual. Fresenius Medical Care. https://laz2qm2bxvodlae4oellp3es-wpengine.netdna-ssl.com/wp-content/uploads/2018/09/490136_Rev_K.pdf.

Bengtsson et al., Haemo dialysis software architecture design experiences. Proceedings of the 1999 International Conference on Software Engineering. IEEE Cat. No. 99CB37002. New York, NY. 1999:516-25.

Choppy et al., Architectural patterns for problem frames—relating software requirements and architectures. IEEE Proceedings: Software, IEE. Stevenage, GB. Aug. 5, 2005;52(4):198-208.

Gentilini et al., Automatic controllers capable of regulating mutliple patient outputs for higher-quality anesthesia treatment. IEEE Engineering in Medicine and Biology Magazine. IEEE Service Centers. Piscataway, NJ. Jan. 1, 2001;20(1):39-53.

Harel et al., Statecharts: A visual formalism for complex systems. Retrieved from the Internet: http://www.wisdom.weizmann.ac.il/~harel/Statecharts87.pdf> Retrieved on Jul. 2, 2002.

Krasner et al., A cookbook for using the model-view-controller user interface paradigm in smalltalk-80. JOOP. Aug. 1, 1988;1(3):26-49.

Mineshima et al., Efficacy of internal filtration enhanced hemodialysis. Artifical Organs. 1999;28(1):127-33.

U.S. Appl. No. 17/107,495, filed Nov. 30, 2020, Demers et al.
U.S. Appl. No. 17/067,605, filed Oct. 9, 2020, Wilt et al.
U.S. Appl. No. 16/916,039, filed Jun. 29, 2020, Kamen et al.
U.S. Appl. No. 15/469,065, filed Mar. 24, 2017, Wilt et al.
U.S. Appl. No. 16/901,897, filed Jun. 15, 2020, Wilt et al.
U.S. Appl. No. 16/901,926, filed Jun. 15, 2020, Wilt et al.
U.S. Appl. No. 17/128,667, filed Dec. 21, 2020, Tracey et al.

(56) References Cited

OTHER PUBLICATIONS

U.S. Appl. No. 15/012,764, filed Feb. 1, 2016, Demers et al.
U.S. Appl. No. 16/207,349, filed Dec. 3, 2018, McGill et al.
U.S. Appl. No. 16/263,950, filed Jan. 31, 2019, Wilt et al.
U.S. Appl. No. 16/691,806, filed Nov. 22, 2019, Scarpaci et al.
U.S. Appl. No. 17/026,804, filed Sep. 21, 2020, Grant et al.
U.S. Appl. No. 17/107,645, filed Nov. 30, 2020, Grant et al.
U.S. Appl. No. 16/723,053, filed Dec. 20, 2019, Wilt et al.
U.S. Appl. No. 16/723,408, filed Dec. 20, 2019, Wilt et al.
U.S. Appl. No. 16/247,204, filed Jan. 14, 2019, Beavers et al.
SG 11201609765V, dated Nov. 3, 2017, **Search Report, Written Opinion and claims as pending.

* cited by examiner

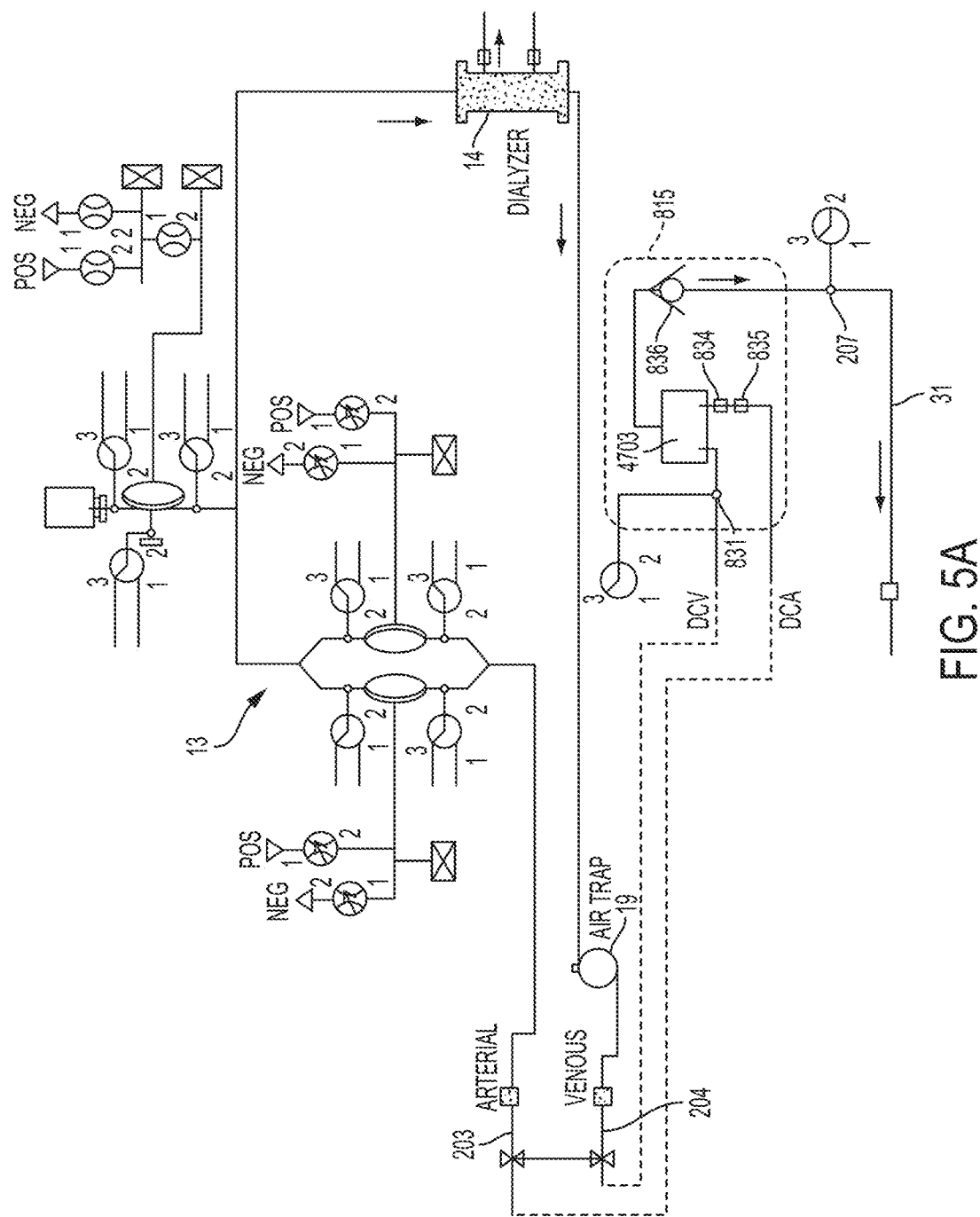

Section A-A

SYSTEMS AND METHODS FOR DETECTING VASCULAR ACCESS DISCONNECTION

RELATED APPLICATIONS

This application is a division of U.S. patent application Ser. No. 14/723,221, entitled "Systems and Methods for Detecting Vascular Access Disconnection," filed on May 27, 2015, now U.S. Pat. No. 9,999,717, which is a continuation in part of U.S. patent application Ser. No. 14/122,166, entitled "Hemodialysis System," filed on Nov. 25, 2013, now U.S. Pat. No. 9,724,458, issued on Aug. 8, 2017, which is a 35 U.S.C. '371 Application of International Patent Application Serial No. PCT/US2012/039369, entitled "Hemodialysis System," filed May 24, 2012, which claims the benefit, under 35 U.S.C. § 119(e), of U.S. Provisional Patent Application Ser. No. 61/489,464, entitled "Hemodialysis System," filed on May 24, 2011.

U.S. patent application Ser. No. 14/723,221 also claims the benefit, under 35 U.S.C. § 119(e), of U.S. Provisional Patent Application Ser. No. 62/121,980, entitled "Hemodialysis System," filed Feb. 27, 2015 and U.S. Provisional Patent Application Ser. No. 62/003,346, entitled "Hemodialysis System," filed May 27, 2014. All of the above-referenced applications are incorporated herein by reference in their entireties.

FIELD OF INVENTION

The present invention generally relates to hemodialysis and similar dialysis systems, e.g., systems able to treat blood or other bodily fluids extracorporeally.

BACKGROUND

Many factors make hemodialysis inefficient, difficult, and expensive. These factors include the complexity of hemodialysis, the safety concerns related to hemodialysis, and the very large amount of dialysate needed for hemodialysis. Moreover, hemodialysis is typically performed in a dialysis center requiring skilled technicians. Therefore any increase in the ease and efficiency of the dialysis process could have an impact on treatment cost or patient outcome.

SUMMARY OF INVENTION

Aspects of the invention generally relate to hemodialysis and similar dialysis systems. Illustrative embodiments described herein involve, in some cases, interrelated products, alternative solutions to a particular problem, and/or a plurality of different uses of one or more systems and/or articles. Although the various systems and methods described herein are described in relation to hemodialysis, it should be understood that the various systems and method described herein are applicable to other dialysis systems and/or in any extracorporeal system able to treat blood or other bodily fluids, such as hemofiltration, hemodiafiltration, etc.

In one aspect of the invention, a method for detecting an access disconnection, the method includes measuring the electrical impedance from a venous line to an arterial line via a vascular access site, determining an electrical quantity from the measured electrical impedance, comparing the electrical quantity to a first predetermined threshold, initiating a counter when the electrical quantity crosses a first threshold, and declaring an access disconnection if the counter reaches a predetermined value before the electrical quantity crosses a second threshold. The counter may count units of time, blood volume pumped to the vascular access site or the number of strokes of a blood pump. The electrical quantity may be raw or filtered value of the impedance between the probes, the time derivative of the impedance, or the difference between a first filtered value of the impedance with a first time constant and a second filtered value of the impedance with a second time constant that is longer than the first time constant. The method for detecting an access disconnect may determine the electrical quantity from the measured impedance only while a blood pump is flowing fluid through the arterial line or the venous line. Further, a controller in communication with the blood pump, the occluder and the user interface may in response to the ADS algorithm declaring an access disconnect, stop the action of the blood pump, close the occluder and/or signal the user. The controller in the event of a declared access disconnect may ask the user to verify the position of arterial and venous needles at the vascular access site and then allow the user to select resume therapy or end therapy.

In another aspect of the invention, method for detecting an access disconnection, the method includes measuring the electrical impedance from a venous line to an arterial line via an vascular access site at regular intervals, determining an electrical quantity from the measured electrical impedance, completing the stroke of a pump delivering blood to the patient, reducing the driving force on the pump plunger to a lower value, declaring an access disconnection when the electrical quantity exceeds a first predetermined threshold. The electrical quantity may the raw or filtered electrical impedance or the time derivative of the impedance or the difference between a first filtered value of the impedance with a first time constant and a second filtered value of the impedance with a second time constant that is longer than the first time constant.

In another aspect of the invention, a method for detecting an access disconnection, the method includes measuring the electrical impedance from a venous line to an arterial line via an vascular access site, determining an electrical quantity from the measured electrical impedance, comparing the electrical quantity to a first predetermined threshold, setting a provisional flag when the electrical quantity crosses a first threshold, clearing the provisional flag when the electrical quantity crosses a second threshold, and declaring an access disconnection when the provisional flag is consistently set for more than a given period.

In another aspect of the invention, a system for detecting an access disconnection, the system includes a venous line and arterial line each connected to a blood pump at one end and to an vascular access site on a patient at the other end, a circuit capacitively coupled to blood in the venous line and the arterial line capable of measuring the electrical impedance through part of the venous line, part of the arterial line and through the vascular access site, and a controller in communication with the blood pump and the circuit which, determines an electrical quantity from the measured electrical impedance, compares the electrical quantity to a first predetermined threshold, initiates a counter when the electrical quantity crosses a first threshold, and declares an access disconnection if the counter reaches a predetermined value before the electrical quantity crosses a second threshold.

A system controller can be configured to detect dislodgment of a catheter or needle in a vascular access comprising a first and second catheter or needle in a blood vessel, fistula or graft. The system comprises a first line fluidly connecting the first catheter or needle to an inlet of a pump; a second line fluidly connecting the second catheter or needle to an outlet of the pump; a first connector connecting the first line to the first catheter or needle; a second connector connecting the second line to the second catheter or needle, each connector having an electrode in fluid communication with a fluid-carrying lumen of its connector; an electronic circuit electrically connected to the electrodes of the first and second connectors, and configured to measure electrical impedance of fluid between the first connector and the second connector via a conductive path through the blood vessel, fistula or graft; and a controller configured to receive a series of sampled electrical impedance values from the electronic circuit, and to process the electrical impedance values as a signal. Operation of the pump may comprise extracorporeal circulation of a portion of a user's blood.

In an embodiment, the controller can be configured to sample and filter or smooth the signal using a first time constant, yielding a first filtered signal; sample and filter or smooth the signal using a second longer time constant, yielding a second filtered signal; provisionally set a disconnection flag and initiate a counter if at a point in time the difference between the first filtered signal and the second filtered signal is greater than a first threshold value; clear the disconnection flag if the difference between the first filtered signal and the second filtered signal decreases to less than a second lower threshold value before the counter has reached a pre-determined count; and declare a vascular disconnection if the disconnection flag is not cleared before the counter has reached the pre-determined count.

Optionally, the declaration may cause the controller to activate one or more mechanical line occluders to stop a flow of fluid in the first and second lines, stop the pump, or notify a user of the occurrence of a possible vascular disconnection. Notification of the user may comprise requesting that the user verify the position of the first and second catheters or needles at the vascular access. The controller may be configured to receive from the user a command to resume operation of the pump or to discontinue further operation of the pump. The controller may be configured to raise the first threshold value if a plurality of declarations of a vascular disconnection are each followed by a user command to resume operation of the pump. The controller may continue to process the electrical impedance values if a declaration of a vascular disconnection is made and the mechanical line occluders are activated, and the controller may be configured to confirm a vascular disconnection if the difference between the first filtered signal and the second filtered signal exceeds a third threshold value that is greater than the first threshold value.

The counter may count units of time, the pre-determined count being a pre-determined time interval; may count units of blood volume pumped to the vascular access, the pre-determined count being a pre-determined volume of blood; or may count strokes of the pump, the pre-determined count being a pre-determined number of strokes.

The signal may be a time derivative of the electrical impedance values.

The controller may stop processing the electrical impedance values if the pump stops pumping fluid through the first and second lines.

In an embodiment, the controller may conduct any of all of the above processes without filtering the signal data, or by using a filtered version of the signal data. The controller may conduct any or all of the above processes by using a difference between a first filtered signal using a first time constant and a second filtered signal using a second longer time constant. Alternatively, the processed signal may be a ratio between the first filtered signal and the second filtered signal, comparing the ratio to first, second and/or third values to set provisional flags or to initiate or terminate a counter. The controller may conduct any or all of the above processes without using a counter or setting a provisional disconnection flag.

The controller may perform a signal test to determine whether a dislodgment event has been obscured by a conductive pathway between the electrodes outside of the blood vessel, fistula or graft. The controller may sample and filter or smooth the signal using a first time constant, yielding a first filtered signal; sample and filter or smooth the signal using a second longer time constant, yielding a second filtered signal; initiate a counter and set a provisional disconnection flag if a difference between the first filtered signal and the second filtered signal exceeds a first threshold value; temporarily clear the provisional disconnection flag if the difference between the first filtered signal and the second filtered signal drops below a second lower threshold value before the counter reaches a preset count; command an actuator of the pump to apply a force to a pumping chamber of the pump to complete a fluid delivery stroke to the first or second catheter or needle; command the actuator to apply a reduced force to the pumping chamber; and declare an access disconnection if the difference between the first filtered signal and the second filtered signal exceeds a third threshold value that is equal to or greater than the first threshold value.

In an embodiment, the controller may be able to detect a transition from a blood-filled blood tubing set to a dialysate-filled blood tubing set during a rinseback procedure. A delayed or incomplete transition may be an indication, for example, of an occlusion at or distal to the connectors. The controller may be configured to measure the signal or a filtered form of the signal as dialysate is pumped through the dialyzer to the blood tubing set; determine whether the signal or a filtered form of the signal has a first value approximately equal to an expected value of the signal for blood in the first and second fluid lines, or has a second value approximately equal to an expected value of the signal for dialysate solution in the first and second fluid lines; determine a point in time when the signal or a filtered form of the signal changes from the first value to the second value; and provide a first notification to a user if the controller detects a change from the first value to the second value, or provide a second notification to the user if the controller detects a change from the first value that is less than approximately the second value within a pre-determined period of time.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Aspects of the invention are described with reference to illustrative embodiments, which are described with reference to the drawings in which like numerals reference like elements, and wherein:

FIG. 5A is a schematic fluid flow diagram illustrating a flow path for a drain assembly in an illustrative embodiment;

FIG. 20 B is a rear exploded view of the blood pump cassette of FIG. 20A;

DETAILED DESCRIPTION

Figure 1:
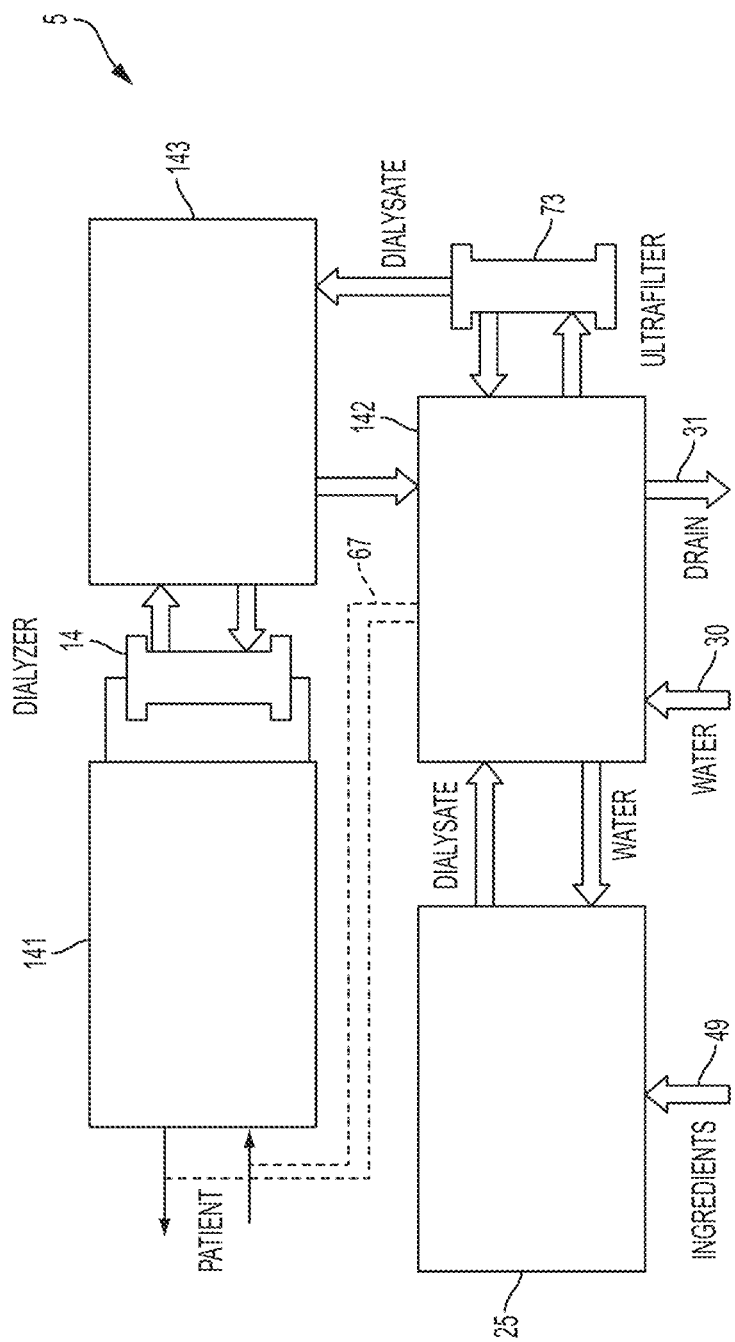
FIG. 1 is a schematic representation of fluid handling components of a hemodialysis system in an illustrative embodiment.

Various aspects of the invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed below, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same or catheter needle (e.g., the two lines or lumens may both be present within the same needle, i.e., a form of "dual lumen" flow). In still other embodiments, a "Y" site or "T" site is used, where blood is drawn from the patient and returned to the patient through one patient connection having two branches (one being the fluid path for the drawn blood, the second the fluid path for the return blood, i.e., a form of "single needle" flow). The patient may be any subject in need of hemodialysis or similar treatments, including non-human subjects, such as dogs, cats, monkeys, and the like, as well as humans.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. The dialysate in some cases may be re-circulated in a "multi-pass" arrangement, which may be beneficial in capturing larger molecules having low mobility across the dialyzer. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a pore size chosen to prevent species such as these from passing therethrough. For instance, the pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium, chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically are separated by a semi-permeable membrane. Typically, the semipermeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases (such as high-flux dialyzers), even larger molecules, such as beta-2-microglobulin, may pass through the membrane. In some cases, for example, ions and molecules may pass through the dialyzer by convective flow if a hydrostatic pressure difference exists across the semi-permeable membrane.

It should be noted that, as used herein, "fluid" means anything having fluidic properties, including but not limited to, gases such as air, and liquids such as water, aqueous solution, blood, dialysate, etc.

FIG. 1 shows a schematic block diagram of fluid circuitry for a hemodialysis system that incorporates various aspects of the invention. In this illustrative embodiment, the dialysis system 5 includes a blood flow circuit 141 that draws blood from a patient, passes the blood through a dialyzer 14, and returns the treated blood to the patient. A balancing circuit or an internal dialysate circuit 143 receives dialysate from an ultrafilter 73, passes the dialysate through the dialyzer 14, and receives used dialysate from the dialyzer 14. A directing circuit or an external dialysate circuit 142 provides fresh dialysate to the ultrafilter 73, and receives used dialysate from the internal dialysate circuit 143 (which may be directed to a drain 31). The directing circuit 142 can also receive water from a water supply 30 and pass it to a mixing circuit 25. The mixing circuit 25 forms dialysate using water from the directing circuit 142 and reagent ingredients 49, such as citric acid, salt and a bicarbonate, that may be received from a renewable source. The mixing circuit 25 may prepare dialysate, for example, on an as-needed basis, during and/or in advance of dialysis. New dialysate prepared by the mixing circuit 25 may be provided to the directing circuit 142, which may provide the dialysate to the ultrafilter 73, as described above. The directing circuit 142 may include a heater to heat the dialysate to a suitable temperature and/or to heat fluid in the system for disinfection. Conduits 67 (shown in dotted line) may be connected between the blood flow circuit 141 and the directing circuit 142, e.g., for disinfection of the hemodialysis system.

Figure 2:
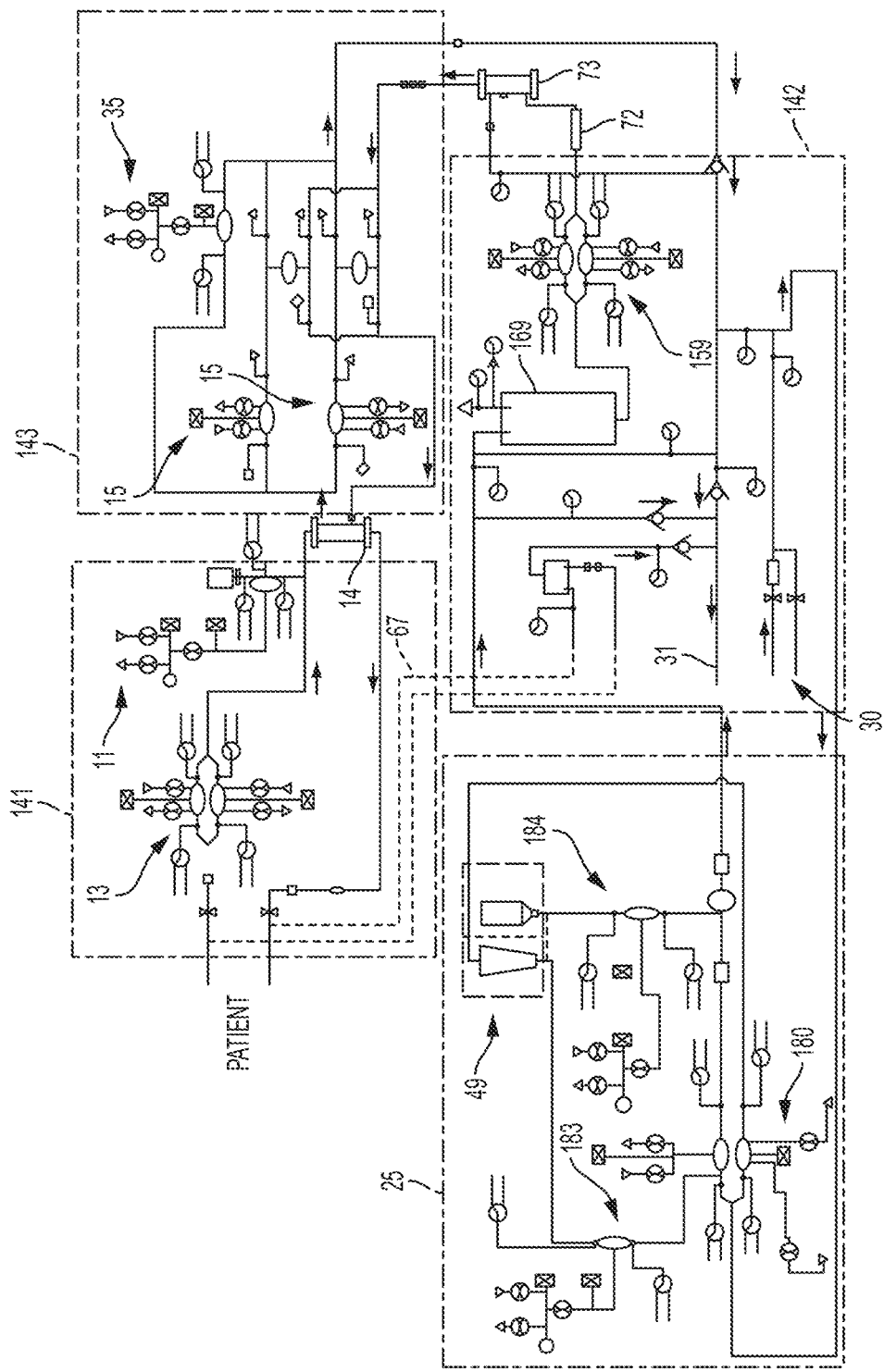
FIG. 2 shows a schematic fluid flow diagram for the dialysis system of FIG. 1.

FIG. 2 is a schematic diagram showing a more detailed circuit arrangement for the dialysis system 5 shown in FIG. 1. It should be understood, of course, that FIG. 2 is only one possible embodiment of the general hemodialysis system of FIG. 1, and in other embodiments, other fluid circuits, modules, flow paths, layouts, etc. are possible. Examples of such systems are discussed in more detail below, and also can be found in the following, each of which is incorporated herein by reference: U.S. application Ser. No. 12/072,908, filed Feb. 27, 2008, U.S. Provisional Application 60/903,582, filed Feb. 27, 2007, U.S. Provisional Application 60/904,024, filed Feb. 27, 2007, U.S. patent application Ser. No. 11/871,680, filed Oct. 12, 2007, U.S. patent application Ser. No. 11/871,712, filed Oct. 12, 2007, U.S. patent application Ser. No. 11/871,787, filed Oct. 12, 2007, U.S. patent application Ser. No. 11/871,793, filed Oct. 12, 2007, or U.S. patent application Ser. No. 11/871,803, filed Oct. 12, 2007.

The blood flow circuit 141 includes an anticoagulant supply 11 and a blood flow pump 13 which pumps blood from a patient through a dialyzer 14 and returns the blood to the patient. The anticoagulant supply 11, although shown in the path of blood flowing towards the dialyzer, may be instead located in another suitable location. e.g., any location upstream or downstream from blood flow pump 13. The balancing circuit 143 includes two dialysate pumps 15, which pump dialysate into the dialyzer 14, and a bypass pump 35. The flow of blood through the blood flow circuit 141 in some cases, is synchronized with the flow of dialysate in the dialysate flow path. In an embodiment, the flow of dialysate into and out of the dialyzer 14 and the balancing circuit 143 is balanced volumewise using balancing chambers in the balancing circuit 143. The directing circuit 142 includes a dialysate pump 159, which pumps dialysate from a dialysate tank 169 through a heater 72 and/or the ultrafilter 73 to the balancing circuit 143. The directing circuit 142 also receives waste fluid from balancing circuit 143 and directs it to a drain 31. In some cases, the blood flow circuit 141 can be connected via conduits 67 to the directing circuit 142, e.g., for disinfection, as discussed below. Dialysate in the dialysate tank 169 is provided by the mixing circuit 25, which produces the dialysate using water from a water supply 30 provided via the directing circuit 142 and dialysate ingredients 49 (e.g., bicarbonate and acid). A series of mixing pumps 180, 183, 184 are used to mix the various components and produce the dialysate.

Figure 3:
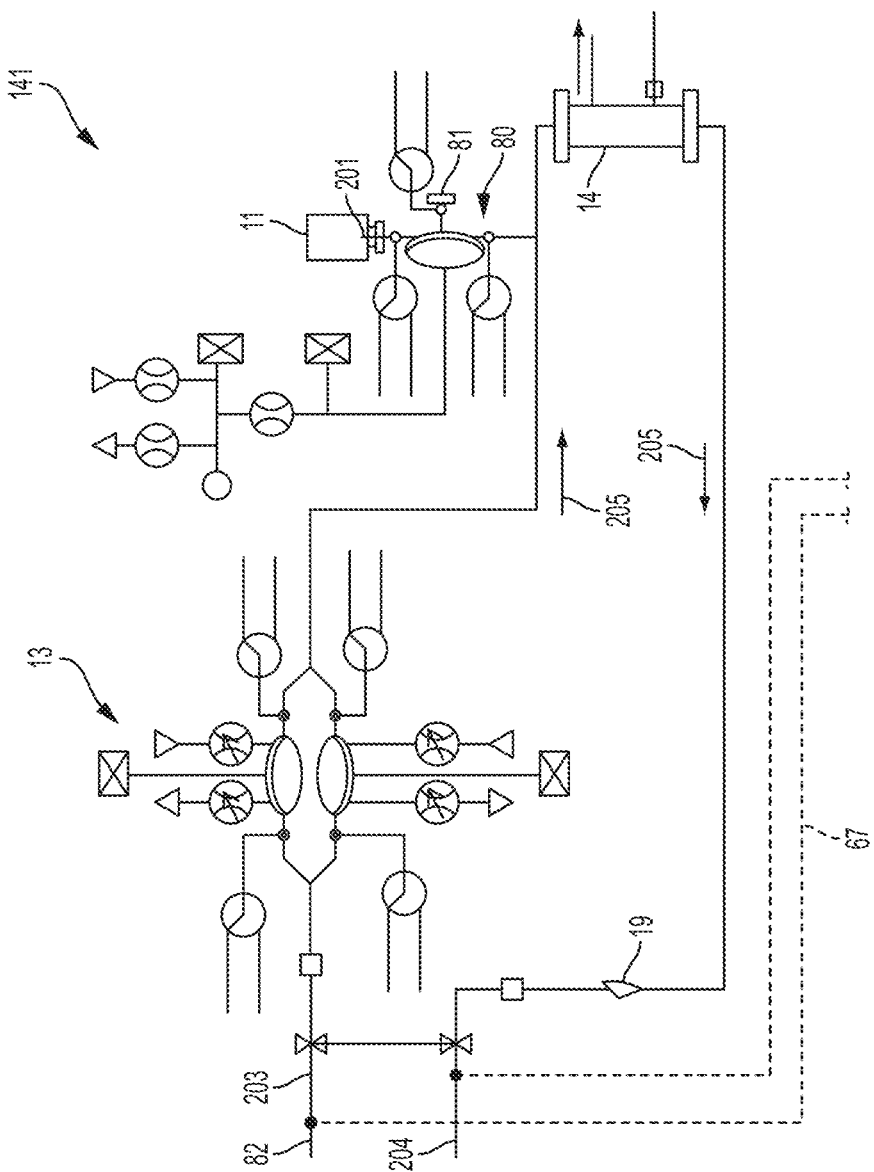
FIG. 3 is a schematic fluid flow diagram for the blood flow circuit of the FIG. 2 embodiment.

FIG. 3 shows a close-up view of the blood flow circuit 141 in this illustrative embodiment. Under normal operation, blood flows from a patient through arterial line 203 via blood flow pump 13 to the dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. After passing through dialyzer 14 and undergoing dialysis, the blood returns to the patient through venous line 204, optionally passing through an air trap and/or a blood sample port 19. The pump 13 may include, for instance, pumps 23 that are actuated by a control fluid.

For example, in one embodiment, the blood flow pump 13 may comprise two (or more) pod pumps 23. Each pod pump, in this particular example, may include a rigid chamber with a flexible diaphragm or membrane dividing each chamber into a pumping compartment and control compartment. There may be four entry/exit valves for these compartments, two for the pumping compartment and two for the control compartment. The valves for the control compartment of the chambers may be two-way proportional valves, one connected to a first control fluid source (e.g., a high pressure air source), and the other connected to a second control fluid source (e.g., a low pressure air source) or a vacuum source. The fluid valves can be opened and closed to direct fluid flow when the pod pumps 23 are operating. Non-limiting examples of pod pumps are described in U.S. Provisional Application 60/792,073, filed Apr. 14, 2006, or in U.S. patent application Ser. No. 11/787,212, filed Apr. 13, 2007, each incorporated herein by reference. If more than one pod pump is present, the pod pumps may be operated in any suitable fashion, e.g., synchronously, asynchronously, in-phase, out-of-phase, etc. For instance, in some embodiments, the two-pump pumps can be cycled out of phase to affect the pumping cycle, e.g., one pump chamber fills while the second pump chamber empties. A phase relationship anywhere between 0° (the pod pumps fill and empty in unison) and 180° (one pod pump fills as the other empties) can be selected in order to impart any desired pumping cycle. A phase relationship of 180° may yield continuous flow into and out of the set of pod pumps. This is useful, for instance, when continuous flow is desired, e.g., for use with dual needle or dual lumen catheter flow. Setting a phase relationship of 0°, however, may be useful in some cases for single needle/single lumen flow or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer.

An anticoagulant (e.g., heparin, or any other suitable anticoagulant) may be contained within a vial 11 (or other anticoagulant supply, such as a tube or a bag), and blood flow circuit 141 may include a spike 201 (which, in one embodiment, is a needle) that can pierce the seal of the vial. The spike 201 may be formed from plastic, stainless steel, or another suitable material, and may be a sterilizable material in some cases, e.g., the material may be able to withstand sufficiently high temperatures and/or radiation so as to sterilize the material.

An anticoagulant pump 80, which can act as a metering chamber in some cases, can be used to control the flow of anticoagulant into the blood circuit. The anticoagulant pump 80 may be a pod pump or a membrane-based metering pump, and/or may be actuated by a control fluid, such as air. For example, the anticoagulant pump 80 may include a rigid chamber with a flexible diaphragm dividing the chamber into a pumping compartment and a control compartment. One valve for the control compartment of the chamber may be connected to a first control fluid source (e.g., a high pressure air source), and the other valve connected to a second control fluid source (e.g., a low pressure air source) or a vacuum source. Valves for the pumping compartment of the chamber can be opened and closed in coordination with the control compartment, thus controlling the flow of anticoagulant into the blood. In one set of embodiments, air provided through a filter 81 may also be introduced into the blood flow path by the anticoagulant pump 80, e.g., to provide air into the vial 11 after or before anticoagulant is withdrawn from the vial.

Fluid Management System ("FMS") measurements may be used to measure the volume of fluid pumped through a pump chamber during a stroke of the membrane, or to detect air in the pumping chamber. FMS methods are described in U.S. Pat. Nos. 4,808,161; 4,826,482; 4,976,162; 5,088,515; and 5,350,357, which are hereby incorporated herein by reference in their entireties. In one illustrative embodiment, the volume of liquid delivered by an anticoagulant pump, a dialysate pump, or other membrane-based fluid pump is determined using an FMS algorithm in which changes in chamber pressure are used to calculate a volume measurement at the end of a fill stroke and at the end of a delivery stroke. The difference between the computed volumes at the end of fill and delivery strokes may be used to determine the actual stroke volume. This actual stroke volume can be compared to an expected stroke volume for the particular sized chamber. If the actual and expected volumes are significantly different, the stroke has not properly completed and an error message can be generated.

The blood flow circuit 141 may also include an air trap 19 to remove air bubbles that may be present within the blood flow path. In some cases, the air trap 19 is able to separate any air that may be present from the blood due to gravity, and/or may include a port for sampling blood.

Figure 4:
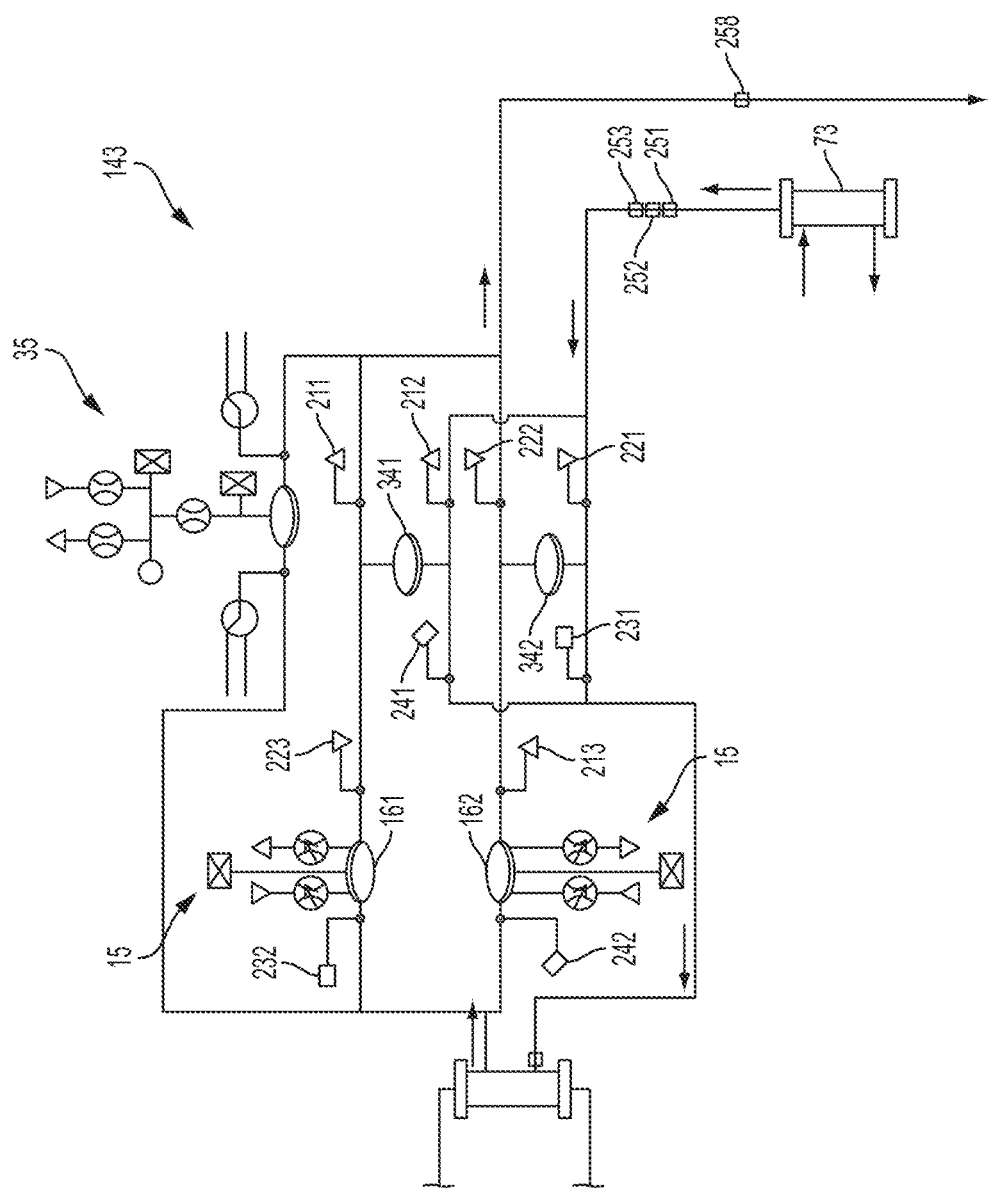
FIG. 4 is a schematic fluid flow diagram for the balancing circuit of the FIG. 2 embodiment.

FIG. 4 shows a close-up view of the balancing circuit 143 in the FIG. 2 embodiment. In the balancing circuit 143, dialysate flows from the optional ultrafilter 73 into a dialysate pump 15. In this embodiment, the dialysate pump 15 includes two pod pumps 161, 162, two balancing chambers 341, 342, and a pump 35 for bypassing the balancing chambers 341, 342. The balancing chambers 341, 342 may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Application 60/792,073, filed Apr. 14, 2006, or in U.S. patent application Ser. No. 11/787,212, filed Apr. 13, 2007.

In one embodiment, balancing of flow in the internal dialysate circuit works as follows. A set of pneumatically operated valves 211, 212, 213, 241, 242 has its operation synchronized and controlled together, where valves 211, 212, 213 are ganged and valves 241 and 242 are ganged, and a second set of pneumatically operated valves 221, 222, 223, 231, 232 similarly have its operation synchronized and controlled together, where valves 221, 222, 223 are ganged, and valves 231 and 232 are ganged. At a first point of time, the first set of valves 211, 212, 213, 241, 242 is opened while the second set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161.

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer 14 (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer 14. In an embodiment, the fluid (e.g. pneumatic) pressures on the control side of the balancing chamber valves are monitored to ensure they are functioning (e.g., opening and closing) properly.

As a specific example, a vacuum (e.g., 4 p.s.i. of vacuum) can be applied to the port for the first set of valves, causing those valves to open, while positive pressure (e.g., 20 p.s.i. of air pressure) is applied to the second set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

The bypass pump 35 can direct the flow of dialysate from the dialyzer 14 through balancing circuit 143 without passing through either of pod pumps 161 or 162. In this embodiment, the bypass pump 35 is a pod pump, similar to those described above, with a rigid chamber and a flexible diaphragm dividing each chamber into a fluid compartment and a control compartment. This pump may be the same or different from the other pod pumps and/or metering pumps described above. When control fluid is used to actuate the bypass pump 35, the additional drop in pressure on the exiting (spent) dialysate side of the dialyzer causes additional ultrafiltration of fluid from the blood in the dialyzer. This may cause a net efflux of fluid from the patient's blood, through the dialyzer, and ultimately to drain. Such a bypass may be useful, for example, in reducing the amount of fluid a patient has, which is often increased due to the patient's inability to excrete excess fluid (primarily water) through the kidneys. As shown in FIG. 4, the bypass pump 35 may be controlled by a control fluid (e.g., air), irrespective of the operation of pod pumps 161 and 162. This configuration may allow for easier control of net fluid removal from a patient, without having to operate the inside dialysate pumps either out of balance or out of phase with the blood pumps in order to achieve such fluid withdrawal from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be kept at pressures above atmospheric pressure. In contrast, however, the blood flow pump and the directing circuit pumps use pressures below atmosphere to pull the diaphragm towards the chamber wall to complete a fill stroke. Because of the potential of fluid transfer across the semi-permeable membrane of the dialyzer and because the pumps of the balancing circuit run at positive pressures, the balancing circuit pumps may be able to use information from the blood flow pump(s) in order to synchronize the delivery strokes of the balancing circuit chambers to the dialyzer with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the inside dialysate pump operates. When the blood flow pump is not delivering blood, the valves that control the flow from the dialyzer to the inside dialysate pumps (and other balancing valves ganged together with these valves, as previously discussed) may be closed to prevent any fluid transfer from occurring from the dialysate side to the blood side. During the time the blood flow pump is not delivering, the inside dialysate pumps are effectively frozen, and the inside dialysate pump delivery stroke resumes once the blood flow pump starts delivering again. The inside dialysate pump fill pressure can be set to a minimal positive value to ensure that the pump operates above atmosphere at minimal impedance. Also, the inside dialysate pump delivery pressure can be set to the blood flow pump pressure to generally match pressures on either side of the dialyzer, minimizing flow across the dialyzer during delivery strokes of the inside dialysate pump.

In another embodiment, the inside dialysate pump delivers dialysate to the dialyzer at a pressure slightly above the pressure at which blood is delivered to the dialyzer. This ensures that a full balance chamber of clean dialysate gets delivered to the dialyzer. On the return side, the inside dialysate pump can fill with spent dialysate from the dialyzer at a slightly lower pressure than the outlet pressure on the blood side of the dialyzer, ensuring that the receiving dialysate pump chamber can fill. This in turn ensures that there is enough dialysate available to complete a full stroke in the balancing chamber. Flows across the semi-permeable membrane caused by these differential pressures will tend to cancel each other; and the pumping algorithm otherwise attempts to match the average pressures on the dialysate and blood sides of the dialyzer.

It is generally beneficial to keep the blood flow as continuous as possible during therapy, as stagnant blood flow can result in blood clots. In addition, when the delivery flow rate on the blood flow pump is discontinuous, the balancing pump may pause its stroke more frequently, which can result in discontinuous and/or low dialysate flow rates. However, the flow through the blood flow pump can be discontinuous for various reasons. For instance, pressure may be limited within the blood flow pump, e.g., to +600 mmHg and/or −350 mmHg to provide safe pumping pressures for the patient. For instance, during dual needle flow, the two pod pumps of the blood flow pump can be programmed to run 180° out of phase with one another. If there were no limits on pressure, this phasing could always be achieved. However to provide safe blood flow for the patient these pressures are limited. If the impedance is high on the fill stroke (due to a small needle, very viscous blood, poor patient access, etc.), the negative pressure limit may be reached and the fill flow rate will be slower then the desired fill flow rate. Thus the delivery stroke must wait for the previous fill stroke to finish, resulting in a pause in the delivery flow rate of the blood flow pump. Similarly, during single needle flow, the blood flow pump may be run at 0° phase, where the two blood flow pump pod pumps are simultaneously emptied and filled. When both pod pumps are filled, the volumes of the two pod pumps are delivered. In an embodiment, the sequence of activation causes a first pod pump and then a second pod pump to fill, followed by the first pod pump emptying and then the second pod pump emptying. Thus the flow in single needle or single lumen arrangement may be discontinuous.

One method to control the pressure saturation limits would be to limit the desired flow rate to the slowest of the fill and deliver strokes. Although this would result in slower blood delivery flow rates, the flow rate would still be known and would be more continuous, which would allow for more accurate and continuous dialysate flow rates. Another method to make the blood flow rate more continuous in single needle operation would be to use maximum pressures to fill the pods so the fill time would be minimized. The desired deliver time could then be set to be the total desired stroke time minus the time that the fill stroke took. However, the less continuous the blood flow, the more the dialysate flow rate may have to be adjusted upward during blood delivery to the dialyzer to make up for the time that the dialysate pump is stopped when the blood flow pump is filling. If this is done with the correct timing, an average dialysate flow rate taken over several strokes can still match the desired dialysate flow rate.

Figure 5:
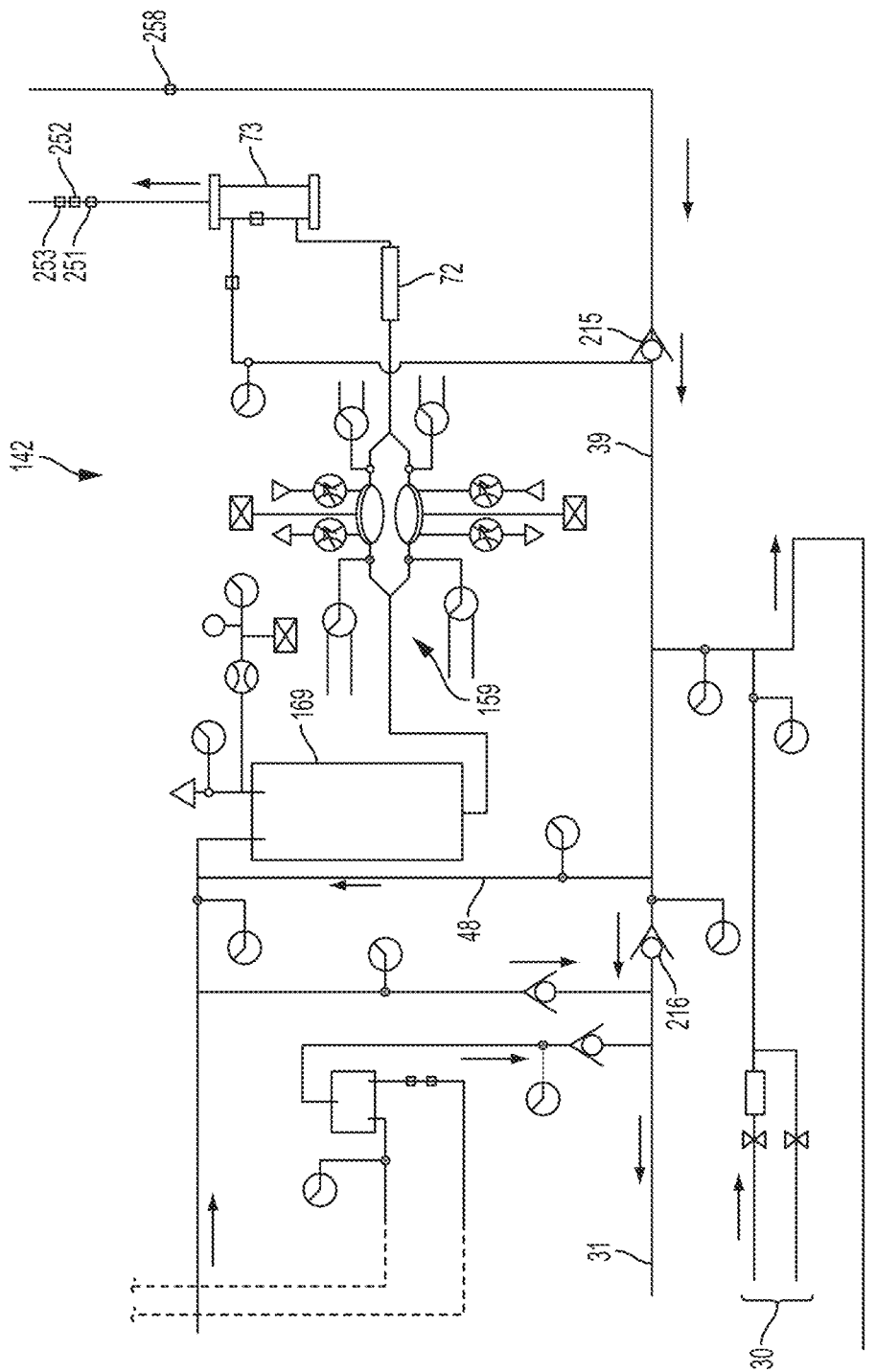
FIG. 5 is a schematic fluid flow diagram for the directing circuit of the FIG. 2 embodiment.

FIG. 5 shows a close up of the directing circuit 142 in the FIG. 2 embodiment. In this embodiment, the directing circuit 142 can provide dialysate from a dialysate tank 169 via a dialysate pump 159 to a heater 72 and the ultrafilter 73. The heater 72 may be used to warm the dialysate to body temperature, and/or a temperature such that the blood in the blood flow circuit is heated by the dialysate, and the blood returning to the patient is at body temperature or higher. In some cases, the heater 72 may be connected to a control system such that dialysate that is incorrectly heated (i.e., the dialysate is too hot or too cold) may be recycled (e.g., back to the dialysate tank 169) or sent to drain instead of being passed to the dialyzer. The heater 72 may also be used, in some embodiments, for disinfection or sterilization purposes. For instance, water may be passed through the hemodialysis system and heated using the heater such that the water is heated to a temperature able to cause disinfection or sterilization to occur, e.g., temperatures of at least about 70° C., at least about 80° C., at least about 90° C., at least about 100° C., at least about 110° C., etc.

The flow of dialysate through the directing circuit 142 may be controlled (at least in part) by operation of the dialysate pump 159. In addition, the dialysate pump 159 may control flow through the balancing circuit 143. For instance, as discussed above, fresh dialysate from the directing circuit 142 flows into balancing chambers 341 and 342 of balancing circuit 143. The dialysate pump 159 may be used as a driving force to cause the fresh dialysate to flow into these balancing chambers. In one set of embodiments, dialysate pump 159 includes a pod pump, e.g., similar to those described above.

The dialysate may also be filtered to remove contaminants, infectious organisms, pathogens, pyrogens, debris, and the like, for instance, using an ultrafilter 73. The ultrafilter 73 may be positioned in any suitable location in the dialysate flow path, for instance, between the directing circuit and the balancing circuit, e.g., as shown, and/or the ultrafilter 73 may be incorporated into the directing circuit or the balancing circuit. If an ultrafilter is used, its pore size may be chosen to prevent species such as these from passing through the filter.

In some cases, the ultrafilter 73 may be operated such that waste from the filter (e.g., the retentate stream) is passed to a waste stream, such as waste line 39 in FIG. 5. In some cases, the amount of dialysate flowing into the retentate stream may be controlled. For instance, if the retentate is too cold (i.e., heater 72 is not working, or heater 72 is not heating the dialysate to a sufficient temperature, the entire dialysate stream (or at least a portion of the dialysate) may be diverted to waste line 39, and optionally, recycled to dialysate tank 169 using line 48. Flow from the filter 73 may also be monitored for several reasons, e.g., using temperature sensors (e.g., sensors 251 and 252), conductivity sensors (for confirming dialysate concentration, e.g., sensor 253), or the like. An example of such sensors is discussed below; further non-limiting examples can be seen in a U.S. patent application Ser. No. 12/038,474, filed Feb. 27, 2008.

The ultrafilter and the dialyzer may provide redundant screening methods for the removal of contaminants, infectious organisms, pathogens, pyrogens, debris, and the like. Accordingly, any contaminant would have to pass through both the ultrafilter and the dialyzer before reaching a patient's blood. Even in the event that either the ultrafilter or dialyzer integrity fails, the other may still be able to maintain dialysate sterility and prevent contaminants from reaching the patient's blood.

The directing circuit 142 may also be able to route used dialysate coming from a balancing circuit to a drain, e.g., through waste line 39 to drain 31. The drain may be, for example, a municipal drain or a separate container for containing the waste (e.g., used dialysate) to be properly disposed of. In some cases, one or more check or "one-way" valves (e.g., check valves 215 and 216) may be used to control flow of waste from the directing circuit 142 and from the system 5. Also, in certain instances, a blood leak sensor (e.g., sensor 258) may be used to determine if blood is leaking through the dialyzer 14 into the dialysate flow path. In addition, a liquid sensor can be positioned in a collection pan at the bottom of the hemodialysis unit to indicate leakage of either blood or dialysate, or both, from any of the fluid circuits.

The directing circuit 142 may receive water from a water supply 30, e.g., from a container of water such as a bag, and/or from a device able to produce water, e.g., a reverse osmosis device. In some cases, the water entering the system is set at a certain purity, e.g., having ion concentrations below certain values. The water entering into the directing circuit 142 may be passed on to various locations, e.g., to a mixing circuit 25 for producing fresh dialysate and/or to waste line 39. In some cases, valves to the drain 31 and various recycle lines are opened, and conduits 67 may be connected between directing circuit 142 and blood flow circuit 141, such that water is able to flow continuously around the system. If heater 72 is also activated, the water passing through the system will be continuously heated, e.g., to a temperature sufficient to disinfect the system.

Figure 6:
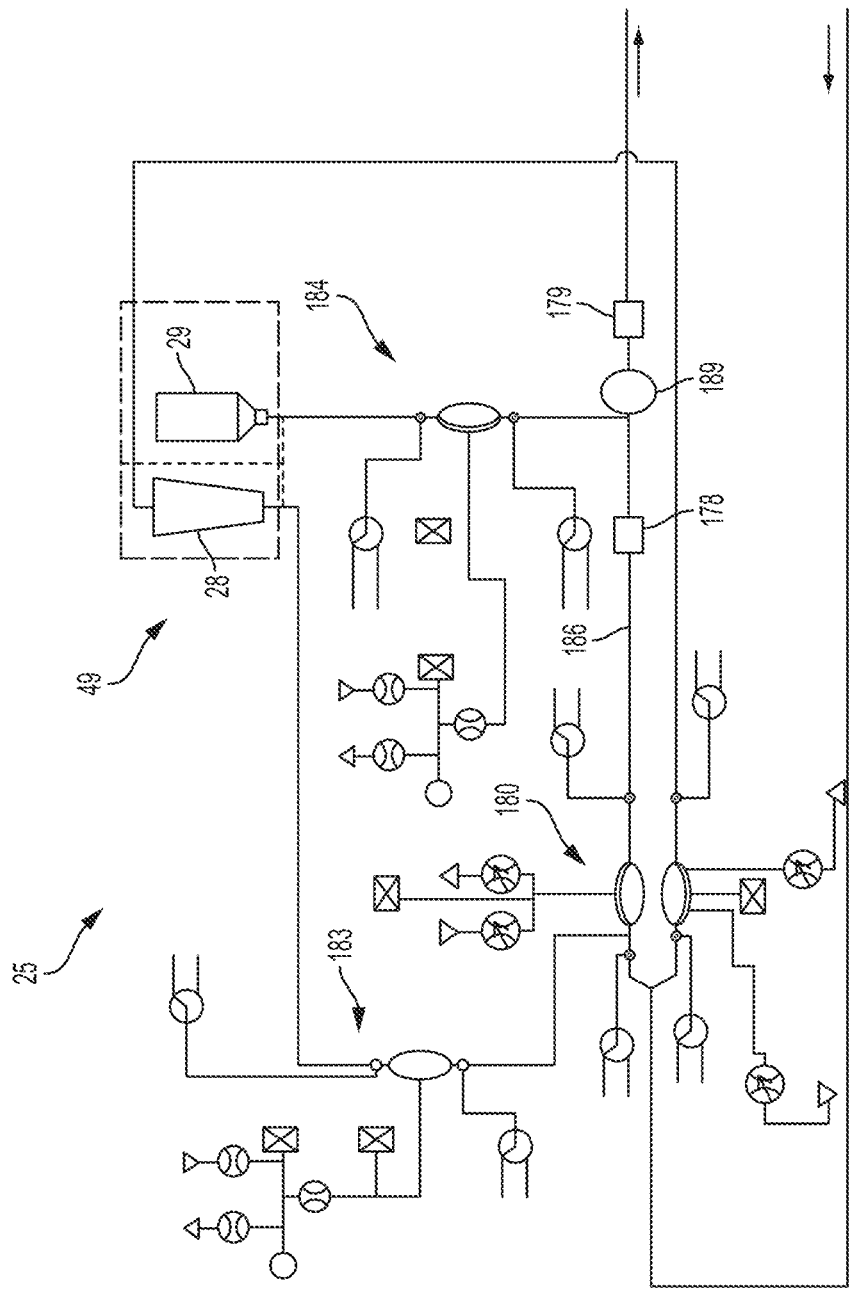
FIG. 6 is a schematic fluid flow diagram for the mixing circuit of the FIG. 2 embodiment.

FIG. 6 shows a close-up view of the mixing circuit 25 in the illustrative embodiment of FIG. 2. Water from the directing circuit 142 flows into the mixing circuit 25 due to action of a pump 180. In this embodiment, the pump 180 includes one or more pod pumps, similar to those described above. In some cases, a portion of the water is directed to reagent ingredients 49, e.g., for use in transporting the ingredients, such as the bicarbonate 28, through the mixing circuit 25. In some cases, sodium chloride and/or the sodium bicarbonate 28 may be provided in a powdered or granular form, which is mixed with water provided by the pump 180. Bicarbonate from bicarbonate source 28 is delivered via bicarbonate pump 183 to a mixing line 186, which also receives water from the directing circuit 142. Acid from an acid source 29 (which may be in a liquid form) is also pumped via an acid pump 184 to the mixing line 186. The ingredients 49 (water, bicarbonate, acid, NaCl, etc.) are mixed in mixing chamber 189 to produce dialysate, which then flows out of mixing circuit 25 to the directing circuit 142. Conductivity sensors 178 and 179 are positioned along mixing line 186 to ensure that as each ingredient is added to the mixing line, it is added at proper concentrations. The volumes delivered by the water pump 180 and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Figure 7:
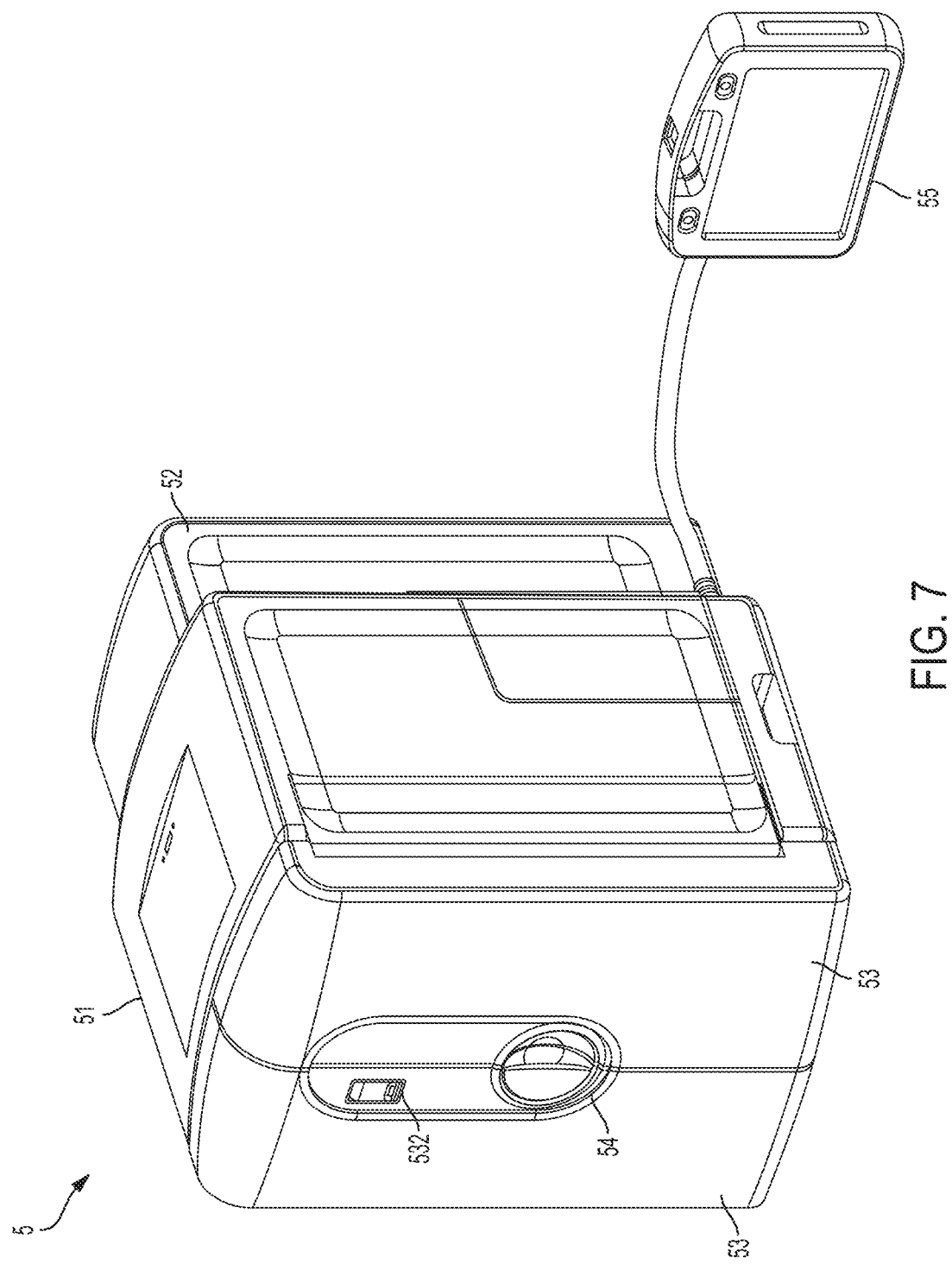
FIG. 7 is a right front perspective view of a hemodialysis system in an illustrative embodiment.

FIG. 7 shows a perspective view of a hemodialysis system 5 that incorporates various aspects of the invention. In accordance with one aspect of the invention, the system 5 includes a dialysis unit 51 and a power unit module 52 that are shown joined together. In this embodiment, the dialysis unit 51 has a housing that contains suitable components for performing hemodialysis, such as a dialyzer, one or more pumps to circulate blood through the dialyzer, a source of dialysate, and one or more pumps to circulate the dialysate through the dialyzer. For example, the dialysis unit 51 may include the mixing circuit 25, blood flow circuit 141, the balancing circuit 143 and the directing circuit 142 as described above. The dialysis unit 51 may also include all blood circuit connections and dialysate fluidic connections needed for operation of the system 5. Patient access and other connections may be revealed by opening side-by-side vertical doors 53 via a handle 54 at a front side of the dialysis unit 51 housing. In this embodiment, the dialysis unit 51 includes a control interface 55 (attached to the housing by a flexible cable in this embodiment) that a user may use to control operation of the dialysis unit 51. The control interface 55 may include a display screen with a touch sensitive overlay to allow touch control and interaction with a graphical user interface presented on the screen. The control interface 55 may also include other features, such as push buttons, a speaker, a microphone for receiving voice commands, a digital camera, and so on. The back side of the control interface 55 may include a retractable "kick-stand" (not shown) that allows the control interface 55 to be positioned on top of the dialysis unit 51 housing. Deploying the retractable "kick-stand" permits the control interface 55 to be placed in a near-vertical position to allow proper viewing of the display screen. In other embodiments, control interface 55 may comprise a tablet-style computer or handheld electronic communications device, either of which may communicate wirelessly with a controller housed within dialysis unit 51. Examples of wireless communications means may include Bluetooth® technology or wireless local area network technology such as Wi-Fi®.

The power unit 52 housing may contain suitable components for providing operating power to the dialysis unit 51, e.g., pneumatic pressure/vacuum to power the pumps, valves and other components of the dialysis unit 51. "Pneumatic," as used herein, means using air or other gas to move a flexible diaphragm or other member. (It should be noted that air is used by way of example only, and in other embodiments, other control fluids, such as nitrogen ($N_2$), $CO_2$, water, an oil, etc., may be used). As discussed above, the pumps and valves of the dialysis unit 51 may operate on pneumatic power, and thus the power unit 52 may provide one or more pneumatic sources for use by the dialysis unit 51. In this way, the dialysis unit 51 need not necessarily be arranged to generate and/or store the necessary pneumatic power needed, but instead may rely on the power unit module 52. The power unit 52 may include one or more pneumatic pumps to generate desired air pressure and/or vacuum, one or more accumulators or other devices to store pneumatic power, valves, conduits and/or other devices to control flow of pneumatic power in the power unit 52, as well as a controller having suitable components, such as a programmed general purpose data processor, memory, sensors (e.g., to detect pressure, temperature, etc.), relays, actuators, and so on.

In one embodiment, the pneumatic power (e.g., air under suitable pressure/vacuum) may be supplied by the power unit 52 to the dialysis unit 51 via one or more supply tanks or other pressure sources. For instance, if two tanks are used in the power unit 52, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pump pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for all of the dialysis unit 51 functions.

In one embodiment, the power unit 52 may include two independent compressors to service the supply tanks. Pressure in the tanks can be controlled using any suitable technique, for instance, with a simple "bang-bang" controller (a controller that exists in two states, i.e., in an on or open state, and an off or closed state), or with more sophisticated control mechanisms, depending on the embodiment. As an example of a bang-bang controller, for the positive tank, if the actual pressure is less than a set point, the compressor servicing the positive tank is turned on. If the actual pressure is greater than a set point, the compressor servicing the positive tank is turned off. The same logic may be applied to the vacuum tank and control of the vacuum compressor with the exception that the sign of the set point term is reversed. If the pressure tanks are not being regulated, the compressor is turned off and the valves are closed.

Tighter control of the pressure tanks can be achieved by reducing the size of the hysteresis band, however this may result in higher cycling frequencies of the compressor. If very tight control of these reservoirs is required, the bang-bang controller could be replaced with a proportional-integral-derivative ("PID") controller and using pulse width modulation ("PWM") signals on the compressors. Other methods of control are also possible.

Other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. A non-limiting example of a negative pressure is −400 mmHg. In some cases, the negative pressure source may be a vacuum pump, while the positive pressure pump may be an air compressor.

Figure 7A:
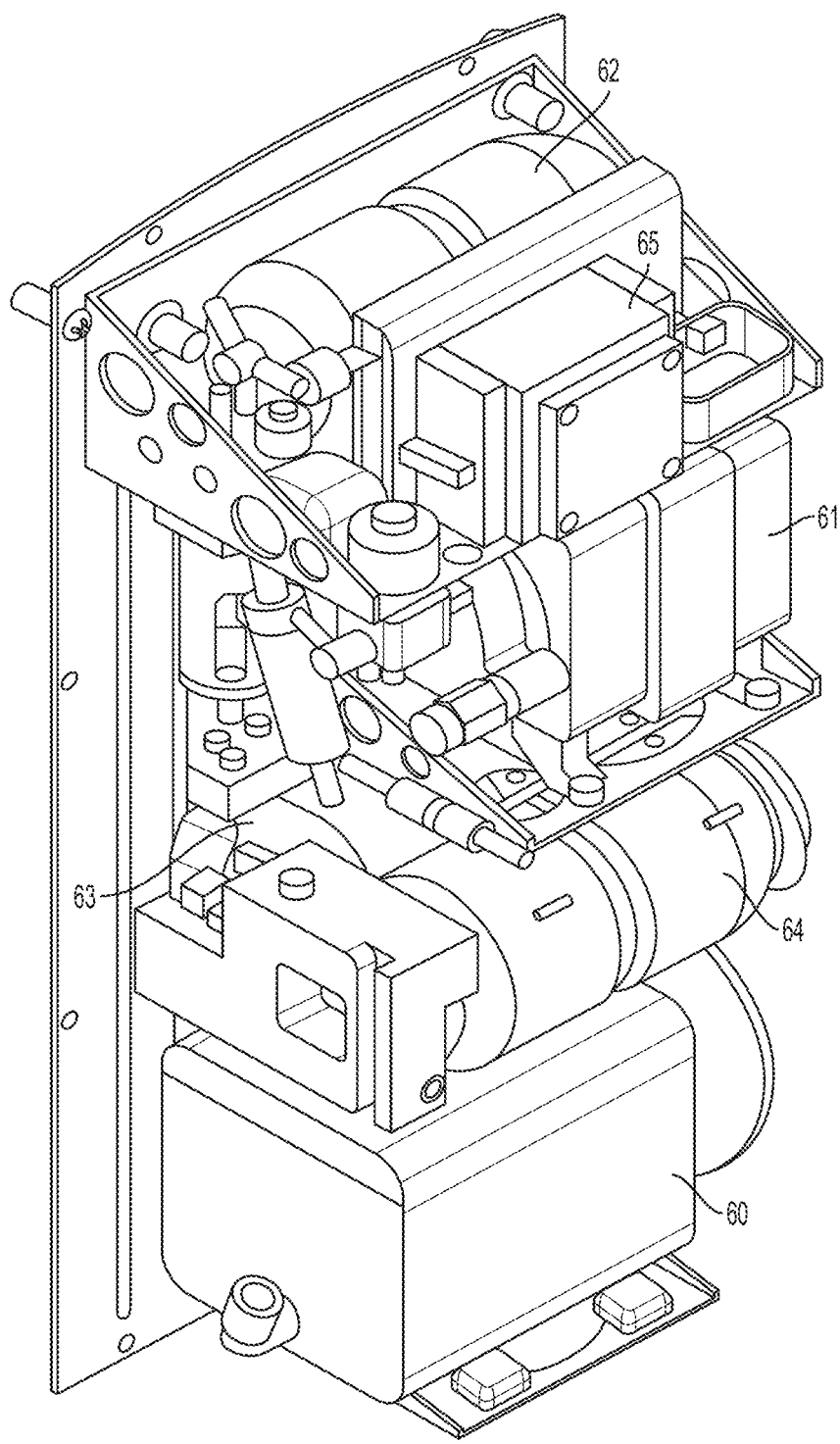
FIG. 7a is perspective view of selected components of a power unit in an illustrative embodiment.

In an embodiment, power unit 52 comprises a housing that may contain components as shown in FIG. 7a. In this example, a pump and pneumatic storage assembly is arranged to fit within power unit 52, and comprises a positive pressure pump 60, a negative pressure or vacuum pump 61, a high-positive pressure reservoir 62, a lower-positive pressure reservoir 63, a negative pressure reservoir 64, and a dehumidification or 'chiller' unit 65. The high-positive pressure reservoir 62, for example, may store air at pressures of about 1000-1100 or more mmHg, and the lower-positive pressure reservoir 63, for example, may store air at pressures of about 700-850 mmHg. The pressurized air generated by positive pressure pump 60 may be used to fill reservoir 63 by interposing a pressure regulator (not shown) between the outlet of pump 60 and the inlet of reservoir 63.

Figure 7B:
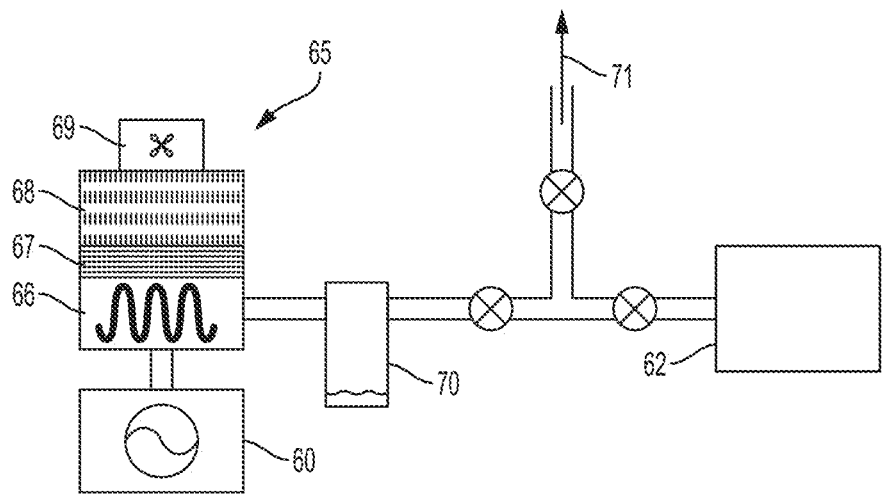
FIG. 7b is a schematic view of an air dehumidifier arrangement in an illustrative embodiment.
Figure 7C:
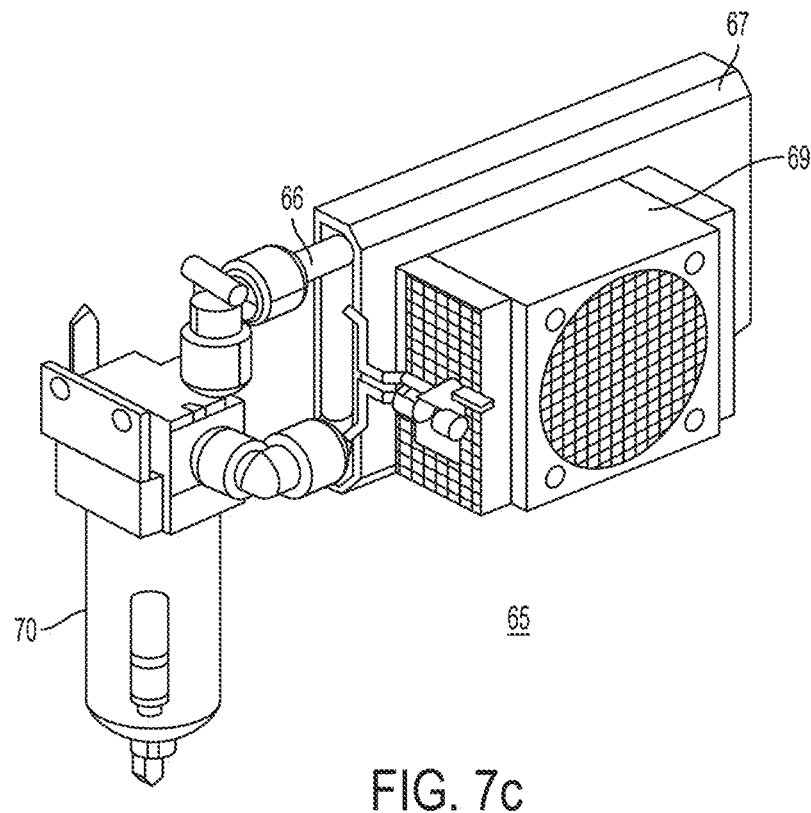
FIG. 7c is a perspective view of a dehumidifier arrangement in the FIG. 7a embodiment.

Chiller 65, or another suitable dehumidifier, may be interposed between the outlet of positive pressure pump 60 and the inlet of the one or more positive pressure reservoirs 62 and/or 63. De-humidification of the pressurized air may prevent water condensation inside pneumatic lines or manifold passages and valves driven by the positive pressure reservoirs 62 and/or 63. As shown schematically in FIG. 7b, the chiller 65 may include a metal coil conduit 66 through which air from compressor 60 is passed, and in which water may be condensed from the compressed air. A cooling element 67 may separate the compressed air coils from a heat exchanger 68, through which ambient air may be drawn, warmed and exhausted by fan 69. The heat exchanger rejects heat to the ambient environment, and a water trap 70 separates the condensed water from the compressed air. The dried compressed air is then available for storage in reservoir 62 (or via a pressure regulator for storage in low pressure reservoir 63), or for delivery to downstream devices 71 such as a valved pneumatic manifold. Cooling element 67 may be a commercially available electrically powered Peltier device such as device model C1-34-1604 from Tellurex, Inc. FIG. 7c shows an example of how chiller 65 may be arranged and configured to fit within the confines of power unit 52.

Figure 8:
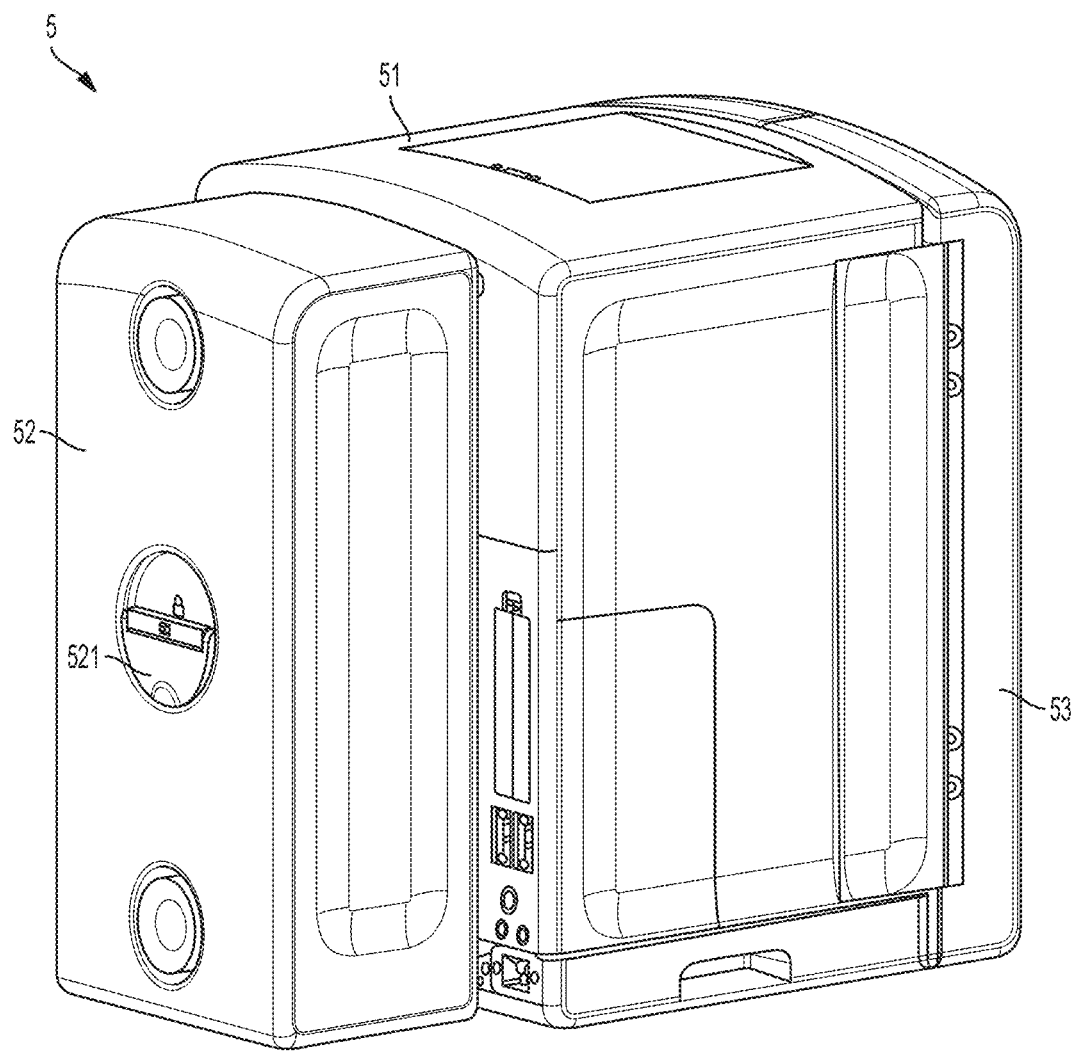
FIG. 8 is a left rear perspective view of the hemodialysis system of FIG. 7.

Moreover, the power unit 52 may be selectively connectable to the dialysis unit 51, e.g., to allow different power units 52 to be interchanged. For example, the dialysis unit 51 may be arranged to work with different types of power units 52, such as power units 52 that use electrical power to generate the pneumatic power supply, as well as power units 52 that use stored pneumatic power (e.g., pressurized air stored in one or more high pressure tanks). Thus, a power unit 52 may be interchanged for another unit 52, in case of failure or other requirements. For example, it may be desired to use the system 5 in an area where noise generation is unacceptable, such as when nearby people are sleeping. In this case, it may be desirable to use a power unit 52 that uses stored pneumatic power, rather than a unit 52 that generates pneumatic power by running pumps or other noise generating equipment. As shown in FIG. 8, the power unit 52 may be disconnected from the dialysis unit 51 by manipulating a handle 521. For example, turning the handle 521 may unlock the power unit 52 from the dialysis unit 51, disengaging not only mechanical connections between the housings, but also power and/or communications connections between the two. An interface (not shown) between the dialysis unit 51 and the power unit 52 may permit the units to exchange pneumatic power (from the power unit 52 to the dialysis unit 51) as well as electrical power, control communications, and other. The dialysis unit 51 may have connection points for electrical power (e.g., standard 115V, 15 amp power found in most home power outlets), external communication (such as Ethernet, or any other suitable connection suitable for communication), a water supply, and so on. The dialysis unit 51 may provide electrical power or other connections to the power unit 52, if desired.

The dialysis unit 51 may include a controller to control flow of control fluid for various components of the system 5, as well as perform other desired functions. In some cases, the control fluid may be held at different pressures within the various tubes or conduits. For instance, some of the control fluid may be held at positive pressure (i.e., greater than atmospheric pressure), while some of the control fluid may be held at negative pressures (less than atmospheric pressure). In addition, in certain embodiments, the controller may have components that are kept separate from the various liquid circuits. This configuration has a number of advantages. For example, in one embodiment, the liquid circuits in the dialysis unit 51 may be heated to disinfection temperatures and/or exposed to relatively high temperatures or other harsh conditions (e.g., radiation) to effect disinfection, while electronic components of the controller may not be exposed to such harsh conditions, and may even be kept separate by an insulating wall (e.g., a "firewall") or the like. That is, the dialysis unit housing may have two or more compartments, e.g., one compartment with electronic and other components that may be sensitive to heat or other conditions, and another compartment with liquid circuit components that are heated or otherwise treated for disinfection.

Thus, in some embodiments, the system 5 may include a "cold" section (which is not heated), and a "hot" section, portions of which may be heated, e.g., for disinfection purposes. The cold section may be insulated from the hot section through insulation. In one embodiment, the insulation may be molded foam insulation, but in other embodiments can be any type of insulation, including but not limited to a spray insulation, an air space, insulation cut from sheets, etc. In one embodiment, the cold section includes a circulation system, e.g., a fan and/or a grid to allow air to flow in and out of the cold box. In some cases, the insulation may be extended to cover access points to the "hot" section, e.g., doors, ports, gaskets, and the like. For instance, when the "hot" section is sealed, the insulation may completely surround the "hot" section in some cases.

Non-limiting examples of components that may be present within the "cold" section include power supplies, electronics, power cables, pneumatic controls, or the like. In some cases, at least some of the fluids going to and from the "hot" section may pass through the "cold" section; however, in other cases, the fluids may pass to the "hot" section without passing through the "cold" section.

Non-limiting examples of components that may be present within the "hot" section include cassettes (if present), fluid lines, temperature and conductivity sensors, blood leak sensors, heaters, other sensors, switches, emergency lights, or the like. In some cases, some electrical components may also be included in the "hot" section. These include, but are not limited to, a heater. In one embodiment, the heater can be used to heat the hot box itself, in addition to fluid. In some embodiments, the heater 72 heats the entire "hot" section to reach a desired temperature.

Figure 9:
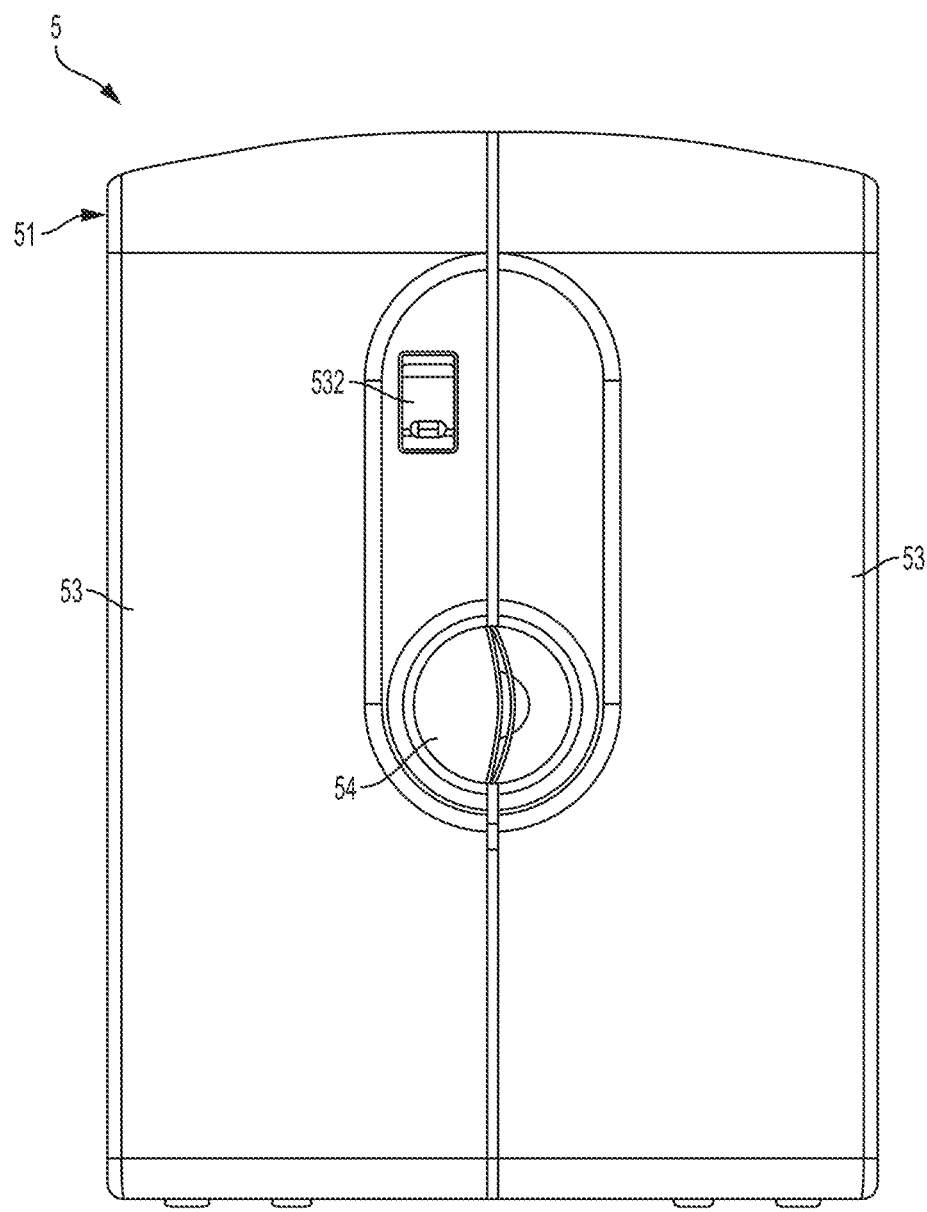
FIG. 9 is a front view of the hemodialysis system of FIG. 7.
Figure 10:
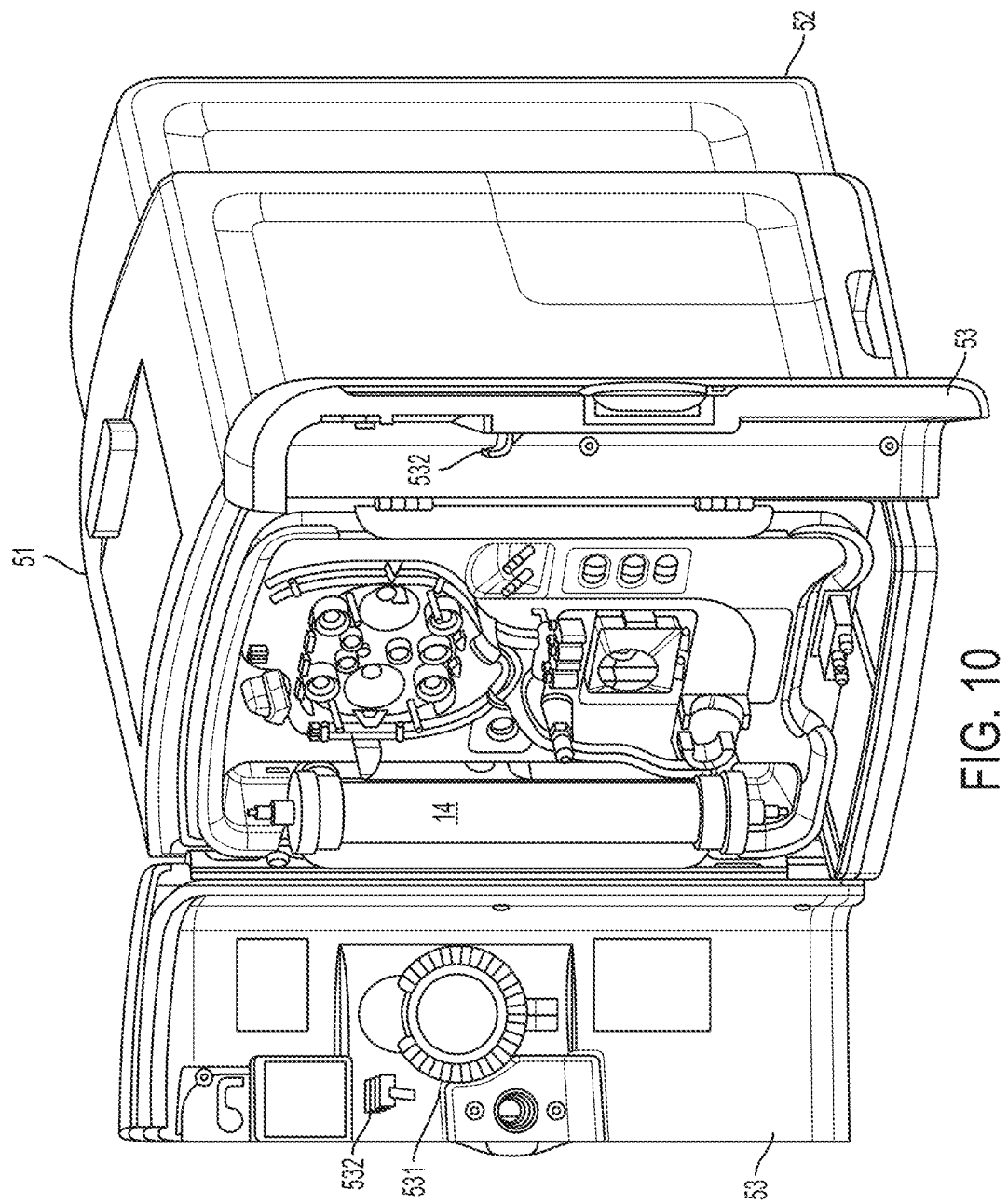
FIG. 10 is a right front perspective view of the view of the hemodialysis system of FIG. 7 with the doors in a first open position.
Figure 11:
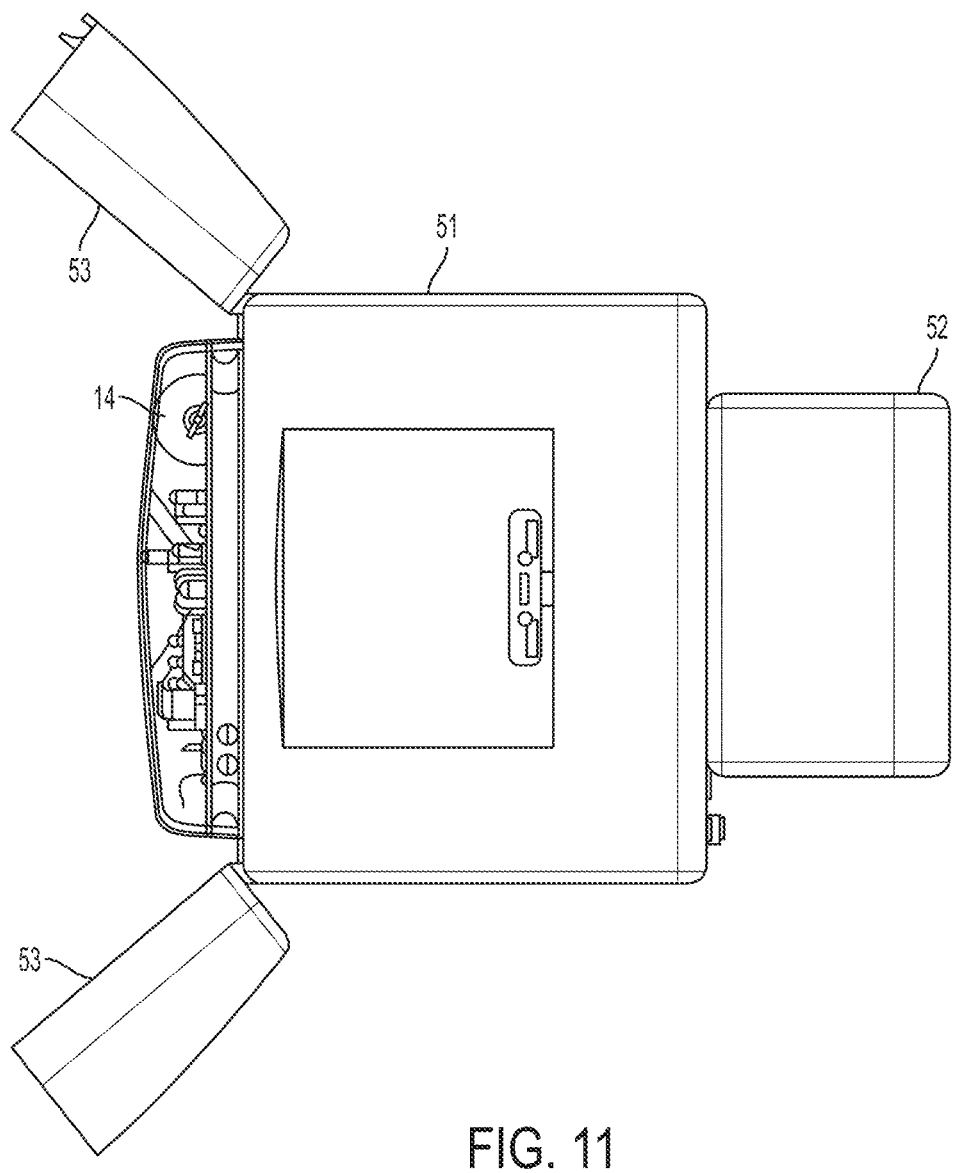
FIG. 11 is a top view of the hemodialysis system of FIG. 10.
Figure 12:
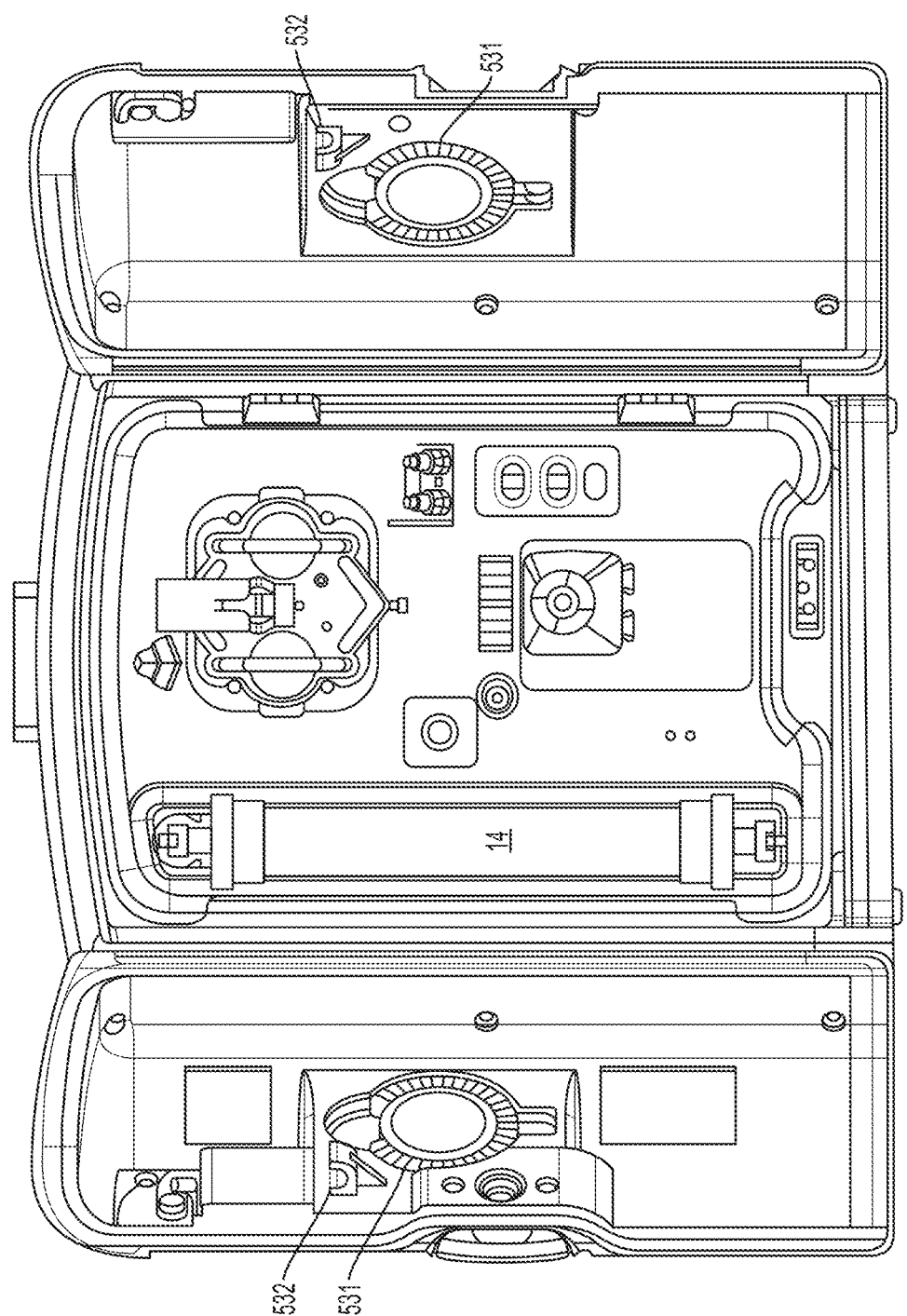
FIG. 12 is a front view of the hemodialysis system of FIG. 10.
Figure 13:
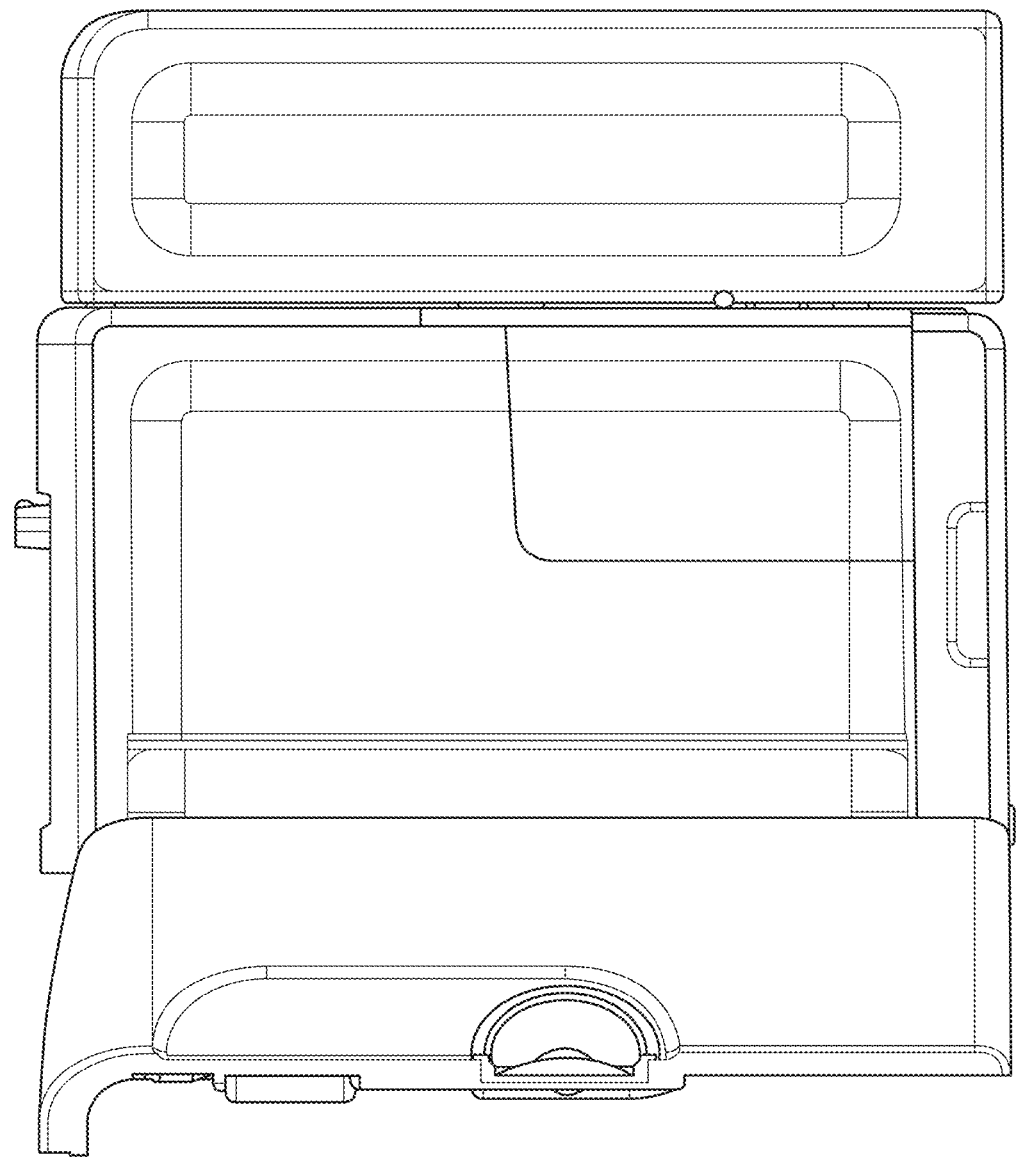
FIG. 13 is a right side view of the hemodialysis system of FIG. 10.

In accordance with an aspect of the invention, the dialysis unit 51 housing may include vertical side-by-side doors that can be opened to expose all mechanical interface points for blood flow circuitry and connections for dialysate circuitry, i.e., all connection points for patient blood connections and acid/bicarbonate connections, that must be made by a user to use the dialysis unit 51. FIG. 9 shows a front view of the dialysis unit 51 with the vertical side-by-side doors 53 in a closed state. In this arrangement, the doors 53 may block access to connection points for patient blood connections and acid/bicarbonate connections as well as seal the interior of the unit housing so as to allow heat retention suitable for disinfection. The seal provided by the doors 53 may be hermetic, preventing or substantially resisting any air exchange between the housing interior and an exterior environment, or may be of a somewhat lesser quality yet still allow for disinfection.

In this embodiment, the doors 53 are connected to the dialysis unit 51 housing by a dual hinge arrangement such that the doors 53 can be opened to two different states of opening. FIGS. 10-13 show the doors 53 in a first state of opening. In this state, the doors 53 expose all user-made connections for the blood circuit connections and for the dialyzer circuitry, including the dialyzer 14 itself and for reagent materials, such as consumable acid/bicarbonate materials. This position also exposes several other features, such as holders 531 for an acid/bicarbonate container (not shown) and hooks 532 that may be used to hold any suitable item, such as the control interface 55, which may be hung by its handle on one of the hooks 532. (See also FIG. 7 which shows a hook 532 on the front of the left door 53 which may be folded out to receive the control interface 55 or other item.) The holders 531 in this embodiment may be folded down from their position shown in the figures (i.e., folded up and into recesses in the doors 53) so as to extend horizontally from the doors 53. The holders 531 have a "C" shaped receiving section to receive and hold an acid/bicarbonate container, but of course could be shaped or otherwise arranged in any suitable way.

Figure 14:
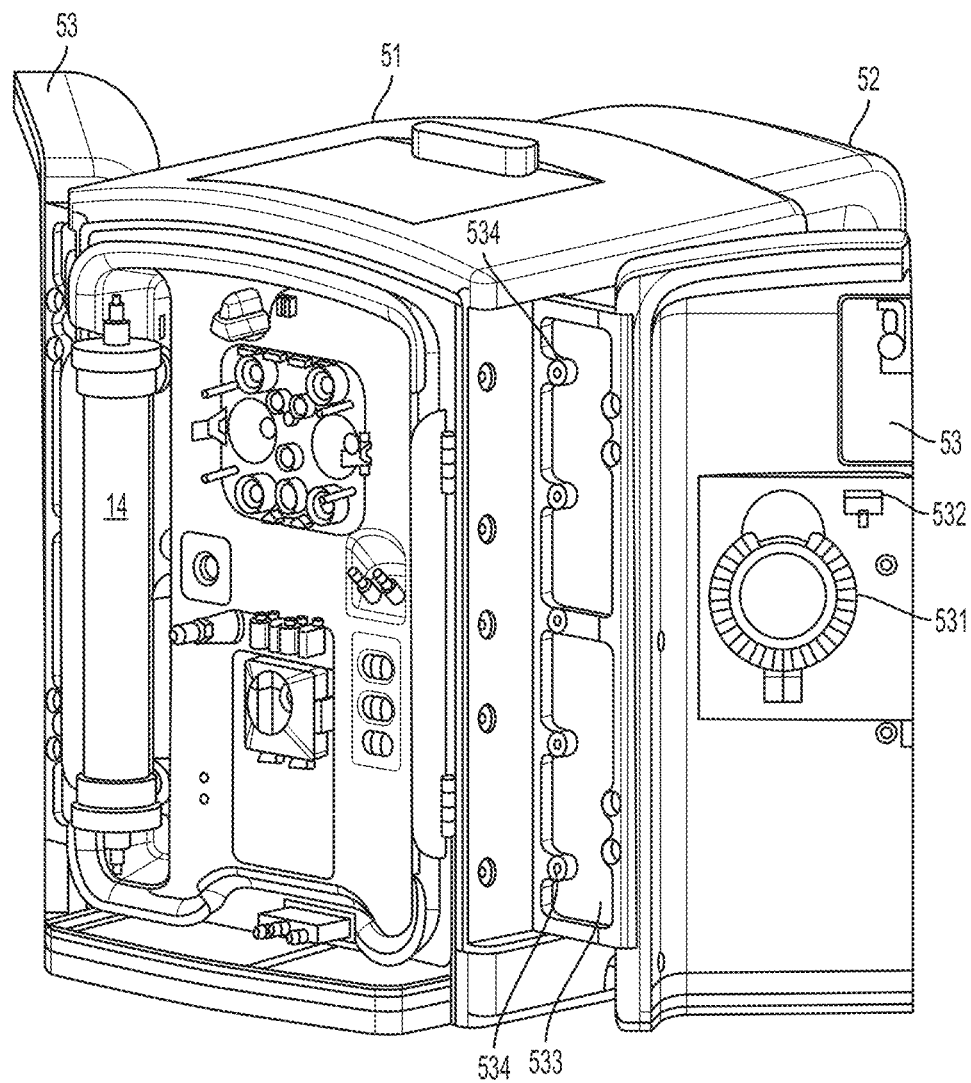
FIG. 14 is a right front perspective view of the view of the hemodialysis system of FIG. 7 with the doors in a second open position.
Figure 15:
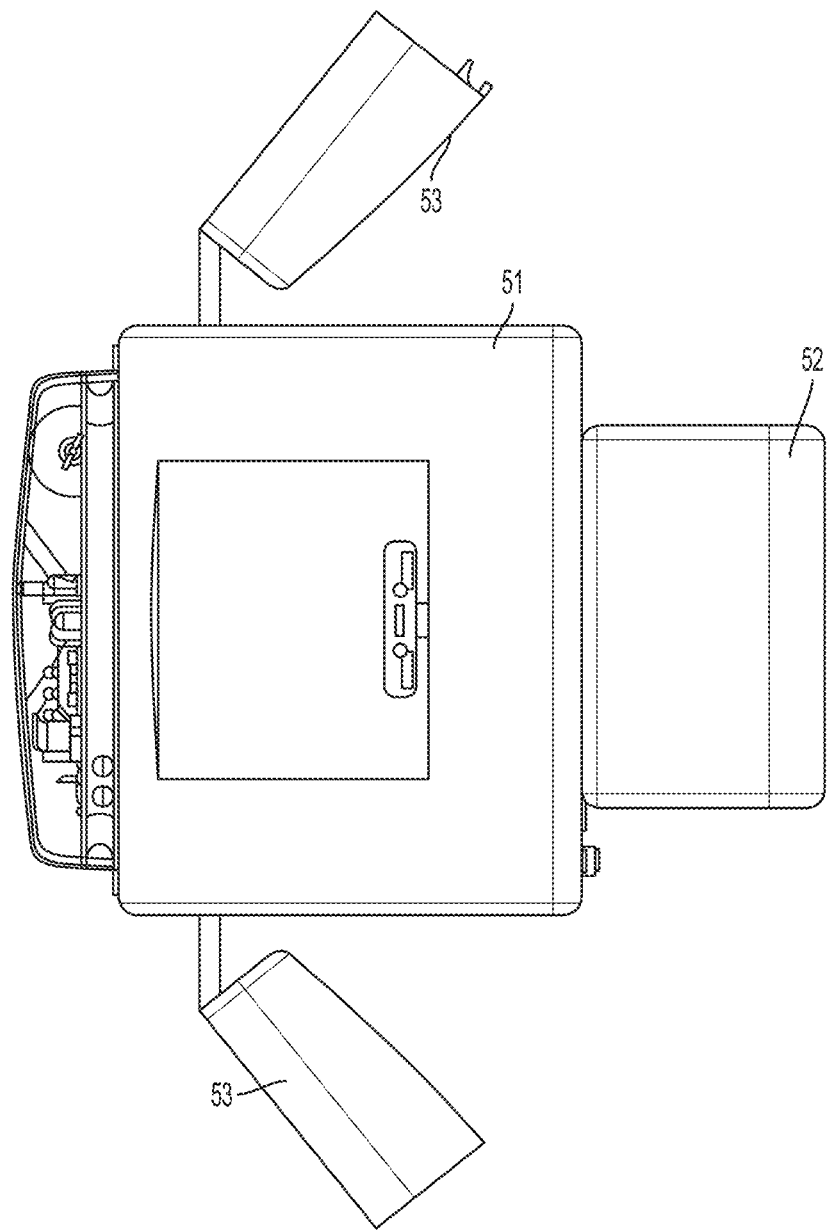
FIG. 15 is a top view of the hemodialysis system of FIG. 14.
Figure 16:
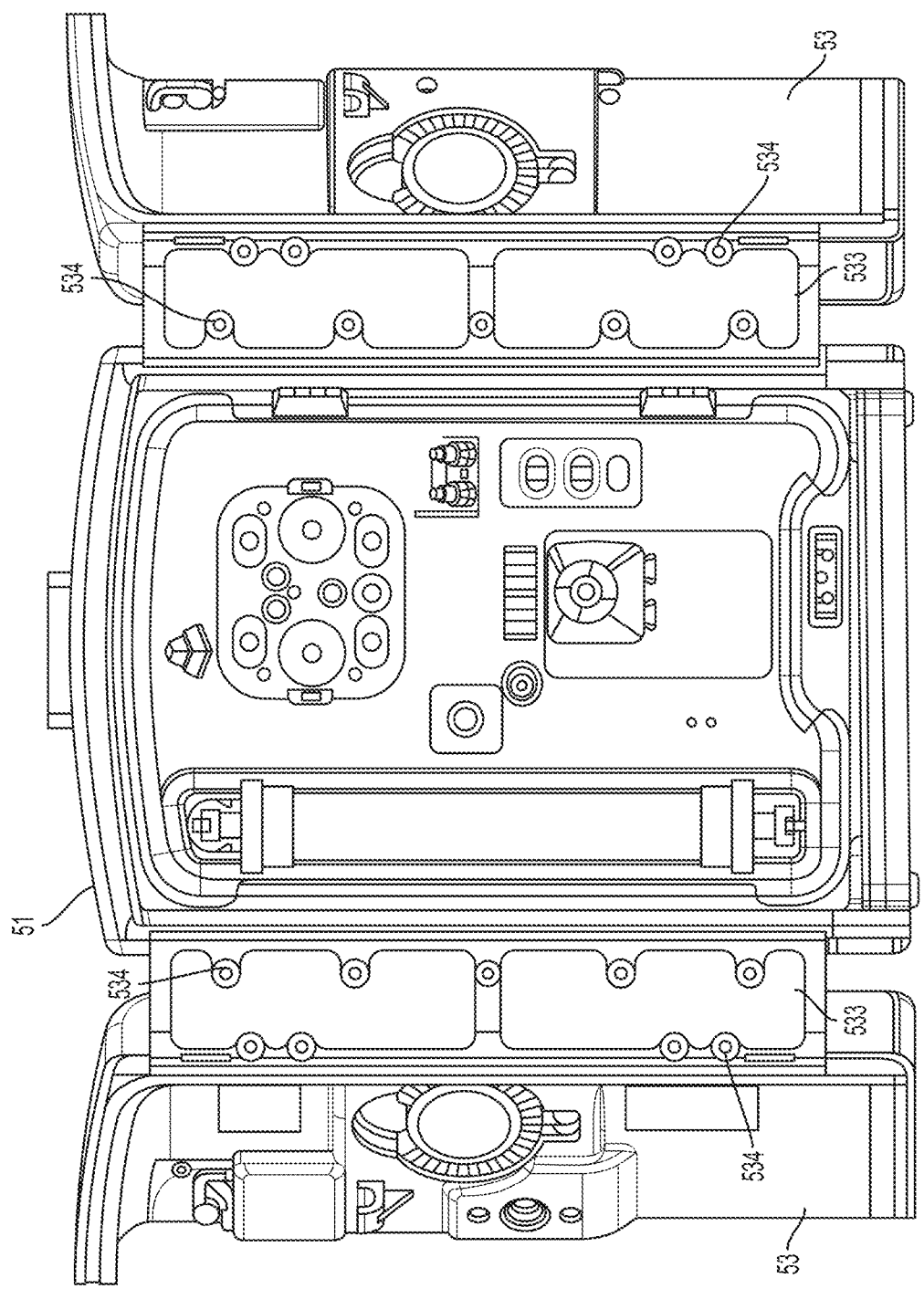
FIG. 16 is a front view of the hemodialysis system of FIG. 14.

FIGS. 14-16 show the doors 53 in a second state of opening in which a hinge plate 533 for each door 53 is pivoted outward and away from the dialysis unit housing 51. The hinge plates 533, which in this embodiment extend vertically along almost the entire height of the dialysis unit housing 51, are pivotally attached to the doors 53 at a first, outer end, and are pivotally attached at a second inner end to the dialysis unit housing 51. (Of course, it should be understood that the hinge plates 533 could be arranged and/or positioned differently, e.g., at the top and bottom of the doors 53 as is found in many refrigerator door arrangements, each plates 533 may include two or more portions that are vertically separated from each other, etc.) Magnets 534 attached to the hinge plates 533 may interact with corresponding magnets (or other suitable components, such as a steel elements) attached to the dialysis unit housing 51 so as to attract the hinge plates 533 toward the dialysis unit housing 51, thus tending to keep the hinge plates 533 in the position shown in FIGS. 10-13. (Of course, the magnets 534 could be positioned on the unit housing, and the hinge plates 533 could have suitable elements (such as pieces of steel) that are attracted to the magnets 534.) The doors 53 in this embodiment also include magnets attached near the hinge plates 533 so that when the doors 53 are opened to the first state as shown in FIGS. 10-13, the magnets interact with corresponding magnets in the hinge plates 533 to help keep the doors 53 in an open position relative to the hinge plate 533. These magnets will also help maintain the relative position of the doors 53 and the hinge plates 533 when the hinge plates 533 are opened to the second state shown in FIGS. 13-16.

Although magnets are used in this illustrative embodiment as part of a retainer member to help the doors 53 and/or hinge plates 533 stay in a particular state of opening or closing, other arrangements for a retainer member are possible. For example, the hinge connection between the doors 53 and the hinge plates 533 and/or the connection between the hinge plates 533 and the housing 51 may include a detent arrangement that serves to resiliently hold the door 53 or hinge plate 533 in a particular position relative to the other part (the hinge plate or housing, respectively). In another embodiment, one or more springs may be used to help maintain the doors 53 in an open position relative to the hinge plates 533. In yet another embodiment, the hinge plates 533 may have a friction or interference fit with a portion of the housing 51 that tends to maintain the hinge plates 533 in the closed position (adjacent the housing). Accordingly, a retainer member that functions to help maintain a door 53 in a particular position relative to its hinge plate 533, and/or that functions to help maintain a hinge plate 533 in a particular position relative to the housing 51, may take any one of a number of possible arrangements.

Figure 17:
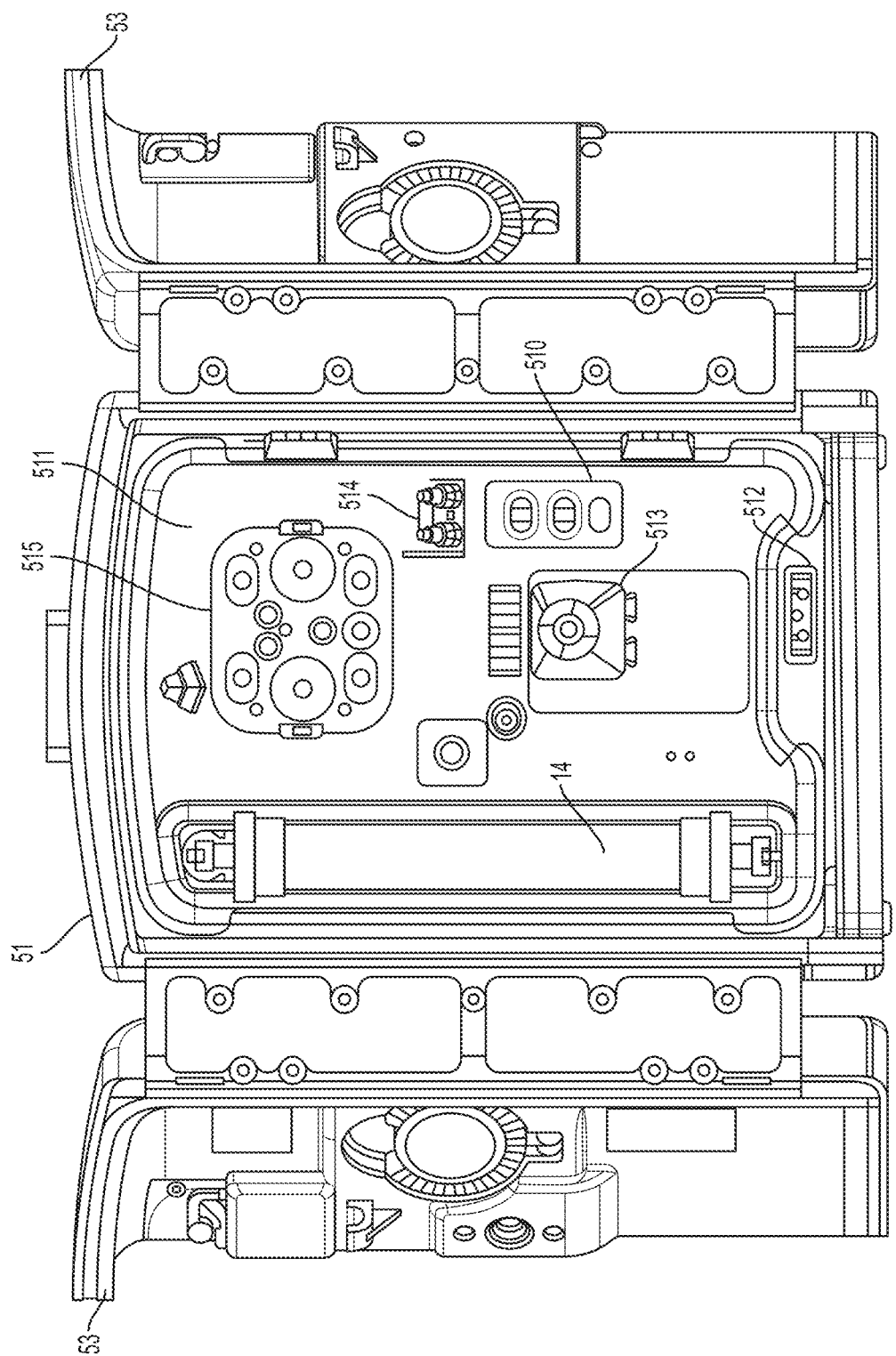
FIG. 17 is a front view of the hemodialysis system of FIG. 7 with the doors in an open position exposing a front panel of the system.

In accordance with another aspect of the invention, opening of the doors to the dialysis unit housing may reveal all of the user-made connections for blood circuit connections and dialysate fluidic connections needed for operation of the system 5. For example, as shown in FIG. 17, with the doors 53 in an open position (either the first or second state of opening) a front panel 511 of the dialysis unit 51 may be exposed. In this embodiment, the front panel 511 carries several items or connection points that must be accessed by a user. For example, the dialyzer 14, which must be periodically replaced, is mounted to the front panel 511. The dialyzer 14 must be connected not only to the blood flow circuit 141, but also the balancing circuit 143. Also, a connection point 512 for an acid/bicarbonate source 49 is located at a lower end of the front panel 511. It is at this connection point 512 that a user may connect a source of consumable reagent ingredients 49 used by the dialysis unit 51 in making dialysate. An occluder 513 is also mounted on the front panel 511. The occluder 513 receives tubes of the blood flow circuit and controls the open/closed state of the tubes based on system operation. The function of the occluder 513 is discussed in more detail in U.S. application Ser. No. 12/198,947, filed Aug. 27, 2008 and below. In short, the occluder 513 allows flow through the arterial and venous lines of the blood flow circuit unless there is a system problem, such as a leak, pump failure, overpressure situation, etc. In such case, the occluder 513 automatically closes the blood lines to prevent all flow to or from the patient. Also exposed on the front panel 511 are blood line connection points 514 for connecting the arterial and venous blood lines 203, 204 of the blood flow circuit 141 with the directing circuit 142 (as explained above with reference to FIGS. 2 and 3, the blood flow circuit 141 may be connected to the directing circuit 142). This connection is normally made at the end of treatment to allow the system to clean and disinfect the blood flow circuit 141. The front panel 511 also has a set of control ports 515 that mate with corresponding control ports on the blood pump portion of the blood flow circuit 141. The control ports 515 provide controlled levels of air pressure and/or vacuum to control the open/closed state of valves and to power the pumps of the blood flow circuit 141.

Figure 17A:
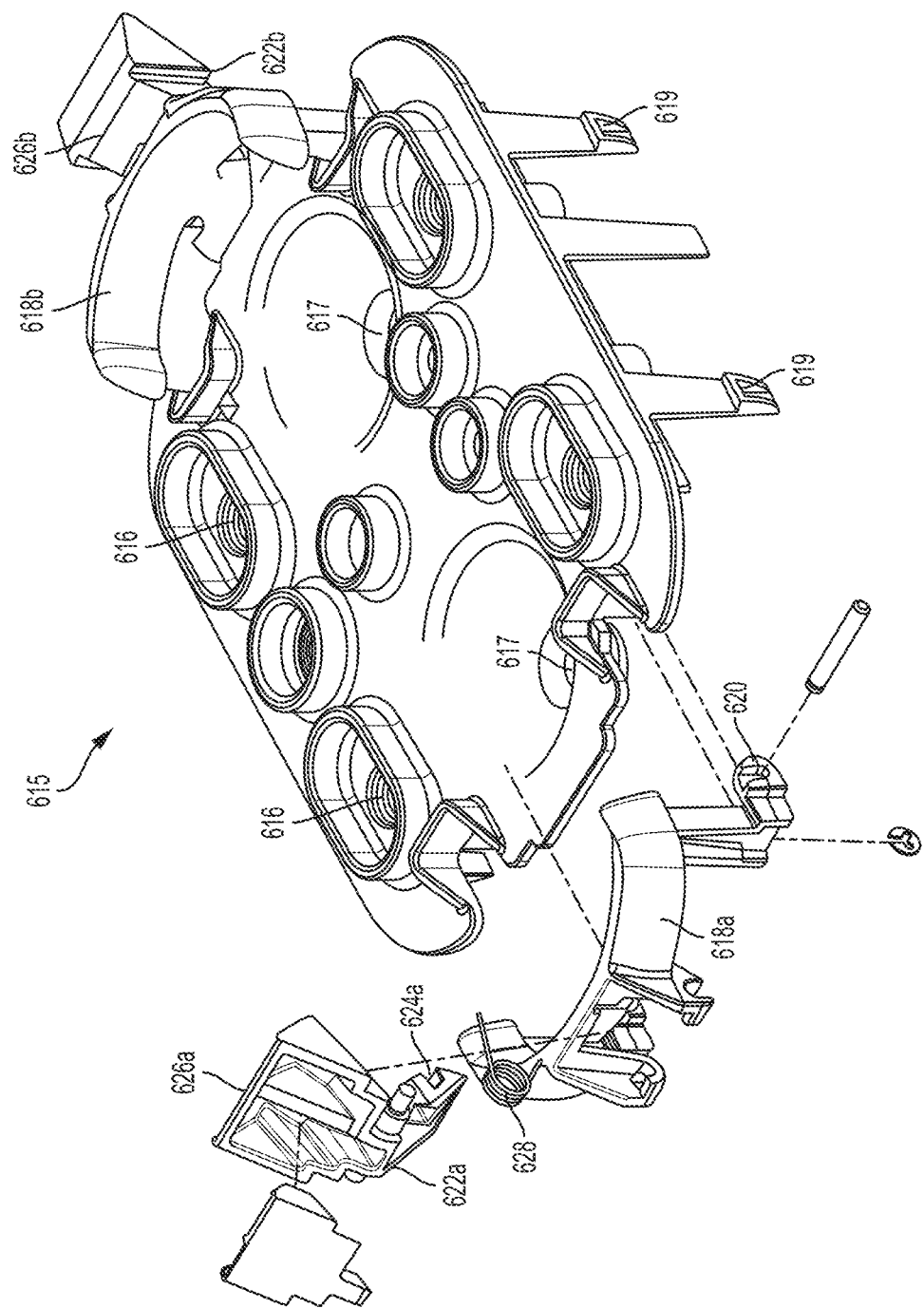
FIG. 17a is an exploded perspective view of a control port assembly arranged to interface with a blood pump assembly in an illustrative embodiment.
Figure 17B:
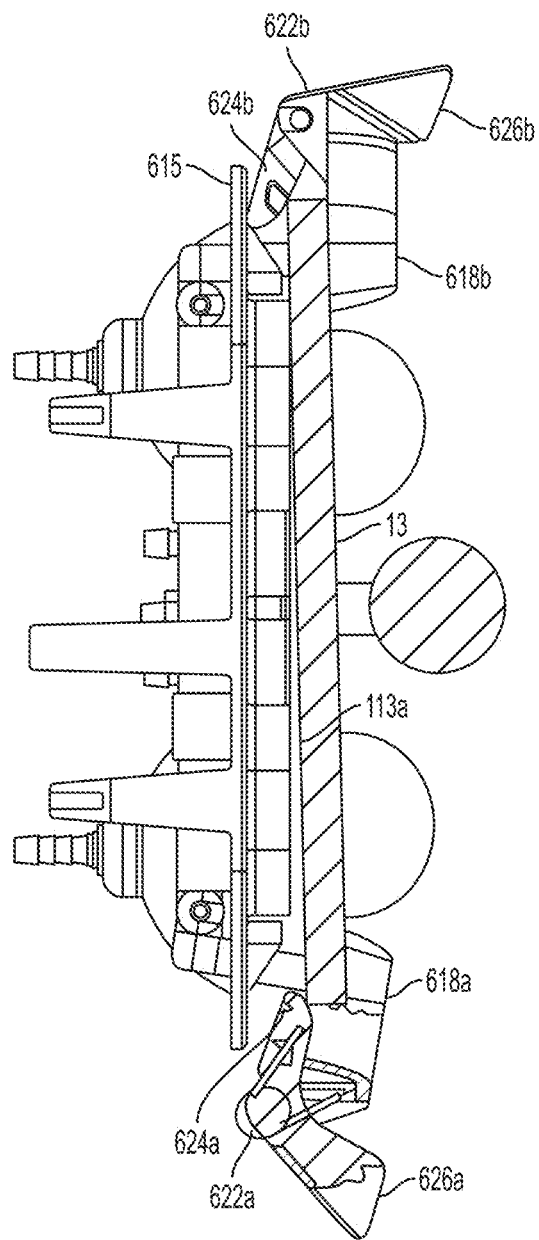
FIG. 17b is a cross sectional side view of the FIG. 17a embodiment with an engaged blood pump assembly.

In another aspect of the invention, FIG. 17a shows a perspective view of a control port assembly 615 onto which a blood pump assembly 13 may be mounted, and with which the fluidic control ports of the blood pump assembly 13 can connect. Shown, for example, are control ports 616 for controlling the actuation of valves on a blood pump assembly 13, and control ports 617 for controlling the actuation of pumps on a blood pump assembly 13. In order to secure a blood pump assembly 13 onto control port assembly 615, a latch member or other engagement device may be provided at one or more sides of, or within, control port assembly 615, or at a portion of front panel assembly 511 adjacent to, or within, the location of the control port assembly 615. (In the example shown, control port assembly 615 may be reversibly mounted onto front panel assembly 511 via retaining tabs 619). Alternately, or in addition, a disengagement or other ejection feature for a blood circuit assembly may be provided to help with removal of a blood pump assembly or other parts of a blood circuit assembly from the front panel 511. For example, a pair of cassette latching and ejection assemblies may be mounted on opposite sides of the control port assembly 615. In the FIG. 17a embodiment, a blood circuit assembly engagement device includes latch or retainer members 618a and 618b pivotably mounted to the sides of control port assembly 615. Preferably, the pivotal connections (e.g., pivotal connection 620) of latch members 618a and 618b are biased by a suitably disposed spring to urge latch members 618a and 618b to rotate toward each other and toward the surface of control port assembly 615, so that they can maintain contact with the edges or other parts of a blood pump assembly 13 (shown in cross-section in FIG. 17b) mounted on the control port assembly 615. This is more clearly shown in FIG. 17b, which is a top, sectional view of control port assembly 615, onto which is mounted a blood pump assembly 13. Latch member 618b is shown in FIG. 17b in its normally biased position, securing the outer edge of blood pump assembly 13 in connection with control port assembly 615. Latch member 618a, on the other hand, is shown in a partially retracted position, allowing blood pump assembly 13 to be partially separated from control port assembly 615. In a fully retracted position (not shown), latch member 618 a or 618b clears the front edge of blood pump assembly 13, allowing it either to be removed from or installed or mounted onto control port assembly 615.

As shown in FIGS. 17a and 17b, in addition to a latch or retainer member 618a and 618b that may help to hold blood pump assembly 13 onto control port assembly 615, a separation assist member (or ejector element or member) 622a or 622b may also be included to assist a user in separating blood pump assembly 13 from control port assembly 615, and lifting it away from control port assembly 615. The separation assist member 622a or 622b may be pivotably mounted on the front panel assembly 511 in a location suitable for a contacting portion 624a or 624b of the separation assist member 622a and 622b to contact an edge of the undersurface 113a of blood pump assembly 13 to help lift it off the control port assembly 615 when the separation assist member 622a or 622b is rotated in an outward fashion. The engagement device may include an actuator to actuate the retainer members 618 and/or the ejector elements 622, such as a thumb- or finger-contacting element 626a or 626b that can be pressed laterally by a user to pivot separation assist member 622a or 622b outward to engage contacting portion 624a or 624b with the undersurface 113a of blood pump assembly 13. Preferably, a spring 628 may be included near the pivotal connection of separation assist member 622a or 622b, and suitably disposed to bias separation assist member 622a or 622b to urge contacting portion 624a or 624b away from contact with the undersurface 113a of blood pump assembly 13. That way, no intrinsic force from separation assist member 622a or 622b is acting to push blood pump assembly 13 away from control port assembly 615. In another preferred embodiment, separation assist member 622a or 622b may be pivotably mounted to latch member 618a or 618b, as shown in FIG. 17a. In this embodiment, a user may engage separation assist member 622a or 622b with the undersurface 113a of blood pump assembly 13, and simultaneously disengage latch member 618a and 618b from contact with the front edge or surface of blood pump assembly 13 by means of a single outward push of thumb- or finger-contacting element 626a or 626b. Thus, with the outward push of one or more actuators, such as a single element 626a or 626b, blood pump assembly 13 may be alternately seated and secured onto control port assembly 615, or separated from control port assembly 615, facilitating the installation and/or removal of blood pump assembly 13.

Figure 17C:
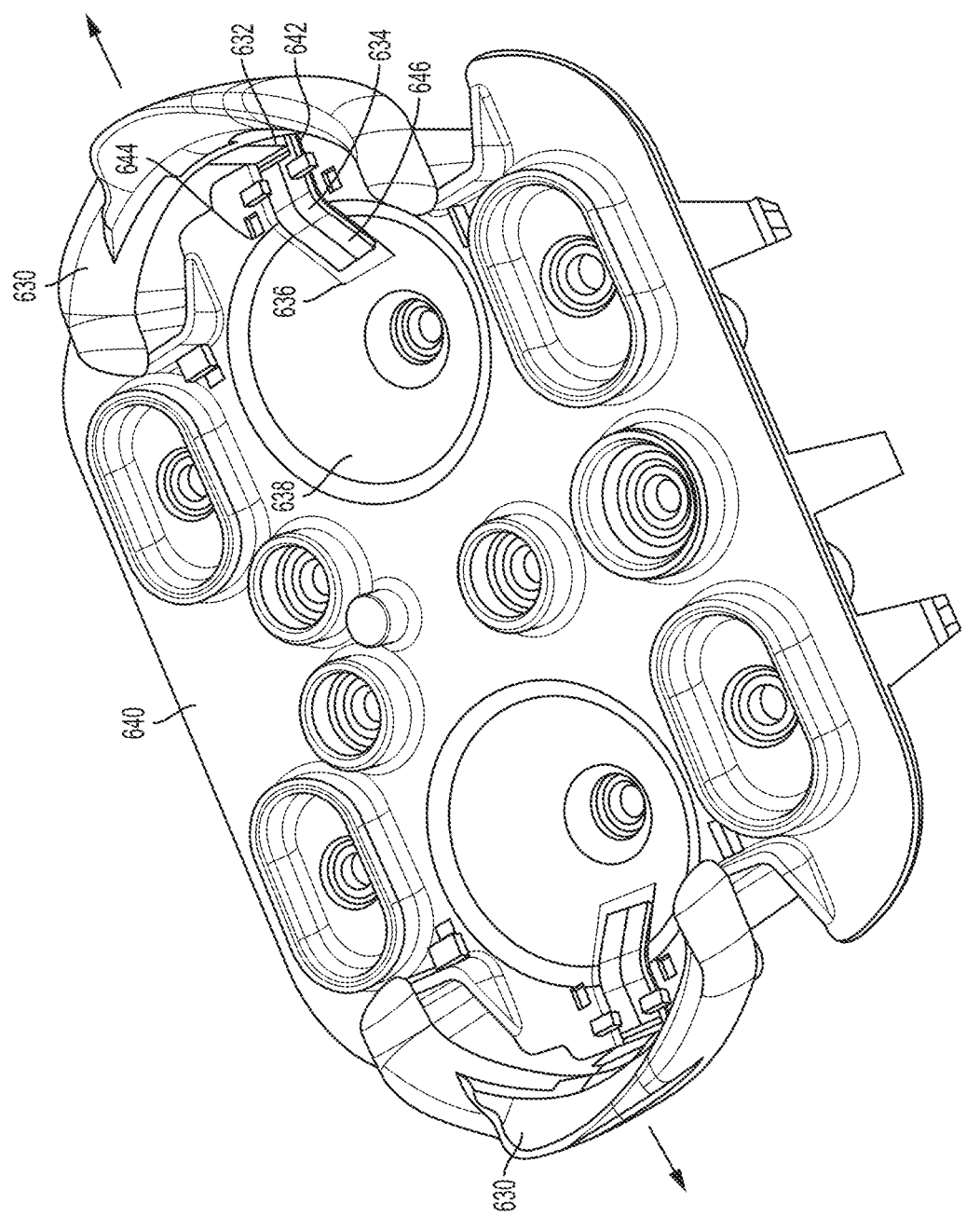
FIG. 17C shows a perspective view of a control port assembly with a pair of blood pump cassette latching and ejection assemblies in an illustrative embodiment.
Figure 17E:
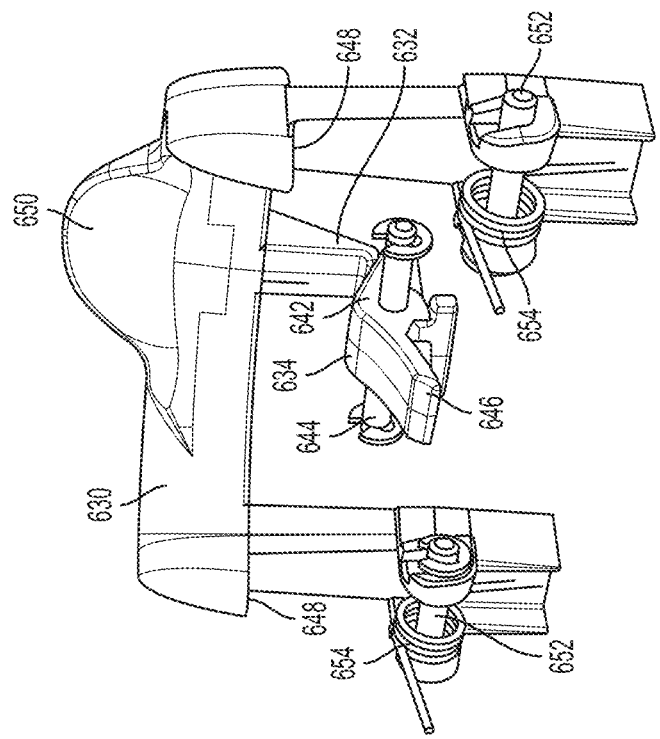
FIG. 17E shows an isolated view of the latching assembly of FIG. 17D with an ejection member in an extended position in an illustrative embodiment.
Figure 17D:
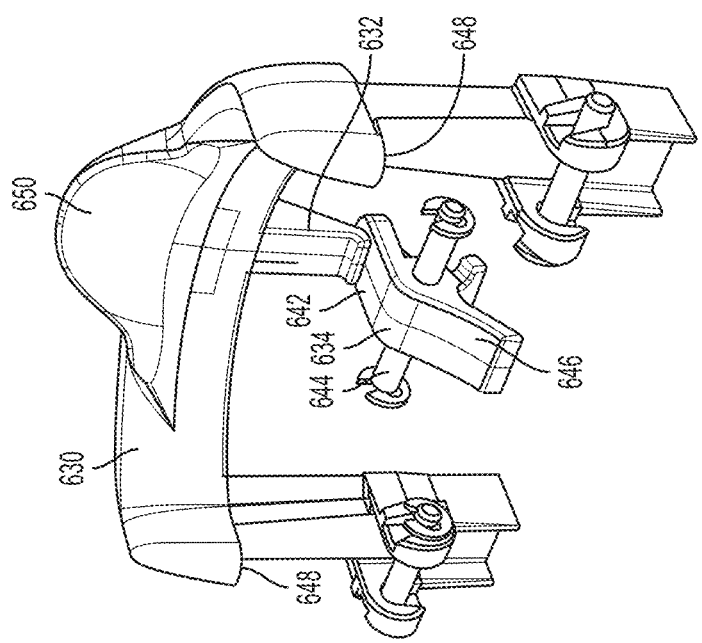
FIG. 17D shows an isolated view of a latching assembly with an ejection member in a retracted position in an illustrative embodiment.
Figure 17G:
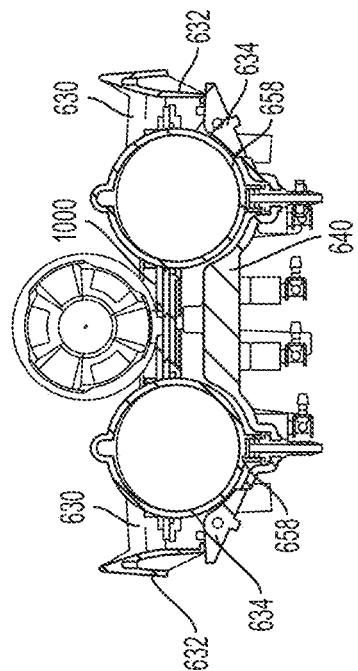
FIG. 17G shows a cross-sectional view along the line 17G-17G in FIG. 17F.
Figure 17H:
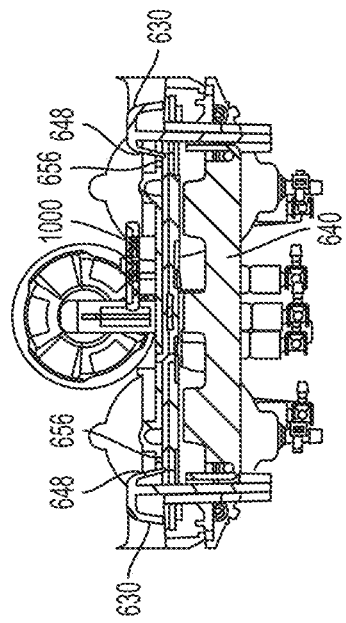
FIG. 17H shows a cross-sectional view along the line 17H-17H in FIG. 17F.
Figure 17F:
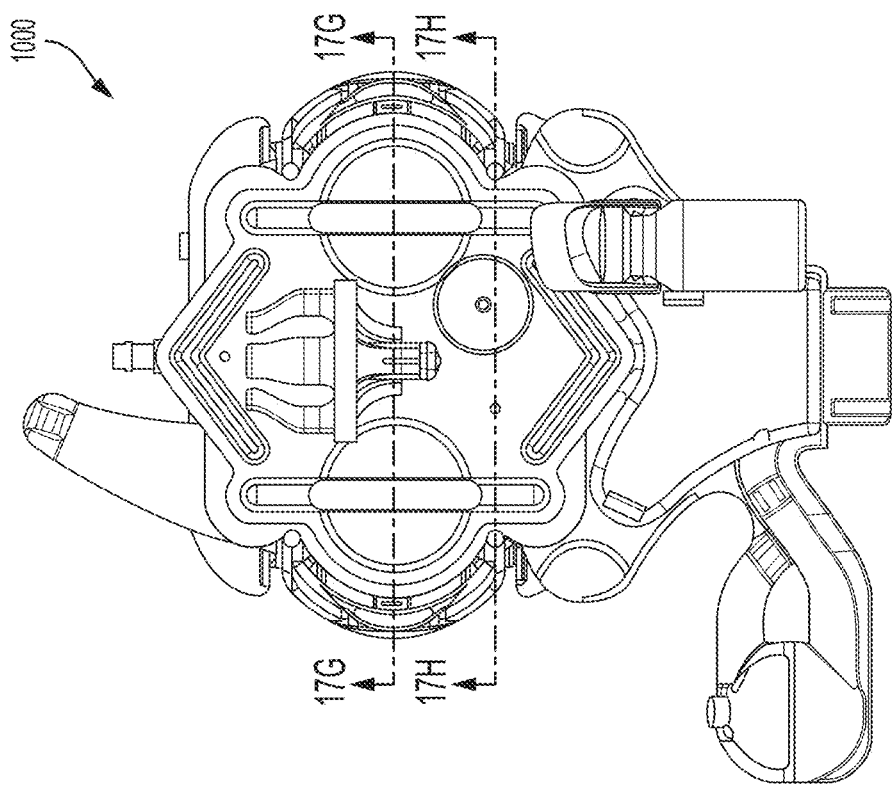
FIG. 17F shows a front view of a blood pump cassette in a retained condition on a panel of a dialysis unit in an illustrative embodiment.

FIG. 17C shows another embodiment of a blood circuit assembly engagement device, that in this embodiment includes a pair of blood pump cassette retainer and ejector elements. In this embodiment, cassette retainer element 630 includes a contacting member 632 that makes contact with an ejector (or separation assist) element 634. In a retracted state, ejector element 634 is positioned in a recessed area 636 of the blood pump pod recess 638 in the control port assembly 640. As retainer elements 630 are pivoted outward (direction of arrows in FIG. 17C), contacting member 632 presses against a proximal end 642 of the ejector element 634, whereupon ejector element 634 rotates about pivot axis 644, causing a distal end 646 of ejector element 634 to lift out of recess 636 to engage the rigid back wall of the actuation chamber of a mounted pump cassette, which is positioned within the blood pump pod recess 638. FIGS. 17D and 17E show isolated views of the engagement device, with a ejector element 634 in retracted (FIG. 17D) and extended (FIG. 17E) positions. In FIG. 17D, retainer element 630 is in a retaining position, with retention elements 648 rotated inward toward the center of control port assembly 640, and ejector element 634 in a recessed position with proximal portion 642 elevated and distal portion 646 depressed. In FIG. 17E, retainer element 630 is in a release position, with retention elements 648 rotated outward away from the center of control port assembly 640, and ejector element 634 in a raised position with proximal portion 642 lowered by contacting member 632 and distal portion 646 raised out of recess 636 to eject a cassette mounted in control port assembly 640. Thumb rest (actuator) 650 is shaped to conveniently allow a user to apply an outward force to release a cassette by applying one thumb on each of the opposing latching members 630 in a complete assembly as shown in FIG. 17C. In an embodiment, retainer element 630 rotates about an axis formed by pinions 652, equipped with springs 654 biased in a latching or retaining direction to help keep a cassette securely mounted on control port assembly 640. FIG. 17F shows a front view of a blood pump cassette 1000 (which is part of a blood circuit assembly) mounted to a panel of a dialysis unit, such as an exposed front panel 511. FIGS. 17G and 17H show cross-sectional views of blood pump cassette 1000 along the lines 17G-17G and 17H-17H, respectively, with the cassette 1000 properly seated on control port assembly 640. FIG. 17G shows the relationship between contacting members 632, ejector elements 634, and the rigid back walls 658 of the pump actuation chambers of cassette 1000. Ejector elements 634 are shown to be in fully retracted positions in their respective recessed areas 636 to allow pump cassette 1000 to be fully seated. FIG. 17H shows the relationship between retention elements 648 and the front plate 656 of cassette 1000. In this case, retention elements 648 are brought into apposition with the front plate 656, securing cassette 1000 onto control port assembly 640.

Figure 17J:
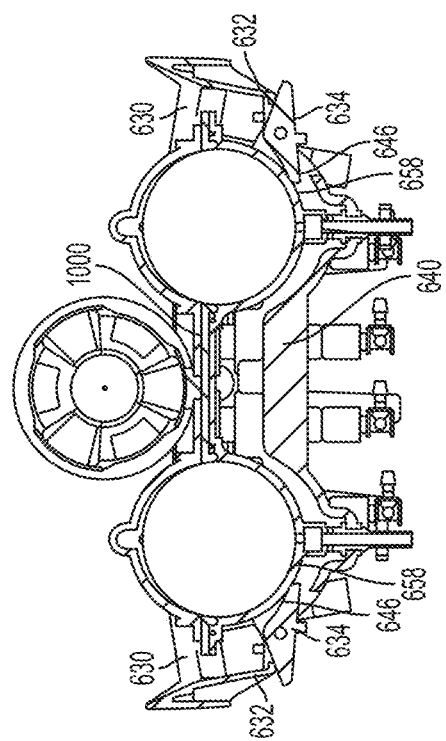
FIG. 17J shows a cross-sectional view along the line 17J-17J in FIG. 17I.
Figure 17K:
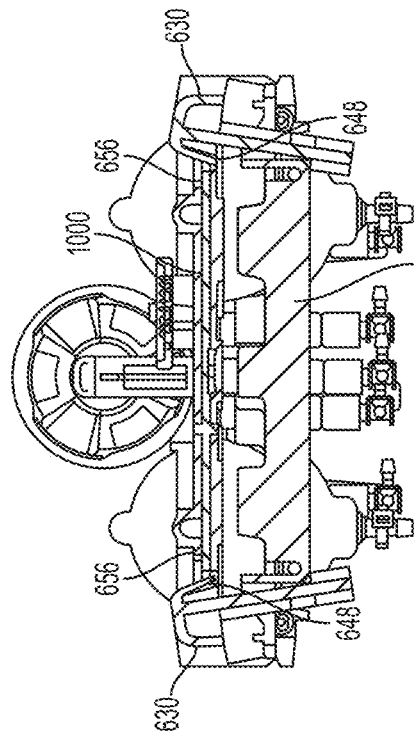
FIG. 17K shows a cross-sectional view along the line 17K-17K in FIG. 17I.
Figure 17I:
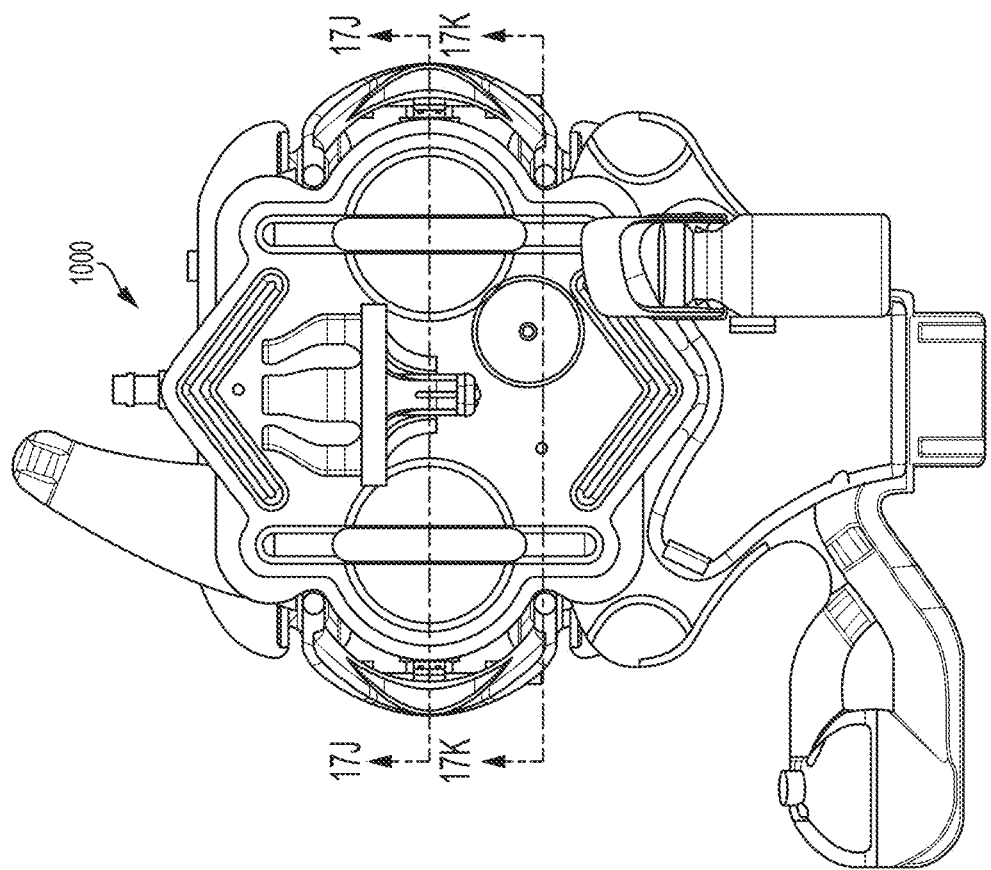
FIG. 17I shows a front view of a blood pump cassette in an ejecting condition in an illustrative embodiment.

FIG. 17I shows a front view of the blood pump cassette from FIG. 17F in the process of being disengaged from the panel 511 of a dialysis unit. FIGS. 17J and 17K show cross-sectional views of blood pump cassette 1000 with the cassette 1000 partially lifted from its engagement with control port assembly 640. FIG. 17J shows the relationship between contacting members 632, ejector elements 634, and the rigid back walls 658 of the pump actuation chambers of cassette 1000. In this case, the distal ends 646 of ejector elements 634 are contacting and elevating cassette 1000 from its fully seated position in control port assembly 640. FIG. 17K shows the relationship between retention elements 648 and the front plate 656 of cassette 1000. In this case, the front plate 656 has been elevated above the retaining surface of retainer elements 648.

Also exposed on the front panel 511 in FIG. 17 is a user control panel 510. The user control panel 510 includes one or more buttons permitting the user to bypass the graphical user interface on control interface 55, providing an alternate method to control certain functions (e.g., critical functions) during hemodialysis. This may be important, for example, if the control interface 55 should ever fail during a dialysis treatment session. Non-limiting examples of critical functions can include a "stop dialysis" or "pause dialysis" command and an "infuse dialysate solution" command.

Figure 18:
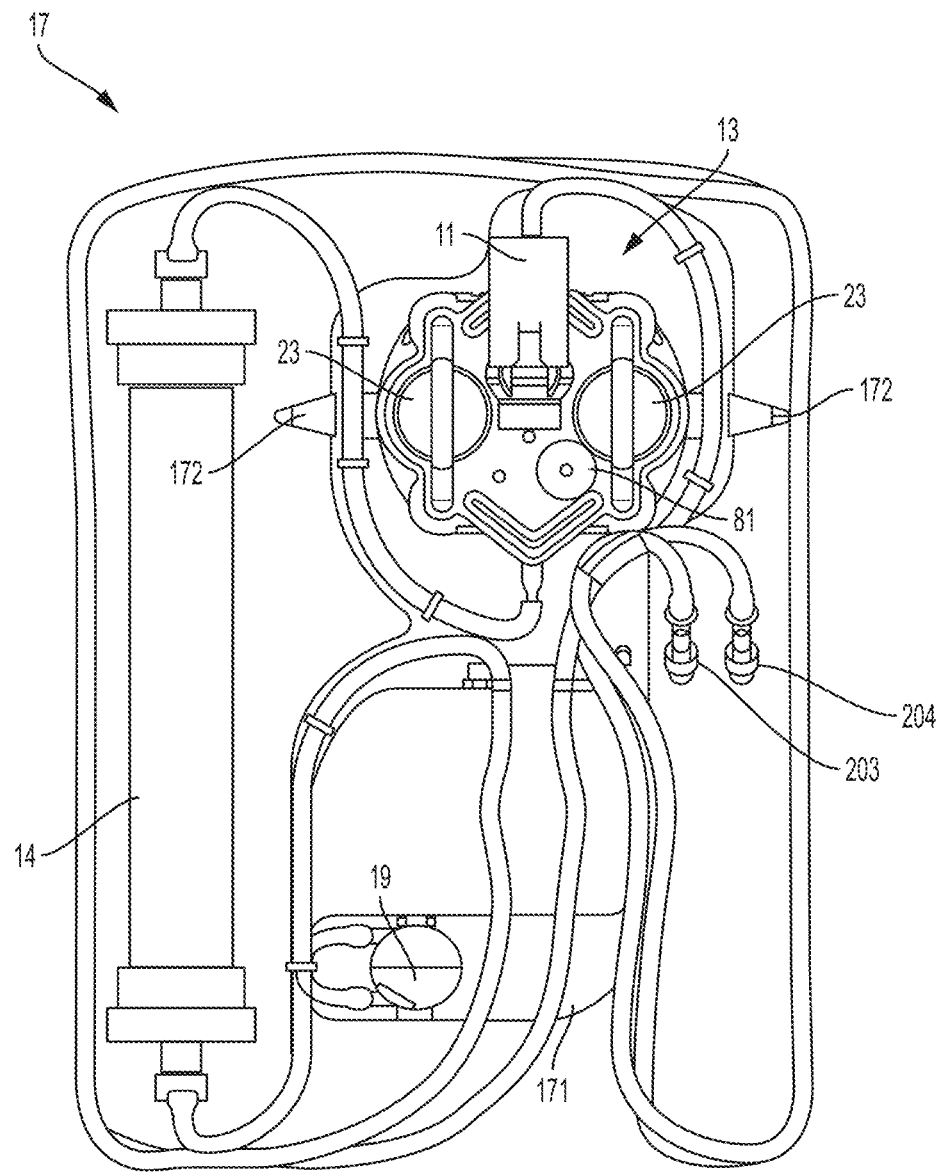
FIG. 18 is a front view of a blood circuit assembly for use with the system of FIG. 7.

FIG. 17 does not show the arterial and venous lines 203, 204 for the blood flow circuit 141 because in this embodiment and in accordance with another aspect of the invention, the blood flow circuit 141 is formed as a blood circuit assembly that is removable from the front panel 511 of the dialysis unit 51, and the blood circuit assembly is not mounted on the front panel 511 in FIG. 17. FIG. 18 shows a front view of the blood circuit assembly 17 in this embodiment along with the dialyzer 14. The blood circuit assembly 17 includes various components discussed above, for example with reference to FIG. 3, that are mounted to a blood circuit organizing tray 171. The arterial and venous lines 203 and 204 (e.g., including lengths of flexible silicone tubing) are terminated with blood line connectors that, in one aspect of the invention, are arranged to provide a plug-in or press-in connection with the blood line connection points 514 as well as provide a screw-type connection used with standard patient access points (e.g., luer type patient access connectors). The arterial line 203 leads to an inlet at the top of the blood pump 13, which includes two pod pumps 23, valves and other components for controlling blood flow. Associated with the blood pump 13 are an air filter 81, an anticoagulant pump 80 (not shown), and an anticoagulant supply 11 (such as a vial of heparin). (Details regarding the blood pump 13 in this illustrative embodiment may be found in U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; and U.S. patent application Ser. No. 11/871,803, filed Oct. 12, 2007, entitled "Cassette System Integrated Apparatus.") Blood output from the blood pump 13 (the outlet is located at a bottom of the pump 13) flows to an inlet of the dialyzer 14 (at the top of the dialyzer 14), and out of the dialyzer (the dialyzer blood outlet is located at the bottom of the dialyzer 14) to the inlet of the air trap 19. The outlet of the air trap 19 is connected to the venous blood line 204. Connections to the inlet and outlet blood ports of the dialyzer 14 are made with typical screw-type connections.

Figure 18A:
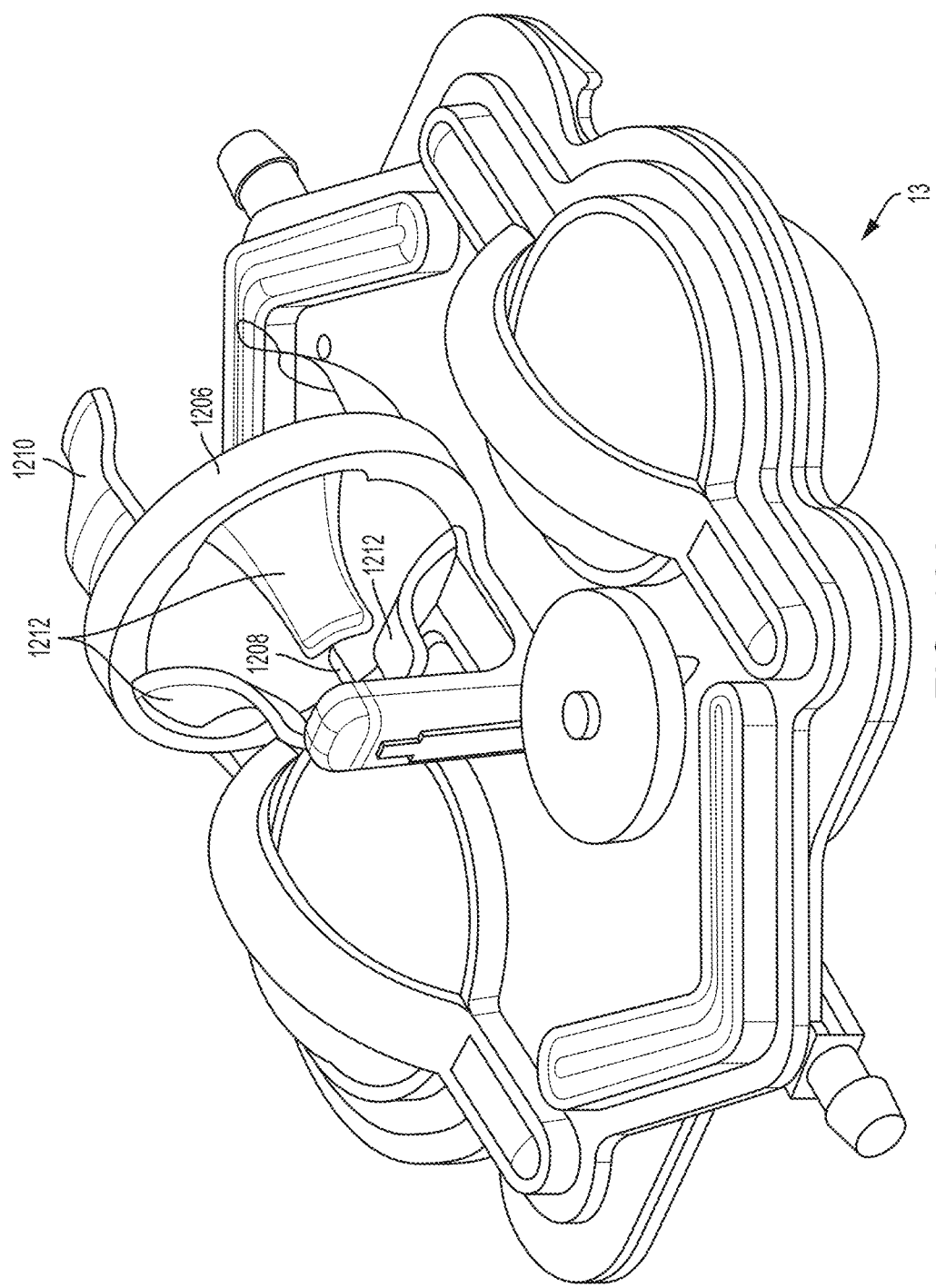
FIG. 18a is a perspective view of a blood pump having a medication holder in an illustrative embodiment.

FIG. 18a shows a perspective view of a blood pump 13 with an alternative embodiment of a vial receptacle or vial holder 1206 for holding or cradling a vial of medication 11 (such as, e.g., an anticoagulant) onto a hollow spike 1208 that is in fluid communication with pump 80 (schematically shown in FIG. 3) of the blood pump 13. In this embodiment, flexible upper arms 1210 serve to hold the body of vial 11 in place, and can flex to accommodate vials of various sizes. Lower arms 1212 help to align the inverted top of vial 11 with spike 1208 in order to prevent vial 11 from being spiked at an angle with respect to the inverted top of vial 11. Spiking the top of vial 11 in a substantially perpendicular manner may help to avoid any leaking of fluid from within vial 11 around the outside of spike 1208.

In accordance with another aspect of the invention, the air trap 19 is placed in the blood flow path after the blood exits the dialyzer and before it is returned to the patient. In an embodiment, air trap 19 can have a spherical or spheroid-shape container (i.e., a container having an approximately spherical inner wall), and have its inlet port located near the top and offset from the vertical axis of the container, and an outlet at a bottom of the container. (The vertical axis of the container is arranged in a vertical direction passing through the top and bottom "poles" of the approximately spherical container.) With the inlet port offset from the vertical axis (in this case set back toward the tray 171), blood is introduced into the container in a direction that is approximately perpendicular to the vertical axis of the container and that is approximately tangential to the spherical inner wall of the container. The curved shape of the inside wall of the trap can thus direct the blood to circulate along the inside wall as the blood gravitates to the bottom of the container (e.g., in a spiral like fashion), facilitating the removal of air bubbles from the blood. Air present in the blood exiting the outlet of the dialyzer 14 will enter at the top of the air trap 19 and remain at the top of the container as blood flows out the outlet at the bottom and to the venous blood line 204. By locating the inlet port near the top of trap 19, it is also possible to circulate blood through the trap with minimal or no air present within the container (as a "run-full" air trap. The ability to avoid an air-blood interface for routine circulation of blood in the trap can be advantageous. Placing the inlet port at or near the top of the container also allows most or all of the air present in the trap to be removed from the trap by reversing the flow of fluid through the blood tubing (i.e. from the bottom to the top of the trap 19, exiting through the inlet port of the trap 19).

In an embodiment, a self-sealing port, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection, e.g., by reversing flow through the air trap using a dialysate or other cleaning fluid. Also, the inlet, outlet and internal wall of the container and the self-sealing port may be arranged to substantially eliminate stagnation regions, i.e., allow for few or no regions where blood can stagnate or clot. The self-sealing port can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Figure 19:
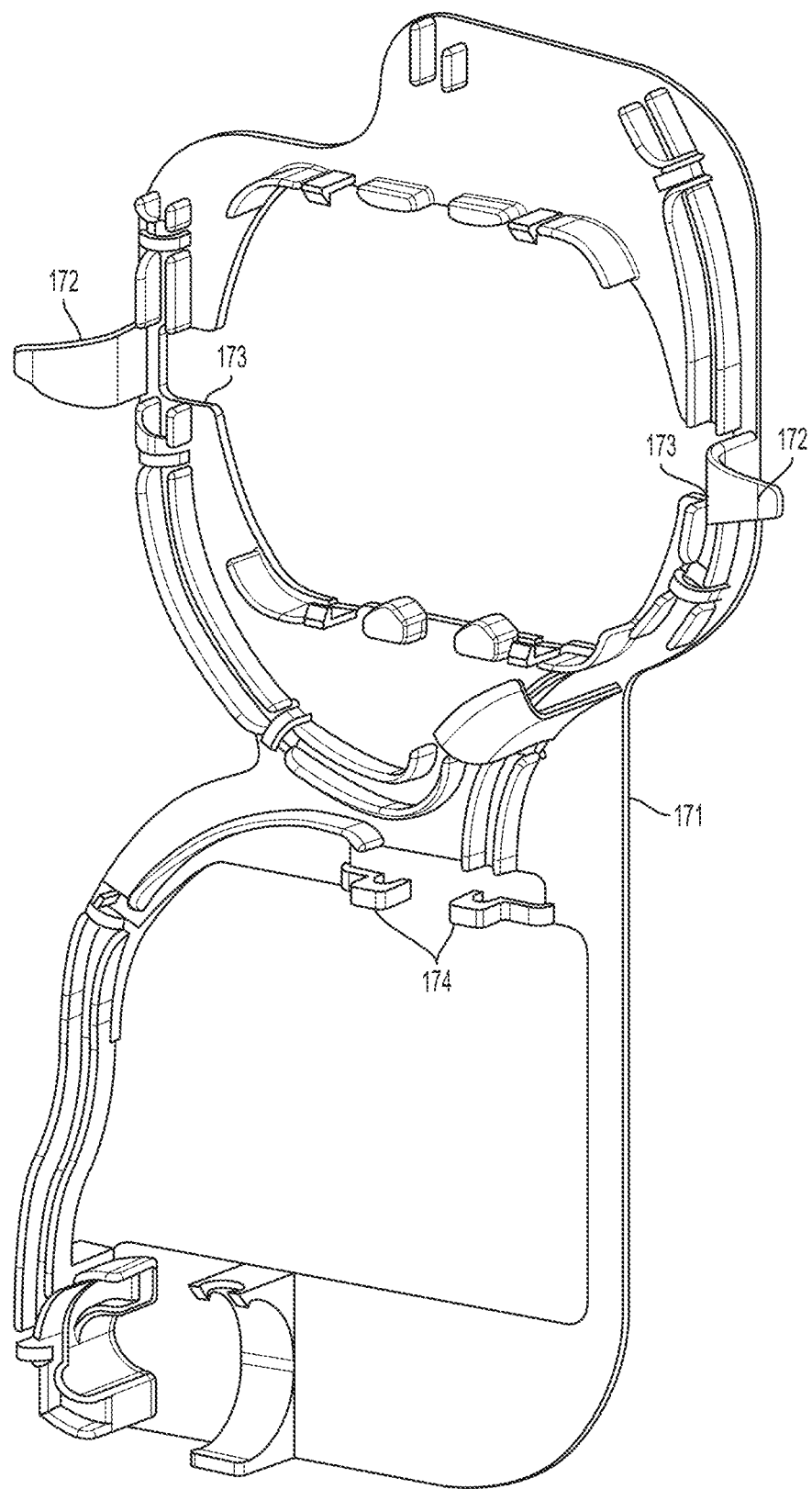
FIG. 19 right perspective view of a organizing tray for the blood circuit assembly of FIG. 18.

FIG. 19 shows the organizing tray 171 for the blood circuit assembly 17 without the various blood circuit assembly 17 components mounted. In accordance with one aspect of the invention, the organizing tray 171 includes handles 172 (in this embodiment, finger pulls) that a user can grip when mounting/dismounting the blood circuit assembly 17 to the front panel 511. Inward of the handles 172 are openings 173 that allow spring tabs on the front panel 511 to pass through and engage with the organizing tray 171 and/or the blood pump 13 cassette to hold the blood circuit assembly 17 in place on the front panel 511. In accordance with another aspect of the invention, the organizing tray 171 includes blood line engagement members 174 that each have a C-shaped recess or other hole through which a corresponding blood line 203, 204 passes. (In this context, a "hole" includes a recess like that shown in FIG. 19, a throughbore that has a continuous wall, e.g., as may be made by a drill, or other suitable opening.) As described in more detail below, the blood line engagement members 174 are used when mounting the blood lines 203, 204 in the occluder 513. In short, when mounting the blood lines 203, 204 in the occluder 513, the blood lines 203, 204 must be pulled and stretched downwardly (so as to reduce the outside diameter of the line) while being pushed horizontally into slots for the occluder 513. The blood line engagement members 174 function to both resist downward pulling on the blood lines 203, 204 (e.g., each line 203, 204 may include a stop ring above the respective engagement member 174 that cannot be pulled through the recess in the engagement member 174) as well as permit the user to press inwardly on the engagement member 174 to seat the lines 203, 204 in the occluder slots. The engagement members 174 are formed integrally with the organizing tray 171 so that a "living hinge" or relatively flexible portion of the organizing tray is positioned between the engagement member 174 and the main body of the organizing tray 171. This arrangement allows the engagement members 174 to be pushed inwardly relative to the organizing tray 171 as the connection portion between the engagement members 174 and the organizing tray main body flexes.

Figure 20:
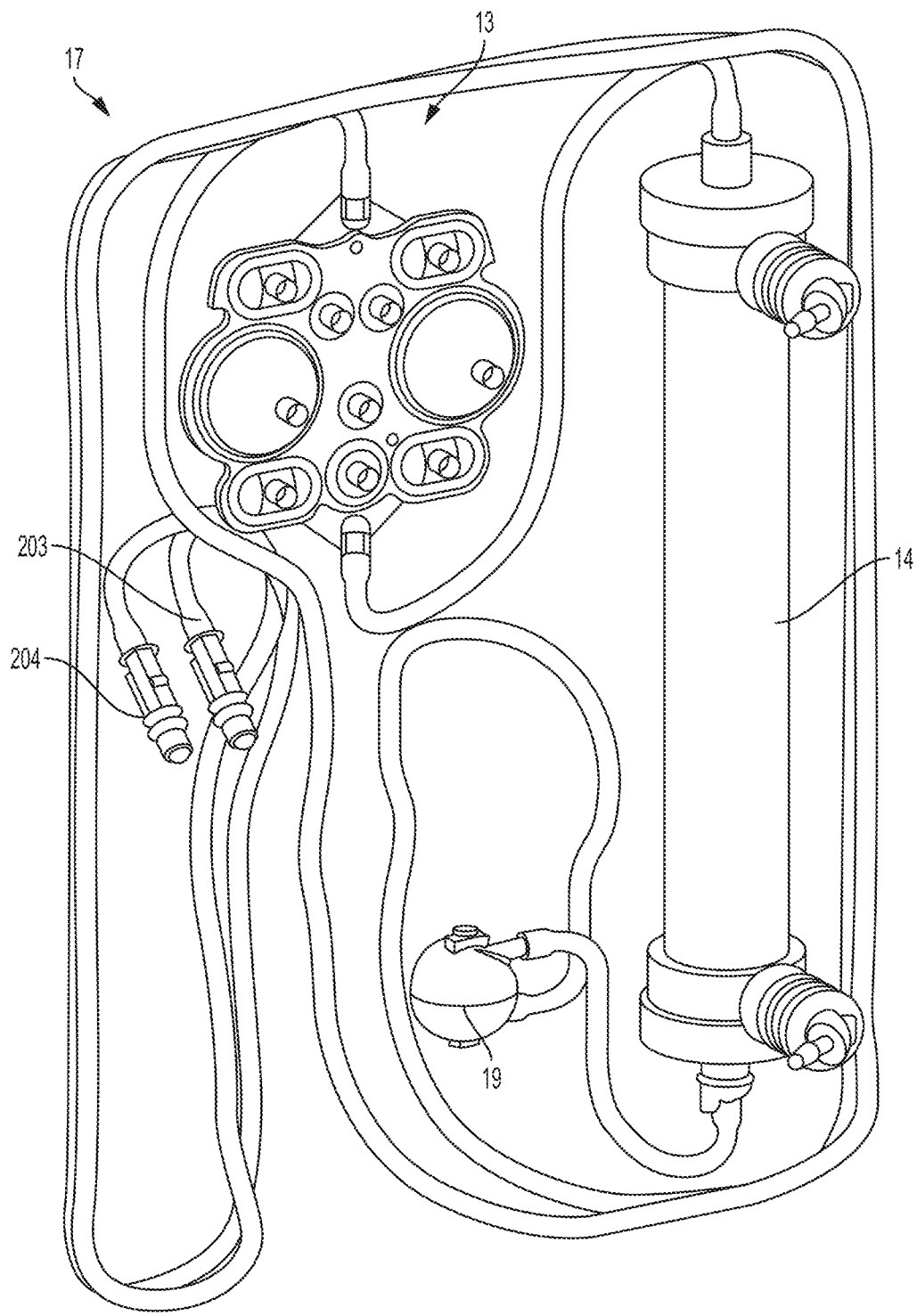
FIG. 20 is a left rear perspective view of the blood circuit assembly of FIG. 18.

FIG. 20 shows a rear view of the blood circuit assembly 17 with the organizing tray 171 removed. This view shows the rear side of the blood pump 13 section with control ports exposed. These control ports mate with corresponding ports 515 on the front panel 511 (see FIG. 17) so that pneumatic control (e.g., suitable air pressure or vacuum) can be applied to the pumps and valves to control their operation and flow through the blood circuit assembly 17. FIG. 20 also shows the offset of the inlet port of the air trap 19, i.e., the inlet port at the top of the air trap 19 is arranged to the rear of the vertical axis of the generally spherical container portion of the air trap 19.

Figure 20A:
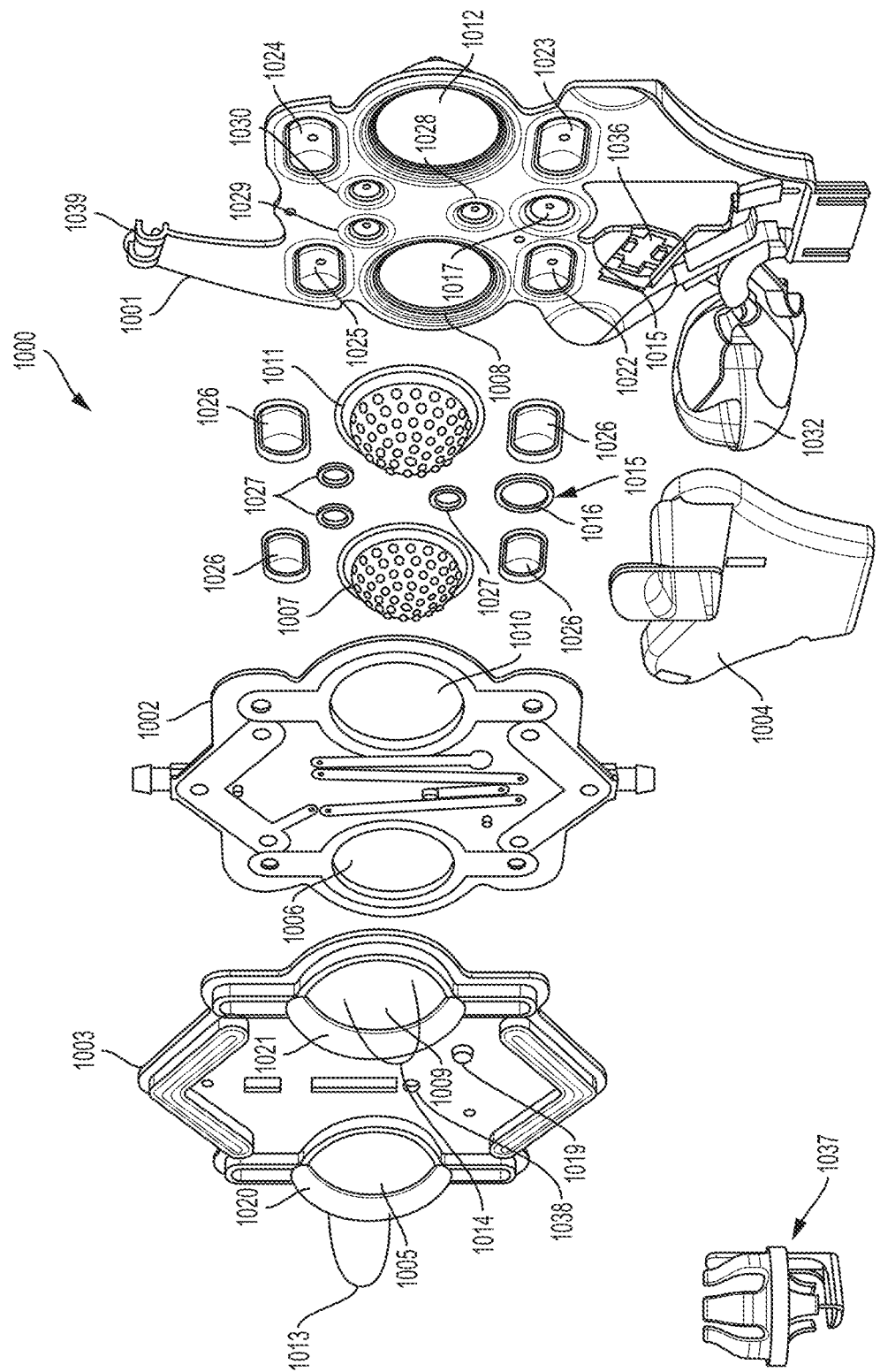
FIG. 20A is an front exploded view of an alternate embodiment of a blood pump cassette.
Figure 20B:
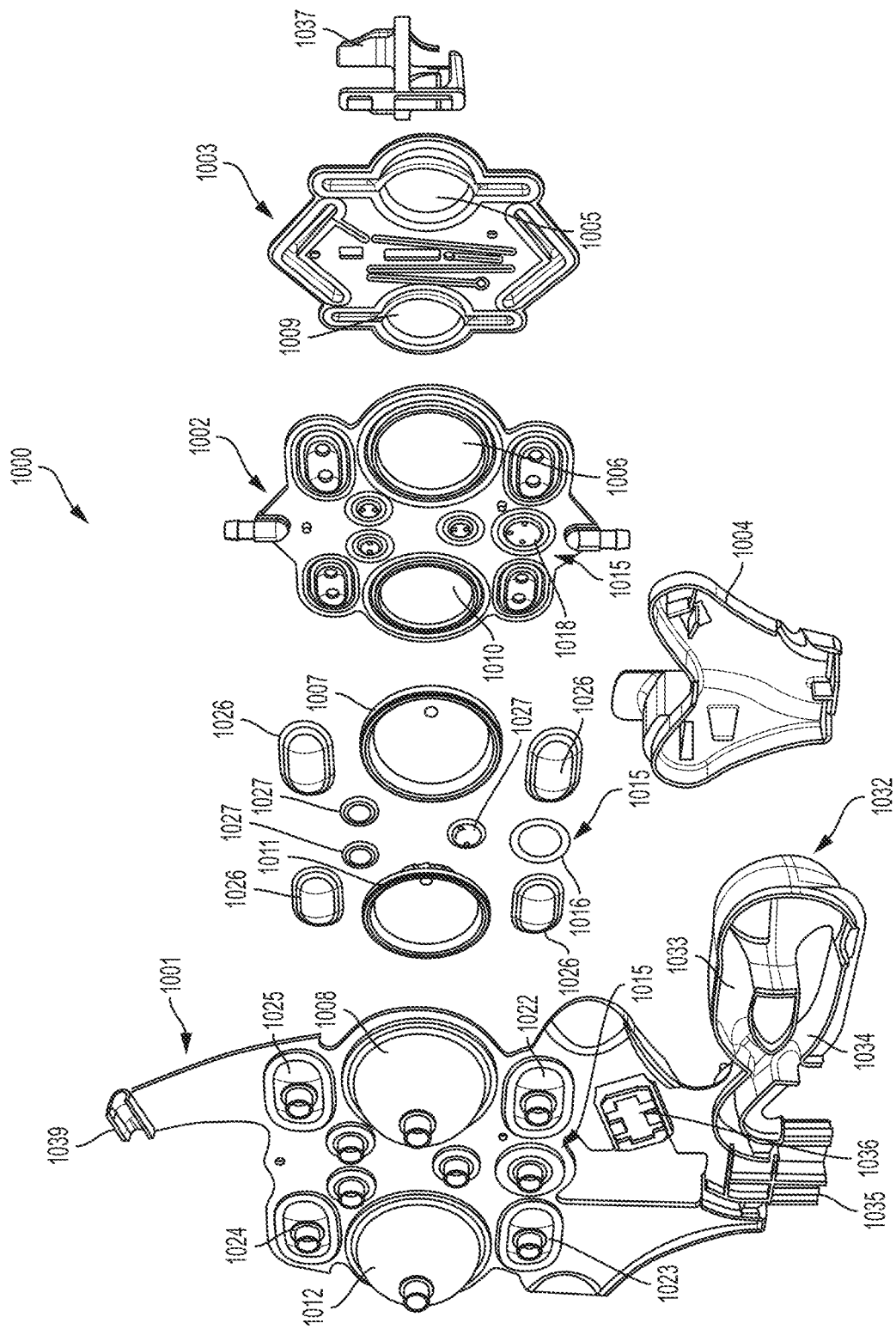
FIG. 20C is a front view of a bottom plate or back plate of the blood pump cassette of FIG. 20A.
FIG. 20D is a back view of a bottom plate or back plate of the blood pump cassette of FIG. 20A.

FIGS. 20A and 20B show exploded, perspective views of an alternative embodiment of a blood pump cassette 1000. FIG. 20A shows a front-perspective, exploded view of the cassette 1000 having a back (actuation side) plate 1001 that includes a tubing organizer formed with the back plate on a single molded piece of material. FIG. 20B shows a back-perspective, exploded view of the cassette 1000 of FIG. 20A. The cassette 1000 shown in FIGS. 20A-20D may be used in place of cassette 13 of FIG. 18A and organizing tray 171 of FIG. 19, combining many of the features of these components and substantially reducing the cost and complexity of manufacturing and assembling them.

The cassette 1000 includes a back plate 1001 that forms rigid outer walls of the actuation chambers of various valves and pumps, a mid plate 1002 that holds various valve and pump diaphragms and helps to define various flow paths in cassette 1000, and a front plate 1003 that forms rigid outer walls of some of the fluid chambers of the various valves and pumps of cassette 1000. The cassette 1000 optionally further includes a protective cover 1004 that is attachable to the front side of back plate 1001. The protective cover 1004 may include a holding arm for holding a vial that may be used for later mounting onto vial holder 1037. The protective cover 1004 can temporarily hold either an empty or full vial prior to inserting the vial into a vial holder 1037 for use during a procedure. That is, a vial may be coupled to a vial holder 1037 having a hollow spike that places the vial in vial holder 1037 in fluid communication with a fluid port 1038 in the front plate 1003. The vial may be filled, for example with anticoagulant medication for use during dialysis, or it may be empty and available for use during cleaning and disinfection procedures either before or after a dialysis treatment.

The cassette 1000 includes blood flow pumps 1013 and 1014 for moving liquid through the fluid flow side of the cassette 1000. That is, the cassette 1000 includes a left pump 1013 and a right pump 1014 for pumping fluid, which may be blood in the case of a hemodialysis apparatus. The pumps 1013 and 1014 (also referred to herein as pod pumps) may be actuated by a control fluid, such as air, a liquid, a gas, or other fluid that enters cassette 1000 through ports on back plate 1001. The left pod pump 1013 includes a rigid chamber wall 1005 formed on the front (or top) plate 1003, a rigid chamber wall 1008 formed on the back (or bottom) plate 1001, a hole 1006 formed on the middle plate 1002, and a flexible membrane 1007 that can flex between the rigid chamber walls 1013 and 1008. The space between the rigid chamber wall 1013 and the flexible member 1007 defines the fluid or blood side (i.e., fluid chamber) of the left pump 1013 and the space between the flexible membrane 1007 and the rigid chamber wall 1008 defines the pneumatic side (i.e., control chamber) of the left pump 1013. Likewise, the right pod pump 1014 includes a rigid chamber wall 1009 formed on the top plate 1003, a rigid chamber wall 1012 formed on the bottom plate 1001, a hole 1010 formed on the middle plate 1002, and a flexible membrane 1011 that can flex between the rigid chamber walls 1009 and 1012. The space between the rigid chamber wall 1009 and the flexible member 1011 defines the fluid or blood side (i.e., fluid chamber) of the right pump 1009 and the space between the flexible membrane 1011 and the rigid chamber wall 1012 defines the pneumatic side (i.e., control chamber) of the right pump 1014.

Each of the pod pumps 1013 and 1014 may include a pair of membrane-based entry/exit valves having fluid flow compartments formed from the top plate 1003 and control compartments formed from the bottom plate 1001. The valves may be actuated by the application of positive or negative fluid (e.g., pneumatic) pressure on individual flexible membranes via control ports on the bottom plate 1001. The fluid valves can be opened and closed to direct fluid flow when the pod pumps are pumping. Depending on how the valve actuations are sequenced in relation to the actuation of their associated pump, fluid may be pumped either in a forward direction, or in a backward direction. Non-limiting examples of pod pumps are described in U.S. patent application Ser. No. 11/787,212, filed Apr. 13, 2007, entitled "Fluid Pumping Systems, Devices and Methods," incorporated herein by reference. The pod pumps 1013 and 1014 may be operated in any suitable fashion, e.g., synchronously, asynchronously, in-phase, out-of-phase, etc., with fluid flow in either direction.

For hemodialysis applications, in some cases, an anticoagulant (e.g., heparin, or any other anticoagulant known to those of ordinary skill in the art) may be mixed with the blood within blood flow cassette 1000. For example, the anticoagulant may be contained within a vial (or other anticoagulant supply, such as a tube or a bag), and blood flow cassette 1000 may be able to receive the anticoagulant vial with a vial holder 1037 (which, in one embodiment, includes a needle or hollow spike) that can pierce the seal of the vial. The spike may be formed from plastic, stainless steel, or another suitable material, and may be a sterilizable material in some cases, e.g., the material may be able to withstand sufficiently high temperatures and/or chemical exposure so as to sterilize the material. As an example, the spike may be used to pierce the seal of the vial, such that anticoagulant can flow into blood flow cassette 1000 to be mixed with the blood in the blood flow path. In other cases, the vial may be filled or partially filled with water or dialysate during cleaning, disinfecting or priming operations.

A third pump 1015, which can act as a metering pump in some cases, in cassette 1000 can be used to control the flow of medication from an attached vial (such as anticoagulant) into a fluid path within the cassette 1000. Metering pump 1015 may be of the same or of a different design from the pumps 1013 and 1014. For example, metering pump 1015 may be a pod pump and may be actuated by a control fluid, such as air. For example, as is shown in FIGS. 20A-20D, the metering pump 1015 may include a rigid chamber wall 1015 formed within the back plate 1001, a rigid chamber wall 1018 formed on the mid plate 1002 (see FIG. 20B), and a flexible diaphragm 1015 dividing the pod into a fluid compartment or chamber and a control compartment or chamber. Valves 1028, 1029, 1030 may be connected to fluid flow paths joining in various combinations fluid port 1038, vent port 1019, a fluid flow path leading to or from a first or second pump (such as pump 1013), and a fluid flow path leading to or from metering pump 1015. The flow of medication (e.g., anticoagulant) or other fluid from an attached vial into a main fluid flow path in the cassette 1000 may thus be controlled by metering pump 1015; and periodically, air may be introduced from vent port 1019 by metering pump 1015 into an attached vial through port 1038 to equalize pressure within an attached vial with ambient pressure as medication or other fluid is withdrawn from the vial.

The cassette 1000 may also include an air vent coupled to a port 1019. Air may be introduced into the flow path of metering pump 1015 to equalize pressure in an attached vial with ambient pressure. In this case, valve 1029 closes flow between metering pump 1015 and the main flow path of the first 1013 (or second 1014) pump. In some cases, metering pump 1015 may also introduce air into the main flow path of the first 1013 or second 1014 pumps in order to allow a system controller to control the emptying of the blood or liquid carrying components of the system.

The pod pumps 1013 and 1014 include raised flow path 1020 and 1021 on the chambers 1005 and 1009, respectively. The raised flow paths 1020 and 1021 allow fluid to continue to flow through the pod pumps 1013 and 1014 after the diaphragms (i.e., flexible membranes) 1007 and 1011 reach the end of a stroke.

The cassette 1000 includes several valves 1022, 1023, 1024 and 1025 formed within the back plate 1001. The actuation (or pneumatic) side of the valves 1022-1025 and 1028-1030 are formed from bottom plate 1001, and have corresponding actuation ports for the entry or egress of control (e.g. pneumatic) fluid. Several diaphragms 1026 and 1027 installed on midplate 1002 complete the valves, while diaphragms 1007, 1011 and 1016 complete the pod pumps 1013, 1014 and metering pump 1015. The metering pump 1015 is completed by diaphragm 1016. In a preferred embodiment, the valves are actuated pneumatically, and as the valve diaphragm is pulled away from the adjacent holes in midplate 1002, liquid is drawn in, and as the diaphragm is pushed toward the holes, liquid is pushed through. The fluid flow is directed by the appropriate sequencing of the opening and closing of the valves 1022-1025, and 1028-1030.

The metering pump 1015 includes three passageways connected to the fluid chamber 1018 defined in the mid plate 1002. One passageway allows air from vent 1019 to be pulled into the metering pump 1015, a second passageway allows the air to be pushed to the spike/source container connected to vial holder 1037, and also alternately draws liquid from the source container or vial, and the third passageway allows the liquid from the source container to be pushed by the metering pump 1015 to a main fluid line connected to first pump 1013 (or pump 1014 in an alternate embodiment). Valves 1028, 1029, and 1030 determine whether the metering pump 1015 moves fluid or air, and in which direction.

Figure 20C:
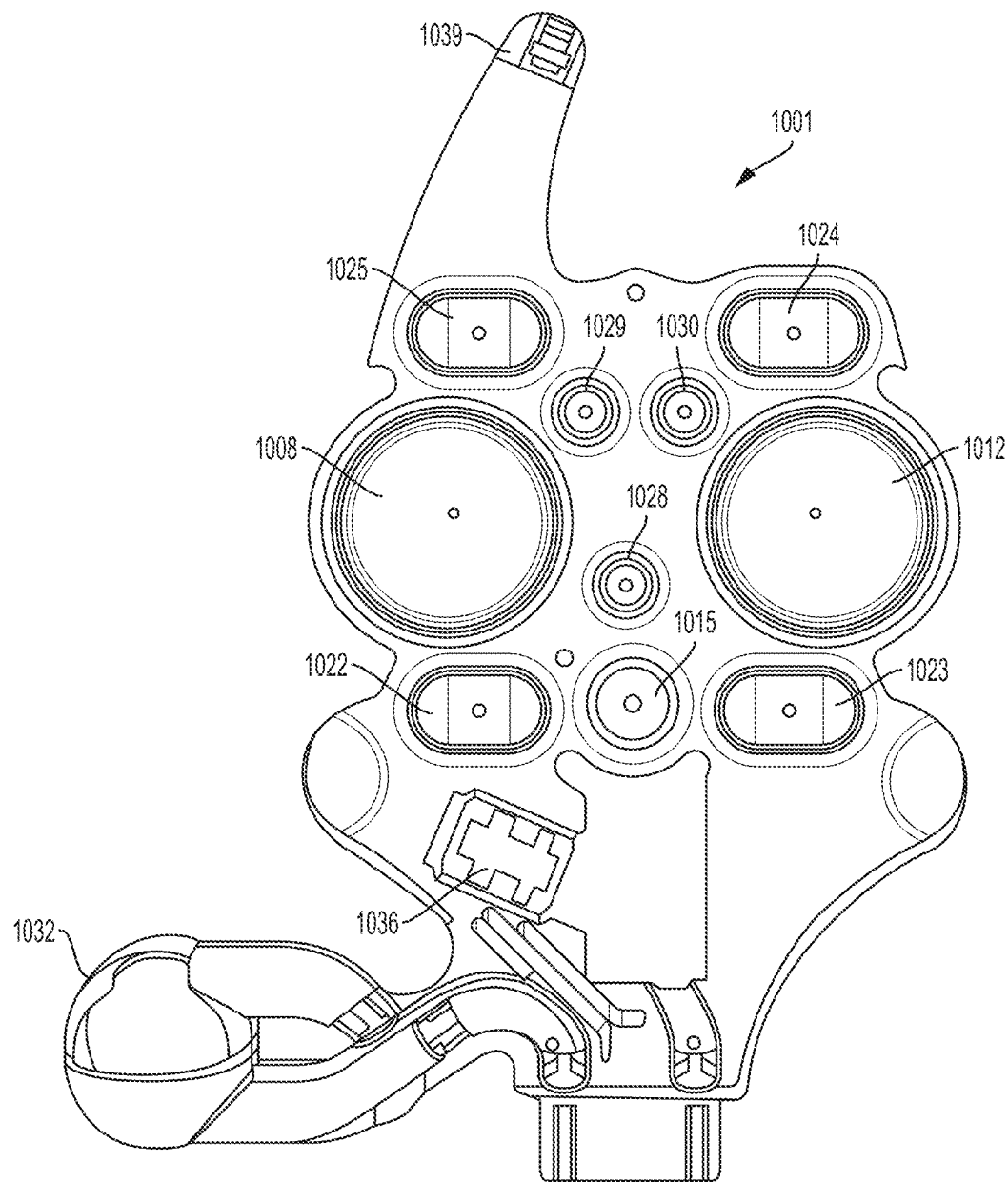
Figure 20D:
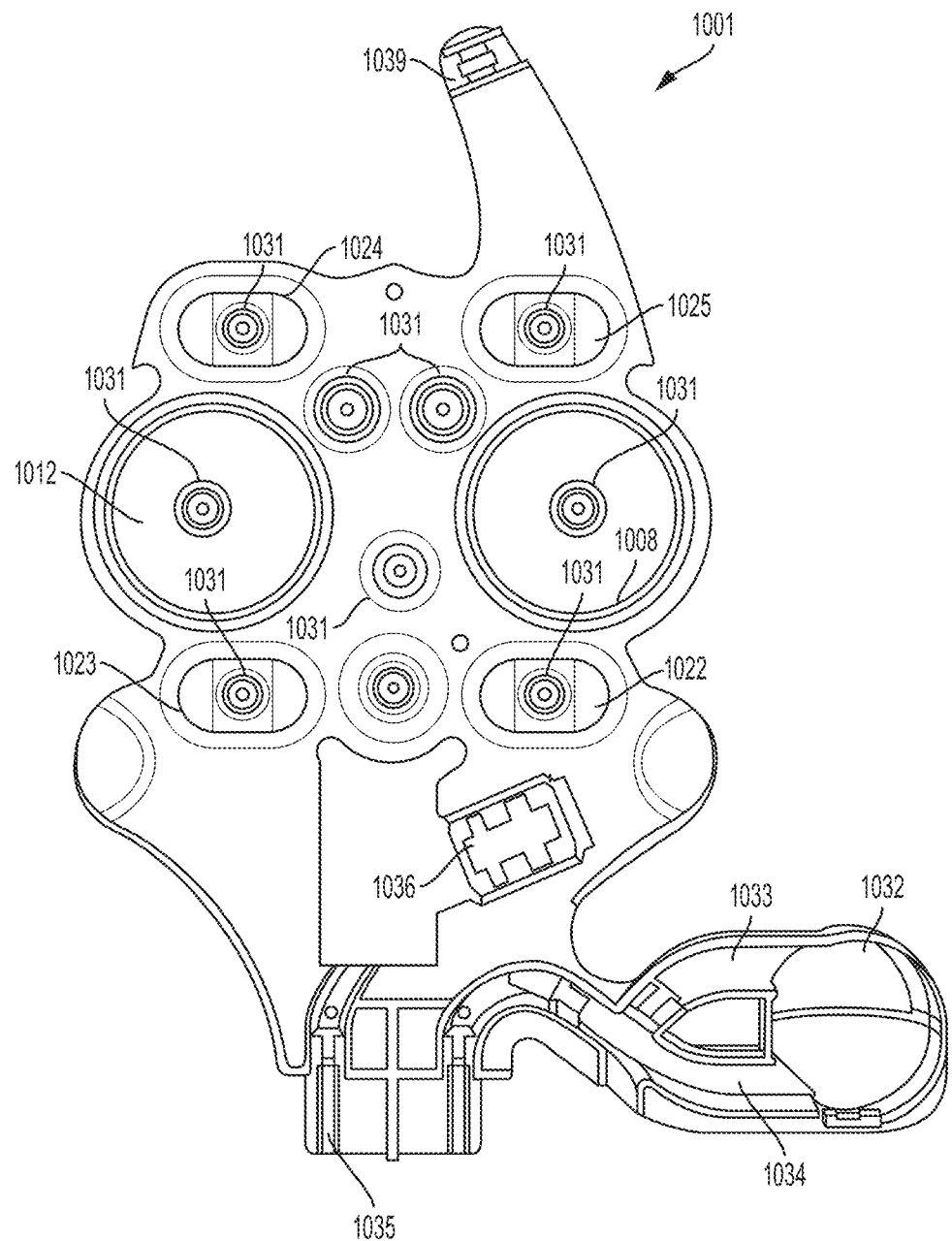

Referring next to FIG. 20C, the inner view of the bottom plate 1100 is shown. The inside view of the pod pumps 1008 and 1012, the metering pump 1015, and the valves 1022, 1023, 1028, 1025, 1029, 1030, and 1024 actuation/air chambers are shown. The pod pumps 1008 and 1012, the metering pump 1015 and the valves 1022, 1023, 1028, 1025, 1029, 1030, and 1024 are actuated by a pneumatic air source. Referring now to FIG. 20D, the outer side of the bottom plate 1100 is shown. The source of control fluid (e.g. air under positive or negative pressure) is connected to this side of the cassette. In one embodiment, tubes connect to various ports 1031. In other embodiments, the ports 1031 are arranged to plug into a control port assembly (e.g., control port assembly 615 in FIG. 17A) on the front panel of dialysis unit 51 (e.g., front panel 511 in FIG. 17).

Figure 21:
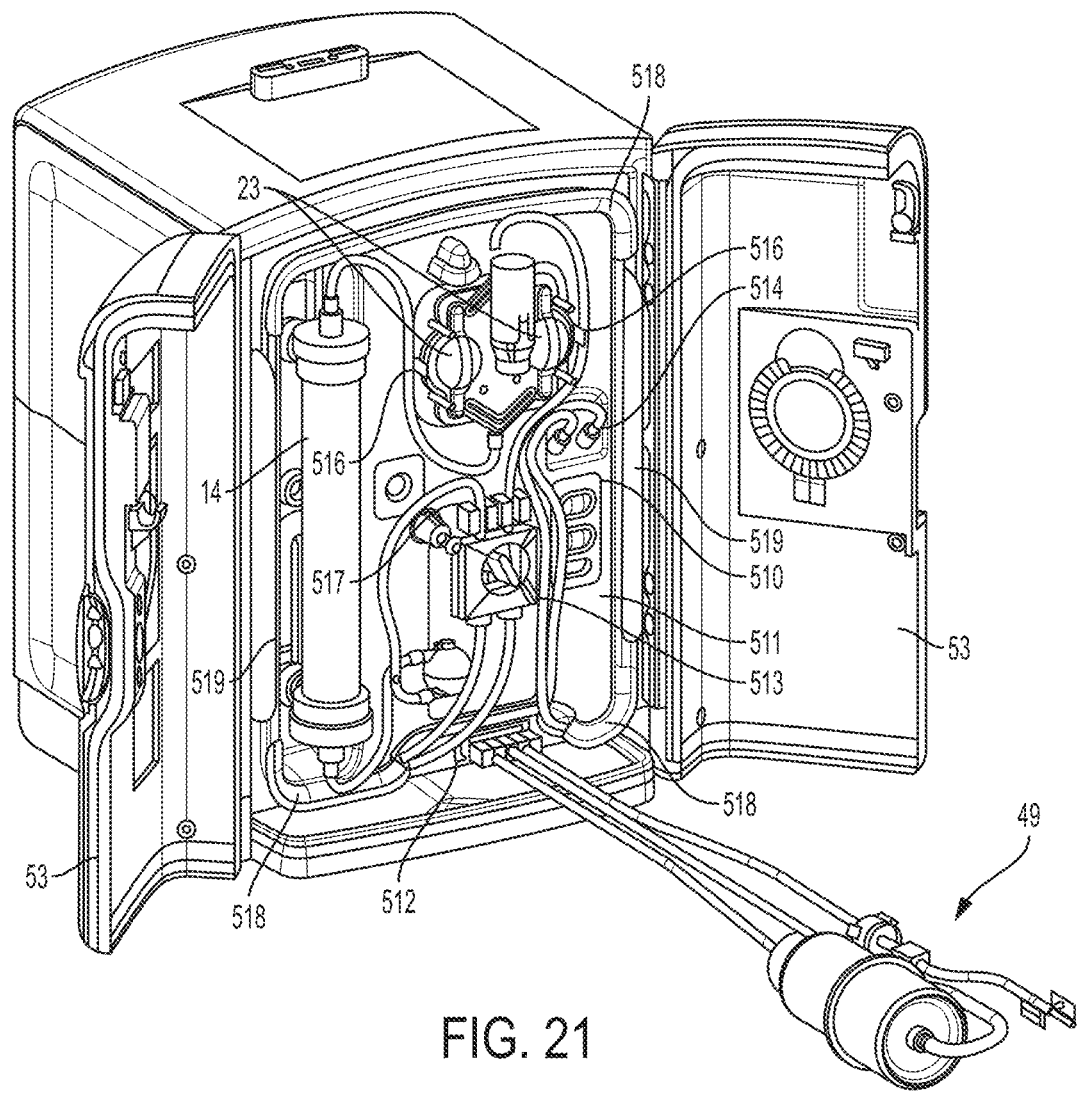
FIG. 21 shows a left front perspective view of the front panel of the system of FIG. 7.
Figure 22:
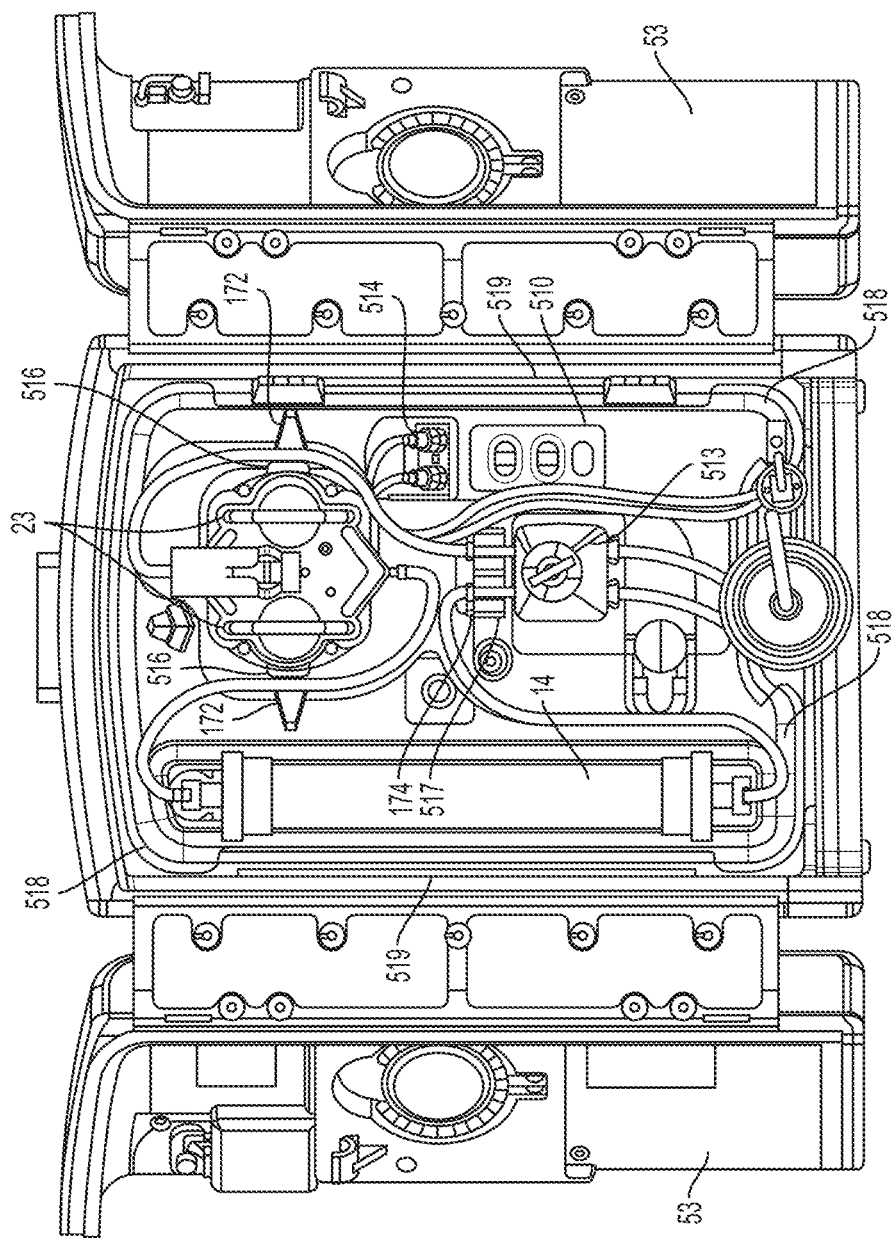
FIG. 22 shows a front view of the front panel of the system of FIG. 7.

Referring now to FIGS. 20A-20D, the bottom plate 1001 includes various organizer features integrated thereon. The bottom plate 1001 includes an air trap retaining member 1032 having tube guides 1033 and 1034 defined on the bottom plate 1001. The tube guides 1033 and 1034 guide a tube to and from an air trap disposed within the air trap retaining member 1032. The bottom plate 1001 also includes additional tube guides 1035 and 1039. The bottom plate 1001 also defines a receiving portion 1036 to receive an electrical connector that may be used in an arrangement to monitor for disconnection of the arterial or venous lines from a patient during therapy. FIG. 21 shows a perspective view of the front panel 511 of the dialysis unit 51 with the blood circuit assembly 17 mounted to the front panel 511 without the organizing tray 171. (Normally, the blood circuit assembly 17 would include the organizing tray 171, but the tray 171 is not shown in the example so as to more clearly show components at the front panel 511.) On opposite sides of the blood pump 13 cassette, the front panel 511 has spring tabs 516 that extend forwardly and resiliently engage with the blood pump cassette and/or the organizing tray 171 to retain the blood circuit assembly 17 in place. The tabs 516 may include a barb or other feature to help retain the blood circuit assembly 17 in place. The spring tabs 516 may be flexed outwardly to release their hold on the blood circuit assembly 17, allowing its removal. However, in the absence of an outwardly directed force on the spring tabs 516, the tabs 516 will remain engaged with the blood circuit assembly 17. FIG. 22 shows a front view of the front panel 511 with the organizing tray 171 of the blood circuit assembly 17 included. To remove the blood circuit assembly 17 from the front panel 511, a user may place index fingers behind the handles 172 while simultaneously placing thumbs on the inner side of the spring tabs 516 (the sides nearest the blood pumps 23) and flexing the spring tabs 516 outwardly and away from the pumps 23. This causes the spring tabs 516 to release the blood circuit assembly 17, e.g., disengagement of barbs on the tabs 516 from the blood pump 13 and/or the organizing tray 171. Of course, to remove the blood circuit assembly 17, other connections must be removed, including connections to the dialyzer 14 and the blood line connection points 514, as well as removal of the lines 203, 204 from the occluder 513. When mounting the blood circuit assembly 17 to the front panel 511, the organizing tray 171 may be grasped at the handles 172 and properly aligned, e.g., so that the spring tabs 516 are aligned to pass through the openings 173 and the control ports of the blood pump 13 cassette are aligned with the corresponding ports 515 on the front panel 511. The blood circuit assembly 17 may then be simply pushed into place, so that the spring tabs 516 engage with the organizing tray 171 and/or the blood pump cassette. Other connections can then be made, such as connections to the dialyzer 14, mounting of the blood lines 203,204 with the occluder 513, etc.

FIG. 21 also shows the slots 517 that hold the blood lines 203, 204 for leading into the occluder 513. The slots 517 define a channel that is slightly smaller than the outside diameter of the blood lines 203, 204 so that the lines 203, 204 tend to remain in the slots 517 after placement in the slots. This helps to ensure proper association of the lines with the occluder 513. Once the blood circuit assembly 17 is mounted on the spring tabs 516, the user may then engage the blood lines 203, 204 with the slots 517 by stretching the lines 203, 204 downward (with the engagement members 174 on the organizing tray 171 engaging the stop ring or other feature on the respective line 203, 204 and resisting the downward pull) and pushing the lines 203, 204 into a corresponding slot. The lines 203, 204 can be pushed into place by pressing inwardly on the engagement members 174, which as described above, are flexible and bend inwardly relative to the organizing tray 171. The lines 203, 204 can then be routed through the occluder 513.

In accordance with another aspect of the invention, the front panel 511 includes a blood line wrap feature around the periphery of the front panel 511. In this illustrative embodiment, the front panel 511 includes flanged portions 518 along the top edge and at lower corners of the front panel 511. This allows a user to wrap the blood lines 203, 204 around the periphery of the front panel 511 by placing the lines 203, 204 in a channel defined by the flanged portions 518. The lines 203, 204 may be wrapped in a clockwise direction, starting from a point near the bottom of the dialyzer 14, and ending at a point near the lower right corner of the front panel 511. The blood lines 203, 204 may then be connected at the blood line connection points 514, e.g., to allow disinfecting fluid to be circulated through the blood lines 203, 204. As a result, the blood lines 203, 204 can be neatly retained on the front panel 511, allowing easy access to other components on the front panel 511 and allowing the user to close the doors 53 with minimal concern for pinching the blood lines 203, 204 between the doors 53 and the dialyzer unit housing 51. Alternatively, the blood lines 203, 204 may be first connected at the blood line connection points 514, and then wrapped in a clockwise direction, starting from a point near the bottom of the dialyzer 14, and ending at a point near the lower right corner of the front panel 511. This ensures that the blood lines are properly distributed along the flanged portions 518 to reach the connection points 514. Vertical fences 519 may also be provided along the left and right sides of the front panel 511 to help keep the blood lines 203, 204 in a desired position and away from the hinge plates 533 and other possible pinch points.

Figure 21A:
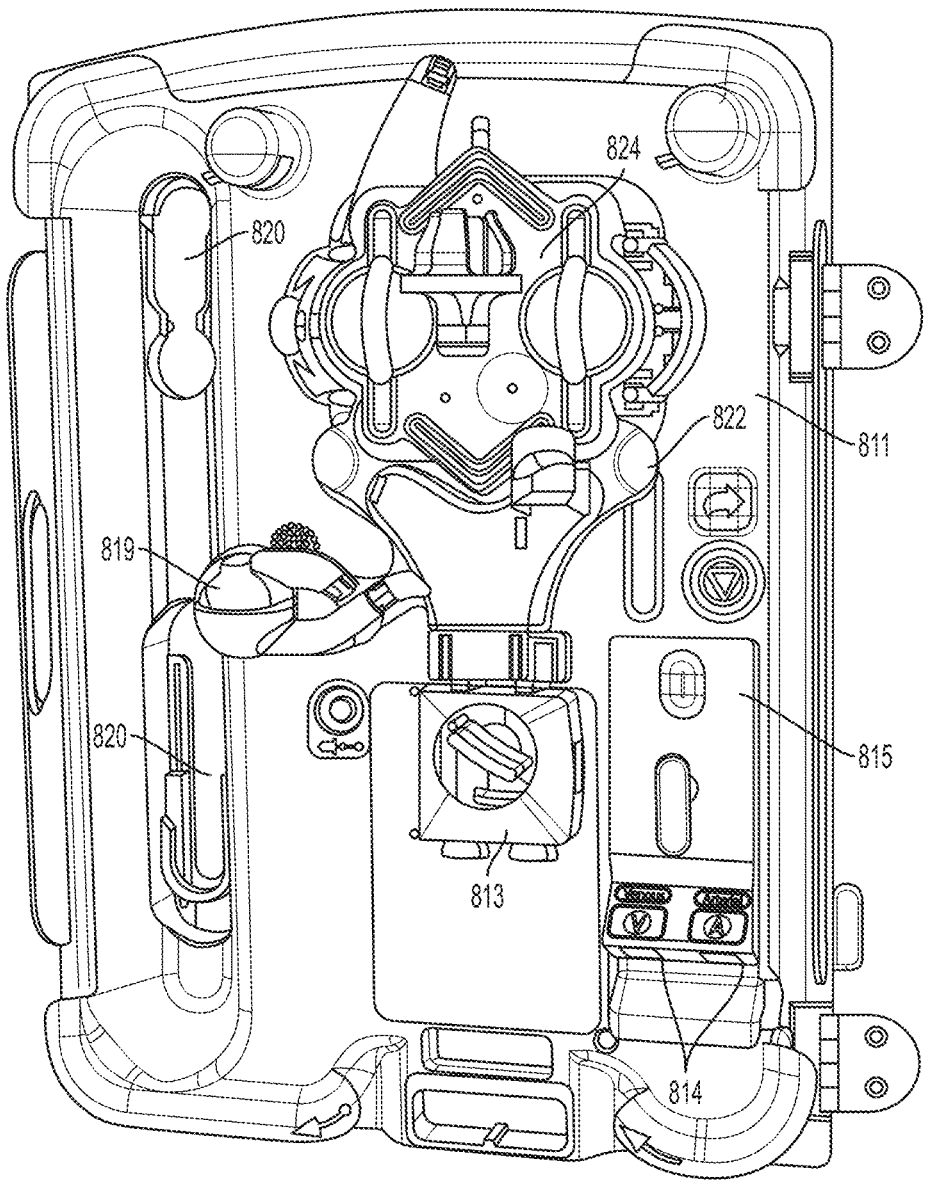
FIG. 21A shows a front view of an alternate embodiment of a front panel assembly in an illustrative embodiment.

In another aspect, as shown in FIG. 21A, an alternate embodiment of a front panel assembly 811 may include a modular drain assembly (or drain cassette) 815 having connection points 814 into which the arterial and venous blood lines may be connected. As shown in FIG. 5A, the drain cassette 815 includes a common pathway to a drain line 31 for both the arterial and venous blood lines during priming, cleaning and disinfecting operations. Water, dialysate solution or another fluid may be introduced into the blood pathways of dialysis system 5 through the semi-permeable membrane of dialyzer 14 in order to expel air from the blood pathways and to prime the blood pathways, or in order to clean and disinfect the blood pathways. The drain cassette 815 may optionally include a valve in one or both arterial or venous blood pathways. In an embodiment, an electronically controlled valve 831 in or near the modular drain cassette 815 in the venous line may permit the blood pumps on the blood pump cassette 13 to sequentially fill or clear the arterial line while the valve 831 in the venous line is closed, and then fill or clear the venous line upon opening of the valve. In this method, any air or contaminants in the arterial line are forced to the drain outlet of the drain cassette 815, rather than into the venous tubing. Alternately, the valve 831 may be arranged to control flow between the arterial line and the drain, e.g., so contents in the venous line can be forced to the drain outlet rather than into the arterial line. The drain cassette 815 may also optionally include conductivity and/or temperature sensors 834, 835. A temperature sensor may be used, for example to monitor the temperature of the fluid circulating through the blood lines during heat disinfection. Conductivity sensors may be used to monitor the conductivity of water or dialysate solution being circulated through the blood lines during tests of the urea or sodium clearance of a dialyzer, for example. An electronically controlled drain control valve 207 may be placed either at the drain outlet of drain cassette 815, or it may be positioned external to the drain cassette 815 (as shown in FIG. 5A). Drain control valve 207 may be useful, for example, when heated water or chemical disinfectant is being circulated within the blood circuit components of dialysis unit 51. The drain cassette 815 may be constructed for ease of connection to and disconnection from the front panel 511 or 811 of dialysis unit 51. A single handle-operated latch (such as a bayonet connection, for example,) may be included which secures the drain cassette 815 onto the front panel by a turn of the handle.

Figure 21B:
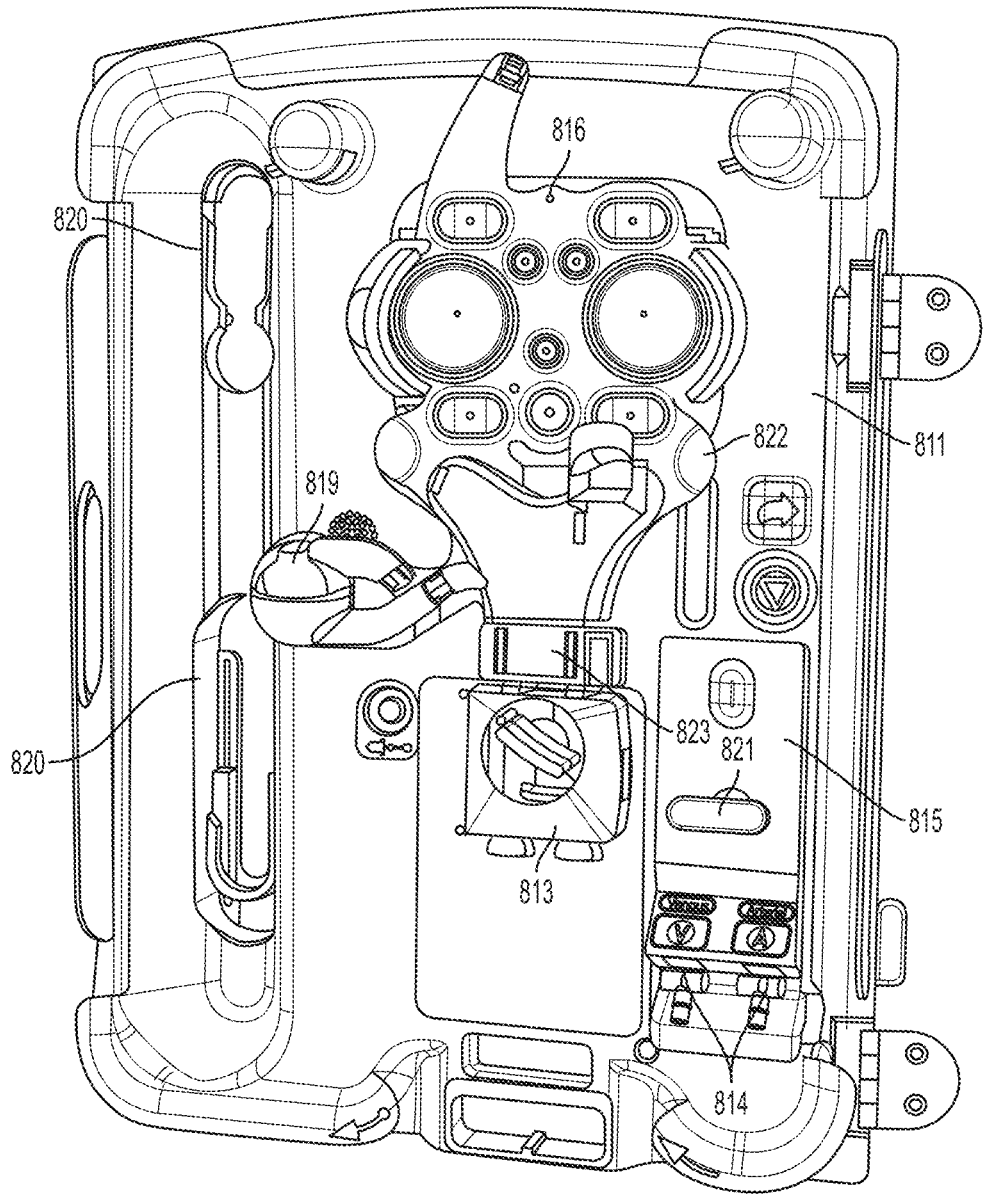
FIG. 21B shows the front panel assembly of FIG. 21A with the top and middle plate components of the blood pump cassette removed for clarity in an illustrative embodiment.

FIG. 21A also shows an alternate embodiment of a blood pump cassette and organizing tray assembly. In some embodiments, the organizing tray 822 may be incorporated in the pneumatic actuation plate (or back plate) of the blood pump cassette 824. FIG. 21B shows the front panel assembly 811 with the top and middle plate components of blood pump cassette 824 removed for clarity. In this example, the organizing tray 822 and the back plate 816 of blood pump cassette 824 have been combined into a single molded piece. In this example, the air trap 819 is supported by an extension of the organizing tray 822 and is located in a vertically more elevated position than in the embodiment shown in FIG. 19 and FIG. 29. Moving the air trap to a higher position relative to the occluder 813 or the air-in-line detectors 823 may increase the ability of the blood pump in a reverse-flow procedure to draw any air bubbles present in the venous tubing into the air trap 819. For example, an inlet of the air trap 819 may be supported by the organizing tray 822 at a position above an outlet of the air trap when the blood circuit assembly is mounted to a dialysis unit. In addition or alternately, the inlet and/or outlet of the air trap may be supported by the organizing tray at a position above a highest point of flexible tubing that extends from the outlet of the air trap to the occluder position. Such an arrangement may help expel any air in the venous tubing into the air trap 819.

In another aspect of the invention, a modular drain cassette may be included, having the function of monitoring and draining fluid (such as water or dialysate solution) flowing through the blood circuit of the dialysis unit 51—the blood circuit including the blood pumps, the blood flow compartments of the dialyzer, the air trap and the arterial and venous blood tubing. As shown in FIG. 5A, when the arterial and venous blood tubing is not connected to a patient, it may be connected to a drain chamber/air trap 4703, which ultimately leads to a drain line 31. This connection allows for the circulation of heated water, for example, for cleaning and disinfection of the blood circuit components, for determination of dialyzer clearance characteristics, or for priming of the blood circuit with dialysate solution. In one aspect of the invention, a drain cassette 815 may comprise a drain chamber/air trap 4703, a valve 831 on one or both of the arterial and venous blood lines, a check valve 836 in the drain line, and temperature and conductivity sensors 834, 835 into one modular component that can be readily connected to or disconnected from the front panel of dialysis unit 51. As shown in FIG. 21A, in an embodiment, the arterial and venous blood lines may be connected to the drain cassette 815 via connection points 814 on front panel 811. The drain cassette 815 may include a channel or chamber which merges fluid flow from the venous and arterial blood lines, exiting via a common outlet to a drain line 31.

As noted previously, the drain cassette 815 may optionally include a valve 831 in the venous path (or, alternatively in the arterial path, or both paths). In a preferred embodiment, the valve 831 is a pneumatically operated membrane valve, which is actuated by an electromechanical valve plumbed to a pneumatic pressure source and under the control of an electronic controller. The drain cassette 815 may also optionally include conductivity and thermal probes 834, 835 in the fluid flow channel or chamber within the housing of the cassette 815. In a preferred embodiment, the drain outlet, the pneumatic control port and the electrical connections for the conductivity and thermal sensors comprise paired connectors, one member of each pair rigidly attached to the housing of the drain cassette 815, and the other member of each pair rigidly attached to the front panel 811 of dialysis unit 51 in order to allow a user to mount or dismount drain cassette 815 quickly and easily from front panel 811. As with the other blood circuit components of the front panel 511 or 811 (including dialyzer 14, blood pump cassette 13 or 824, air trap 19 or 819, and arterial and venous blood lines), drain cassette 815 may be configured to be readily dismountable from dialysis unit 51.

Figure 31:
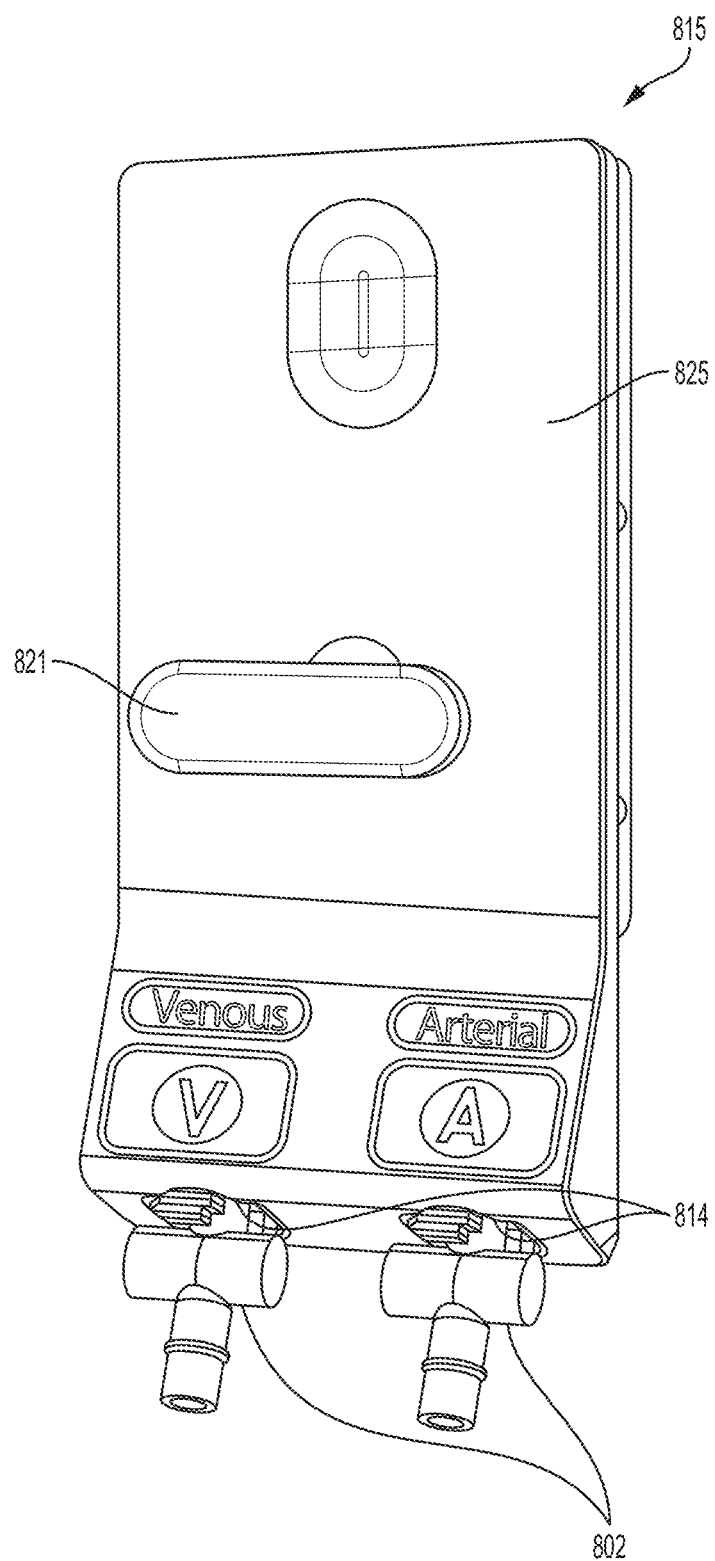
FIG. 31 shows an exemplary modular drain cassette in an illustrative embodiment.

FIG. 31 shows an exemplary modular drain cassette 815. In this view, the escutcheon 825 of the drain cassette 815 includes markings identifying the arterial and venous line connection points 814. A handle 821 anterior to the escutcheon 825 may be grasped with a single hand and turned to engage or disengage the drain cassette 815 from the front panel 811. Blood line connectors 802 for each of the arterial and venous blood lines are shown engaged within their respective connection ports or points 814 on the drain cassette 815.

Figure 32:
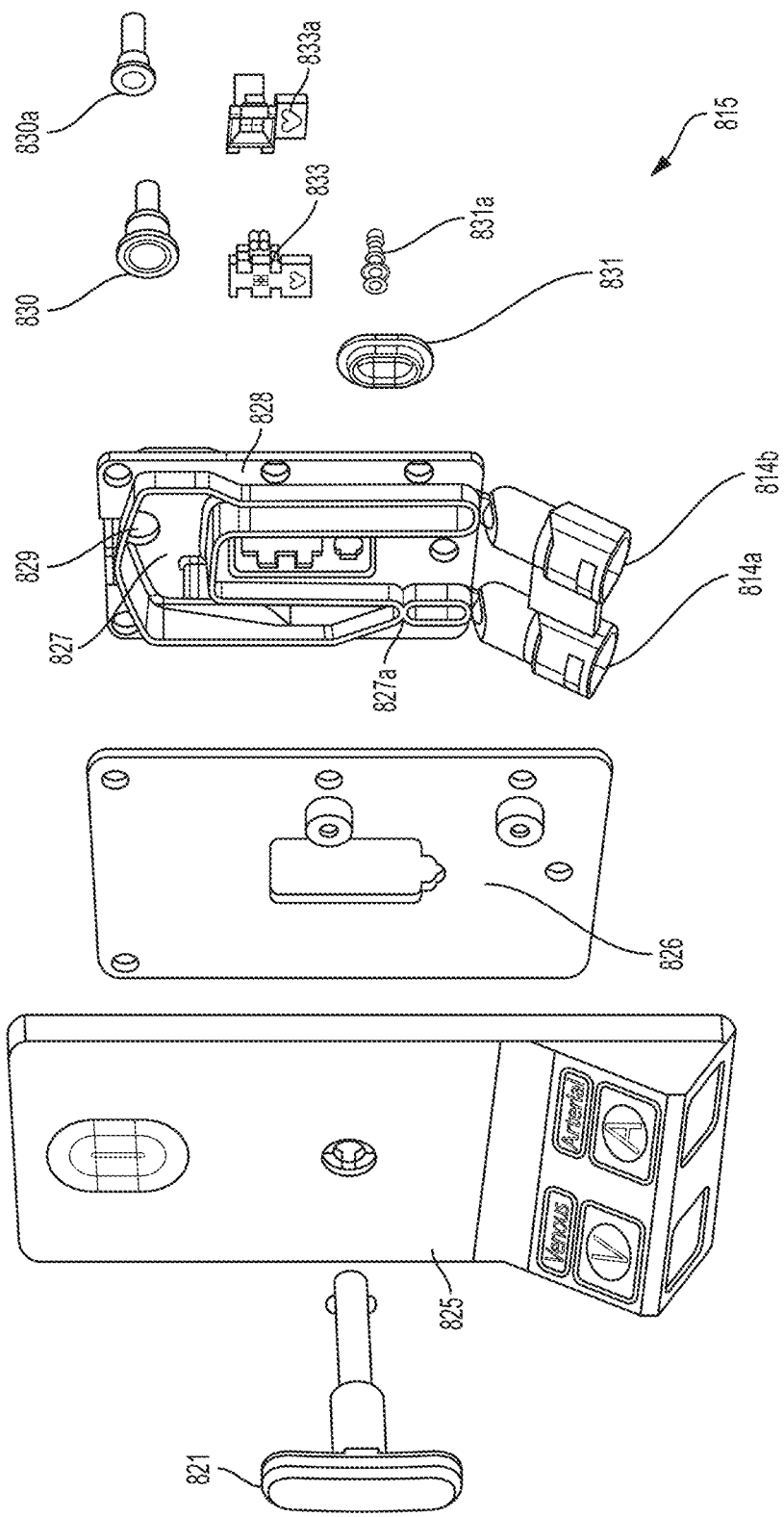
FIG. 32 shows the drain cassette of FIG. 31 in an exploded view with an escutcheon positioned anterior to a front wall of the drain cassette in an illustrative embodiment.

FIG. 32 shows drain cassette 815 in an exploded view, with escutcheon 825 anterior to the front wall 826 of the drain cassette 815. In this example, front wall 826 sealingly forms a front wall for the common channel or chamber 827 of the housing 828 of drain cassette 815. A common outlet 829 to a drain line from the channel 827 is equipped with a fluid connector 830 mounted on the back wall of housing 828, which optionally may include a one-way check valve (e.g., such as a duckbill valve) to prevent fluid within the drain line from re-entering the channel 827. A mating connector 830a is mounted on front panel 811, and is connected to a fluid line ultimately leading to drain. Outlet 829 is preferably positioned higher than either fluid connection points 814a and 814b, in order to trap and ultimately expel to drain any air that may be present in the arterial or venous blood lines when connected to drain cassette 815. In this regard, the fluid channel 827 may have a U shape, with the venous and arterial blood line connectors 802 fluidly coupling with a respective connection port 814a, 814b at ends of the U shape, and the drain outlet port 829 located at the bend of the U shape. A valve 831 may be present on one or both fluid channel portions of channel 827 leading from connection points 814a and 814b. Thus, the valve may controllably open and close fluid communication in the channel 827 between the connection ports 814 and the drain outlet port 829. In embodiments where only one valve 831 is provided in the channel 827, flow between one connection port 814 and the outlet drain port 829 may be controlled by the valve while fluid communication between the other connection port 814 and the drain outlet port 829 may be permanently open. In the illustrated example, a pneumatically actuated membrane valve 831 mounted on the back of housing 828 is positioned over the portion of the channel 827*a* leading from venous blood line connection point 814*a*. A mating pneumatic connector 831*a* mounted on the front panel 811 supplies valve 831 with positive or negative pneumatic pressure to actuate the valve, a pneumatic pressure line extending to front panel 811 from a pneumatic pressure distribution module or manifold located in a rear portion of dialysis unit 51. Both connectors 830 and 831 may be constructed to form radial sealing engagements (e.g., using elastomeric O-rings) with mating connectors 830*a* and 831*a* on the front panel 811 in order to allow for drain cassette 815 to be plugged into or unplugged from front panel 811 with relative ease. Similarly, an electrical connector 833 may be mounted on the back wall of housing 828 to make electrical connections outside of channel 827 with temperature and/or conductivity probes positioned within channel 827. Electrical connector 833 may be constructed to form a keyed connection with a mating electrical connector 833*a* on front panel 811 in order to facilitate engagement and disengagement of the connector when drain cassette 815 is installed or removed from front panel 811. In some embodiments, the connections of the outlet drain port connector 830, the valve control port connector 831 and the electrical connector 833 to respective connectors on the panel 511 may be made essentially simultaneously and/or in a single operation, e.g., by pushing the drain cassette 815 into place on the panel 511.

Figure 33:
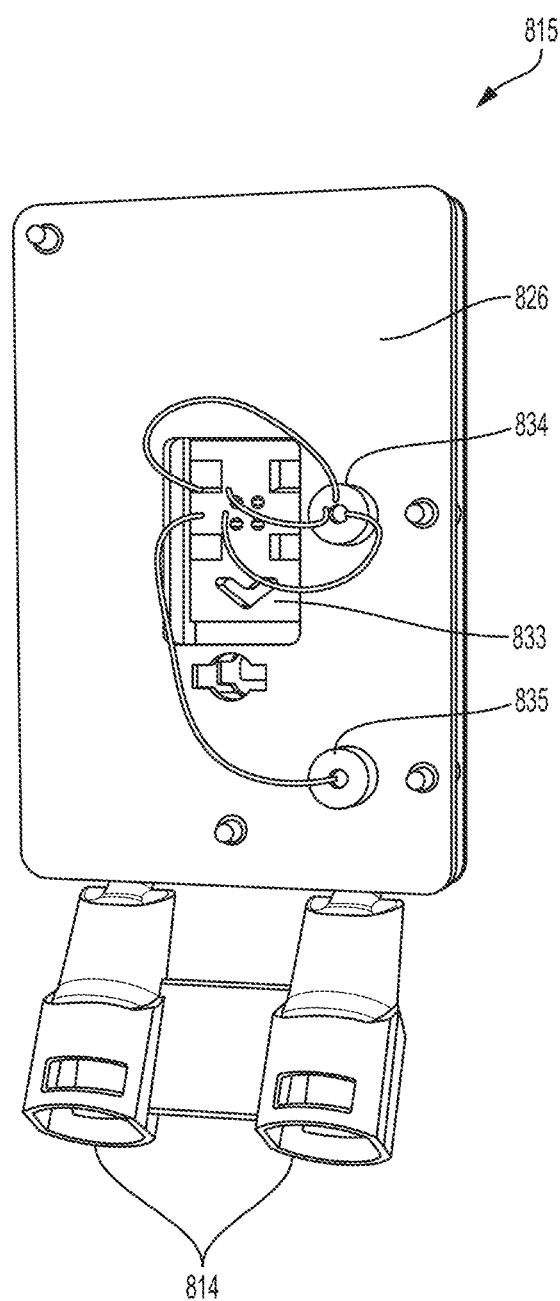
FIG. 33 shows a perspective view of the front wall of the drain cassette of FIG. 31 in an illustrative embodiment.

FIG. 33 shows a perspective view of drain cassette front wall 826. In which electrical connections are illustrated between probes 834 and 835 and connector 833. In this example, probe 834 comprises a thermistor and one of a pair of conductivity sensors, extending into channel 827 to detect both fluid temperature and conductivity. Probe 835 similarly extends into channel 827 as the second probe in a pair of conductivity sensors extending into channel 827.

Figure 34:
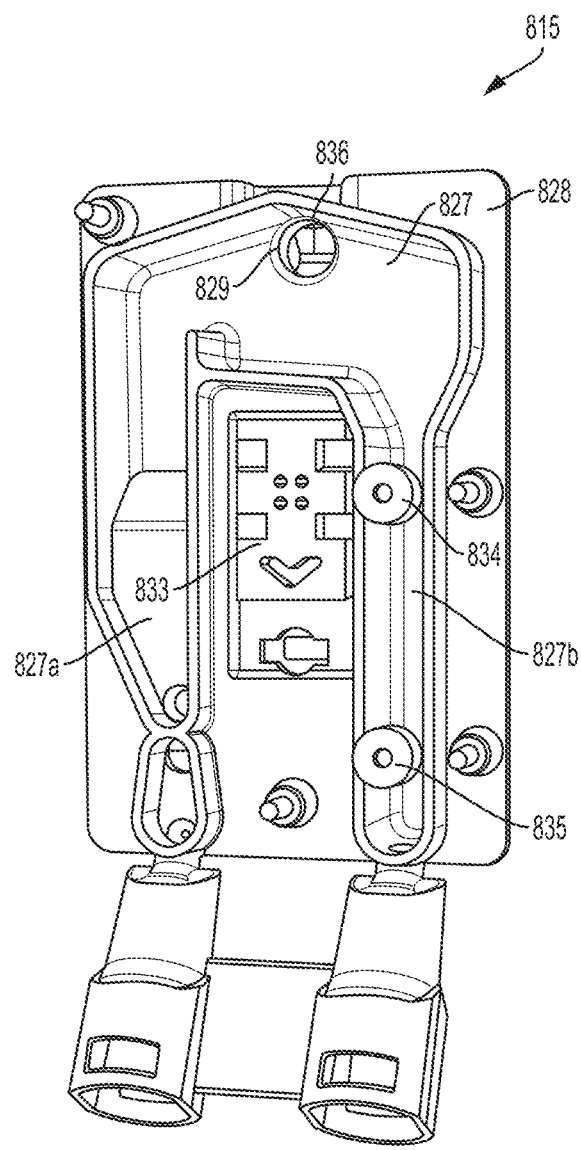
FIG. 34 shows a main housing of the drain cassette of FIG. 31 with the front wall removed for clarity purposes in an illustrative embodiment.

FIG. 34 shows the main housing 828 of drain cassette 815, the front wall 826 having been removed for clarity. Thermal and/or conductivity probes 834 and 835 are shown to illustrate their positioning in a portion 827*b* of fluid flow channel 827. (Each probe, although sealingly installed on front wall 826, has an elongated element that penetrates through front wall 826 to reside in some portion of fluid channel 827). Electrical connector 833 is shown to be positioned in an area of housing 828 that is outside channel 827. In an embodiment, a check valve, such as a duckbill valve 836, may be mounted within drain connector 830 (shown in FIG. 32).

Figure 35:
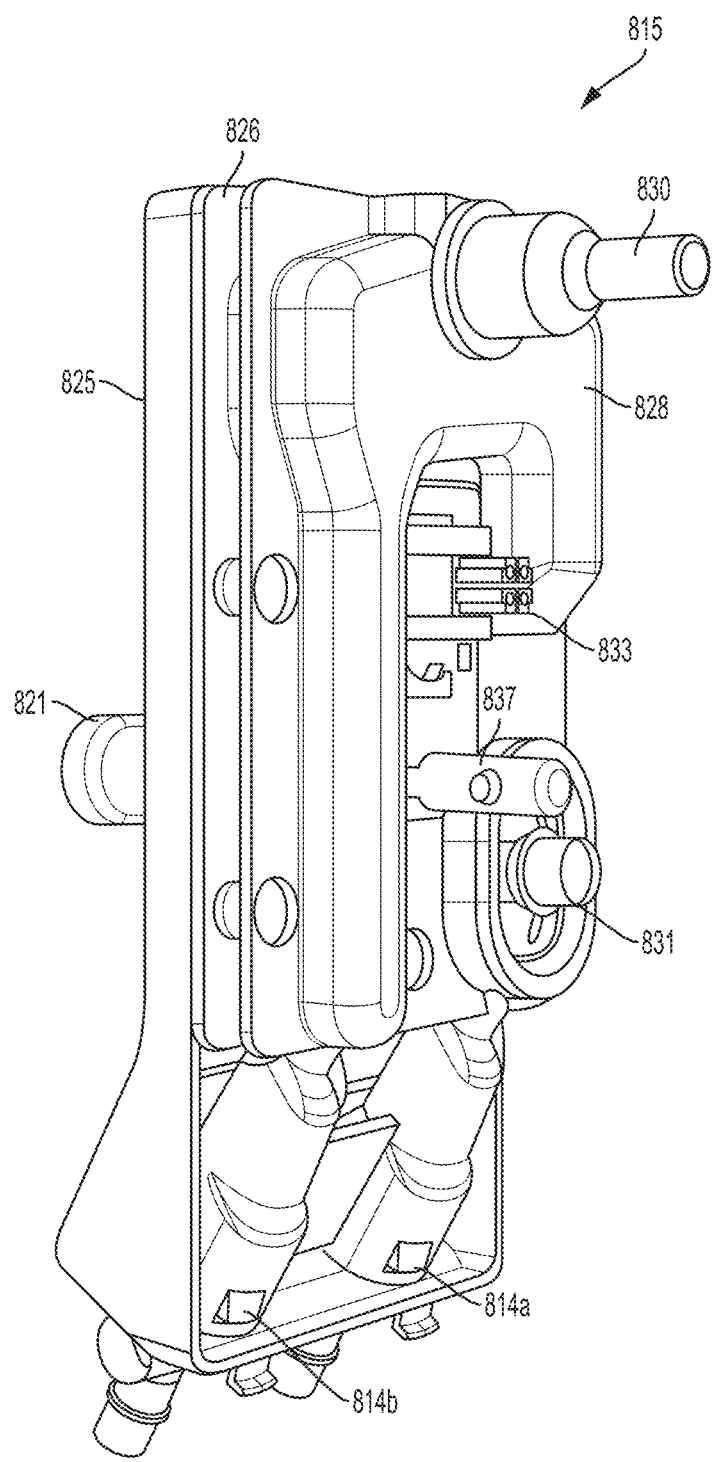
FIG. 35 shows a rear, perspective view of the drain cassette of FIG. 31 in an illustrative embodiment.

FIG. 35 shows a rear perspective view of drain cassette 815. Male fluidic connector 830 is arranged to connect to a mating connector 830*a* on front panel 811, which is connected to a drain line. Male pneumatic connector 831 is arranged to connect to a mating connector 831*a* on front panel 811, which is connected to a pneumatic pressure line. Male electrical connector 833 is arranged to connect to a mating connector 833*a* on front panel 811, which carries electrical connections from thermal and/or conductivity sensors in housing 828 to a system controller in a rear portion of dialysis unit 51. Latch member 837, connected to handle 821, is arranged to insert into a keyhole of front panel 811 in order to engage and lock drain cassette 815 onto front panel 811.

Figure 36:
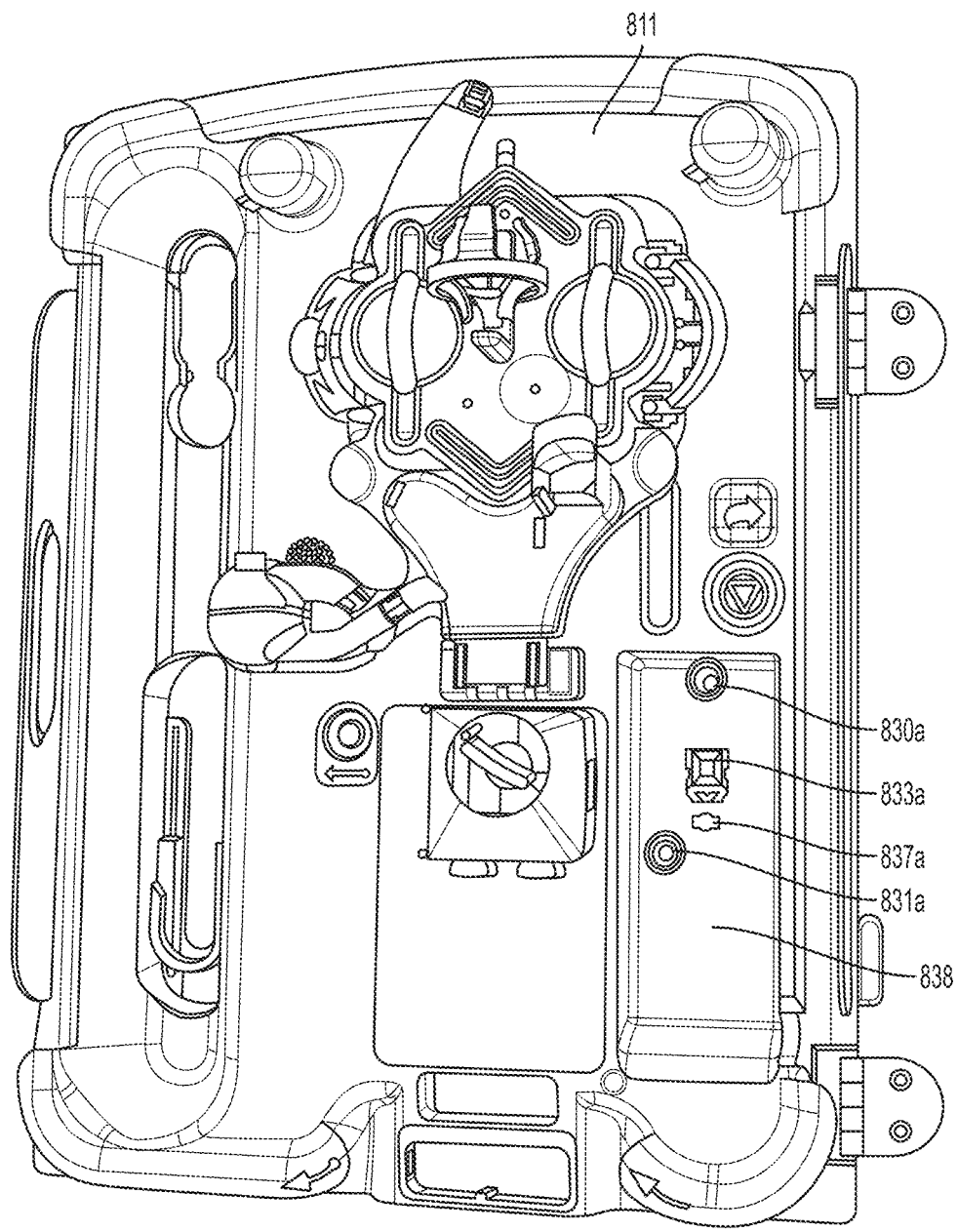
FIG. 36 shows a front panel in which a drain cassette has been dismounted in an illustrative embodiment.

FIG. 36 shows front panel 811 in which drain cassette 815 has been dismounted. Drain cassette recess 838 is arranged to accept drain cassette 815. The user need only align drain connector 830, pneumatic valve connector 831 and electrical connector 833 on drain cassette 815 with their counterpart connectors 830*a*, 831*a* and 833*a* on front panel 811 and push the cassette 815 into place to make the needed pneumatic and electrical connections. Latch member 837 of handle 821 on drain cassette 815 is inserted into keyhole 837*a*, and handle 821 may be turned ¼ or ½ turn to lock drain cassette 815 into recess 838, resulting in an arrangement of the front panel as shown in FIG. 21B.

The modular features of drain cassette 815 advantageously allow a user to easily mount and dismount substantially all of the blood-bearing components of the dialysis system (except possibly for distal portions of drain line 31). Thus, the dialysis unit 51 may be made available for use by more than one individual by simply swapping out the blood bearing components (e.g., a blood circuit assembly and drain cassette), each set of which is assigned to each individual user. The microbiological barriers afforded by the dialyzer semi-permeable membrane, by an ultrafilter for incoming water or dialysate within the dialysate-side circuit, and by the dialysate-side disinfection procedures between each use of the dialysis unit 51 allow for the dialysate-side components to be reusable among different users. Having a modular drain cassette 815 along with the other modular blood circuit components allows the dialysis unit 51 to be used as conveniently in a multi-user clinic setting as in a single-user home setting.

Figure 23:
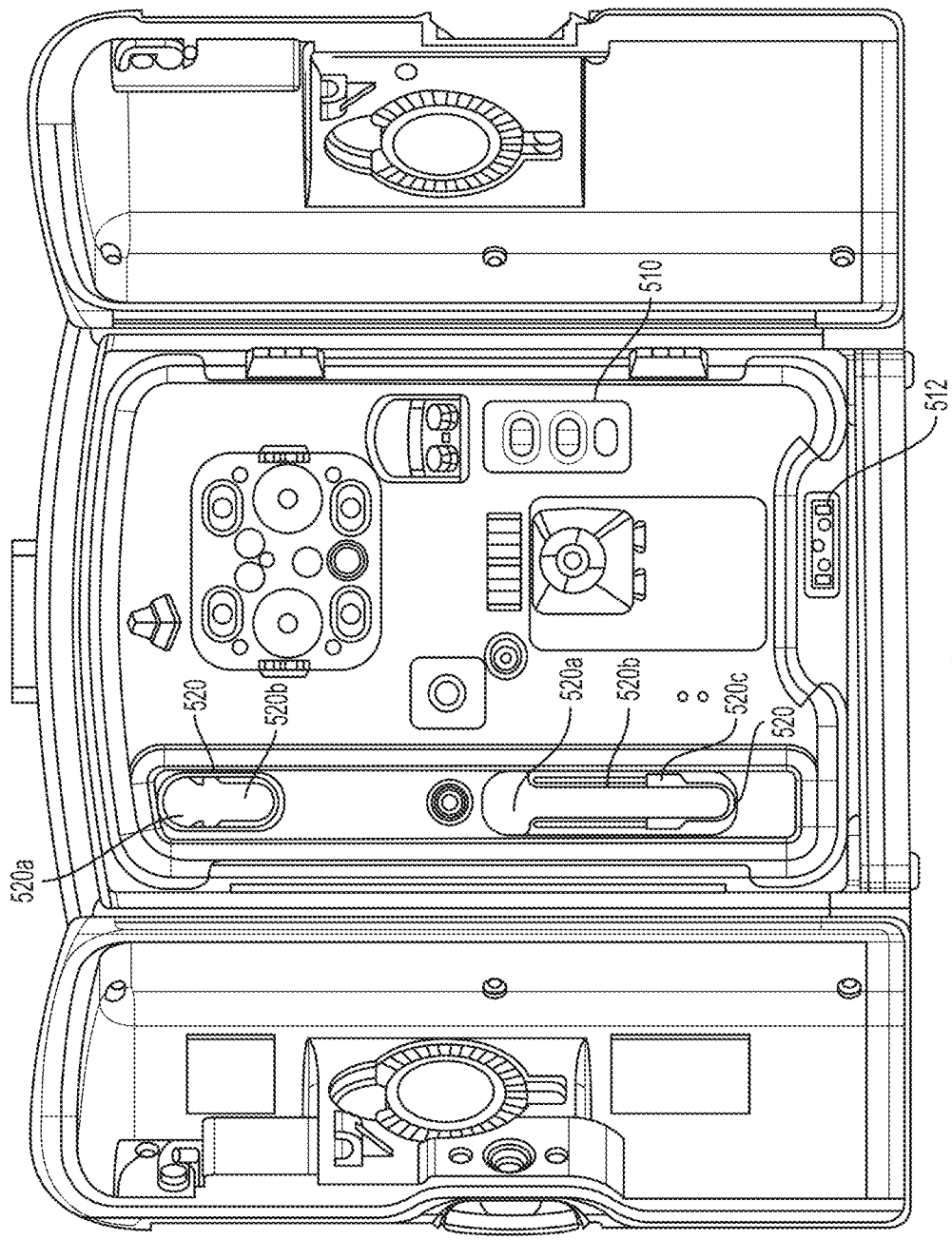
FIG. 23 shows a front view of the front panel of the system of FIG. 7 with a pair of mounting features for the dialyzer.
Figure 24:
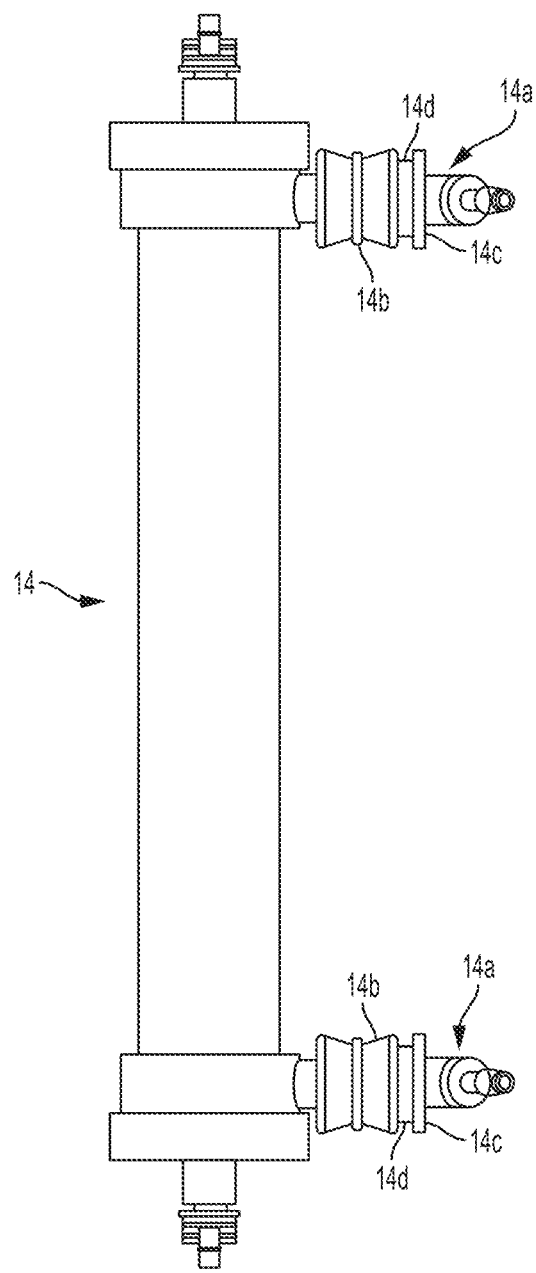
FIG. 24 shows a side view of a dialyzer with quick-connect fittings attached to the dialysate inlet/outlet ports of the dialyzer.

In accordance with another aspect of the invention, the front panel 511 of the dialysis unit 51 (or other suitable component) may be arranged to accommodate a variety of differently sized and/or shaped dialyzer units 14. Different patients, and in some cases even the same patient over time, may be prescribed different dialyzers so as to provide different treatment conditions. Thus, the dialysis unit 51 is preferably arranged to operate with multiple different types of dialyzers 14. In many cases, different dialyzers 14 have different dimensions, such as the overall diameter and/or length of the dialyzer unit. In this illustrative embodiment as shown in FIG. 23, the front panel 511 includes a dialyzer mount with a pair of "keyhole" features 520 that are arranged to engage with a respective dialysate quick-connect fitting on the dialyzer 14. Each keyhole feature 520 includes an upper insertion area 520*a* sized to receive a portion of the quick-connect fitting and a lower flanged portion 520*b* that has a width that is smaller than an overall diameter of the quick-connect fitting and that engages with a grooved area of the quick-connect fitting. So as to aid in understanding of these features, FIG. 24 shows a dialyzer 14 with quick connect fittings 14*a* attached at dialysate inlet and outlet ports of the dialyzer 14. (Blood inlet and outlet ports are located at the extreme top and bottom of the dialyzer 14 shown in FIG. 24.) The quick connect fittings 14*a* shown are of a standard type, and most, if not all, dialyzers 14 have dialysate inlet/outlet ports that are arranged to engage with the standard quick connect fittings 14*a*. The quick connect fittings 14*a* each include a slide element 14*b* that is moved to the right (as shown in FIG. 24) relative to a base 14*c* to allow the fitting 14*a* to be engaged with a dialysate port on the dialyzer 14. When the slide element 14*b* is moved to allow the fitting 14*a* to be attached to the dialyzer 14, a groove 14*d* is closed. However, once the fitting 14*a* is properly seated on the inlet/outlet port of the dialyzer 14, the slide element 14*b* may be released, allowing a spring (not shown) to move the slide to the left as shown in FIG. 24, reestablishing the groove 14*d* to the condition shown in FIG. 24. Thus, when the quick connect fitting 14*a* is properly engaged with the dialyzer 14, the groove 14*d* will be present as shown in FIG. 24.

To mount the dialyzer 14 to the keyhole features 520, the quick connect fittings 14*a* may be partially inserted into the upper insertion area 520a of the top and bottom keyhole features, respectively, so that the groove 14d of each fitting 14a is aligned with a flange of the lower flanged portion 520b of the keyhole features 520. (Note that the upper insertion area 520 of the bottom keyhole feature 520 may be made longer than that shown in FIG. 23 to allow the accommodation of a wider range of dialyzer lengths.) With the grooves 14d aligned with the flanges, the dialyzer 14 may be lowered so that the quick connect fittings 14a are fully received into the lower flanged portions 520b of the keyhole features 520.

In accordance with another aspect of the invention, one or both of the keyhole features 520 may be adjustable so that the weight of the dialyzer 14 is shared by both lower flanged portions 520b of the keyhole features 520. For example, in this illustrative embodiment, the bottom keyhole feature 520 has part of the lower flanged portion 520b adjustable in vertical position relative to the top keyhole feature 520. In this way, the portion of the lower flanged portion 520b may be adjusted in vertical position so that, with the top quick connect fitting 14a supported by the flanged portion 520b of the top keyhole feature 520, the movable portion of the flanged portion 520b of the bottom keyhole feature can be moved, e.g., upwardly, so that the bottom quick connect fitting 14a is also supported by the flanged portion 520b. Thus, the weight of the dialyzer 14 can be shared by both keyhole features 520. The flanged portion 520b may be made adjustable in any suitable way. In this embodiment, the flanged portion 520b has a "U" shaped member 520c that is vertically slidable along the vertical flanges and can be fixed in place by tightening a set of thumb screws. The "U" shaped member 520c may engage the quick connect fitting 14a so that the "U" shaped member 520c supports the weight (at least in part) of the dialyzer 14.

Although in the embodiment above, the dialyzer 14 is supported by keyhole features in the front panel 511, a support arrangement for the dialyzer may be configured in other ways. For example, the upper insertion area 520a is not necessarily required. Instead, only flange portions (e.g., in the shape of a "U" shaped flange having opposed flange portions) may be provided to engage the dialyzer quick connect fittings. The flange portions may be offset from the front surface of the front panel 511 to provide clearance for the fitting and allow the flange portions to engage with the grooves of the quick connect fittings. Also, the flange portions need not be provided in a vertical orientation as shown, but instead may be oriented at an angle to the vertical, e.g., in a horizontal arrangement. The flange portions may have a detent, catch, or other feature to help maintain the dialyzer in place as well.

Figure 25:
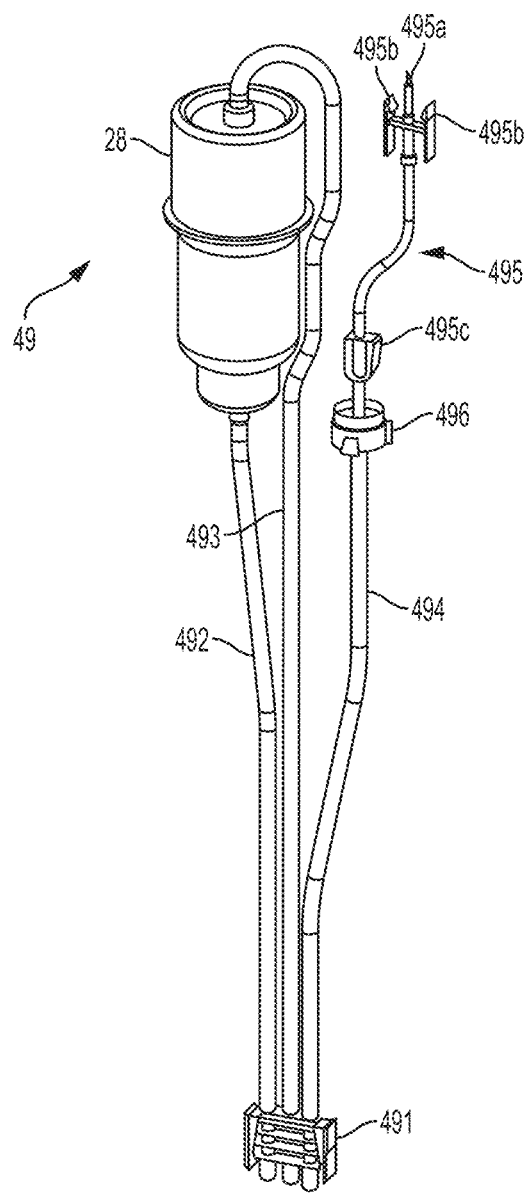
FIG. 25 shows a right perspective view of a reagent supply for use with the system of FIG. 7.

In accordance with another aspect of the invention, a bicarbonate, acid and/or other reagent supply device may be selectively associated with the dialysis unit. As described above, the dialysis unit 51 requires a supply of certain chemicals to generate dialysate and/or other materials needed for system operation. FIG. 25 shows a reagent supply 49 used to provide acid, bicarbonate and/or other materials to the dialysis unit 52. (FIG. 21 shows the reagent supply 49 attached to the acid/bicarbonate connection point 512 on the front panel 511.) The reagent supply 49 in this illustrative embodiment includes an E-prong connector 491 that is arranged to mate with the acid/bicarbonate connection point 512. As with other connections made by the user at the front panel 511, e.g., including the blood line connections at the connection point 514, the mating connectors may be color coded or otherwise marked to help ensure proper connections are made. For example, the E-prong connector 491 and the acid/bicarbonate connection point 512 may be colored orange, while the arterial line 203 and its mating connection at the connection point 514 may be colored red, and the venous line 204 and its mating connection at the connection point 514 are colored blue. Leading from the E-prong connector 491 are a bicarbonate supply line 492, a water supply line 493 and an acid supply line 494. (See FIG. 6 and the accompanying description regarding the function of these lines.) The water supply line 493 provides water to a bicarbonate supply 28 (which in this embodiment is a 750 g Altracart Bicarbonate cartridge (#500750A) sold by Baxter International Inc. that includes a powdered bicarbonate material, but may be any suitable supply), which provides bicarbonate to the dialysis unit 51 via the bicarbonate supply line 492. In this embodiment, the acid supply line 494 leads to an acid bag spike 495, which may be used to pierce and draw a suitable acid from a IV-type bag or other container. In this embodiment, the acid bag spike 495 includes a spike member 495a and a pair of spring clips 495b. The spring clips 495b are joined together at center portions by a connecting bar such that the spring clips 495b and the connecting bar form an "H" shape and allow the spring clips 495b to be pivoted relative to each other when proximal ends of the spring clips 495b are squeezed toward each other. The spring clips 495b may be arranged to engage with a connector element on an acid bag (or other acid supply, not shown) so that the spike member 495a remains engaged with the bag until a user disengages the clips 495b. For example, distal ends of the clips 495b may include barbs that engage with the acid supply, and the clips may be disengaged from the acid supply by squeezing proximal ends of the clips 495b together to disengage the barb elements at the distal ends of the clips 495b from the acid supply. The acid bag spike 495 may also include a valve 495c (in this case, a pinch clamp) to open/close the line of the acid bag spike 495. In accordance with one aspect of the invention, the acid bag spike 495 may be replaced (disconnected from the acid supply line 494 at a cap connector 496) with another component, such as an acid jug straw (not shown) or other arrangement. When used with a jug straw, the cap connector 496 may be engaged with an acid jug opening such that the cap connector 496 covers the opening, like a cap. Alternatively, the jug straw can terminate in a spike, which then has the ability to penetrate a self-sealing (e.g. rubber) membrane covering the opening of the acid jug. Thus, different types of components may be attached to the acid supply line 494 depending on the acid supply arrangement (such as a jug, bottle, bag, or other).

Figure 26:
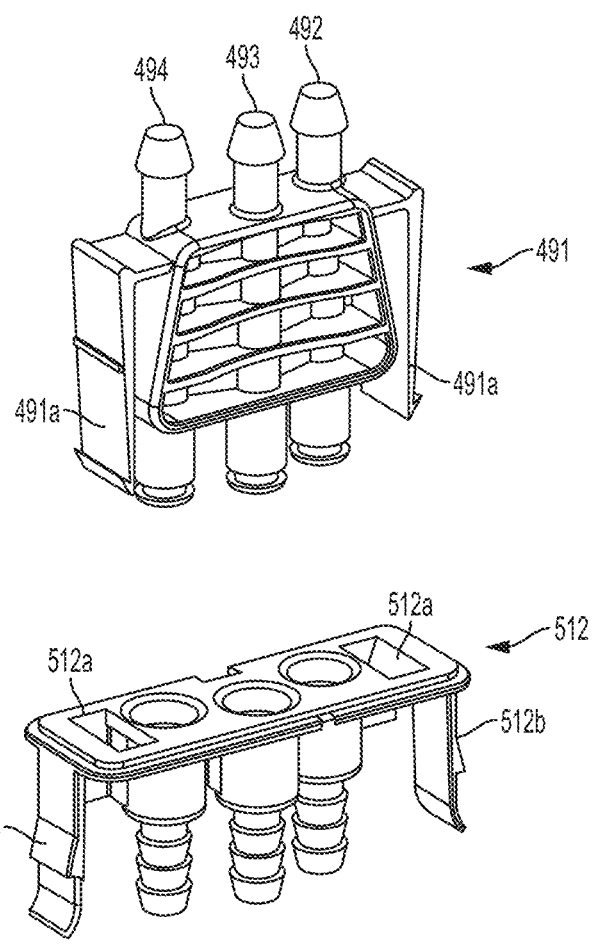
FIG. 26 shows a perspective view of an E-prong connector for the reagent supply of FIG. 25 and a corresponding connection point at the front panel of the hemodialysis system.

FIG. 26 shows a close up view of the E-prong connector 491 and the corresponding connection point 512 at the front panel 511. The E-prong connector 491 has three parallel prongs (corresponding to the bicarbonate and acid supply lines 492 and 494 and the water supply line 493) that that engage with corresponding receiving holes in the connection point 512. The E-prong connector 491 and receiving holes in the connection point 512 are arranged so that a center lumen (the water supply line 493) is arranged above, or otherwise out of, a common plane of the two outer lumens (the bicarbonate and acid supply lines 492 and 494). In this way, it is ensured that the bicarbonate and acid supply lines 492 and 494 are properly connected since the E-prong connector 491 cannot be engaged with the connection point 512 unless appropriately oriented. The E-prong connector 491 includes a pair of spring tabs 491a that can be engaged with corresponding slots 512a in the connection point 512, e.g., when the prongs are properly seated in receiving holes of the connection point 512. With the tabs 491a engaged in the slots 512a, the E-prong connector 491 cannot be easily removed from the connection point 512, helping reduce the likelihood of an accidental disconnection. The E-prong connector 491 may be disconnected by pressing the tabs 491a toward each other so that barbs at the distal ends of the tabs 491a disengage from the slots 512a. The connection point 512 has similar spring tabs 512b which allow the connection point 512 to be connected to and disconnected from the front panel 511.

In accordance with another aspect of the invention, a disinfect connector (not shown) engages with connection point 512 for use during a disinfection procedure. The disinfect connector has three parallel prongs having a similar orientation as the E-prong connector 491, so that the prongs may engage with the receiving holes in connection point 512. The channels in the prongs of the disinfect connector terminate within a common chamber within the disinfect connector. Thus, during a disinfect procedure, the bicarbonate flow line, acid flow line and water flow line are all interconnected, permitting disinfection of each of these flow lines during the disinfect procedure. (This is shown as a dashed inverted "T" line at 49 in FIG. 6).

Figure 27:
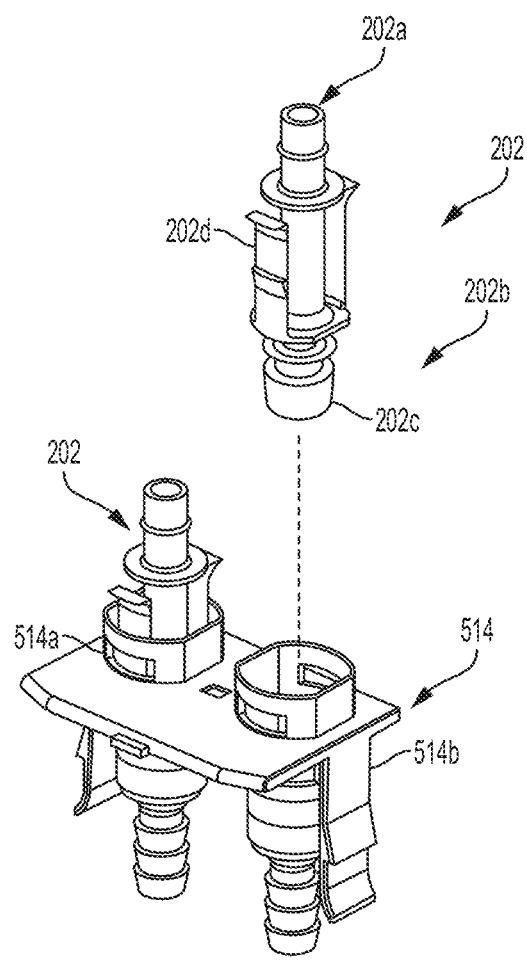
FIG. 27 shows a perspective view of a pair of blood line connectors for the blood circuit assembly and a corresponding connection point at the front panel of the hemodialysis system.
Figure 28:
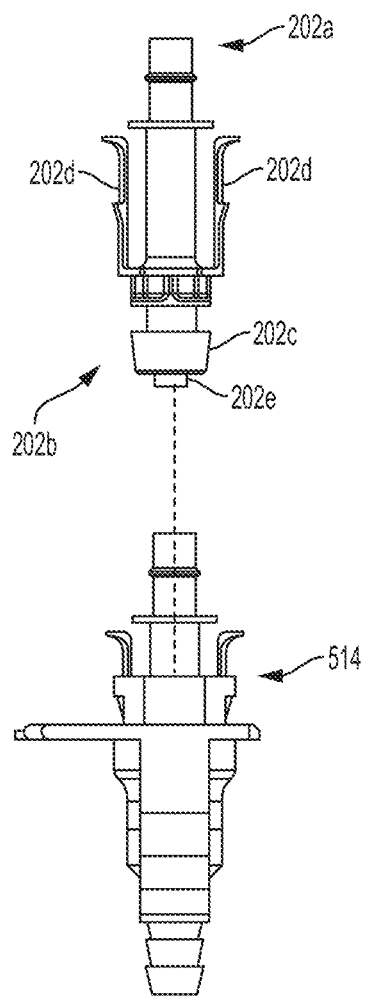
FIG. 28 shows a side view of a blood line connector and connection point of FIG. 27

In accordance with another aspect of the invention, the blood lines 203, 204 are equipped with a connector that enables two types of connections to be made. One type of connection is a plug-in or press-in connection by which the connector can be pushed into a receiving lumen and a leakfree connection made without requiring rotation of the connector or the receiving lumen. A second type of connection is a screw-type connection by which a leakfree connection can be made by a threaded engagement of the connector with a complementary element. For example, FIGS. 27 and 28 show a perspective view and a side view of a blood line connector 202 that is used with the blood lines 203, 204 and that can engage with the blood line connection point 514 on the front panel 511. The connector 202 includes a tube connection end 202a that connects to the corresponding blood line 203, 204, and a patient access connection end 202b that is arranged to connect to both a patient access as well as the connection point 514 to establish a leakfree connection. At the patient access connection end 202b, the connector 202 includes a frustoconical member 202c that has an internally threaded portion arranged to engage with an externally threaded patient access. For example, the frustoconical member 202c may be part of a male-type luer connector that includes the central tube 202e extending from the center of the frustoconical member 202c. When making the luer connection, the tube 202e may extend into a female luer connector at the patient access and the threaded portion on the interior of the frustoconical member 202c may engage with a thread on the female luer connector of the patient access (whether arterial or venous). Such luer connections are standard when connecting blood lines to a patient access. However, the connector 202 may also be engaged with the connection point 514 by simply pushing the patient access connection end 202b into a receiving hole of the connection point 514. When making this connection, the exterior of the frustoconical member 202c may engage with a suitable seat, or other surface or element in the connection point 514 (such as a valve seat, O-ring, or other) so that a seal is formed between the frustoconical member 202c and the connection point 514. The central tube 202e may also, or instead, be used to engage with the connection point 514 to establish a suitable seal. Locking arms 202d that extend rearwardly from the frustoconical member 202c may engage with holes 514a in the connection point 514 (e.g., barbed portions on the arms 202d may engage with the holes 514a) to help maintain the connector 202 in the receiving hole of the connection point 514. The connector 202 may be released by pressing the arms 202d toward each other (e.g., by pressing on finger depression portions at the distal ends of the arms 202d), thereby disengaging the barbs from the holes 514a, and withdrawing the connector 202. Note that the connection point 514 may include spring tabs 514b to allow the connection point 514 to be selectively engaged/disengaged at the front panel 511. The connectors 202 may be made in any suitable way, such as by molding of plastic as a single unitary part.

Figure 29:
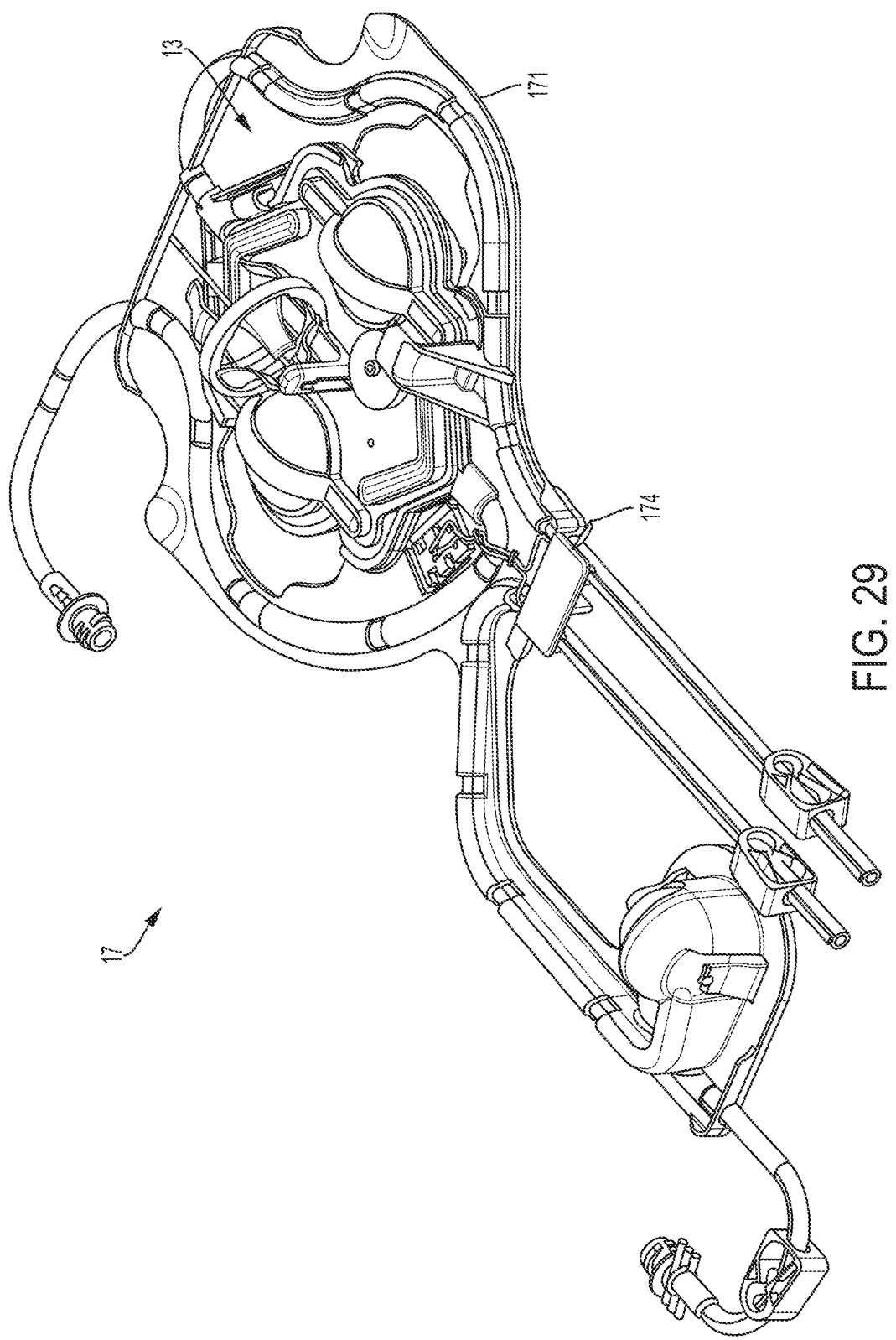
FIG. 29 is a perspective view of a blood circuit assembly in an alternate embodiment.
Figure 30:
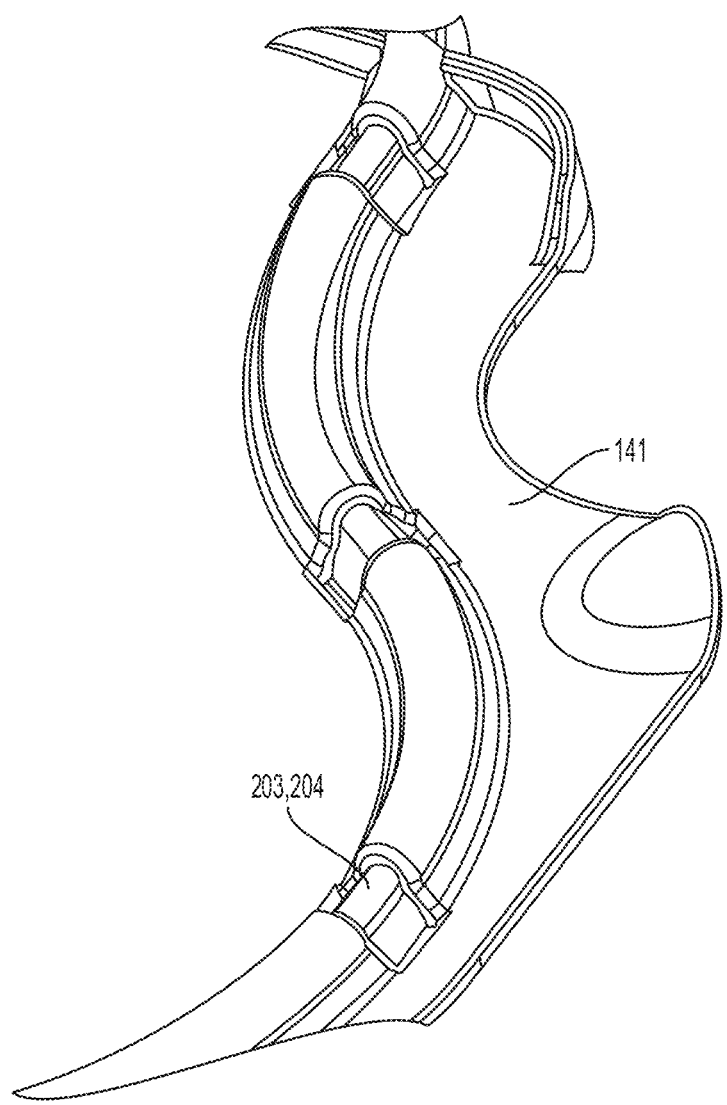
FIG. 30 is a close up view of a portion of the blood circuit assembly of FIG. 29.

FIG. 29 shows a perspective view of a blood circuit assembly 17 in an alternate embodiment. This embodiment is different from that shown in FIGS. 18 and 19 in a few ways. For example, in this embodiment, the blood lines 203 and 204 have a cross section having a shape similar to a "FIG. 8" in which one portion of the "FIG. 8" includes a lumen to carry blood or other fluid, and another portion of the "FIG. 8" carries a conductor. That is, the blood lines 203 and 204 include a lumen through which blood and other fluids may flow, and another lumen through which an electrical conductor may pass. Further detail regarding this and other arrangement is provided below with reference to FIGS. 37-49. As also discussed in more detail below, the electrical conductor may be used to detect disconnection of a blood line 203, 204 from a patient or other connection point, or interruption of vascular access of one or both of a pair of catheters inserted in a blood vessel or fistula. Additionally, the organizing tray 171 in FIG. 29 is different from that shown in FIG. 19 in that the engagement members 174 may include a slot or hole that the blood lines 203, 204 are engaged with, but in this embodiment, the engagement members 174 need not engage the blood lines 203, 204 so as to resist pulling of the lines 203, 204 downwardly, e.g., for mounting the lines in an occluder. Instead, in this embodiment, the blood lines 203, 204 may be allowed to move freely with respect to the engagement members 174. Another modification in the embodiment is that the engagement members 174 include a push plate that spans across both lines 203, 204. This is in contrast to the arrangement in FIG. 19 where each line 203, 204 is engaged by engagement members 174 that are independent of each other. The arrangement in FIG. 29 may provide an advantage in some embodiments that allows a user to engage the lines 203, 204 with respect to slots 517 that lead to an occluder in an single operation. (See FIG. 22) In one embodiment, the slots 517 may each be associated with an air detector that operates to detect whether there are air bubbles in the lines 203, 204 (e.g., by optical detection or other so that air in a line 203 or 204 can be detected by a respective air detector in one of the slots 517). Thus, the engagement members 174 may function to associate the lines with an air detector or other feature in addition to, or instead of, an occluder or other arrangement that positions the lines 203, 204 in a desired way. In this embodiment, the engagement features 174 include slots arranged on an underside of the push plate that engage with a narrower portion of the lines 203, 204 (e.g., the portion that carries the electrical conductor) so as to position the conductor near the push plate. This may help position the lines 203, 204 in the slots 517 in such a way that the conductor does not interfere with an air detector operating to detect air in the lines 203, 204. As mentioned above, the slots on the push plate that engage with the lines 203, 204 may engage the lines so that the lines do not rotate relative to the push plate, but are allowed to move along their length relative to the push plate. FIG. 30 shows a closeup view of a portion of the blood circuit assembly of FIG. 29 and illustrates how a portion of the organizing tray 171 may be arranged to at least partially conform to the shape of a blood line 203, 204 held by the tray 171. Similar to the engagement members 174, the tray 171 portions that engage with the lines 203, 204 may be arranged to orient the lines 203, 204 so that the conductor portion of the line faces outwardly. This may help properly position the lines 203, 204 for the engagement members 174 or other portions of the assembly 17.

It should be understood that any and all of the aspects of invention described herein may be combined with or otherwise incorporated with any of the other aspects of invention and/or embodiments described. For example, a dialysis system incorporating one or more aspects of invention described herein may include a line disconnection or interruption function like that described in connection with FIGS. 37-49. Such a disconnection function may include features such as 1) an electrical circuit or other suitable circuitry to detect a change in voltage, resistance or other characteristic indicative of a disconnection of a blood line 203, 204 with respect to an associated connector, 2) positioning of detection electrodes suitably near a patient or other reference, 3) one or more connector arrangements, 4) blood line tubing arrangements or other suitable arrangements in which a blood line carries both a fluid flow lumen and an electrically conductive feature, and so on. For example, in one aspect of the invention, a blood circuit assembly may include blood lines, one or more blood pumps, an air trap and electrical circuitry components suitable for use in detecting disconnection/connection of one or more blood lines on an organizing tray. Such an arrangement may allow a user to make several different connections, whether fluidic, pneumatic and/or electrical, in a relatively uncomplicated and straightforward way.

Accordingly, aspects of the invention relate generally to systems and methods to detect disconnection of an indwelling vascular line being used in a dialysis treatment, such as a catheter or needle, or its attached tubing. If not quickly detected, a disconnection can lead to rapid exsanguination, particularly when the blood in the catheter or tubing is under positive pressure. Examples of circumstances involving positive intravascular pressure include the positive pressure associated with an artery or arterio-venous fistula, or the positive pressure associated with an extracorporeal blood pump circuit. In hemodialysis, for example, a blood pump can generate blood flow rates of 400-500 ml/min, making rapid, reliable disconnect detection particularly desirable. Indeed any medical treatment involving relatively high flow or high pressure extracorporeal circulation (such as, for example, hemoperfusion or cardiopulmonary bypass) can be made safer by having an effective system to monitor the integrity of the arterial (withdrawal) and venous (return) blood lines.

In hemodialysis, for example, extracorporeal blood circulation can be accomplished with vascular access using either a single indwelling catheter, or two separate indwelling catheters. In a single catheter system, blood is alternately withdrawn from and returned to the body via the same cannula. A disconnection in this system can be quickly detected by placing an air monitor in the line at or near the pump inlet, because air will be drawn into the line from the disconnection site during the blood withdrawal phase of the pumping. On the other hand, in a two-catheter system, blood is typically continuously withdrawn from the body via one catheter inserted in a blood vessel or fistula, and returned to the body via the second catheter inserted in the same vessel some distance from the first catheter, or in a separate blood vessel altogether. In the two-catheter system, it is also possible to monitor for catheter or tubing dislodgement in the blood withdrawal or 'arterial' segment by using a sensor to detect the presence of air being entrained into the arterial tubing as blood is withdrawn from the blood vessel under negative pump pressure and/or positive fistula pressure. However, air-in-line detection cannot reliably detect a disconnection of the venous (return) segment of the extracorporeal circuit. In this case, if the blood-withdrawal path remains intact, air will not be introduced into the line. Thus it is particularly important to be able to detect a disruption in the continuity of the return line from the extracorporeal pump to the vascular access site.

In one aspect, the invention comprises a system for detecting whether a vascular access device, such as a needle, cannula, catheter, etc. becomes disconnected or dislodged from a blood vessel or vascular graft. In another aspect, the system is configured to detect by electrical conductivity or impedance whether the vascular access device is occluded. The system includes a fluid delivery device that provides for the flow of a liquid through a tube or conduit into the blood vessel via an indwelling needle or catheter at a first site on the blood vessel or graft. The fluid may be an electrolyte solution or other solution suitable for intravenous infusion, or it may be blood or blood components. An electrode is disposed to be in contact or fluid communication with the lumen of the conduit, and a second electrode is disposed to be in fluid communication with blood within the blood vessel or graft via a second on the blood vessel or graft. An electronic circuit is connected to the first and second electrodes, and configured to deliver a control signal to the first and second electrodes in order to measure the electrical resistance of the fluid between the first and second electrodes, such that at least one of the electrodes is located closer to the blood vessel or graft than to the fluid delivery device. In some embodiments the electrode is located at about 50-70% of the distance from the fluid delivery device to the blood vessel or graft. In other embodiments, the electrode is located at about 70-90% or more of the distance from the fluid delivery device to the blood vessel or graft. The fluid delivery device can include a pump, either for blood or for other therapeutic or diagnostic fluid. The fluid delivery device can be part of a hemodialysis blood flow circuit, which may or may not include a blood pump, a dialyzer cartridge, or an air trap and associated tubing. The second electrode may be placed in contact with the lumen of a second conduit or tube that is in fluid communication with the blood vessel or graft at the second site. The second conduit may form part of a fluid flow path from the blood vessel or graft to the fluid delivery device. The fluid in the second conduit may be blood being delivered to an extracorporeal blood flow circuit.

The system may comprise a first and second connector connecting a pair of vascular access catheters accessing a blood vessel segment or vascular graft segment at two different sites. The first and second connectors may each connect to a flexible tube leading to the fluid delivery device. Each connector may include an electrode that is exposed to the lumen of the connector. A wire may be attached to each connector, the wire being connectable on its other end to the electronic circuit. The flexible tubes may be double lumen tubes having a first lumen for carrying fluid and a second lumen for carrying a wire. The wires of each tube may be connected on the other end of the tube to a connector for connection to the electronic circuit.

The electronic circuit or an associated microprocessor may be configured to convert the voltages measured across terminals connected to the electrodes by the electronic circuit into resistance values. The system may comprise a controller configured to receive a signal from the electronic circuit or microprocessor, the signal representing the electrical resistance between the electrodes, the controller being programmed to trigger an alert signal when the electrical resistance value exceeds a pre-determined threshold. The alert signal may be an audible or visual signal to the person whose blood vessel is being accessed, and optionally an alert signal may include an electrical command to a tubing occluder apparatus. The tubing occluder apparatus may be actuated to mechanically occlude one or more of the tubes leading from the vascular access sites. The tubing occluder may operate in a number of ways, such as, for example electromechanically, hydraulically, or pneumatically.

In another aspect, the invention comprises an apparatus for monitoring the continuity between a vascular access device and a blood vessel or vascular graft segment, comprising, a first and second vascular connector, the first connector being attached on a proximal end to a distal end of a fluid-carrying lumen of a first double-lumen tube, and the second connector being attached on a proximal end to a distal end of a fluid-carrying lumen of a second double-lumen tube. The first connector comprises a first electrode in contact with a lumen of the first connector and electrically connected to a wire within a wire-carrying lumen of the first double-lumen tube, and the second connector comprises a second electrode in contact with a lumen of the second connector and electrically connected to a wire within a wire-carrying lumen of the second double-lumen tube. The wire within the first double-lumen tube and the wire within the second double-lumen tube are each connected to an electrical connector at a proximal end of the double-lumen tubes. The distal end of each connector may be configured with a locking feature to provide a reversible, air-tight connection between the connector and a mating connector of a vascular catheter. The proximal end of the double-lumen tubes can be connected to a blood pump on an arterial side, and an air trap on a venous side; and in a hemodialysis system, the blood pump and air trap may each be reversibly connectable to a dialyzer cartridge.

In another aspect, the invention comprises a vascular connector comprising a proximal fluid connection end, a distal fluid connection end, and an electrode configured to electrically connect a fluid-carrying lumen of the connector with a wire external to the vascular connector. The proximal end of the connector may be configured to connect with a flexible tube, and the distal end of the connector may be configured to connect with a mating connector of a vascular catheter. The electrode may be installed in a conduit on the connector that connects the lumen of the connector to the exterior of the connector. The electrode may be lodged into the conduit in a manner to provide an air-tight seal between the lumen and the exterior of the connector. An elastomeric member such as an O-ring may be installed between the electrode and the conduit to contribute to the air-tight seal.

In another aspect, the invention comprises an electrical circuit for measuring the resistance of a liquid between a first and second electrode, the first electrode connected to a first terminal of the electrical circuit, and the second electrode connected to a second terminal of the electrical circuit, comprising a capacitor C1 connected on a first end to the first terminal and a capacitor C2 connected on a first end to the second terminal; a known reference resistance Rref connected on a first end to a second end of capacitor C1; switching means for connecting either (a) a first reference voltage V+ to a second end of Rref, and a lower second reference voltage V− to a second end of C2 to form a first switch configuration or; (b) the first reference voltage V+ to the second end of C2 and the lower second reference voltage V− to the second end of Rref to form a second switch configuration; and measuring means for measuring a voltage Vsense at the connection between C1 and Rref; such that the electrical circuit is configured to determine the value of the resistance of the liquid based on the known reference resistance Rref and the observed voltage Vsense for each of the first and second switch configurations. The resistance Rref may be chosen to be a value that permits conductivity measurement of an electrolyte solution or other solution suitable for intravenous infusion. The electrolyte solution may include dialysate solution. The resistance Rref may also be chosen to permit measurement of the resistance of a volume of blood between the first and second electrodes.

Conductivity Circuit

Figure 37:
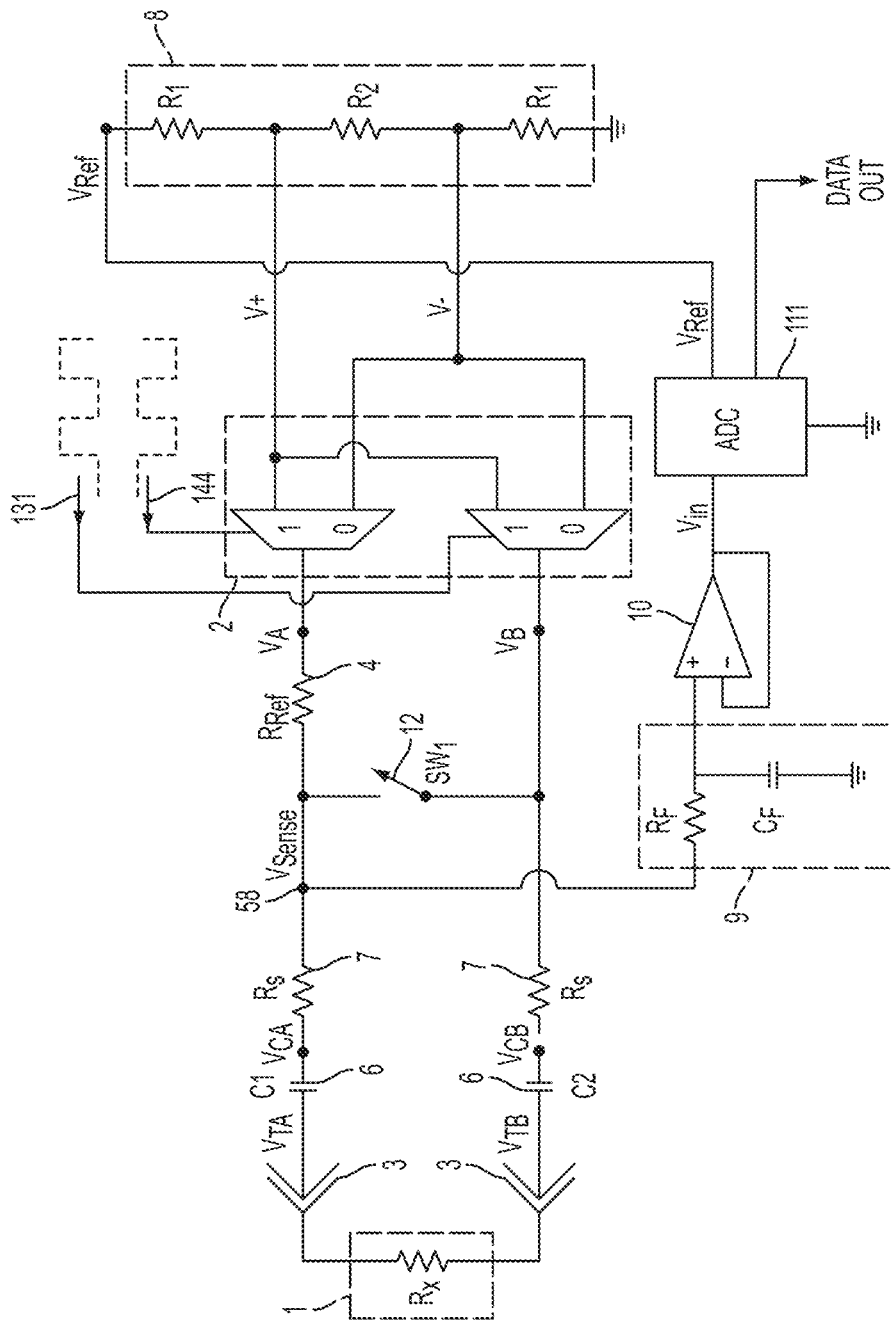
FIG. 37 is a schematic representation of a conductivity circuit in an illustrative embodiment.

An exemplary electrical circuit shown in FIG. 37 can be used to measure the electrical conductivity or resistance of a subject fluid. In one embodiment, the fluid may be an electrolyte solution or dialysate fluid, and the circuit may ultimately provide a measurement of the conductivity of the fluid to ensure its compatibility for intravascular administration. In addition to monitoring the concentration of dissolved solutes in the fluid, the electrical circuit can also monitor for any interruption in the continuity of the fluid between the electrodes connected to the circuit. For example, it can be used to monitor an intravenous fluid line for the presence of air bubbles, or for the presence of a contaminating substance. In another embodiment, the fluid may be blood, and a change in the measured electrical resistance of a blood flow path (for example, in a conduit) may be used to indicate if a discontinuity occurs between the blood flow path and measuring electrodes. For example, the blood flow path may comprise a column of blood between two electrodes that includes indwelling needles or catheters in a segment of a blood vessel, arterio-venous fistula or graft. Vascular access disconnection can result in the introduction of air into the blood flow path, causing a change in the resistivity of the blood column between the electrodes. The electrical circuit can be readily modified (depending on its application) to adjust for the difference between the impedance of a blood flow path and that of dialysate fluid.

The circuit shown in FIG. 37 may be used to measure an unknown resistance Rx of a subject media 1 using inexpensive electronic components, particularly where the unknown resistance involves a conductive path through an electrolytic fluid. A switching network 2 comprising a pair of multiplexers allows the connection of nodes VA and to reference voltages V+ and V−. The subject media 1 having unknown resistance Rx is connected to terminals VTA and VTB 3, and forms a voltage divider with reference resistor Rref 4. To make a conductivity measurement, alternating voltages can be presented to the subject media 1 via switching network 2 to the voltage divider created by the known reference resistor Rref 4 (680 ohms, for example, in the case of dialysate fluid) and the unknown resistance Rx of the subject media 1. The midpoint of the voltage divider is measured. The signal Vsense at point 8 is buffered by amplifier 10 to make the input signal Vin of the analog-to-digital converter (ADC) 111. Vsense switches between two values as the voltage divider is driven first one way and then the other way. This signal is valid only for a short period of time after switching because the fluid in the conductivity cell 1 is AC coupled into the circuit through capacitors C1 and C2 6. Thus DC-blocking capacitors C1 and C2 6 may be used to prevent DC currents from passing through the unknown resistance (which may include a conductive path through electrolytic fluid or blood). In an embodiment, series capacitors C can each comprise two capacitors in parallel, one having a value, e.g., of 0.1 uF, and the other having a value, e.g., of 10 uF. Series resistors 7 may be used to reduce exposure by the switch network and other sense circuitry to noise and surge voltages. ADC 111 can take multiple samples of the signal as the circuit is switched between the two configurations.

Figure 38:
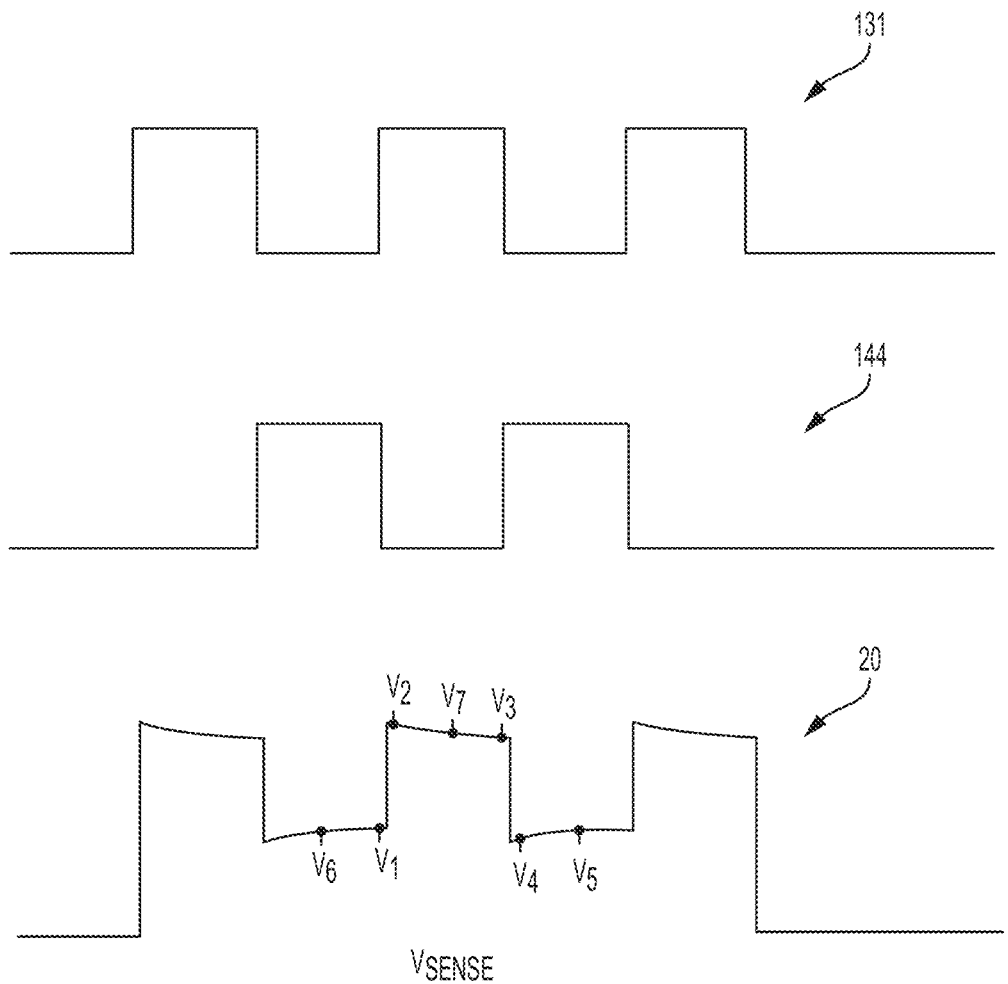
FIG. 38 is a diagram of the electrical waveforms processed by the circuit of FIG. 37.

The switching network 2 can be driven by a pair of alternating binary control signals 131, 144 that connect VA to V+ and VB to V− during one half-cycle, and VB to V+ and VA to V− during the other half-cycle. The binary control signals 131, 144 may be characterized by the duration of the cycle (T) or the frequency of the signal (f=1/T), The binary control signals 131, 144 may be further characterized by an active period in which the signals are alternating as shown in FIG. 38 between high and low values and an inactive period in which both signals are off. In one embodiment, the active period consists of a first control signals supplying 3 high half-cycles, while the second control signal supplies 2 high half-cycles. Applying the binary control signals 131, 141, to a circuit similar to the circuit in FIG. 37 produces a waveform at the Vsense node 58 that is similar to the waveform 20 shown in FIG. 38. In other embodiments, the number of high half-cycles for each control signal 131, 144 during the active period may be any integer number of high half-cycles for signal 131 alternating with any integer of high half-cycles for signal 144. Alternatively, during the active period the control signal 131 may produce one high half-cycle alternated with one high half-cycle in control signal 144.

In this embodiment, Vref is 4 volts, resulting in a Vsense amplitude of less than 4 volts, as shown in FIG. 38. A voltage divider 8 creates the voltages V+ and V− that are near the positive reference voltage Vref and near ground, respectively. In one embodiment, R1 can have a value of 10 ohms, and R2 can have a value of 2K ohms When both multiplexers of switching network 2 are commanded to zero, the circuit is at rest and the lower voltage is presented to terminals VTA and VTB 3. When VA is high and VB is low, the higher voltage is presented to the reference resistor Rref 4 and the lower voltage is presented to the subject media 1 having unknown resistance Rx. When VB is high and VA is low, the higher voltage is presented to the subject media 1 having unknown resistance Rx and the lower voltage is presented to the reference resistor Rref 4.

A change in voltage ΔVsense before and after each square wave edge, can be shown to depend only on the reference resistance Rref 4, the unknown resistance Rx of subject media 1, and any series resistance (including, e.g., Rs 7), and is generally independent of series capacitance C1 or C2 6, since during this short time period the capacitor acts as an incremental short circuit. In particular, $$\Delta\alpha=\Delta V\text{sense}/(V+-V-)=(Ry-Rref-Rth)/(Ry+Rref+Rth)=(\rho-1)/(\rho+1)$$

where Ry=Rx+2Rs+Rth, where Rth=source series resistance from multiplexer 2 and voltage divider 8, and ρ=Ry/(Rref+Rth). (Source series resistance Rth, can be derived as the sum of the resistance of multiplexer 2 and the Thevenin equivalent resistance of the voltage divider 8. For example, for R1=10 ohms, R2=2K ohms, then Rth=R1·parallel·(R1+R2)=9.95 ohms). Thus, if Ry is a short circuit, then ρ=0 and Δα=−1. The sense node's change in voltage ΔVsense is then equal to the voltage change at VB which has an amplitude opposite to the drive node at VA. If Ry is an open circuit, then ρ=∞ and Δα=1. The sense node's change in voltage ΔVsense is then equal to the voltage change at the drive node VA. Accordingly, if this change in voltage is measured, the preceding equations can be solved for the unknown resistance Rx:

$$Rx=\rho(Rref+Rth)-2Rs-Rth, \text{ where } \rho=(1+\Delta\alpha)/(1-\Delta\alpha)$$

As shown in FIG. 37, a low-pass filter 9 can be formed by resistor Rf and capacitor Cf, to filter out high-frequency noise. In one exemplary arrangement, Rf can have a value of 1K ohms, and Cf can have a value of 0.001 uF. Buffer amplifier 10 and analog-to-digital converter (ADC) 111 can then measure the sensed voltage for a computer or digital signal processor (not shown).

The reference voltages V+ and V− may be advantageously derived from a voltage divider 8 so that V+ is close to the reference voltage Vref of the ADC 111, and V− is close to the ground reference voltage of the ADC 111. For example, for R1=10 ohms, R2=2 Kohms, and Vref=4.0V, then V+=3.980V, and V−=0.020V. This places both voltages within but near the edges of the active sensing region of the ADC 111, where they can be used for calibration (discussed below). Switch SW1 12 may be used to help calibrate the load resistance sensing.

Several improvements may decrease errors related to variations of component values. First, a calibration step can be introduced where VA is switched to V+ for a relatively long period of time, until settles and is approximately equal to V+, at which point ADC 111 can take a measurement of Vsense. A second calibration step can involve switching VA to V− for a relatively long period of time, until Vsense settles and is approximately equal to V−, at which point ADC 111 can take another measurement of Vsense. This allows the ADC 111 to measure both V+ and V−.

Secondly, as shown in FIG. 38, while the square wave is switching, ADC 111 readings before and after both edges of the switching waveform may be used to compute the dimensionless quantity Δα:

$$\Delta\alpha=\Delta V\text{sense}/(V+-V-)=[(V2-V1)+(V3-V4)]/2(V+-V-)$$

As a result, both edges of the waveform can be used to measure ΔVsense=[(V2−V1)+(V3−V4)]/2, so that asymmetric responses to the circuit are likely to be canceled out. Alternatively, an average voltage at about the midpoint of the waveform may be used; so that, for example, Δα=ΔVsense/(V+−V−)=[(V7−V6)+(V7−V8)]/2(V+−V−), and ΔVsense=[(V7−V6)+(V7−V8)]/2. In addition, only differential measurements of the input signal Vin of the ADC 111 can be used. Thus, any offset errors of the buffer amplifier 10 and ADC 111 can be canceled out. Also, Δα is a ratiometric quantity based on measurements using the same signal path. Thus, any gain errors of the ADC 111 can also be canceled out.

The reference resistor Rref 4 may be optimally chosen to be equal to the geometric mean of the endpoints of the desired range of unknown resistances, taking series resistances Rs 7 into account. For example, if Rs=100 ohms and Rx varies from 100 ohms to 3000 ohms, then Ry=Rx+2R, varies from 300 ohms to 3200 ohms, and Rref should be approximately the square root of (300 ohms*3200 ohms)= 980 ohms. To measure an unknown resistance in the range of 100 k-300 k ohms (as in, for example, a column of blood extending from one electrode to another via an arteriovenous fistula), the reference resistor Rref 4 can be changed to approximately 200 k ohms and the filter capacitor Rf of low pass filter 9 at the input to the buffering amplifier 10 can be removed completely.

Because a voltage divider's output is a nonlinear function of its resistance ratio, errors or noise in readings from the ADC 111 produce their lowest fractional error (sensitivity) in the resultant calculation of Ry when it is equal to Rref, and the sensitivity increases the more Ry diverges from the reference resistance Rref. Specifically, it can be shown that the sensitivity in resistance ratio is as follows:

$$Sp=(1/\rho)\cdot\partial\rho/\partial\Delta\alpha=2/[(1+\Delta\alpha)(1-\Delta\alpha)]=2/[1-(\Delta\alpha)2]$$

When Ry=Rref, ρ=1, Δα=0 and Sp=2. Thus, for a change in Δα of 0.001 (0.1% of the ADC full-scale) around this point, the calculated resistance Ry changes by 0.002 or 0.2%. The sensitivity increases as ρ diverges from 1, as shown in Table 1.

TABLE 1

| ρ | Δα | Sp |
|---|---|---|
| 1 | 0 | 2 |
| 2, 0.5 | .+−.0.333 | 2.25 |
| 4, 0.25 | .+−.0.6 | 3.13 |
| 5.83, 0.172 | .+−.0.707 | 4 |
| 10, 0.1 | .+−.0.818 | 6.05 |
| 20, 0.05 | .+−.0.905 | 11.03 |

Figure 39:
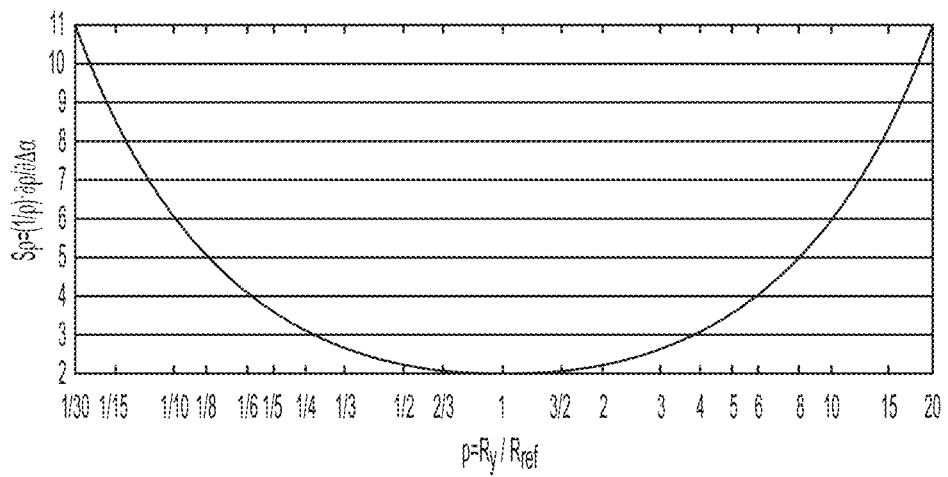
FIG. 39 is a representative graph of the noise/error sensitivity of the circuit of FIG. 37 plotted against the ratio of unknown/reference resistance in the circuit.

FIG. 39 shows that the noise/error sensitivity doubles at about a 6:1 ratio of unknown/reference resistance, and triples at a 10:1 ratio. Resistance measurements outside this range may suffer in their increased sensitivity to noise and error.

For calibration purposes, a switch SW1 12 can be used to make resistance measurements to calibrate out a point at Rx=0. Preferably this switch 12 should be placed across the terminals VTA and VTB 3, or as close to the terminals as feasible, which would give a true zero-point calibration. In practice, however, locating the switch 12 close to the terminals VTA and VTB 3 may make the switch 12 prone to external noise and surge voltages, and may introduce DC leakage current into the subject media 1.

The series capacitances C1 and C2 6, and the use of square waves are important for unknown resistances that include an electrolytic conductive path. There are at least two reasons for this. First, it may be important in many applications to prevent DC current from flowing through an electrolyte solution or a bodily fluid having similar properties; otherwise electroplating and/or electrolysis of electrodes at the terminals VTA and VTB 3 can occur. In this circuit, the capacitors C1 and C2 6 block DC currents. Furthermore, because the capacitors may allow very small currents to flow (microamps or less), using an alternating square wave voltage may help to limit the average current further.

Secondly, in the event that a small electrochemical DC voltage is induced in the subject media 1 (for example, the electrodes in a fluid path may oxidize over time at different rates), this DC voltage can be blocked by the capacitors C1 and C2 6. Because the method for calculating resistance takes differential measurements, any residual DC voltage may be canceled out through the process of calculating the unknown resistance Rx of subject media 1.

The applied voltage and duration of the high half-cycles during the active period are selected to saturate capacitive elements between the voltages VA and VB, whereby the determined impedance is equal to the pure resistance component of the unknown impedance Rx. Further, the period between active periods may be selected to limit the leakage current to which the patient may be exposed.

Referring now to the circuit in FIG. 37 and the waveform plots in FIG. 38. The unknown resistor Rx in FIG. 37 may have a complex impedance consisting of a pure resistance and a capacitive resistance. The pure resistance is the resistance to the flow of DC current, whereas capacitive resistance is the resistance to alternating current. In some embodiments, the electrical lines, between the capacitors C1, C2 and the terminals VTA, VTB, may be capacitively coupled. The capacitive coupling provides a resistance in parallel to the unknown impedance Rx which lowers the measured voltage signal Vsense and thus the measured impedance. In applications, such as measuring the conductivity of the dialysate or detecting a disconnected vascular access, the pure resistance portion of the complex impedance Rx is of greater interest.

In cases where capacitive elements exist either in series with the unknown resistance Rx or in parallel with the unknown resistance, the measured voltage signal Vsense and thus the measured impedance will depend on the voltage and frequency of the signal applied at VA and VB in FIG. 37. In one embodiment, the binary voltage signals 131, 144 operate at a sufficient low frequency during the active phase that the capacitive elements in series with or in parallel with the unknown impedance Rx are fully charged or saturated. The resulting Vsense waveform 20 reaches a stabilized value during a half cycle so that V7 is approximately equal to V3. The resistance calculated from a stabilized Vsense is minimally affected by the capacitive elements and the resulting measured resistance reflects primarily the pure resistive element of Rx. The frequency of the binary voltage signals 131, 144 that produces a measurement unaffected by capacitive elements in the unknown impedance Rx may be determined based on measurements or calculations of the capacitance or may be determined empirically.

In one embodiment, a controller varies the frequency of the binary voltage signals 131, 144 to determine the capacitance-rejecting frequency below which capacitive elements do not affect the measurement of the unknown resistance Rx. The controller may start the search for a frequency to minimize capacitive elements by starting with a high frequency and decreasing the frequency of the voltage signals 131, 144, thereby extending the duration of the high half-cycle, while monitoring the resulting Vsense waveform 20. The controller may continue to reduce the frequency of the voltage signals until the controller detects that the Vsense waveform 20 has reached steady state by the end of the half-cycle. In one embodiment, steady state may be defined as the Vsense voltage V7 at the middle of the half cycle at which it is greater than a predetermined fraction of the final voltage V3 at the end of the half cycle. In one embodiment, the Vsense waveform 20 has reached steady state with when V7 is greater than about 75% of V3. In another embodiment the Vsense waveform 20 has reached steady state with when V7 is greater than about 90% of V3. Alternatively, the Vsense waveform 20 may be declared to have reached steady state when the rate of change of V3 is less a predetermined threshold.

Alternatively, the controller may start the frequency search with a low frequency value and increase the frequency until the Vsense waveform 20 is no longer at steady state by the end of the half cycle.

The controller may determine the capacitance-rejecting frequency for the binary control signals 131, 144 at the beginning of therapy and then use that frequency throughout the rest of the therapy. The determination of the capacitance-rejecting frequency may occur after a predetermined volume of blood has been has been pumped or a predetermined number of blood-pump strokes have occurred.

In another embodiment, the capacitance-rejecting frequency may be determined periodically to assure that any capacitance between the wires in the arterial blood circuit tubing 108 and the venous catheter tubing connector 128 (FIG. 40) tubes has not changed. In one embodiment, the capacitance-rejecting frequency is determined every 50 strokes of the blood pump.

In one embodiment, the inactive period of the binary voltage signals may be extended to limit the current leakage from the circuit in FIG. 37. The active period may have a short duration and comprise only a few cycles at which point the circuit is turned off for a relatively much longer period of time. For example, the active period may consist of 6 pulses each having a 420 microsecond duration with the active period occurring every 80 milliseconds.

Vascular Disconnect Detector

With the appropriate modifications of a conductivity measurement circuit such as the one described above, it is possible to detect the conductivity and changes in the conductivity of blood. More specifically, it is possible to detect the change that occurs in the conductivity of a volume of blood when air enters the volume. This situation can occur, for example, when an intravascular access site becomes dislodged in an extracorporeal blood circuit.

The circuit shown in FIG. 37 can be used to measure the resistance of a volume of fluid in a conductivity cell or conduit 1. For measurements of Rx of a conductivity cell 1 representing the resistance or conductivity of a volume of dialysate solution, a convenient value for the reference resistor Rref 4 can be chosen to be approximately 680 ohms. For measurements of Rx of a conduit 1 representing the resistance or conductivity of a column of blood extending from a first cannula or needle, through an arterio-venous fistula, to a second cannula or needle, a convenient value for the reference resistor Rref 4 can be chosen to be approximately 200 k ohms.

The advantages of using this circuit to monitor the continuity of a column of a bodily fluid such as blood or plasma include the following: Capacitive coupling to the conductivity cell or conduit 1 blocks DC current which could cause plating and corrosion of electrodes at terminals VTA and VTB; Voltages and current levels are very low and decoupled for patient safety; Current only flows briefly while the measurement is being taken. No current flows between measurements.

With the lower reference resistor Rref 4 value (e.g. 680 ohms), this circuit is appropriately configured for dialysate conductivity measurements. With a much higher reference resistor Rref 4 value (e.g. 200 k ohms) this circuit is appropriately configured for measuring the resistance between an arterial needle and a venous needle to detect vascular needle dislodgement from an arterio-venous fistula.

Electrode Placement

The continuity of a fluid column leading from a fluid delivery apparatus to a patient's blood vessel or vascular graft can be monitored using the electronic circuit described above. The fluid being delivered may include blood or any electrolyte solution, including dialysate fluid. Although the following discussion will involve a hemodialysis system, the same principles of operation of the invention can apply to any device that is configured to deliver a fluid to a patient via a vascular access. In an embodiment illustrated by FIG. 40, the conductivity of a volume of blood or other fluid within a fluid flow circuit 100 of a hemodialysis machine 200 can be monitored electronically, using electrodes on each end of the volume that make direct contact with the blood or other fluid. Using an electrical circuit such as the one shown in FIG. 37, one electrode can be connected to the VTA terminal, and the other electrode can be connected to the VTB terminal of the circuit. The voltages applied to the electrodes by the circuit can be sufficiently small (e.g., about 4 volts or less), sufficiently brief, and with DC voltages sufficiently decoupled so as to prevent any harm to the patient. In this example, a fluid flow circuit 100 is shown, including an arterial access needle 102, an arterial catheter tubing 104, an arterial catheter tubing connector 106, arterial blood circuit tubing 108, a transition 110 between the blood circuit tubing 108 and hemodialysis machine 200, a blood pump inlet line 112, a blood pump 13, a blood pump outlet line 116, a dialyzer 14, a dialyzer outlet line 120, air trap 122, a transition 124 between hemodialysis machine 200 and venous blood circuit tubing 126, a venous catheter tubing connector 128, a venous catheter tubing 130, a venous access needle 132, and the intraluminal volume of that portion of the patient's blood vessel or fistula 134 that lies between the arterial access needle 102, and the venous access needle 132. It should be noted that the invention described herein also encompasses circumstances in which the arterial access needle may reside in one blood vessel of a patient, while the venous access needle may reside in a separate blood vessel some distance away from the arterial access site. Furthermore, the circuit described above may be used to monitor the integrity of a vascular access in a fluid delivery system that does not have the venous return line shown in FIG. 40. In that case, for example, an electrode at location B could be paired with an electrode in contact with fluid in a dead-end line communicating with a second needle or cannula accessing the blood vessel or vascular graft. In another example, an indwelling hollow cannula or solid trocar in the vascular segment can be equipped with a conductive wire which could then serve as the second electrode in the monitoring system. The vascular segment being accessed may be a surgically constructed arterio-venous fistula, and may also include an artificial conduit such as a GoreTex® vascular graft. The term 'arterial' is used herein to denote the portion of the blood flow circuit that conducts blood away from the patient and toward the hemodialysis machine 200. The term 'venous' is used to denote the portion of the blood flow circuit that conducts blood away from the hemodialysis machine 200 and back toward the patient. The term 'access needle' is used to denote a needle or catheter device that penetrates the patient's vascular segment or fistula. In different embodiments it may be permanently fused or reversibly connected to a corresponding catheter tubing 104, 130.

The continuity of any segment of the fluid flow circuit 100 can be monitored by positioning two electrodes in contact with the fluid on either side of the fluid and blood-containing segment of interest. In order to monitor for a disconnection of the arterial access needle 102, or the arterial catheter tubing 104, or the venous access needle 132 or venous catheter tubing 130, one electrode can be placed in continuity with the lumen of the venous side of the blood flow circuit, while a second electrode is placed in continuity with the lumen of the arterial side of the blood flow circuit. In one embodiment, the two electrodes can be positioned on or near the dialysis machine 200, with an electrode in contact with blood upstream of blood pump 110, and a second electrode in contact with blood downstream of the dialyzer 14 and/or air trap 122. For example, the electrodes can be incorporated into transition locations 110 and 124.

In another embodiment, one of the electrodes can be positioned to be in contact with the fluid in the fluid flow circuit 100 at a point that is closer to the vascular access site 134 than it is to the equipment (e.g. a dialysis machine) used to deliver fluid flow to the accessed blood vessel or vascular graft. In a preferred embodiment, both electrodes can be positioned to be nearer to the patient's blood vessel or vascular graft than the equipment associated with the dialysis machine 200. This may further reduce electrical interference associated with the dialysis machine 200. An electrode A can be conveniently placed at or near the arterial catheter tubing connector 106 and a second electrode B can be conveniently placed at or near the venous catheter tubing connector 128. In this arrangement, the electrical continuity pathway from the first electrode through the patient's vascular access to the second electrode is much shorter—and the electrical resistance lower—than the pathway extending back toward the dialysis machine 200. In some cases, the access catheters 104 and 130 can be as short as about a foot, whereas the arterial and venous tubings 108 and 126 can be about six feet long. Because of the electrical conductive properties of the fluid in the circuit, the electrical resistance associated with the pathway incorporating tubing 108 and 126, and components of the dialysis machine 200, can be many times greater than the electrical resistance associated with the pathway through the patient's blood vessel or fistula 134.

Electrical interference associated with the dialysis machine 200 is thus reduced, and a change in electrical resistance due to an access-related disconnection can more easily be detected. Preferably, the electrodes A and B are positioned to be more than 50% of the distance from the dialysis machine to the patient. More preferably (and more conveniently), the electrodes A and B are located near the last disengageable fluid connection before reaching the patient. In one embodiment of a hemodialysis system, the blood tubing 108 and 126 is approximately 6 feet in length, and the arterial and venous catheter tubes 104, 130 are about two feet or less in length. A convenient location for electrodes A and B would then be at the arterial line and venous line connectors 106, 128 (which can be, e.g. Luer type connectors or modifications thereof) that connect the arterial and venous blood circuit tubes 108, 126 with the arterial and venous catheter tubes 104, 130.

Connector Electrodes

Figure 41A:
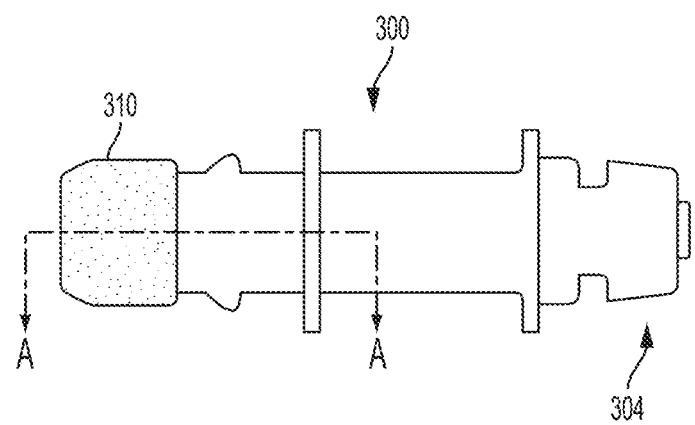
FIG. 41A is a side view of a connector that may be used in the blood flow circuit of FIG. 40.
Figure 41B:
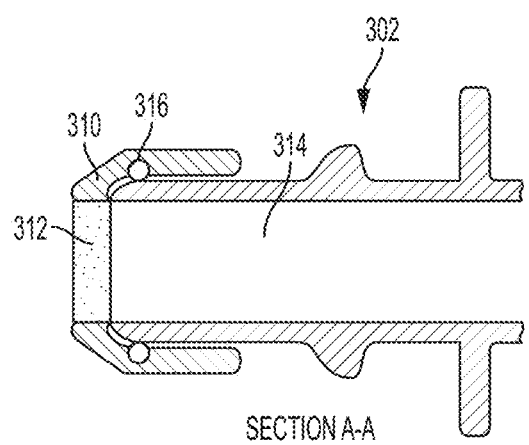
FIG. 41B is a cross-sectional view of the connector of FIG. 41A.

As shown in FIGS. 41A and 41B, in one embodiment, a blood line connector for the blood circuit of a hemodialysis system may incorporate electrodes that can make contact with any liquid within the lumen of the connector. In one aspect, the electrode can comprise an annular conductive cap 310 placed at the tube-connection or proximal end 302 of any suitable connector, such as, for example connector 300. The electrode is preferably constructed from a durable and non-corrosive material, such as, for example, stainless steel. The distal coupling end 304 of connector 300 can be constructed to make a sealing engagement with a corresponding Luer-type connector of an arterial or venous catheter, for example. The inner annular surface 312 of the cap 310—in part or in whole—can make contact with any liquid present within the lumen 314 of the connector. As shown in FIG. 41B, an O-ring 316 or a suitable sealant can be placed between the cap electrode 310 and the proximal end 302 of the connector to maintain a fluid-tight connection between the connector and any flexible tubing attached to the connector.

An elastomeric O-ring may be particularly useful in hemodialysis or other extracorporeal systems in which the blood-carrying components are subjected to disinfection or sterilization using heated liquids. The thermal coefficients of expansion of the plastic components of a connector may be sufficiently different from that of an incorporated metal electrode that a permanent seal may not be preserved after one or more sterilization or disinfection procedures. Adding an elastomeric component such as an O-ring at the junction between an electrode and the connector seat on which it is positioned may preserve the seal by accommodating the different rates of expansion and contraction between the electrode and the connector.

Figure 42:
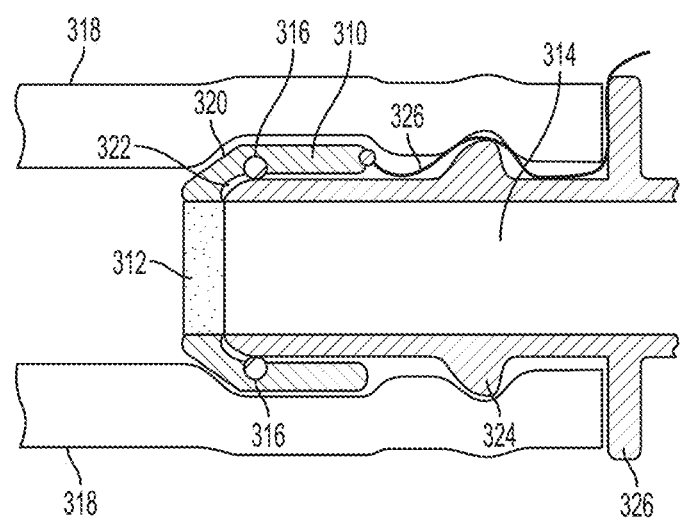
FIG. 42 is a cross-sectional view of the connector of FIGS. 41A and 41B, with an attached wire and flexible tubing.

As shown in FIG. 42, in one embodiment, a conductive electrode 310 (constructed of, e.g., stainless steel) can be incorporated into a portion of a connector 300 (either at its proximal end 302, or alternatively at its distal connecting end 304), over which the end of a flexible tubing 318 can be placed. In this embodiment, the electrode 310 is generally cylindrical, and has a taper 320 on a proximal end to permit an easier slip-fit attachment of the end of a segment of flexible tubing 318 over the outside surface of the electrode 310. As shown in FIG. 42, the internal surface of the electrode 310 has an internal ledge 322 that allows the electrode cap 310 to slip over and abut a proximal end 302 of connector 300. Connector 300 can be constructed of any suitable hard material, including metal or more typically a plastic material. The ledge 322 helps to ensure that a smaller diameter inner surface 312 of electrode 310 is properly positioned to make contact with any liquid (e.g. blood) that passes through the lumen 314 of connector 300. The connections between connector 300 and electrode 310, and electrode 310 and the termination of an overlying flexible tubing 318 can be made air tight or permanent with any suitable adhesive compatible with the compositions of the components.

To ensure a more secure seal to prevent blood leakage between the connector and electrode, and to limit the area under the electrode where blood elements may migrate and become lodged, an O-ring 316 can be incorporated into the inner surface of electrode 310 near the electrode internal ledge 320. This is seen in enlarged detail in FIG. 42. In this example, the O-ring 316 seals between the stainless steel electrode 310 and the distal end 302 of connector 300. A barb element 324 on the proximal end 302 of connector 300 can be incorporated in the connector design in order to hold the stretched end of the flexible tubing 318 onto the proximal end 302 of connector 300. In an embodiment, the electrode 310 is held in place by the portion of the flexible tube that is stretched over both the electrode 310 and the barb 324 of connector 300.

A wire 326 can be soldered, welded or otherwise secured onto the outer surface of electrode 310, and can travel under the overlying stretched tubing 318 until exiting more distally along the connector 300. The wire can thus conduct electrical signals to and from the electrode 310 as the internal surface 312 makes contact with the intraluminal fluid (e.g. blood). In the example shown, wire 326 is soldered to a distal portion of electrode 310 and travels under tubing 318, to emerge at the abutment of tubing 318 with a corresponding stop 326 of connector 300.

Figure 43A:
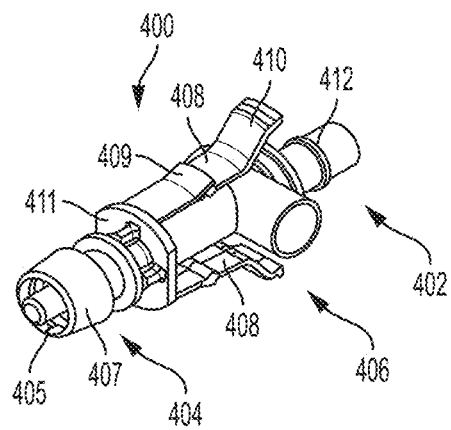
FIG. 43A is a perspective view of an alternate embodiment of a connector that may be used in the blood flow circuit of FIG. 40.
Figure 43B:
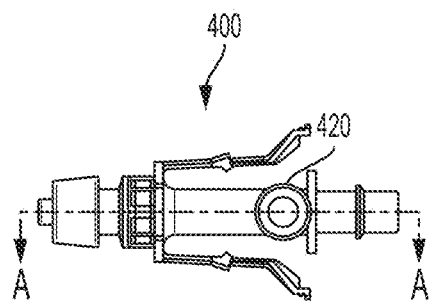
FIG. 43B is a top view of the connector of FIG. 43A.
Figure 43C:
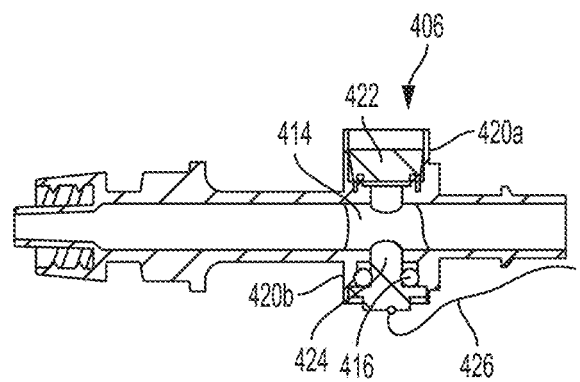
FIG. 43C is a cross-sectional view of the connector of FIG. 43B.

In another embodiment as shown in FIGS. 43A-43C, a connector 400 as described in U.S. Patent Application Publication No. 2010/0056975 (the contents of which are hereby incorporated by reference) has been modified so that a mid-portion 406 of the connector 400 can incorporate an electrode. Placement of the electrode along the mid-portion 406 of the connector 400 avoids having to alter the distal coupling end 404 of the connector, and avoids any alteration of the interaction between the termination of the flexible tubing and the proximal end 402 of the connector. In this example, the blood line connector 400 is constructed to make two different types of sealing connections on its distal coupling end 404, including an internal screw-type connection 405 for a Luer-type connector of a patient access line, and an external press-in type connection 407 with a dialysis machine port for recirculation of priming and disinfecting fluid through the blood carrying components of a dialysis system. The press-in feature 407 is formed having a frustoconical shape on the outside surface of the distal end 404 of the connector 400, while the Luer-compatible screw-type feature 405 is formed on the corresponding internal surface of the distal end 404 of the connector 400. The outside surface of the frustoconical member is constructed to make sealing engagement with the seat of a mating connector of a dialysis machine 200 or other device. A pair of locking arms 408 extending proximally from the distal coupling end 404 of the connector 400 can each have a barbed portion 409 to engage a corresponding locking feature on a mating connector on the dialysis machine, and a finger depression portion 410 to aid in disengaging the barbed portions 409 from the dialysis machine. The barbed portion 409 helps to lock the frustoconical member in sealing engagement with its mating connector on the dialysis machine when making a press-in type of connection. The distal ends of the locking arms can be constructed to attach to the connector via a flange 411 located proximal to the frustoconical portion 407 of the connector 400. The connector 400 has a proximal tubing attachment end 402 to sealingly engage a flexible tube. The tubing attachment end 402 may have one or more barb features 412 to help prevent disengagement of the end of a flexible tube from the connector 400.

FIG. 43B shows a side view of connector 400, bringing into view an access feature or port 420 that can permit placement of an electrode in direct communication with the lumen of connector 400. In other embodiments, the access feature may house an elastomeric stopper—with or without a septum—to permit sampling of fluid from within the lumen 414 of connector 400 using a syringe with a sharp or blunt needle. Alternatively, the feature may serve as a port to allow connection of another fluid line to the lumen 414 of connector 400.

In yet another embodiment, the mid-portion 406 of connector 400 may have two access ports, as shown in the cross-sectional view of FIG. 43C. A fluid access port 420a can serve as a sampling port, and an electrode port 420b can serve as an electrode cradle. An elastomeric stopper 422 within sampling port 420a can be shaped to extend to the lumen 414 of connector 400, simultaneously permitting sampling of fluid in the lumen 414 with a needle, while maintaining an air-tight seal. Alternatively, a Luer-type connector having a separated cap or seal can be incorporated into the port, which is capable of connecting with a syringe or catheter having a mating Luer-type connector. An electrode port 420b can serve as a seat or cradle for an electrode 424. In can be press-fit or cemented into position, and sealed with an adhesive, or with an O-ring 416 as shown. A wire 426 can be soldered, welded or otherwise secured onto the outer surface of electrode 424, and can travel proximally toward dialysis machine 200 with the arterial tubing 108 or venous tubing 126 to which connector 400 is attached.

In any of the above electrode embodiments, the electrodes may be replaced by a suitably sized thermistor, or combination of a thermistor and electrical conductor, for the additional purpose of monitoring the temperature of the fluid passing through connector 300, 400 or variants thereof.

Wire Assembly

In one embodiment, the wires carrying electrical signals to or from a pair of electrodes on connectors 106, 128 (one on the arterial side and one on the venous side of the blood flow circuit) can travel separate and apart from the blood tubing 108, 126 back toward dialysis machine 200, where they ultimately terminate and connect to, a conductivity detecting circuit, such as the conductivity circuit shown in FIG. 37. The conductivity circuit, in turn, provides an appropriately configured signal to a processor on the dialysis machine to determine whether a change in fluid conductivity consistent with an access disconnection has occurred. If so, the processor can trigger an alarm condition, or can initiate a shut-down of blood pump 13, and trigger a mechanical occlusion of blood tubing 108 and/or 126, for example.

Figure 44A:
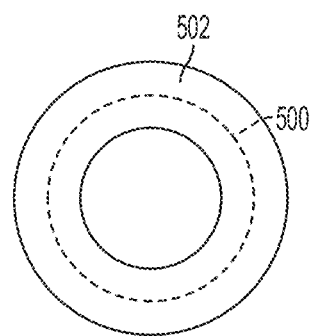
FIGS. 44A-D are various cross-sectional views of a flexible tube incorporating a conductive wire.
Figure 44B:
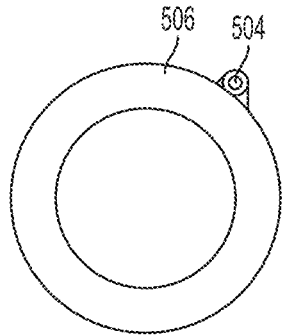
Figure 44C:
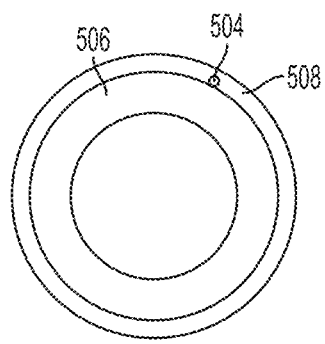
Figure 44D:
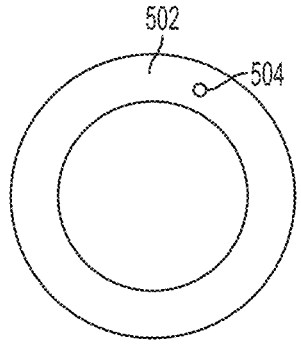

Wires that extend together or separately between the dialysis machine and the patient are at risk of getting tangled, broken or becoming disconnected. Therefore, preferably, each wire 326 or 426 can be attached, fused, or otherwise incorporated into its associated tubing 108, 128. Incorporating a wire into its associated tubing provides a convenient way of protecting the wires and connections, and simplifying the interface between the patient and the dialysis apparatus. Exemplary methods of achieving this are shown in FIGS. 44A-44D. In a preferred embodiment, the tubing is comprised of a flexible material (e.g., silicone) that can be formed in an extrusion process. As shown in FIG. 44A, a loose wire mesh may be embedded in the flexible silicone tubing as it is formed and extruded, similar to fiber reinforcement of flexible tubing. As shown in FIG. 41A, a wire mesh 500 can be embedded within the wall of the flexible tubing 502 during extrusion, in a manner similar to the construction of a fiber-reinforced tube. As shown in FIG. 44B, an insulated wire 504 can be joined to the external surface of its adjacent tubing 506, either during a secondary extrusion process, or a process in which the two structures are joined by an adhesive, for example. As shown in FIG. 44C, a second extrusion producing a secondary concentric layer of tubing material 508 can be made to capture a wire running along the external surface of the tubing after the primary extrusion. As shown in FIG. 44D, the tubing 502 during formation can also be co-extruded with a wire 504 embedded in the wall of the tubing.

Figure 45:
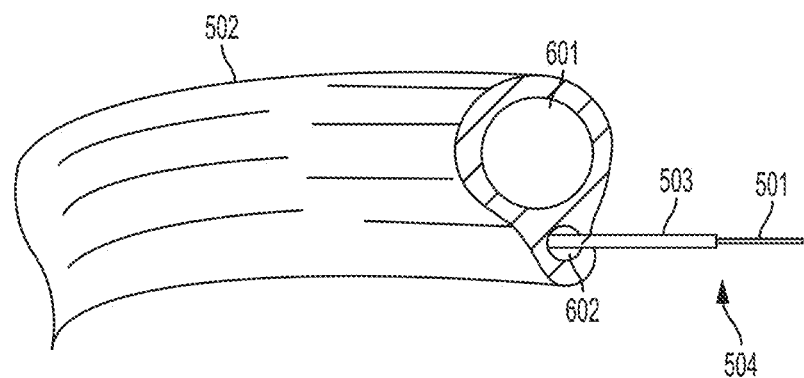
FIG. 45 is a perspective view of a flexible double-lumen tube having a fluid-carrying lumen and a wire-carrying lumen.

In some of the above methods, the resulting tube-wire combination may have a tendency to curl because of the difference in thermal coefficients of expansion between the wire and the silicone material of the tubing. As the material cools after extrusion, the silicone may capture the embedded wire tightly, causing the cooled tube-wire bundle to curl. In a preferred embodiment, the wire lumen of the extrusion die is constructed to be large enough to accommodate a cross-sectional area significantly larger than the cross-sectional area of the wire to be embedded. Then as the silicone cools, the passageway surrounding the wire does not shrink to the point of tightly encasing the wire. A co-extrusion process incorporating an insulated wire can generate a tube-wire bundle as shown in FIG. 45. In this example, flexible tubing 502 is a co-extrusion of a fluid-carrying lumen 601 and a wire-carrying lumen 602. Preferably, the wire 501 is multi-stranded for flexibility and durability, and is coated or sheathed in a durable, flexible synthetic insulating material 503, such as, for example, PTFE. A PTFE-based sheath 503 of the stranded wire 501 can sustain the high temperatures associated with the silicone tubing extrusion process, so that its integrity is maintained along the section 504 of the wire that ultimately exits the tubing for connection either to the dialysis machine 200 or the patient line connectors 106, 128.

Figure 46:
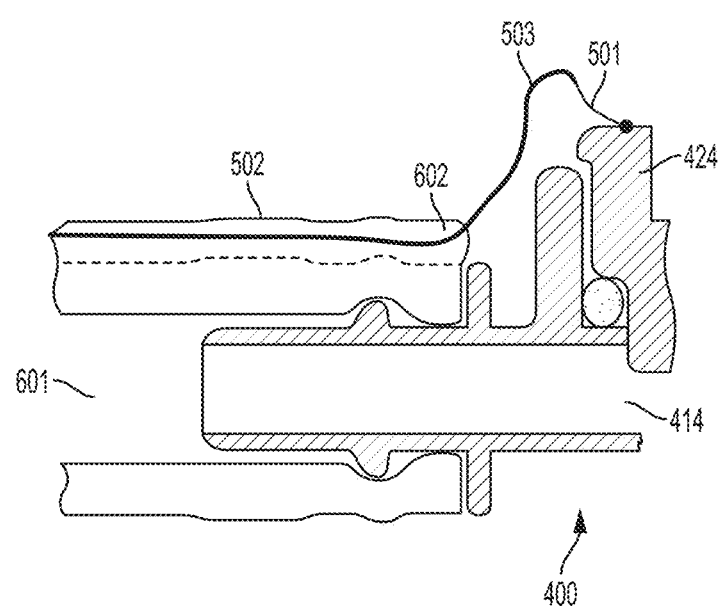
FIG. 46 is a cross-sectional view of a connector similar to the connector of FIGS. 43A-C, with an attached wire and tubing.

A coating or sheathing may also help prevent the wire from adhering to the side walls of the wire-carrying lumen after extrusion and during cooling. In another embodiment, the sheathing 503 may be eliminated and the wire 301 is bare inside the wire-carrying lumen 602. FIG. 46 shows a cross-sectional view of an exemplary connector-wire-tubing assembly. The proximal tubing connection end of a connector 400 is shown with the end of a double-lumen tubing 502 attached. The fluid-carrying lumen 601 is press-fit and/or cemented to the proximal end of connector 400, allowing for fluid flow through the central lumen 414 of connector 400. Stranded wire 501 is soldered or otherwise attached to electrode 424, which is in conductive contact with any fluid present within the lumen 414 of connector 400. The non-connecting portion of the wire 501 that travels outside tubing 502 is preferably sheathed in an insulating synthetic coating, such as, for example, PTFE. Optionally, this portion of both the exposed and sheathed wire may also be sealed with a sealant, such as RTV. The sheathed wire 503 enters the wire-carrying lumen 602 of tubing 502 near its termination onto connector 400. The wire/tubing bundle then makes its way toward the dialysis machine 200, where the wire emerges from the tubing to make a connection to a conductivity circuit such as the one shown in FIG. 37.

Figure 40:
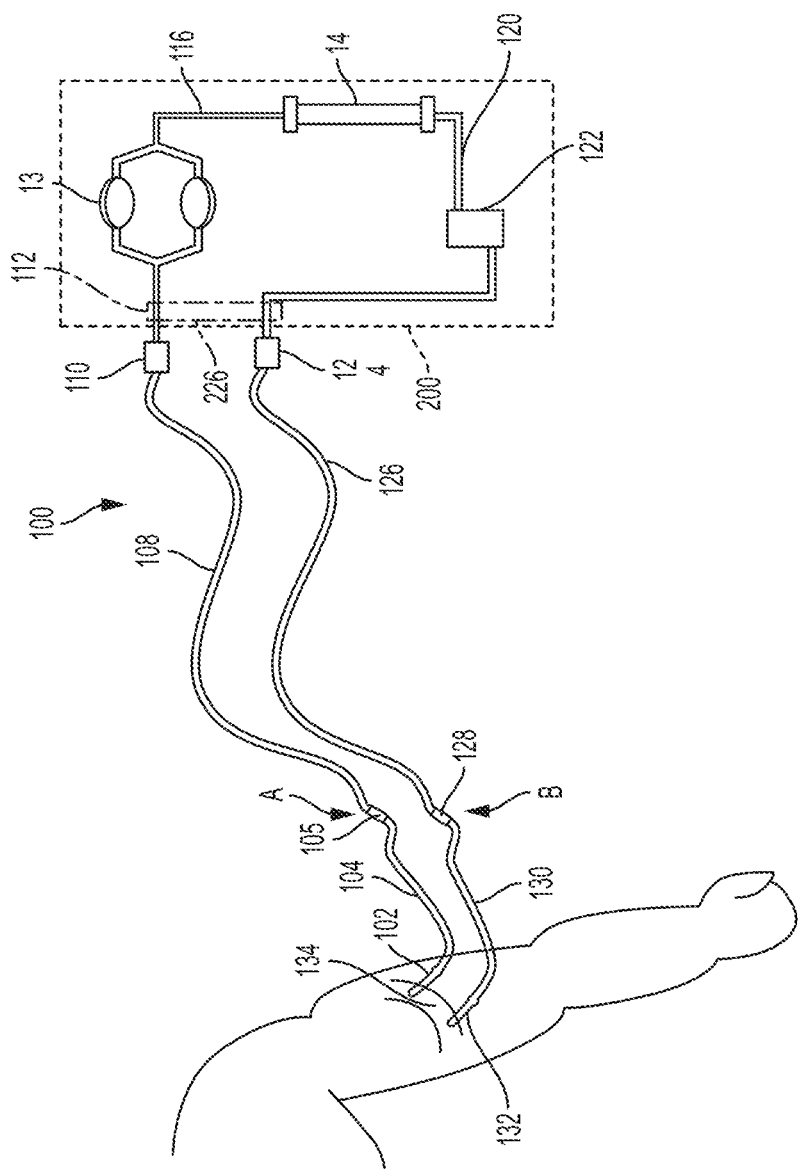
FIG. 40 is a schematic representation of an exemplary blood flow circuit of a hemodialysis system.
Figure 47:
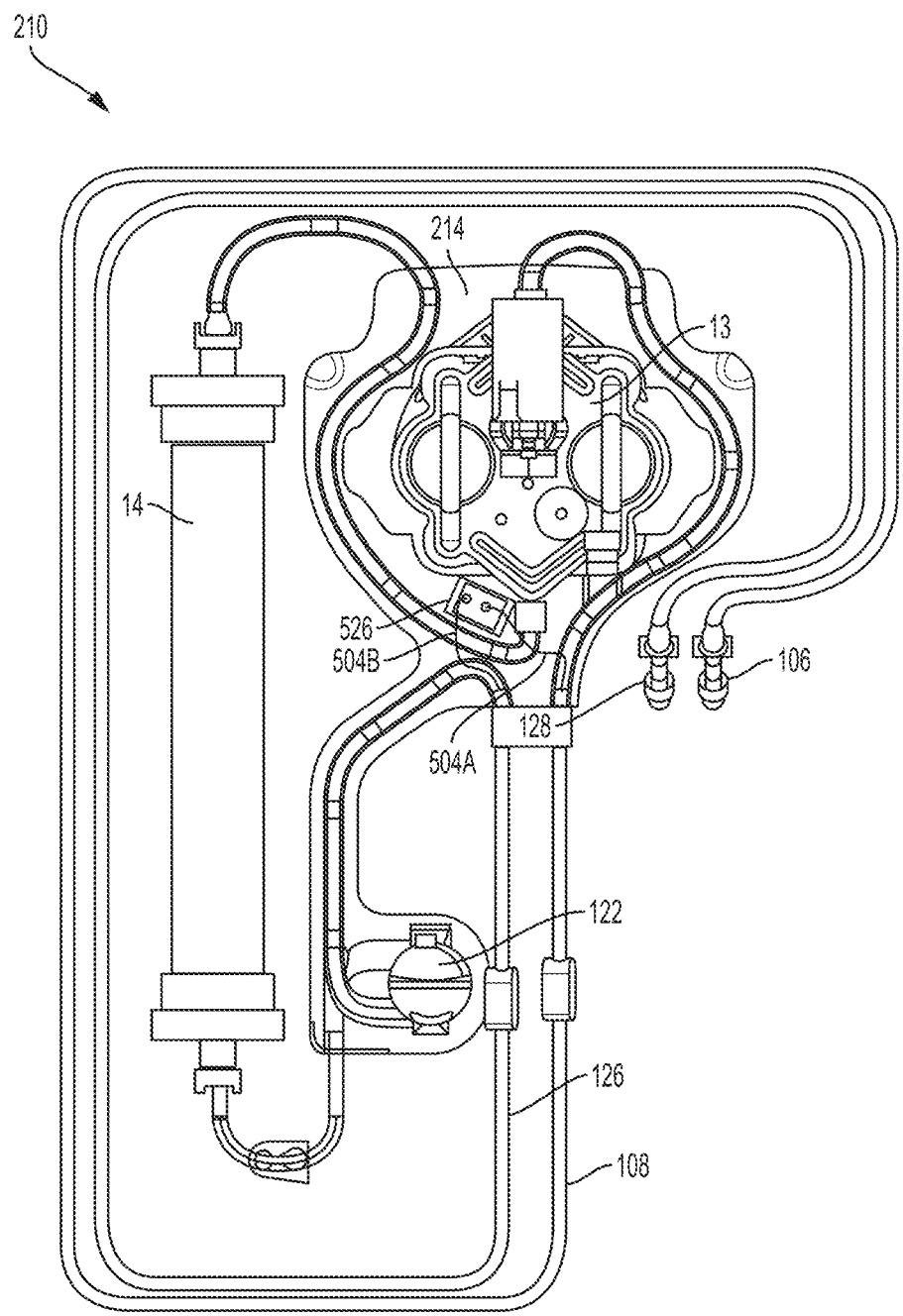
FIG. 47 is a plan view of an extracorporeal blood flow circuit used in a representative hemodialysis system.
Figure 48:
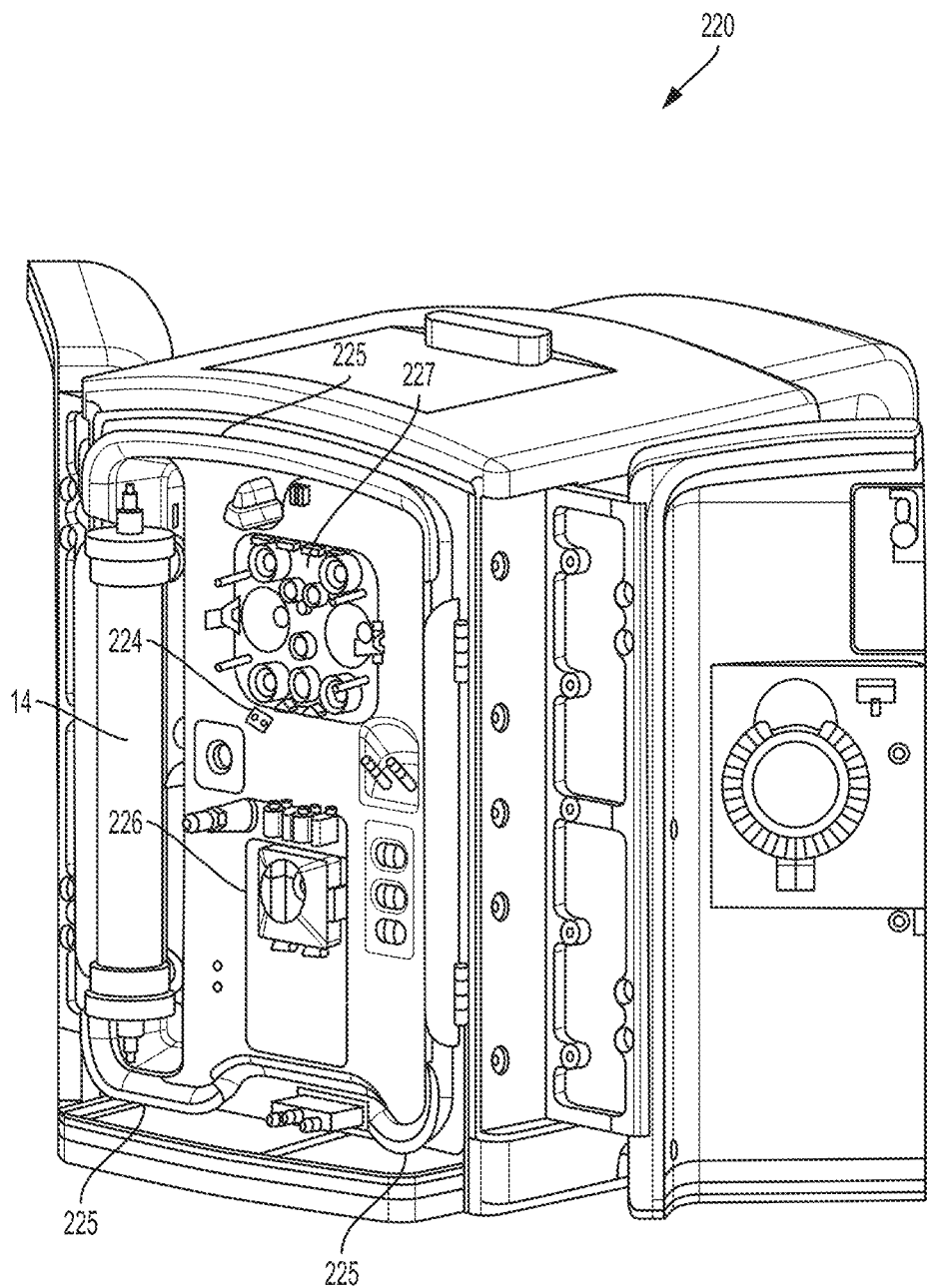
FIG. 48 is a perspective view of a hemodialysis apparatus configured to receive and operate the extracorporeal blood flow circuit of FIG. 47.

FIG. 47 shows an exemplary extracorporeal circuit 210 that may be used as a removable, replaceable unit in a hemodialysis apparatus 220 as shown in FIG. 48. In this embodiment, the extracorporeal circuit comprises a blood pump cassette 13, dialyzer 14, venous return air trap 122, arterial blood tubing 108, venous blood tubing 126, arterial catheter connector 106, and venous catheter connector 128. The arterial 106 and venous 128 connectors may be of a type similar to the connector 300 shown in FIGS. 41A and 41B, or similar to the connector 400 shown in FIGS. 43A-43C, or variants thereof. The arterial 108 and venous 126 blood tubes may be of a type shown in FIGS. 44A-44D, or FIG. 45. Wires forming terminal connections to electrodes on connectors 106 and 128 may exit arterial 108 and venous 126 tubes as segments 504A and 504B to make a connection with a connector that ultimately passes the connection through on the dialysis apparatus to terminals associated with a conductivity circuit such as that shown in FIG. 37. In the embodiment shown, the connector 526 is mounted to a support structure 214 for the blood pump 13 and air trap 122. The segments 504A, 504B, shown in FIG. 47, may be insulated. In another example, the segments 504A, 504B may be bare, but covered with a shield 1004 (FIG. 20A) that connects to the bottom plate 1001 (FIG. 20A). The placement of the wire 501 within the arterial and venous tubes 108, 126 and the relative location of the arterial tube 108 to the venous tube 126 can create a capacitive conductance between the wires 501 in each of the tubes 108, 126. This capacitive conductance may serve as an additional conductive path between the terminals VTA and VTB 3 (FIG. 37) and in parallel with the purely resistive impedance through the blood columns of the catheter tubes 104, 130 and the fistula 134 (FIG. 40). The capacitive conductance between the wires 501 within the arterial and venous tubes 108, 126 will vary with the distance between the tubes. The Vsense measurement made with a circuit similar to FIG. 37 can be made insensitive to the position of the arterial and venous tubes 108, 126 be selecting a frequency of the binary voltage signals 131, 144 low enough to saturate the capacitance between the wires 501 within the arterial and venous tubes 108, 126. In an exemplary embodiment, the binary voltage signals are each operated at a 50% duty cycle at a frequency of about 2174 Hz during periodic active phases. The active phase may be set to occur every 80 milliseconds.

FIG. 48 shows an exemplary hemodialysis apparatus 220 that is configured to receive the extracorporeal circuit 210 shown in FIG. 47. In this illustration, the dialyzer 14 is already mounted onto the apparatus 220. A base unit 227 receives the control ports of a mating blood pump cassette 13. Sets of raceways or tracks 225 help to organize the pair of arterial 108 and venous 126 blood tubes when not extended out and connected with a patient. A connector 224 receives and passes through the connections made between wire segments 504A and 504B and connector 526 to the terminal connections of a conductivity circuit such as that shown in FIG. 1. A tubing occluder 226 is positioned to receive venous blood tube 126 after it exits air trap 122, and arterial blood tube 108 before it reaches blood pump cassette 13. The occluder 226 may be actuated pneumatically or electromechanically, for example, whenever an alarm condition occurs that requires cessation of extracorporeal blood flow. A set of arms of occluder 226 can be configured to rotate against the walls of the flexible tubes, constricting or stopping fluid flow within them. Thus, a controller installed within apparatus 220 can receive a signal from a conductivity circuit similar to FIG. 37, the signal representing the electrical resistance of the column of fluid or blood between the electrodes mounted on connectors 106 and 128. Because the connectors are positioned much closer fluidically to the patient's blood vessel or fistula 134 than to the blood pump 13, dialyzer 14 and air trap 122, the signal associated with the fluid path through the blood vessel or fistula 134 can discriminate between an intact and an interrupted column of blood or fluid between the connectors 106, 128 and the patient's blood vessel or fistula 134. The controller can be programmed to respond to an electrical resistance detected by the conductivity circuit found to exceed a pre-determined value. Depending on the circumstances, the controller may then trigger an alarm to alert the patient to a possible disconnection of blood flow, and may also optionally command the occluder 226 to cease extracorporeal flow to and from the patient.

Operation of the Disconnect Detection Circuit

Figure 49:
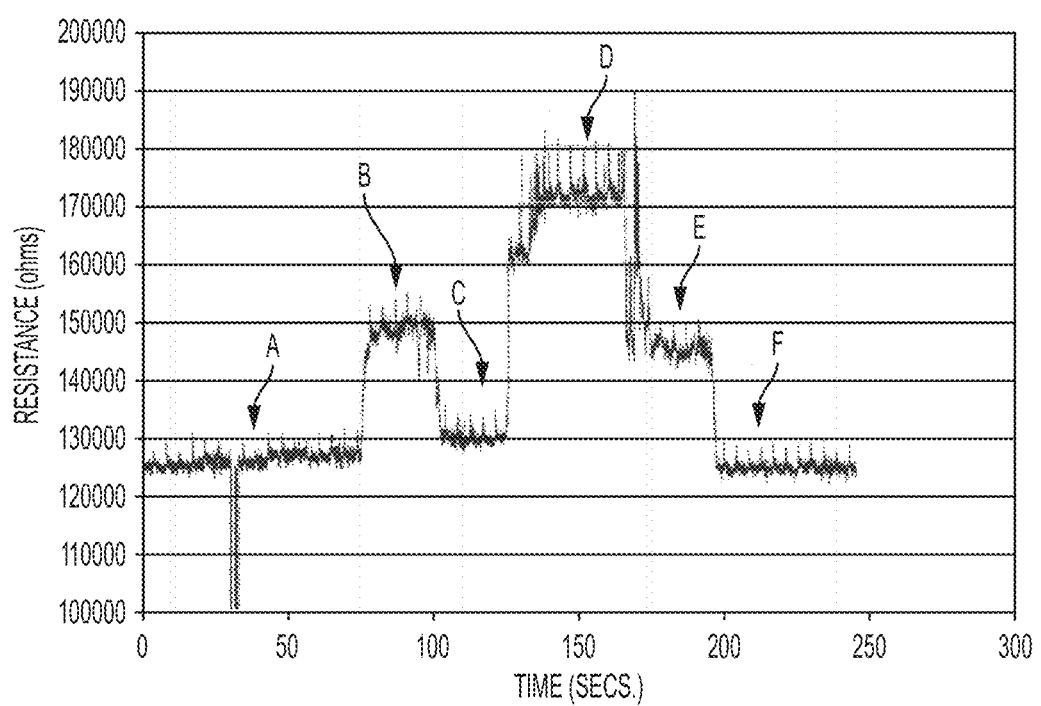
FIG. 49 is a representative plot of the resistance measured by the conductivity circuit of FIG. 37 under various conditions.

FIG. 49 shows test results utilizing the disconnect detection circuit described above and shown in FIG. 37. In this case, a hemodialysis blood circuit and apparatus was employed that is similar to that disclosed in U.S. Patent Application Publication Nos. 2009/01 14582 and 2010/0056975, (the contents of which are hereby incorporated by reference). The extracorporeal circuit 210 shown in FIG. 47, comprises a blood pump 13, dialyzer 14, air trap 122, venous blood circuit tubing 126, and arterial blood circuit tubing 108. Extracorporeal circuit 210 mates to a hemodialysis apparatus 220 similar to the one shown in FIG. 48. The blood flow circuit tested included a pair of membrane-based blood pumps arranged on a blood pump cassette 13 shown in FIG. 47, a dialyzer 14, a venous return air trap 122, an arterial blood tubing set 108, a venous blood tubing set 126, arterial and venous connectors 106 and 128, and catheter tubing sets 104, 130 connected to vascular access needles 102, 132 as shown in FIG. 40. The needles 102, 132 were placed in a container holding anticoagulated bovine blood. The blood tubing set 108 and 126 was approximately six feet long, and the catheter tubing sets 104 and 130 were approximately two feet long or less. The needles were alternately manually placed in or withdrawn from the container during blood flow to simulate disconnection of a needle from a fistula or blood vessel. Periods A, C and F in FIG. 49 represent the times during which the needles were submerged in the blood in the container. The electrical resistance measured by the disconnect detection circuit shown in FIG. 37 during these periods averaged between 120,000 and 130,000 ohms. Periods B and E in FIG. 49 represent the times during which the venous return needle 132 (under positive pressure from the blood pumps) was withdrawn several centimeters above the surface of the blood within the container, forming a stream of blood mixed with air as the blood exited the venous return needle and entered the container of blood below. The electrical resistance measured during these periods averaged between 140,000 and 150,000 ohms. Period D represents the time during which one of the needles was completely removed from the container, creating a fully open electrical circuit. The electrical resistance measured during this period averaged between about 160,000 and 180,000 ohms. Thus a controller can be readily programmed to distinguish the difference in the monitored resistance of the electrical circuit between an uninterrupted and an interrupted flow of blood. These results showed that an interruption of the continuity of the blood between the arterial 102 and venous 132 needles can reliably produce a detectible change in the measured electrical resistance between two electrodes when placed relatively closer to the arterial and venous access sites than to the blood processing components 13, 14 and 122 of the extracorporeal blood circuit. Furthermore, even a partial interruption of the continuity of blood flow (as in the streaming of blood through air) can be reliably detected, albeit with a smaller change in the measured electrical resistance.

ADS Algorithm

The operation of the Access Disconnect Sensor (ADS) may be further understood by referring to FIGS. 40, 48. The controller installed within hemodialysis apparatus 220 (FIG. 48) can control the position of the occluder 226 and the operation of the blood pump through the base unit 227 to minimize loss of blood upon detecting an access disconnection. Referring now to FIG. 40, an access disconnection or needle dislodgment may be deemed to occur when either the venous needle 132 or the arterial needle 102 is removed from the vascular access site, if either is partially dislodged from the vascular access site, or even if either is experiencing an obstruction to fluid flow to or from the vascular access site. More generally, use of the term 'access disconnect' is understood to include any condition in which the electrical impedance or conductivity between two electrodes in a fluid path from a first catheter (or cannula), through the vessel or fistula comprising the vascular access, to a second catheter (or cannula) has been altered through detection algorithms to be described below. The vascular access site refers to the vein, or fistula or shunt 134 where the needles 102, 132 or catheter from the dialysis machine 200 enters the body to access the patient's blood. The removal of either the venous or arterial needle 102, 132 from the vascular access site may result from a number of actions including but not limited to: loosening of tape that may have been applied over the needles 102,132, or tubing proximal to the needles; inadvertently pulling lines 104,108, 126, or 130 upon movement of the patient's body or limb; or action by a patient to remove the needle 102, 132 or catheter from the vascular access site; etc.

The controller may detect an access disconnection based on one or more inputs including but not limited to the signal of a conductivity circuit similar to FIG. 37, pressure information from one or more sensors monitoring the operation of the blood pump, or the commanded position of the valves on the blood pump and controller commanded pumping operation. The Data Out signal from a conductivity circuit similar to that shown in FIG. 37 that is connected to the patient as described above may be referred to as the Access Disconnect Sensor signal or ADS signal. In one embodiment, the ADS signal is the electrical impedance between the probes in the connectors 106, 128 shown in FIG. 40. In another embodiment, the ADS signal is a filtered value of the Data Out signal in FIG. 37 or measured electrical impedance between the probes in the connectors 106, 128 in FIG. 40. Other electrical quantities may be calculated from the measured electrical impedance or from the ADS signal, including but not limited to: filtered values of the impedance at a variety of time constants; time derivative of the impedance: averaged values of the impedance; peak values; peak values over a moving window of data; minimum values over a moving window of data, or averaged values over a moving window of data.

Referring again to FIG. 40, in an embodiment, upon detecting a needle dislodgment or access disconnection, the controller commands a freeze state, stopping the blood pump blood 13 and/or closing the occluder 226 and signaling the patient. In the case of an access disconnection the controller signals the patient or user to check the condition and/or positioning of their needles 102, 132. Once this is completed, the patient may be given the option to resume treatment or stop treatment. The patient may be allowed to resume treatment if they confirm that the needles are properly positioned. If the patient chooses to resume treatment, the controller will open the occluder 226, restart the blood pump 13 and other components of the hemodialysis apparatus 220 as needed to restart therapy. If the patient chooses to end treatment without reestablishing vascular access, the controller may direct the patient to disconnect from the machine and the controller will initiate end of treatment procedures without returning the blood in the extracorporeal circuit 100 to the patient. In one embodiment, the controller may communicate to the patient via the control interface 55 (FIG. 7)

In an example, the controller runs a software sub-routine or function referred to here as the ADS algorithm that identifies an access disconnection based on the ADS signal and other inputs that may be generated by other sensors, or by other software components in the controller. The controller, upon receiving an access disconnection signal from the ADS algorithm, will control the blood pump, occluder and/or control interface to minimize loss of blood and allow the patient to select the next action for the hemodialysis machine 200. In other embodiments, a separate machine-level controller may be programmed to track and/or filter the ADS signals, set signal thresholds, timing or pump stroke counters, flags or triggering events, and transmit one or more triggering signals to a higher level controller (e.g. therapy controller and/or user interface controller) as needed to initiate a suspension of pumping operations, occlusion of blood lines, a user notification, or a user command.

As noted above, an access disconnection will break the conductive path between the probes and generate a high ADS signal. The ADS algorithm preferably identifies an access disconnection based on the ADS signal, and ignores other high ADS signals due to a variety of non-dislodgement events. Referring now to FIG. 40, non-dislodgement events may include but are not limited to an air bubble in either of the needle lines 104, 130, a kinked, pinched or occluded needle line 104, 130, a compressed vein between the two needles 102, 132, or electrically grounding the patient. The ADS algorithm may be able to discriminate between a spurious ADS signal and one that is likely to represent an access disconnection through one or more software subroutines, functions or classes that process the ADS signal and other information received from the controller. Higher order functions in the controller software may then control the blood pump, occluder and/or control interface to minimize loss of blood and allow the patient to select the next action for the hemodialysis machine 200.

The ADS algorithm is preferably insensitive to a number of physical conditions that may change the ADS signal, including but not limited to: changes in the hematocrit level during treatment, changes in the hematocrit level from day to day and from patient to patient, differences in the vein, fistula or access due to differences in patient characteristics, or the type of needle used, The ADS algorithm preferably rejects false needle dislodgment signals due to such changes. The ADS algorithm may detect needle dislodgements and differentiate other events causing a high ADS signal using one or more multi-step methods. One embodiment of the ADS algorithm includes a first step in which a potential needle disconnect is recognized based on a first value derived from the measured electrical impedance between the probe on the venous line and the probe on the arterial line exceeding a first threshold value, triggering the initiation of a counter. In the second step, a second value derived from the measured impedance is monitored as the counter is incremented. If the second derived value drops below a second threshold value, the counter is stopped. In the third step, a needle dislodgement or access disconnection is declared if the counter reaches a third threshold value and the second derived value remains above the second threshold value.

In an alternative embodiment, the multi-step ADS algorithm may comprise the following steps. In the first step, a potential needle disconnect is recognized based on a first value derived from the measured electrical impedance between the probe on the venous line and the probe on the arterial line. If the first value exceeds or crosses a first threshold value, a counter is initiated. In the second step, a second value derived from the measured impedance is monitored as the counter is incremented. If the second derived value drops below or crosses a second threshold value, the counter is stopped. In the third step, an occlusion is declared and the blood lines are occluded if the counter reaches a third threshold value and the second derived value has not crossed the second threshold value. In the fourth step, the occlusion declaration is replaced by needle dislodgment declaration, if a third value derived from the measured electrical impedance crosses a fourth predetermined threshold value.

In an alternative embodiment, the multi-step ADS algorithm may comprise the following steps. In the first step, a potential needle disconnect is recognized in based on a first value derived from the measured electrical impedance between the probe on the venous line and the probe on the arterial line exceeding or crossing a first threshold value, and a counter is initiated. In the second step, a second value derived from the measured impedance is monitored as the counter is incremented. If the second derived value drops below or crosses a second threshold value, the counter is stopped. In the third step, if the second value crosses the second threshold value, then the blood pump is paused and all the valves are closed except the outlet valve from the pump chamber delivering blood. That pump chamber is fully delivered and then the delivery pressure is reduced to near-atmospheric pressure. In a fourth step, a needle dislodgement or access disconnection is declared if a third value derived from the measured electrical impedance between the probe on the venous line and the probe on the arterial line exceeds or crosses a third threshold value related to the first threshold value.

Figure 62:
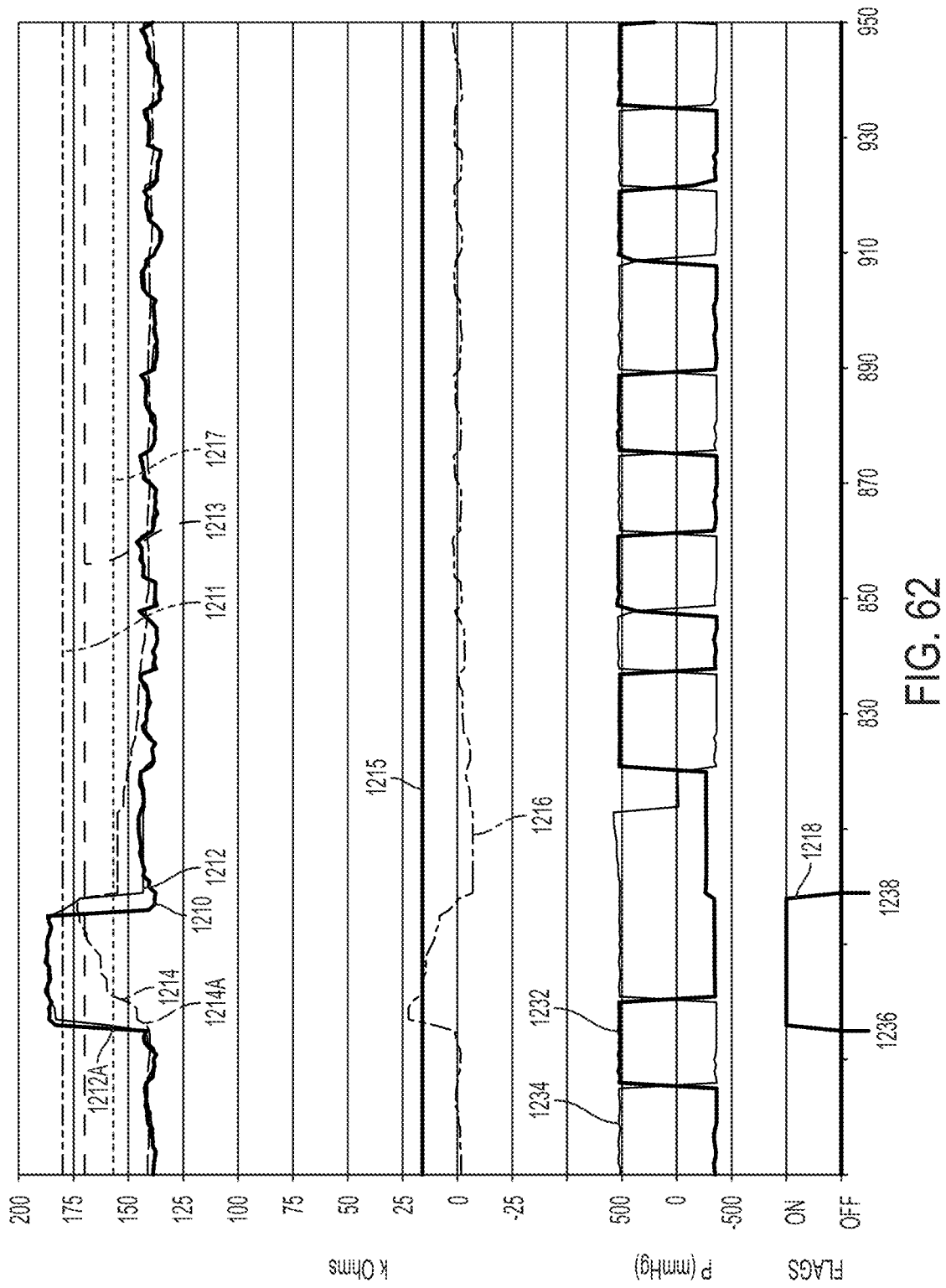
FIG. 62 shows raw and processed signals from the Access Disconnect Sensor system and pumping pressures for a non-dislodgement event.
Figure 63:
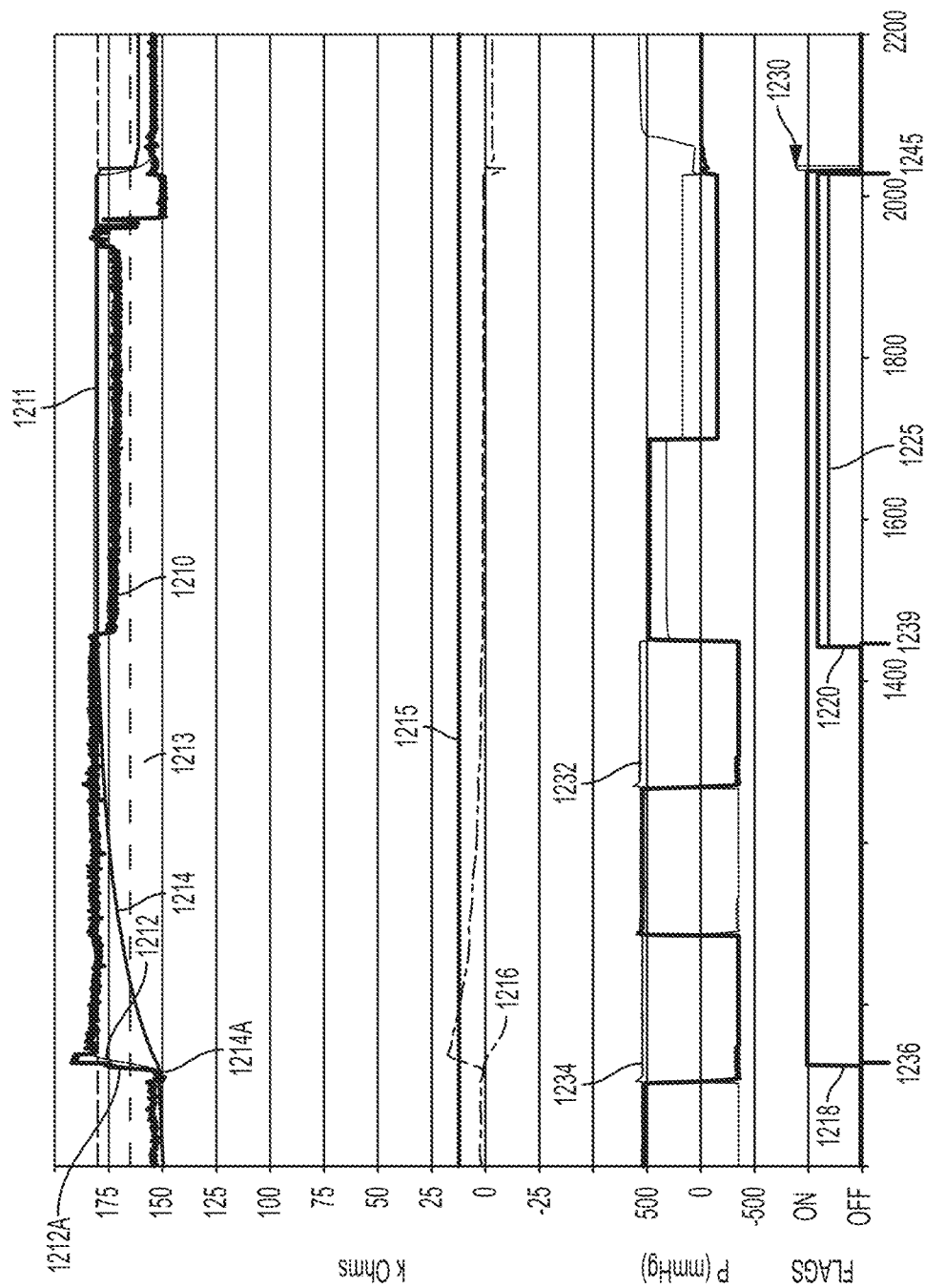
FIG. 63 shows raw and processed signals from the Access Disconnect Sensor system and pumping pressures for an access disconnect event.

The ADS algorithm can be implemented in several ways. The embodiments will be described with reference to test data plotted in FIGS. 62-64. In these tests, the venous needle and arterial needle were placed in a common beaker of bovine blood and a simulated dialysis therapy was initiated. FIG. 62 plots the results for a test in which the venous line was occluded for several seconds and then unoccluded, which temporarily raised the ADS signal level. FIG. 63 plots the results for a test in which the venous line is removed from the beaker, simulating a needle disconnection. FIG. 62 presents plots of the ADS related signals, blood pump pressures and software flags that may be part of the calculations in the ADS algorithm. The upper part of the plot in FIG. 62 plots the ADS signal and a plurality of derived signals, along with thresholds used in the ADS algorithm. The signals are plotted in resistance units of k-ohms. The state of one or more software flags are graphed at the bottom of the plot in FIG. 62. The software flags are binary values or boolean values stored in memory that are either off or on, which may be represented as being equal to 0 or 1 respectively. The blood pumping pressures (mm Hg) are located between the plots of software flags and the ADS derived signals in FIG. 62. In this example, the two blood pumps alternate pulling blood from the arterial line by applying a negative pressure and delivering blood to the venous line by applying a positive pressure. The pressure of the first blood pump is plotted as the thick line 1232 in units of mmHg. The pressure of the second blood pump is plotted as the thin line 1234 in units of mmHg. The nearly vertical lines represent end of stroke for each blood pump pod. The ADS signals, pumping pressures and flags are plotted against an index of measurements. In the plotted example the index is updated at 20 Hz, so horizontal axis values can be converted into temporal units of seconds by dividing the values by 20.

In FIG. 62, the ADS signal 1210 rises sharply from approximately 135 Kohms to a value of approximately 180 Kohms at time element 1236. The ADS signal 1210 returns to approximately 130 at time element 1238.

In one embodiment, the ADS algorithm starts a counter when the ADS signal 1210 crosses a first predetermined threshold 1211, and the counter continues to increment until the ADS signal crosses a second predetermined threshold 1213. The ADS algorithm declares an access disconnection if the counter reaches a predetermined value. The counter may be reset to zero when the ADS signal crosses the second threshold 1213 or an access disconnection is declared. In one example, the counter increments by time and the ADS algorithm declares an access disconnection when the counter exceeds a predetermined amount of time. In another example, the counter increments by blood volume and the ADS algorithm declares an access disconnection when the counter exceeds a predetermined volume of blood. In another example, the counter increments by blood pump strokes and the ADS algorithm declares an access disconnection when the counter exceeds a predetermined number of blood pump strokes. In one example, the ADS controller will declare a needle dislodgment if the ADS signal exceeds 180 Kohms and remains above 175 Kohms during a plurality of blood pump strokes, or, for example, when more than three blood pump strokes are completed.

An example of a high-ADS event that does not trigger an access disconnection signal is shown in the FIG. 62, in which the action of the blood pump is shown by the pump pressures 1232, 1234. It can be seen that one blood pump stroke is completed after the ADS signal 1210 exceeds the first threshold 1211 at time element 1236 and a second blood pump stroke is started, but is not completed before the ADS signal 1210 drops below the second predetermined threshold 1213 at time element 1238.

An example of a high-ADS event that does trigger an access disconnection signal is shown in the FIG. 63, in which the ADS signal exceeds the first threshold 1211 at time element 1236. Three blood pump strokes are completed by both pumps combined as evidenced by the pump pressures 1232, 1234, by time element 1239, at which time an access disconnection signal 1220 is triggered by the ADS algorithm. Upon triggering of the access disconnection signal, the controller sets a 'frozen' flag 1225 and enters a frozen state, during which the blood pumps are stopped and the occluder is closed (i.e. occluding the fluid lines). (As noted above, these functions may be performed by a single physical controller employing a plurality of software-base subroutines, or may be performed by two or more physical controllers interacting to coordinate the functions triggered by flags or counters). The occluder may be closed immediately and the controller may record the percent-stroke-completion time so that the blood pump may be allowed to resume the current stroke upon restart of pumping operations. At time element 1245, the user commands a resumption of therapy, plotted as 1230, that commands the controller to open the occluder and restart the blood pumps.

In an embodiment, the ADS algorithm may include programming a controller to ignore ADS signals while the 'frozen' flag is set and any time the blood pump is not moving blood or other fluids through the venous line or arterial line.

In another embodiment, the ADS algorithm sets a provisional disconnect flag based on the ADS signal, starts a counter, and then declares an access disconnection if the provisional flag is not cleared before the counter reaches a predetermined value. As described above the counter in one example may increment time and the predetermined value is a period of time. In another example, the counter measures blood flow and the predetermined value is a volume of blood pumped. In another example, the counter increments blood pump strokes and the predetermined value is a number of blood pump strokes. In one example, the ADS algorithm sets the provisional flag if the ADS signal exceeds a first predetermined threshold. In an exemplary embodiment, that first threshold is set at about 180 Kohms. The ADS algorithm will remove or clear the provisional flag if the ADS signal drops below a second threshold. For example, the second threshold may be set to about 175 Kohms. In an exemplary embodiment, the ADS algorithm will declare an access disconnection to higher software levels in the system or system controller if the provisional flag is set for a duration of three or more blood pump strokes (although the threshold number of pump strokes can be set to a different number, if desired).

An example of an embodiment comprising the provisional flag reacting to a high ADS signal event that is not an access disconnection is plotted in FIG. 62. The provisional flag 1218 is set at time element 1236 when the ADS signal 1210 exceeds the first threshold 1211 at time element 1236. At time element 1238, the provisional flag 1218 is cleared when the ADS signal 1218 drops below the second threshold 1213. An access disconnect is not signaled by the ADS algorithm in FIG. 62 because the provisional flag 1218 was cleared before three blood pump strokes were completed.

Applying this same embodiment comprising the provisional flag to an actual access disconnection results in the plot shown in FIG. 63. At time element 1236, the provisional flag is set when the ADS signal 1210 exceeds the first threshold 1211. The ADS signal 1210 remains above the second threshold 1213 and the provisional flag 1218 remains set through the time representing three completed strokes by the pumps combined, as plotted by the blood pump pressures 1232, 1234. At the completion of the third stroke at time element 1239, the ADS algorithm signals an access disconnection and sets the disconnection flag 1220. Upon receiving the access disconnection signal, the controller sets a 'frozen' flag 1225 and enters a frozen state, during which the blood pumps are stopped and the occluder is closed. The occluder may be closed and the pumps stopped immediately; or the blood pump, if pulling from the arterial line may be allowed to complete the current stroke in order to be in a start position to restart pumping. At time element 1245, the user commands a resume, plotted as 1230, that commands the controller to open the occluder and restart the blood pumps.

In another embodiment, the ADS algorithm sets the provisional flag if the ADS signal shows a sharp increase as could be expected in the case of an access disconnection, and clears the provisional flag when the ADS signal drops below a value calculated from the ADS signal when the provisional flag is set. In one example, the ADS algorithm sets the provisional flag if the time derivative of the ADS signal exceeds a first predetermined value. In this example the ADS algorithm records the ADS signal when the provisional flag is set as ADS-entry. The provisional flag is cleared only when the ADS signal drops below ADS-exit which is a predetermined function of ADS-entry. In a further example, the provisional flag may be cleared when ADS signal drops below ADS-exit and the ADS derivative drops below a second predetermined value.

Unfiltered ADS signal data may not be able to provide adequate discrimination between a signal change due to a vascular access disconnect event and other incidents (such as, e.g., signal noise, arm movement, variations in blood composition and conductivity, signal drift during the course of a therapy, or small occlusions developing at the catheter or fistula sites). The baseline signal may also vary from patient to patient, may depend on the anatomy or quality of the fistula or graft, or may vary based on its location on the body. Preferably, an access disconnect algorithm should not require setting individualized parameters based on a number of these variables. Merely filtering the raw signal data may not be enough to resolve the issue of detecting a disconnect event in a reliable and timely manner independent of patient-specific variables. One step toward providing a more reliable detection algorithm can involve the use of provisional flags and timers to eliminate the erroneous declaration of a disconnect event due to a short-lived 'noise' event. To address the effects that longer lasting variables may have on the algorithm, it may be useful to compare the signal data with its filtered counterpart. In one embodiment, a difference may be taken between the raw signal and its filtered counterpart, the filtering being sufficient to isolate a pre-existing bias or a drift over time of the baseline signal. Alternatively, a mildly filtered signal can be compared to a more heavily filtered version of the same signal—a difference between the signal filtered with a first time constant and the signal filtered with a second longer time constant. If a difference is taken between the two values, a threshold impedance can be set at which a triggering event can be declared. The threshold impedance value can be programmed to change in proportion to a change in value of the more heavily filtered version of the signal. If a ratio between the two values is taken, then a threshold ratio can be set at which a triggering event is declared.

Again referring to FIGS. 62, 63, in another embodiment (designated as the delta ADS embodiment), the ADS algorithm compares two filtered values of the ADS signal 1210 that are filtered with different time constants. In the delta ADS embodiment, the controller looks for a rapid increase in the ADS signal as compared to the longer term average value of the ADS signal by monitoring the difference between an ADS value filtered with a short time constant (lightly filtered) and an ADS value filtered with a longer time constant (more heavily filtered). In the delta ADS embodiment, the controller evaluates a rapid increase in the ADS signal as indicative of a needle dislodgement or access disconnect event. The delta ADS embodiment may be less sensitive to differences in the baseline impedance that varies from patient to patient, day to day or during a treatment. The baseline electrical impedance may change from therapy to therapy for a number of reasons, including but not limited to different hematocrit levels, different vascular access locations, and different needles. The baseline electrical impedance can change during a treatment due to changes in the needle position, variation in the hematocrit level, or various other causes. At least some of the thresholds in the delta ADS embodiment are differences between the filtered values (slowADS, medADS), so that changes in the absolute value or baseline value of the ADS signal (e.g., due to signal drift or other factors) are less likely to trigger a false positive detection value. In another embodiment, the controller can take the ratio between the two filtered values, and set the provisional flag based on a pre-determined value for the ratio.

The delta ADS embodiment of the ADS algorithm calculates a value—deltaADS 1216—that is the difference between the faster filtered (or more lightly filtered) ADS (medADS) 1212 and the slower filtered (or more heavily filtered) ADS value (slowADS) 1214. A provisional flag 1218 is set when the deltaADS value 1216 is greater than a third predetermined threshold value 1215. (The third predetermined threshold value can be adjusted upward or downward in proportion to the amount that the slow-filtered ADS value increases or decreases, for example if there is a signal drift). The values of medADS 1212 and slowADS 1214 may be recorded when the provisional flag is set as medADS-entry 1212A and slowADS-entry 1214A. An ADS-exit value 1217 may be calculated as a predetermined function of medADS-entry 1212A and slowADS-entry 1214A. The provisional flag is cleared when the medADS value 1212 value drops below ADS-exit 1217. In one example, a provisional flag is only cleared when both (1) the medADS value 1212 drops below ADS-exit 1217 and (2) deltaADS 1216 is below a fourth predetermined value (not shown).

In some examples of the delta ADS embodiment, the slowADS and/or the medADS values may be reset by the controller after particular pump events. The slowADS and medADS values may be reset to improve detection and/or to reduce false detection of access disconnect in particular situations. In one example, the medADS value is set equal to the slowADS value anytime the blood pump resumes from a freeze state to minimize false detection values.

In another example of the delta ADS embodiment, after a Temp Disconnect State, both the slowADS and the MedADS values are reset to the unfiltered ADS value when the blood pump resumes operation. In the Temp Disconnect state, the user may temporarily disconnect the BTS lines 108, 126 (FIG. 40) from the needle lines 104, 130 and join the BTS lines 108, 126 to each other to allow the blood pump 13 to flow blood through both of the BTS lines. The Temp Disconnect state ends after the user has reattached the needle lines 104, 130 to the BTS lines 108, 126.

In a further modification of the delta ADS embodiment, the slowADS value may be reset to the medADS value while the blood pump 13 is operating in order to improve detection of needle dislodgements. The first step of this embodiment detects potential dislodgements when the medADS is greater than the slowADS by a predetermined amount as described above. In certain situations the ADS signal drops quickly and the slowADS value responds more slowly and is temporarily greater than the medADS value. In order to maintain the ability to detect potential needle dislodgements, the controller of the ADS algorithm resets the slowADS value to the medADS value when the slowADS value is greater than the medADS by a predetermined amount. In certain conditions during a therapy, the ADS signal may rapidly shift to a steady higher value. A rapid and persistent shift of the average or baseline ADS signal may cause repeated false detects of access disconnects. In one example of an embodiment, the slowADS value may be reset to the medADS value when resuming therapy after a freeze state caused by repeated detection of an access disconnect or an occlusion. In one example, the slowADS value is reset to the medADS when the user elects to resume therapy after the third detection of an access disconnect or occlusion within the same therapy session.

In one example, the slowADS value is reset to the medADS value when the user elects to resume therapy after the third detection of an occlusion within the same therapy session. In this example, an occlusion counter is incremented each time therapy is resumed after a freeze state caused by an occlusion in the BTS or needle lines. The occlusion counter is set to zero at the start of therapy and may be reset to zero if the controller under the ADS algorithm detects an access disconnect. The counter is also reset to zero when the slowADS value is reset to the medADS value.

Referring now to FIGS. 62, 63. In an example implementation, the medADS value 1212 is the first order filtered value of the ADS signal 1210 with a time constant of 1 second. The slowADS value 1214 is the first order filtered value of the ADS signal 1210 with a time constant of 20 seconds. The provisional flag is set when deltaADS 1216 exceeds a third predetermined value of 16 Kohms. The ADS-exit 1217, for example, can be set equal to ⅞*medADS-entry+⅛*slowADS-entry. The fourth predetermined threshold to clear the provisional flag can be set to 2 Kohms.

An example of an embodiment comprising the two filtered values of the ADS signal reacting to a high ADS signal event that is not an access disconnection is plotted in FIG. 62. The provisional flag 1218 is set at time element 1236, when the deltaADS 1216 exceeds the third threshold 1215, but the medADS value 1212 drops below the ADS-exit value 1217 before three complete strokes have occurred as evidenced by the pump pressures 1232, 1234.

Applying this same embodiment comprising the two filtered ADS values and the provisional flag to an actual access disconnection results in a plot as shown in FIG. 63. The deltaADS 1216 exceeds the third threshold 1215 at time element 1236 and the provisional flag 1218 is set. The medADS value 1212 remains high through the completion of the next three blood pump strokes as plotted by 1232, 1234. At the completion of the third stroke at time element 1239, the ADS algorithm signals an access disconnection and sets the disconnection flag 1220. Upon receiving the access disconnection signal, the controller sets a 'frozen' flag 1225 and enters a frozen state, during which the blood pumps are stopped the occluder is closed. At time 1245, the user commands a resume, plotted as 1230, that commands the controller to open the occluder and restart the blood pumps.

In one embodiment, the ADS algorithm declares an access disconnection when the ADS signal drops below a low predetermined threshold for more than a predetermined period of time or while more than a predetermined amount of blood is pumped or while more than a predetermined number of blood pump strokes occur. In one example, the provisional flag is set when the ADS signal drops below a first low threshold and only clears when the ADS signal rises above a second low threshold. The ADS algorithm declares an access disconnection, if the provisional flag is set for more than a predetermined period of time or while more than a predetermined amount of blood is pumped, or while more than a predetermined number of blood pump strokes occur. In one example the first low threshold may be set to 20 k-ohms and the second low threshold may be set to 25 k-ohms.

In another embodiment, the ADS algorithm declares an access disconnection when an ADS Signal Test fails. The ADS Signal Test comprises monitoring the ADS signal while executing a pump delay operation. The pump delay operation may include: completing the stroke of the delivering pump pod, then pausing both blood pump pods and the inner dialysate circuit; closing all the valves on the blood pump and preferably the valves between the inner dialysate circuit and the dialyzer; leaving open the outlet valve of the delivering pump pod; then fully delivering blood from the delivering pod by applying a first predetermined pressure for a first predetermined time; lastly, reducing the applied pressure on the pump plunger or diaphragm to a lower second pressure that is near, but greater than atmospheric pressure and holding that second pressure for a second predetermined period of time. In one embodiment, the second pressure applied to the pump plunger or pump diaphragm of a pod pump is near atmospheric in order to apply near zero force on the plunger and fluid in the pump chamber. The ADS algorithm will signal an access disconnection immediately if the provisional flag is set, while the second pressure is applied. The provisional flag may be set if the ADS signal meets any of the following conditions including: ADS signal above a first threshold; derivative of ADS signal above a second threshold; deltaADS signal above a third threshold. The controller will take one or more actions upon the ADS algorithm signaling an access disconnection including but not limited to closing the occluder, stopping the blood pump, signaling the user. The controller may signal the user to inspect the placement of the needles and may allow the user to resume treatment if the needles are properly inserted.

In one embodiment, the ADS algorithm executes the ADS Signal Test only when the provisional flag has been set and cleared without signaling an access disconnection or an occlusion. In this embodiment the ADS algorithm uses the ADS Signal Test to identify needle dislodgments, where either the venous or arterial needle has been removed from vascular access site, but reestablished a conductive path to the other needle outside of the vein or fistula of the vascular access site. In one experiment with the arterial and venous needles in a simulated fistula and in which the venous needle was pulled out of a simulated fistula, the ADS signal initially rose, then returned to a lower value as the blood flow from the dislodged venous needle contacted the arterial needle and reestablished a conductive path. The ADS Signal Test stopped the blood flow, and the resulting high resistance through the blood caused a high ADS signal, which the ADS algorithm detected and signaled as an access disconnection. A similar algorithm can be used in an in-vivo setting.

The ADS signal test can be used at any time to identify a needle dislodgement based on other detected conditions (e.g., air-in-line detection), or through a pre-programmed periodic monitoring protocol during a therapy. Any event that creates an electrical discontinuity between the arterial and venous needles can be detected by the ADS signal test. For example, if a conductive path is re-established between a dislodged needle and its counterpart via a collection of externally pooled blood or other fluid, the introduction of a small air bubble at the distal end of either needle can create an electrical discontinuity sufficient for the controller to recognize that a vascular disconnect has actually occurred. In a compliant blood circuit, the forward momentum of a column of blood in the venous line may be enough to cause a small air bubble to enter the tip of the dislodged needle. Such an air bubble may also enter the distal end of the needle, for example, during a pump delay operation.

Figure 64:
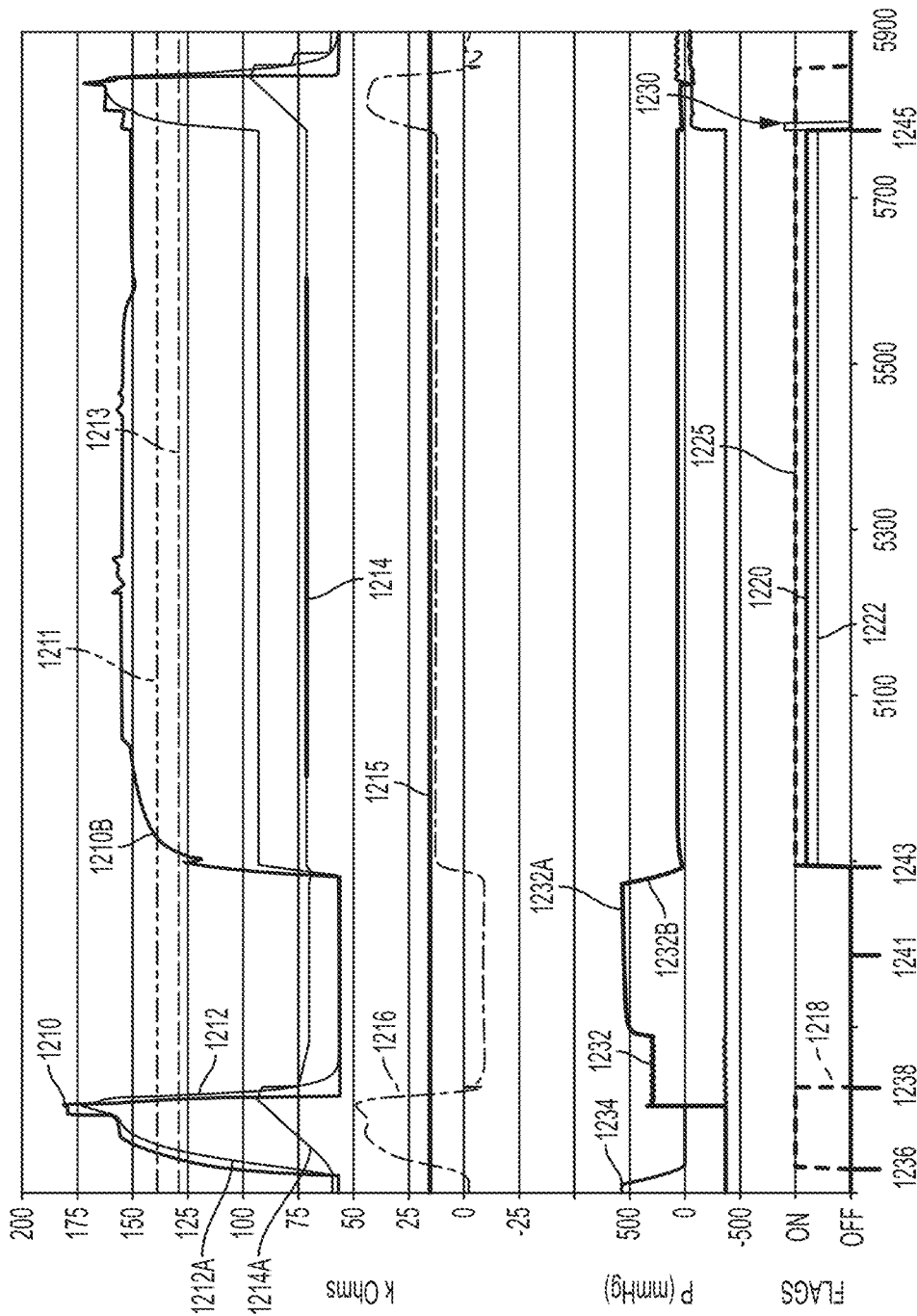
FIG. 64 shows raw and processed signals from the Access Disconnect Sensor system, pumping pressures and the ADS Signal Test for an access disconnect event.

An example of the applying the ADS Signal Test after setting and clearing a provisional flag is presented in FIG. 64. In the test plotted in FIG. 64, the venous needle and arterial needle are initially placed in a first beaker of bovine blood and a simulated dialysis therapy is initiated. The venous line then is removed from the first beaker and placed in a second beaker so that the venous needle is not touching blood pool at the bottom of the second beaker; and lastly a metal wire electrically connects the blood in the two beakers. The ADS signal temporarily rises as the venous needle is removed from the first beaker. Once the venous needle is located in the second beaker, the blood stream from the venous needle, blood pool and wire reestablish an electrical connection back to the arterial needle as long as blood flows through the venous needle. Using the ADS Signal test, the controller stops the blood flow through the venous needle and looks for a rise in the ADS signal to detect needle dislodgement.

The ADS signal rises rapidly and sets the provisional flag 1218 at time element 1236. The provisional flag may be set by the ADS signal 1210 exceeding the first threshold 1211 or by deltaADS 1216 exceeding the third predetermined threshold 1215. At time element 1238, the ADS signal 1210 drops and clears the provisional flag 1218 based on the ADS signal 1210 dropping below the second predetermined threshold 1213, or the medADS 1212 dropping below ADS-exit. The ADS Signal Test begins by applying high pressure 1232A to the blood pump pod that was delivering blood when the provisional flag 1218 cleared at time element 1238. After a period of time, the pressure applied to the delivering blood pump pod was reduced to approximately atmospheric pressure 1232B at time 1243. The provisional flag 1216 was reset and an access disconnection 1220 was signaled at time element 1243 because the ADS signal 1210B exceeded the first threshold 1211 and or deltaADS 1216 exceeded the third threshold 1215.

The ADS algorithm may combine some or all of the above thresholds to set the provisional flag and the corresponding tests to clear the flag. Similarly, an access disconnection may be signaled for any of criteria described above. Referring now to FIG. 63, in one embodiment, the provisional flag will be set if any of the following conditions occur: the ADS signal 1210 exceeds a first threshold 1212; deltaADS 1216 exceeds a third threshold 1215, the ADS signal drops below a low threshold (not shown) or the derivative of the ADS signal exceeds a fifth predetermined threshold. The provisional flag may be cleared based on conditions that correspond to conditions that set the flag in the first place. For example, if the flag was set by the ADS signal exceeding the first threshold 1211, then the flag only clears when the ADS signal drops below the second threshold 1213, or if the flag was set by deltaADS 1216 exceeding the third threshold, then the flag only clears when the medADS 1212 drops below ADS-exit 1217 (see, e.g., FIG. 62). In another example the flag may be cleared by requiring one or more conditions described above. The ADS algorithm signals the higher software levels or the rest of the controller that a needle has dislodged if the provisional flag has been continuously set for a period of time, while a quantity of blood has been pumped or if a number of blood pump strokes have occurred.

The measured resistance values reported in FIGS. 49, 62-64 were made when the binary digital signals 131, 144 in FIGS. 37, 38 were alternating at a frequency of approximately 35 kHz. The frequencies of the digital signals 131, 144 were sufficiently high to allow capacitive coupling between the wires in the arterial and venous lines 108, 126 (FIG. 40). The parallel capacitive circuit reduced the measured resistance values throughout the tests, but most significantly during the open circuit conditions, when the venous needle was removed from the first beaker.

Figure 65:
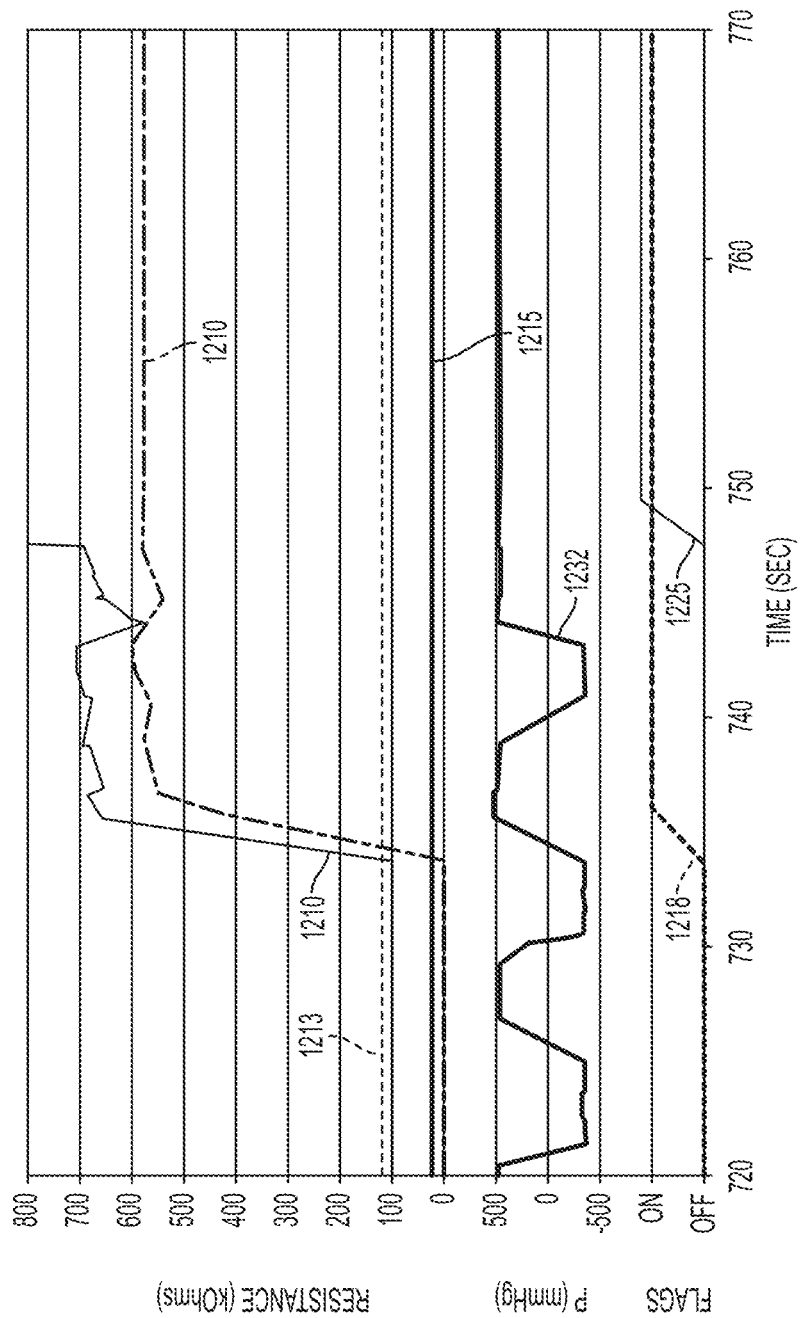
FIG. 65 shows raw and processed signals from the Access Disconnect Sensor system, pumping pressures and the ADS Signal Test for an access disconnect event, with longer duration half cycles than shown in FIGS. 62-64.

In contrast, the measured resistances plotted in FIG. 65 are from an experiment in which the duration of the high half-cycles (FIG. 38) are sixteen times longer than the half-cycles in the experiments plotted in FIGS. 49, 62-64. In the experiment plotted in FIG. 65 the duration of the half cycle is approximately a quarter millisecond. In terms of frequency the binary control signals 131, 144 alternate at a frequency of 2174 Hz during the active phase in the test that is plotted in FIG. 65.

Referring now to FIG. 38, the signals 131 and 144 in one example comprise pulses each having a duration of 420 microseconds. The pulses occur in sets of 6 pulses that repeat every 80,000 microseconds. Between the sets of pulses, the signals 131, 144 are both low. The periods of low signal between the pulses may limit the amount of current leakage that reaches the patient.

The blood flow circuit tested included a pair of membrane-based blood pumps arranged on a blood pump cassette 13 shown in FIG. 47, a dialyzer 14, a venous return air trap 122, an arterial blood tubing set 108, a venous blood tubing set 126, arterial and venous connectors 106 and 128, and catheter tubing sets 104, 130 connected to vascular access needles 102, 132 as shown in FIG. 40. The probes 3 of the circuit in FIG. 37 are mounted in the arterial and venous connectors 106,128. The needles 102, 132 were placed in a container holding anticoagulated bovine blood. The blood tubing set 108 and 126 was approximately six feet long, and the catheter tubing sets 104 and 130 were approximately two feet long or less. The needles were alternately manually placed in or withdrawn from the container during blood flow to simulate disconnection of a needle from a fistula or blood vessel. The period before 730 on the horizontal axis in FIG. 65 represents the times during which the needles were submerged in the blood in the container.

Continuing to refer to FIG. 65, the electrical resistance or ADS signal 1210 during these periods averaged 100 k ohms. At approximately 735 seconds, one of the needles was completely removed from the container, creating a fully open electrical circuit. The electrical resistance measured increased to approximately 670 Kohms. The controller set a provisional flag 1218 based on the large change in the ADS value 1210. The ADS value remained high for the next three pump strokes and a needle dislodgement was declared at approximately 748 seconds and the disconnect flag 1225 was set. The thick line 1232 plots one of the blood pump pod pressures that range from (−)500 to 500 mmHg. Each transition between −500 and 500 mmHg represents a stroke of one of the blood pumps. Blood pump operation is frozen when the disconnect flag 1225 is set and the occluder 226 in FIG. 40 is closed. Continuing to refer to FIG. 40, closing the occluder 226 blocks the conductive path from one electrode A at connector 106 through the blood set tubing 108, 126, the blood pump 13, blood pump lines 112, 116, dialyzer 14, dialyzer line 120 and air trap 122 probe B at connector 128. As described previously the conductive path through the blood set tubing and cassette is a parallel path to conductance through the access site. In cases in which at least one fistula needle is dislodged from the vascular access, the ADS value may become approximately equal to the resistance through the blood tubing set and pump such as the ADS value 1210 between 735 and 748 seconds in FIG. 65. The conductive path through the blood pump is interrupted when the occluder is closed at time 748, so the measured ADS value 1210 rises sharply to values well above 1000 Kohms. In one embodiment, the controller distinguishes between an occlusion or an air bubble in the blood tubing 104, 130 (FIG. 40) and a dislodgement of one of the needles 132, 102 from the vascular access site 134 in a two-step method. When the controller detects a needle dislodgement based on the ADS signal, the blood pump is frozen and the occluder 226 is closed. The controller initially declares an occlusion and displays the occlusion alert to the user. A needle dislodgement or Access Disconnect is not declared and the user is not alerted to a needle dislodgement until the ADS signal or a filtered value of the ADS signal exceeds a predetermined threshold. In one example, the controller does not declare a needle dislodgment until the ADS signal exceeds 1000 k ohms. One possible theory among others is that an occlusion or air bubble in the blood tubing 108, 126 will block the conductive path through the blood pump and raise the measured resistance between the probes at the fittings 106, 128 by removing one of the conductive path through the blood pump 13. In the case of an occlusion in the blood lines, 108, 126, closing the occluder does not change the conductive paths as the occlusion or air bubble had already broken the conductive path through the blood pump 13, while the conductive path through the vascular access 134 remains intact. In this case, closing the occluder does not change the ADS signal. Conversely, if one of the needles 102, 132 has pulled out of the vascular access site 134, then the only remaining conductive path between the probes is through the blood pump 13, and closing the occluder 226 closes that conductive path so the ADS signal rises sharply. In one embodiment, the ADS algorithm starts a counter when a quantity based on the ADS signal 1210 crosses a first threshold 1211 and the counter continues to increment until the ADS signal crosses a second threshold 1213. (See, e.g., FIGS. 62-64). The ADS algorithm declares an access disconnection if the counter reaches a predetermined value. The counter may be reset to zero when the ADS signal crosses the second threshold 1213 or an access disconnection is declared. In this embodiment the first and second thresholds are calculated based on the measured ADS signal 1210. The first and second thresholds may increase as the ADS signal increases. In one example, first threshold has a minimum value for ADS signals below a predetermined low value and a maximum value for ADS signals above a predetermined high value. Between the predetermined high and low ADS values, the first threshold changes proportionally to changes in the ADS value. The second threshold may depend on the ADS values in a similarly proportional manner.

In one example, the controller compares the difference of two filtered values of the ADS signal 1210 to the thresholds, in which two values are filtered with different time constants. The ADS algorithm may calculate a value deltaADS 1216 that is the difference between the faster filtered ADS (medADS) 1212 and the slower filtered ADS value (slowADS) 1214. A provisional flag 1218 is set when the deltaADS value 1216 is greater than a first threshold. In this example, the first and second thresholds are functions of the slowADS value 1214. In one example, the first threshold is 14 Kohms for slowADS values below 60 Kohms. The first threshold is 51K ohms for slowADS values above 170 Kohms. The first threshold increases proportionally with the slowADS value for slowADS values between 60 and 170 Kohms. The second threshold may be a fixed fraction of the first threshold. Alternatively, the second threshold may be a fixed value less than the first threshold.

In some embodiments, the first and second thresholds are increased during defined periods of operation to avoid false detections of needle dislodgements due to noise in the ADS signal. In one example, the first and second thresholds are increased by a fixed amount until a predetermined amount of blood has been pumped by the blood pump 13 (FIG. 40). For example, the first and second thresholds may be increased by about 150% during the first 25 blood pump strokes.

In an embodiment of the blood pump delay test, as described above, the third threshold may be larger by a predetermined factor than the first threshold. In one example of the blood pump delay test, the provisional flag is first set when an electrical quantity based on the ADS signal exceeds a first threshold. The blood pump test may be initiated when the provisional flag is cleared before a needle dislodgement is declared. The blood pump test stops the blood pump and forces all the possible blood from the pod by applying the maximum allowed pressure to the pumping pod. Next the pumping pressure is reduced the near zero and after a delay an electrical quantity is compared to a third threshold. In one example, the third threshold is a fixed factor greater than the first threshold. In an example, the third threshold may be about 150% of the first threshold. In an example, the delay before comparing the electrical quantity to the third threshold is about 10 seconds.

In an embodiment to avoid false detections while the blood pump may not be moving fluid toward the patient, the controller avoids calculating an electrical quantity based on the ADS signal and does not evaluate or compare the ADS signal or a quantity based on the ADS signal to a first threshold. In one example, the controller does not evaluate the ADS value for a plurality of strokes after the blood pump restarts from a freeze condition. The blood pump pressure may start low enough that no blood flows for the first few strokes of the pump. In one example, the controller does not evaluate the ADS signal for the first 2 strokes after resuming from a frozen condition. In another example, during a solution infusion the blood pump is paused while the outer dialysate pump pushes dialysate toward the patient. The controller does not evaluate the ADS signal while the blood pump is paused.

Optionally, the controller evaluates the electrical resistance through the needle lines 104, 130 (FIG. 40) and the vascular access site 134 in order to ensure that a needle dislodgment can be detected. When the electrical resistance through the needle lines 104, 130 and the vascular access 134 approaches the resistance value of a dislodged needle, the ADS algorithm may not detect the disconnection. In order to ensure the controller's ability to detect dislodged needles, the ADS algorithm measures the resistance of the needle lines and vascular access and compares it to a predetermined maximum allowed resistance. If the measured resistance exceeds the predetermined maximum allowed resistance, the controller may inform the user that that the ADS system may not function properly. The user may be given the option to proceed without the protection of the ADS system, or alternatively be given the choice to end therapy.

In one example, the controller allows the ADS algorithm to operate for a period of time sufficient to ensure that the needle lines are full of the patient's blood, then stops the blood pump 13 and closes the occluder 226 before measuring the patient's resistance through the needle lines and vascular access site. If the measured resistance is equal to or less than a predetermined maximum allowed resistance, the controller will restart the therapy. If the measured resistance is greater than the maximum allowed resistance, the therapy may be terminated or the user may be alerted that the ADS system is not active and allowed to choose to continue the therapy without the ADS system. In one example, blood pump executes 10 pump strokes before measuring the resistance through the needle lines and vascular access. In one example the measured allowed resistance is about 800 Kohms. In an embodiment, the ADS algorithm confirms the functionality of the ADS system by evaluating the ADS signal during one or more machine operations before starting therapy or dialyzing the patient. In one example, the ADS algorithm confirms that the ADS signal is above a predetermined minimum value while the blood pump is primed with dialysate and the occluder is open. In another example, the ADS algorithm confirms that the magnitude of the ADS signal changes substantially during the process of connecting the BTS lines 108, 126 (FIG. 40) to the needle lines 104, 130. In this example, the highest ADS signal during the connection process is compared to the lowest ADS value before the first stroke of the blood pump 13 is completed. If the difference between the highest and lowest ADS value is equal to or less than a predetermined value, the therapy will be paused and the controller will enter a freeze state. If the patient resumes the therapy, the ADS algorithm will complete one or more blood pump strokes and compare the lowest ADS value during those strokes to the highest ADS value. If the difference between the highest and lowest ADS value is equal to or less than a predetermined value, the therapy will be paused and the controller will reenter a freeze state.

Rinseback Occlusion Detection

Referring now to FIGS. 5, 5A, the ADS controller may also detect occlusions in the venous line 204 during the rinseback process. The rinseback process occurs at the end of therapy and returns blood from the blood pump 13 and dialyzer 14 to the patient. The rinseback process normally includes using the outer dialysate pump 160 and blood pump 13 to push dialysate across the dialyzer 14 and flush the blood remaining in the blood pump 13 and dialyzer 14 toward the patient through the venous line 204. The standard occlusion detection algorithm may not be able to detect an occlusion during this process.

Referring now to FIG. 40, at the end of therapy and before the rinseback operation starts, the BTS lines 108, 126 and needle lines 104, 130 are fully primed with the patient's blood. As the blood is flushed out and returned to the patient, it is slowly replaced with dialysate and the blood hematocrit decreases in the BTS and needle lines 104, 108, 126, 130. The decreasing hematocrit may lead to a change in the electrical impedance between the ADS probes mounted in the fittings 106, 128 and measured by the ADS sensing circuit similar to the circuit in FIG. 37. If the blood tubing on the venous side of the pump including lines 120, 126, 130 is occluded, then the flow of dialysate is reduced or stopped and the reduction of the hematocrit level in the tubing is attenuated. The attenuated change in the hematocrit corresponds with an attenuated reduction in the ADS signal (i.e. signal impedance or a filtered value of the signal impedance). In this way an occlusion in the venous lines 130, 126, 120 or dialyzer 14 may be detected by a reduction in the change of the ADS signal during the rinseback process.

In one embodiment, the controller records the ADS signal at the start of the rinseback process and compares it to the ADS signal at the end of the rinseback process. The controller declares an occlusion if the ADS signal at the end of the rinseback process is equal to or greater than a predetermined percentage of the ADS signal at the start of the rinseback process. In one example, the predetermined percentage is less than 100%. In another example, the predetermined percentage is 99%. In another example, the predetermined percentage comprises a range of values—e.g., 93% to 97%.

In one example, the controller records a high-rinseback-ADS value as the highest medADS value during the first 12 seconds of the rinse back process. After the rinse back process is completed, the controller records an end-rinseback-ADS value as the medADS value at the end of the rinseback process. The controller declares an occlusion if the end-rinseback-ADS value is not less than 97% of the high-rinseback-ADS value.

Occluder

As mentioned above, an occluder, such as the occluder 513 in FIG. 17, can be used to control flow through lines of a blood circuit assembly, e.g., at a point between a patient connection of the blood lines 203, 204 and other portions of the assembly. Below, various aspects of the invention relating to an occluder, which may be employed alone or in any suitable combination with other features described herein, are described, along with one or more specific embodiments.

In accordance with one aspect of the disclosed invention, an occlusion assembly for compressing at least one flexible tube, for example a pair of flexible tubes is described. The occlusion assembly includes a tube occluder comprising a mechanism configured to occlude fluid flow within one or more flexible tubes, and in certain embodiments one or more pairs of flexible tubes. In certain embodiments, the tube occluder of the occlusion assembly comprises at least one occluding member, and in a specific embodiment comprises an occluding member for each section of tubing placed within the assembly. In certain such embodiments, each occluding member is pressed or otherwise forced or urged into an occluding position by an element that slides along a side of the occluding member, causing the occluding member to pivot at its proximal end and to translate toward the tubing at its distal end. In an embodiment, the element is positioned between two occluding members and acts to spread the distal ends of the occluding members away from each other as they press against their respective tubes. In a preferred option, a main spring urges the spreading element toward the distal ends of the occluding elements into an occluding position. The spreading element may be moved against the biasing force of the main spring into a non-occluding position near the proximal ends of the occluding elements either manually through a button and linkage assembly coupled to the spreading element, or by control of a controller activating an actuator that is also coupled to the spreading element. A hinged door may be configured to cover the occluding elements and their respective sections of tubing. Activation of the actuator may be prevented if the door is not properly closed over the occluding elements. Optionally, a retention element to hold the spreading element in a non-occluding position may be enabled when the door is in an open position. Enabling the retention element allows the spreader to be held in a non-occluding position without continued application of force by a user on the button or by continued activation of the actuator. The retention element may be disabled when the door is closed, so that the spreading element may be free to be moved into and out of an occluding position, either manually or via the actuator.

Figure 50:
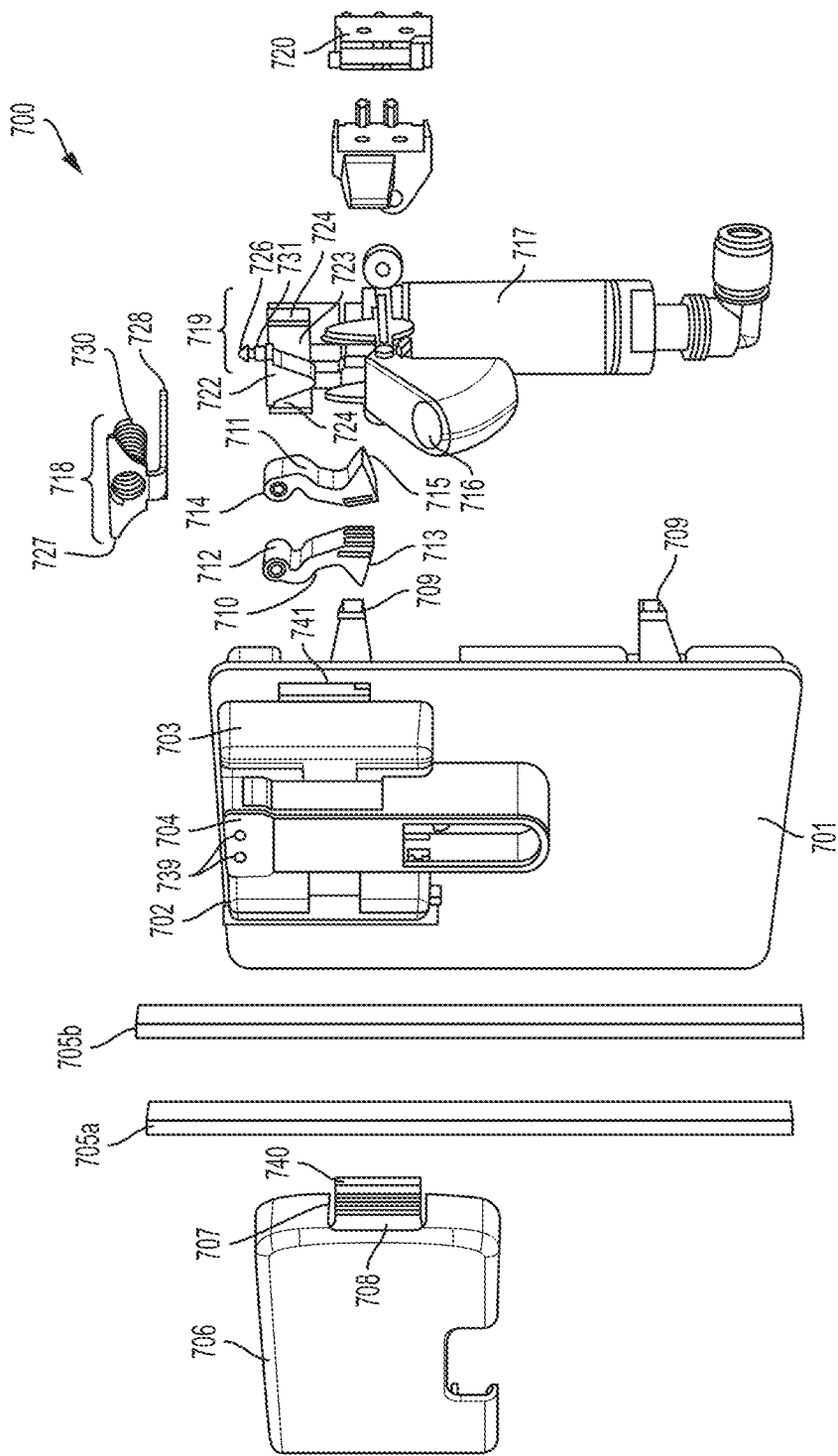
FIG. 50 shows an exploded, perspective view of an occlusion assembly from a front angle in accordance with an embodiment of the present disclosure.
Figure 51:
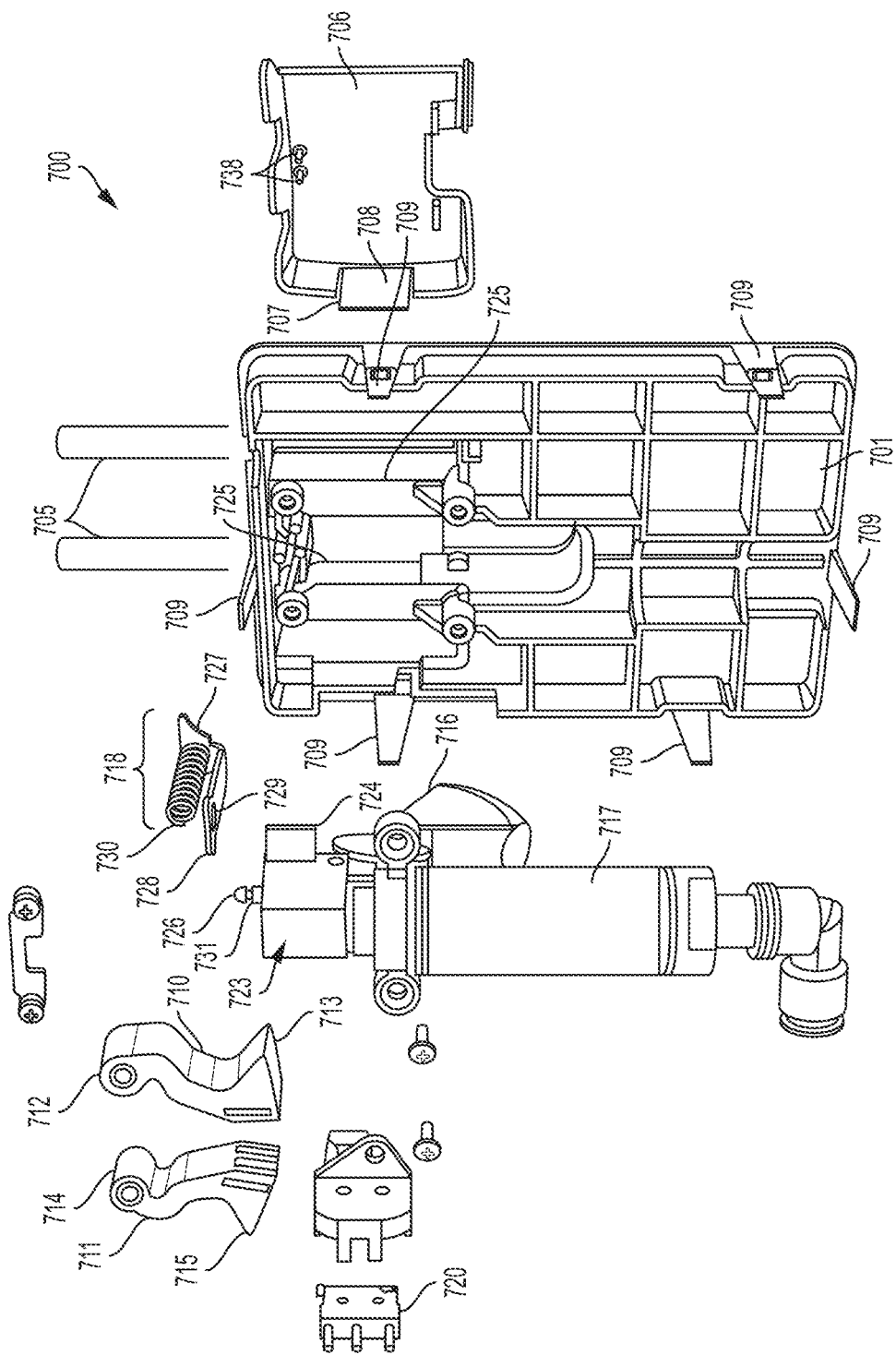
FIG. 51 shows an exploded, perspective view of the occlusion assembly of FIG. 50 from a back angle.

FIGS. 50 and 51 show exploded, perspective views of an occlusion assembly 700 in accordance with an embodiment of the present disclosure. FIG. 50 shows an exploded, perspective view of the occlusion assembly 700 from a front angle and FIG. 51 shows an exploded, perspective view of the occlusion assembly 700 from a back angle.

The occlusion assembly 700 receives a pair of tubes 705 and is configured to occlude the tubes 705 using a pinching action at approximately the same level along the length of assembly 700. The pinching action reduces the size of an inner fluid pathway of each tube 705 to restrict the flow of fluid therethrough. The occlusion assembly 700 may be used with an infusion pump, in a dialysis machine, in hemodialysis, in peritoneal dialysis, in hemofiltration, in hemodiafiltration, in intestinal dialysis, and the like.

The occlusion assembly 700 includes a frame 701. In some embodiments, the frame 701 includes tabs or snaps 709 for securing the frame to corresponding slots on a front panel of a blood filtration device, such as a hemodialysis apparatus.

Figure 52:
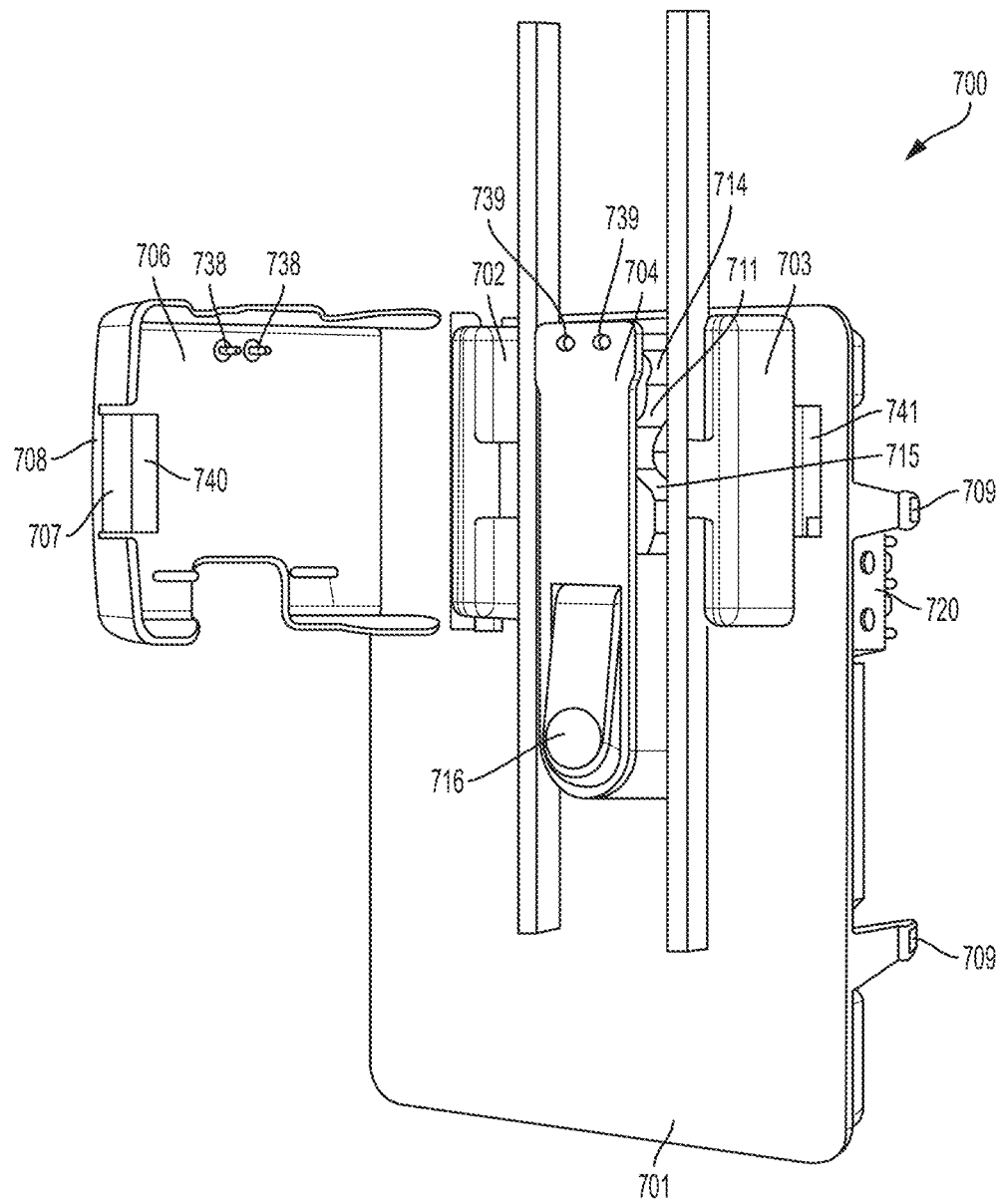
FIG. 52 shows a front, perspective view of the occlusion assembly of FIG. 50 with the door open and the button pressed to illustrate loading of a tube.
Figure 53:
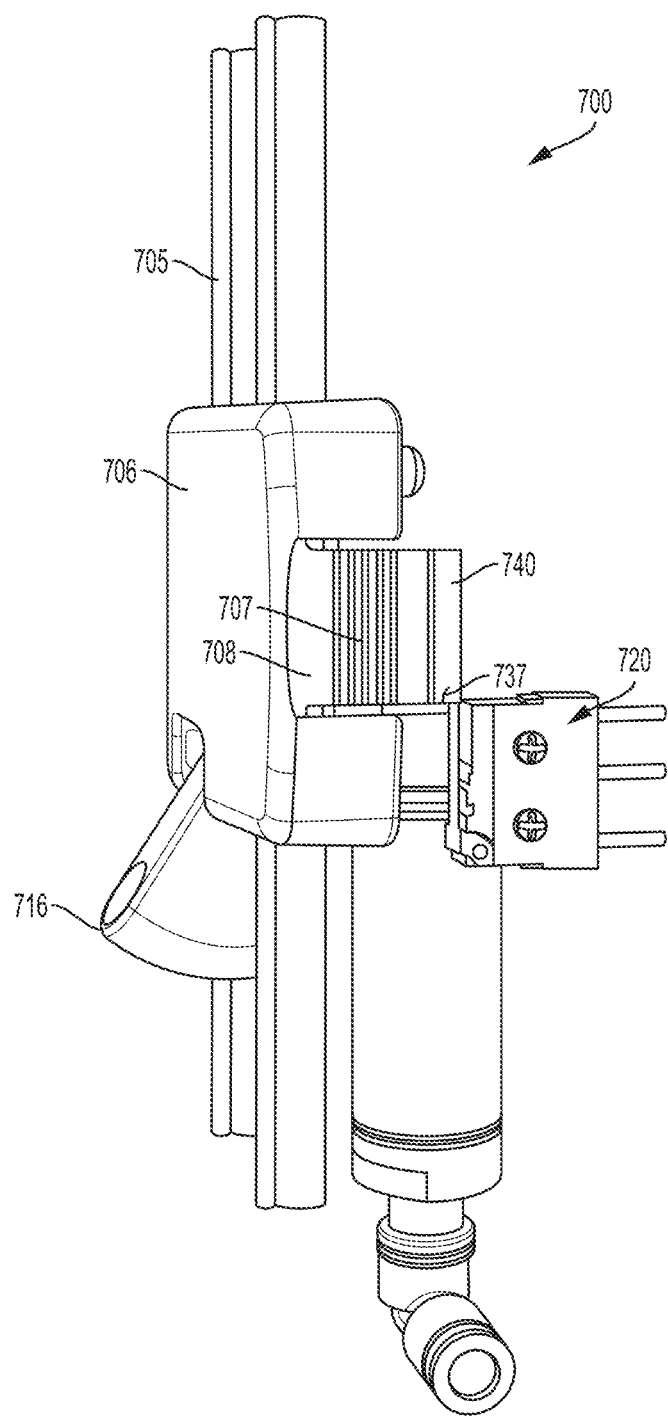
FIG. 53 shows a close-up perspective view of the occlusion assembly of FIG. 50, showing the door engaging a switch when the door is closed.

The frame 701 includes anvils or blocks 702 and 703 against which a tube 705 is compressed by the occluding ends 713 of a pair of occluding arms 710 and 711, and a tube guide 704 to position each tube 705 against blocks 702 and 703. The tube guide 704 and blocks 702 and 703 are configured to each position a tube 705 in a predetermined position adjacent to each of the blocks 702 and 703. The occlusion assembly 700 also includes a door 706 which is pivotally mounted to the frame 701. The door 706 can shut against the frame 701 to secure the tubes 705 between each of the blocks 702 and 703 and the tube guide 704. The door 706 includes a latch 707 co-molded with the door 706 via a resilient, flexible base portion (e.g., via a living hinge) 708 to secure the door 706 to the frame 701 in a closed position. However, the latch 707 could be arranged in other suitable ways, such as including a latch element that is adhered, welded, bolted or otherwise attached to the door 706. As shown in FIGS. 50, 52 and 53, the latch 707 may be pressed laterally to release a catch 740 from engagement with a corresponding slot 741 on frame 701 to open the door 706.

The occlusion assembly 700 includes two arms 710 and 711. The first arm 710 includes a pivoting end 712 and an occluding end 713; likewise, the second arm 711 includes a pivoting end 714 and an occluding end 715. The two arms 710 and 711 operate together to occlude the tubes 705 when a button 716 is released and door 706 is closed, or when an actuator 717 is deactivated.

Figure 54:
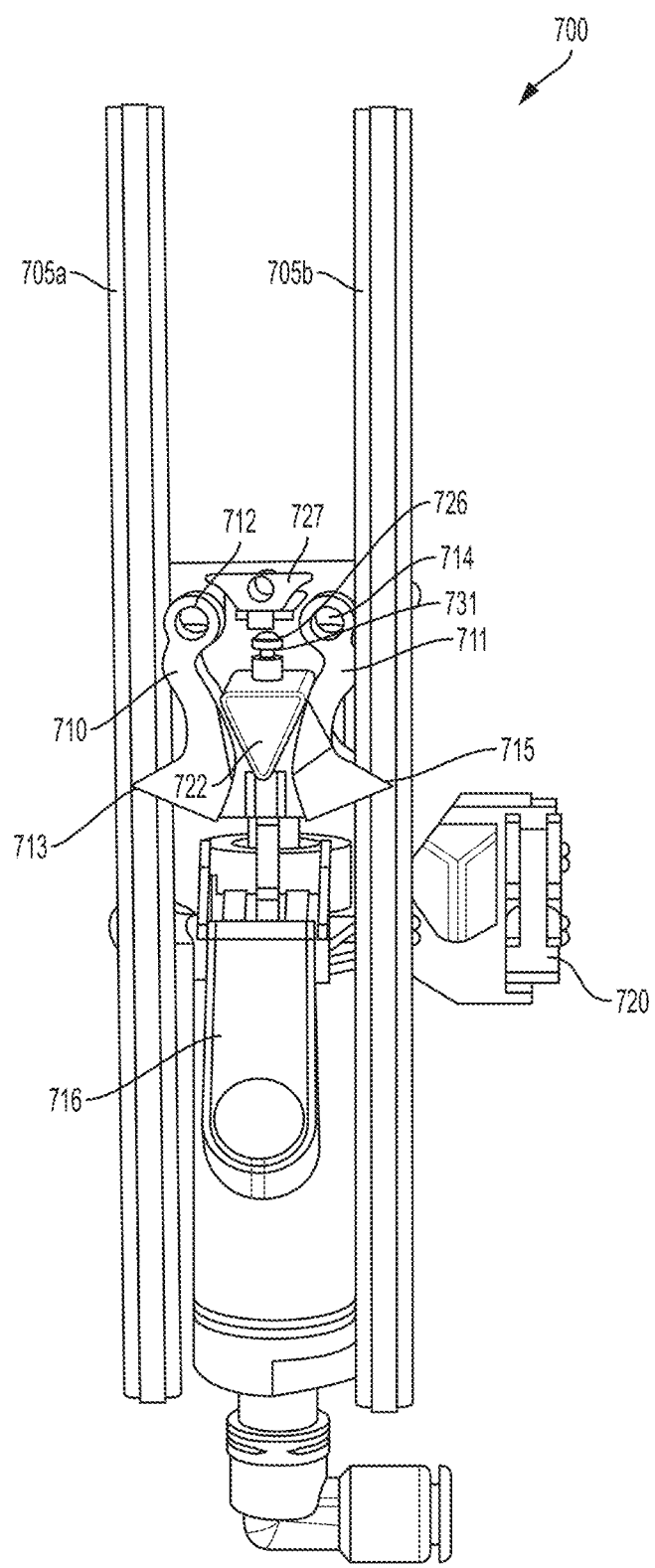
FIG. 54 shows the front of the occlusion assembly of FIG. 50 without the door and frame to illustrate the arms fully occluding flexible tubes.

FIG. 52 shows a front, perspective view of the occlusion assembly 700 with the door 706 open and the button 716 pressed to illustrate release of occluding arms 710 and 711 to permit loading and unloading of the tubes 705 in accordance with an embodiment of the present disclosure. FIG. 54 shows the front of the occlusion assembly 700 of FIG. 50 without the door 706 and frame 701 to illustrate the arms 710 and 711 fully occluding the tubes 705a, b in accordance with an embodiment of the present disclosure. As shown in FIG. 54, a wedge element or spreader 722 contacts the facing sides of occluding arms 710 and 711, which under a spring force can apply pressure to occluding arms 710 and 711 to press the occluding ends 713 and 715 of occluding arms 710 and 711 against a portion of tubes 705a, b. A user may release the occluding arms 710 and 711 by pressing button 716, which causes spreader 722 to withdraw away from occluding arms 710 and 711, releasing the pressure of spreader 722 being applied to the distal ends of occluding arms 710 and 711. In some aspects, the manual actuator (e.g. button 716) acts as an override mechanism to an automated actuator (such as, for example, a pneumatically operated piston/cylinder apparatus) connected to a tubing occluder element (e.g., the spreader 722). The manual actuator is operatively coupled to the tubing occluder to cause essentially linear motion of at least a portion of the tubing occluder, moving the occluding member from an occluding position to a non-occluding position upon manual operation of the override mechanism by a user.

Similarly, activation of an actuator may release occluding arms 710 and 711 by causing spreader 722 to withdraw away from the occluding ends 713, 715 of occluding arms 710 and 711. In one embodiment, as shown in FIG. 50, spreader 722 may be formed of, co-molded with, attached to or otherwise connected to a carriage assembly 723, which in turn is connected to an actuating arm of the actuator (see, e.g., FIGS. 56 and 57). The actuator may comprise, for example, a motor and gear assembly (e.g., rack and pinion assembly or worm-type gear assembly), a solenoid, a hydraulic cylinder or a pneumatic cylinder, among others. In a preferred embodiment, the actuator comprises a pneumatic cylinder 717 that causes an actuating arm comprising a piston arm 742 to extend linearly against a spring force (which in an embodiment may be a coil spring 745 within cylinder 717 as shown in FIG. 60). As shown in FIG. 60, in a perspective side view of a pneumatically operated linear actuator 717, piston arm 742 is connected to carriage 723. When activated by pneumatic pressure, actuator 717 extends piston arm 742 and moves carriage 723 and attached spreader 722 in a direction that withdraws spreader 722 from engagement with the distal ends 713, 715 of the occluding arms 710 and 711. (For clarity, occluding arm 711, frame 701, door 706, block 703 and tube guide 704, among other elements, have been removed from FIGS. 58-60). Preferably, a main spring that is either external or internal to cylinder/actuator 717 may apply a biasing force to piston arm 742 or carriage 723 to cause spreader 722 to move occluding arms 710 and 711 to an occluding position. In the event of a loss of power or pneumatic pressure, the occluding arms 710 and 711 will default to an occluding mode, preventing the flow of fluid through tubes 705. As illustrated in a cross-sectional view of occlusion assembly 700 in FIG. 60, in an embodiment, a coil spring 745 may be placed within the cylinder 743 to provide a biasing force against which piston 744 may move piston arm 742 under pneumatic pressure. Pneumatic pressure may be supplied to linear actuator 717 from a pressure source (e.g., a tank pressurized by a pump) regulated by an intervening electromechanical valve under control of an electronic controller.

Figure 59:
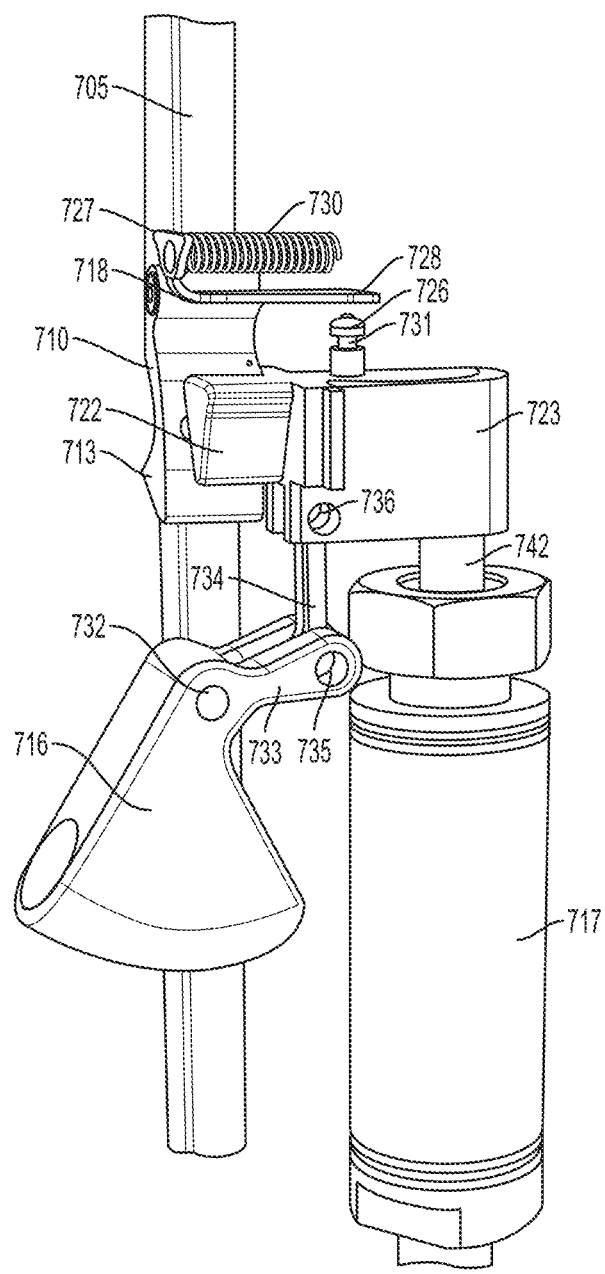
FIG. 59 shows a side perspective view of several working parts of the occlusion assembly of FIG. 50 in an occluding state.
Figure 60:
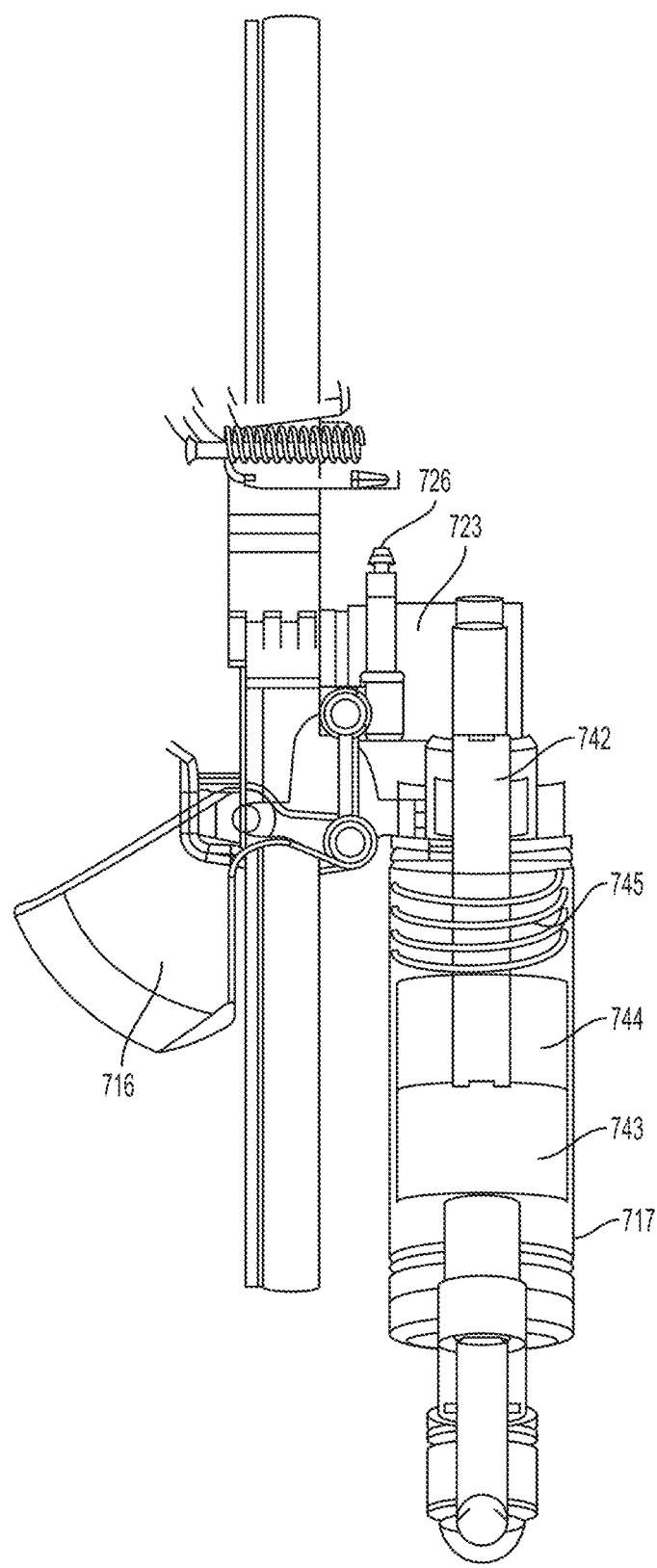
FIG. 60 shows a side, cross-sectional view of an actuator of the occlusion assembly of FIG. 50, illustrating a location for a main spring for the assembly.

As shown in FIGS. 54 and 59, when the linear actuator 717 is fully retracted, the carriage 723 carries spreader 722 along the facing sides of the occluder arms 710 and 711 to rotate them into an occluding position. The first arm 710 pivots about its pivoting end 712 to cause the occluding end 713 to press against first tube 705a that is restrained by block 702 (see FIG. 54). The second arm 711 pivots about its pivoting end 714 such that the occluding end 715 can press against second tube 705b which is restrained by block 703.

Figure 55:
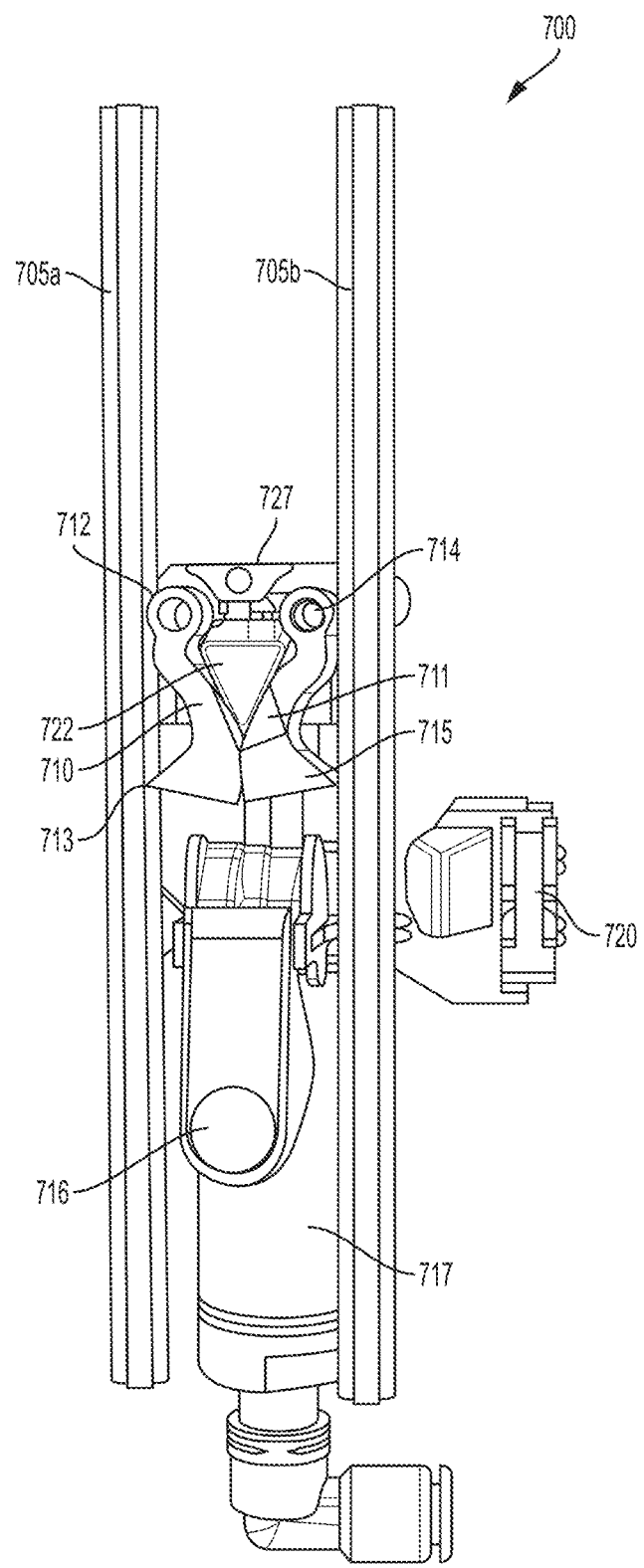
FIG. 55 shows the front of the occlusion assembly of FIG. 50 without the door and frame to illustrate the arms in a non-occluding position.
Figure 58:
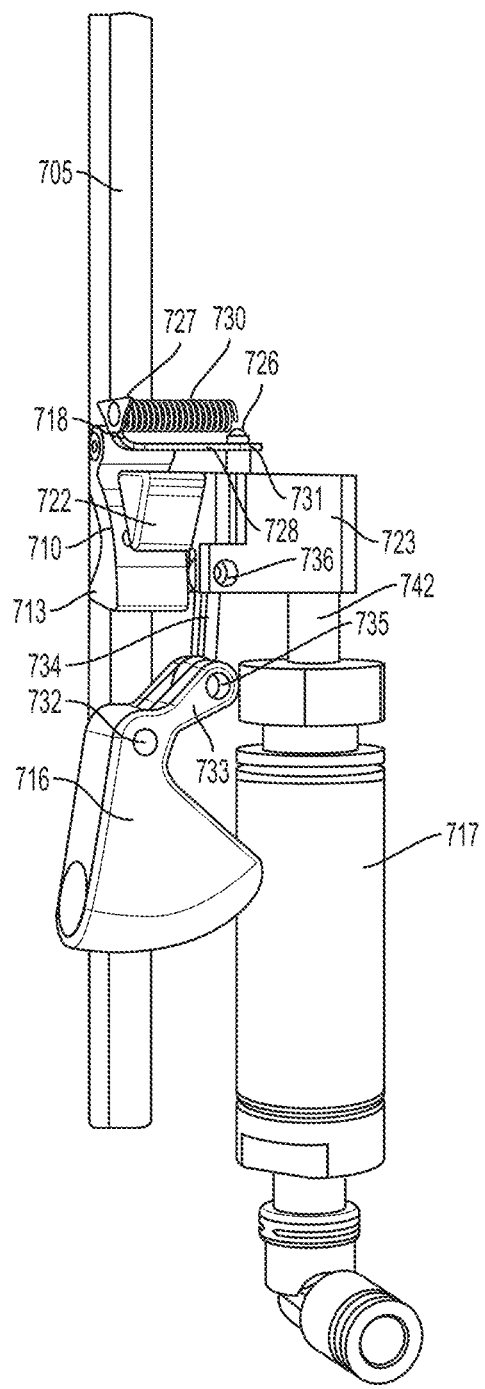
FIG. 58 shows a side perspective view of several working parts of the occlusion assembly of FIG. 50 in a non-occluding state.

FIGS. 55 and 58 show occlusion assembly 700 in a non-occluding state (frame 701, door 706. Blocks 702, 703, and other elements removed for clarity). When the button 716 is pressed or the linear actuator 717 is activated, the carriage 723 and attached spreader 722 move distally away from the actuator 717, allowing occluder arms 710 and 711 to rotate about pivot points 712 and 714 into a non-occluding position. The elastic resilience of the tubes 705a, b may cause the arms 710 and 711 to pivot towards each other. In some embodiments of the present disclosure, small magnets (not explicitly shown) embedded in the arms 710 and 711 pull the arms 710 and 711 towards each other to facilitate the retraction of the occluding ends 713 and 715 away from the tubes 705. In other embodiments, small springs (not shown) may bias occluding arms 710 and 711 to pivot toward each other, the spring constants being weak enough to be overcome by the main spring (e.g., spring 745) biasing carriage 723 or spreader 722 into retracted (occluding) positions.

FIG. 53 shows a perspective side view of the occlusion assembly 700 of FIG. 50 (frame 701 removed for clarity) showing the door 706 engaging a switch 720 when the door 706 is closed in accordance with an embodiment of the present disclosure. As shown in FIG. 53, the hinge portion 708 of latch 707 is coupled to an engagement member or catch 740 that can snap into a cooperating slot 741 of the frame 701 (see, e.g., FIGS. 50 and 53). As the door 706 is closed, a portion of the catch 740 of latch 707 of the door 706 engages a spring-loaded switch 720, which in an embodiment includes a spring arm 737 of the switch 720.

Engagement of switch 720 by closure of door 706 signals an electronic controller (not shown) that the door 706 is properly closed, and that linear actuator 717 may be activated to release occluders 710 and 711 to allow fluid to flow through tubes 705. The door 706 closure signal may also cause the controller to perform other functions, such as, for example, instructing a pump coupled to the tubes 705 to begin pumping fluid within tubes 705.

Figure 56:
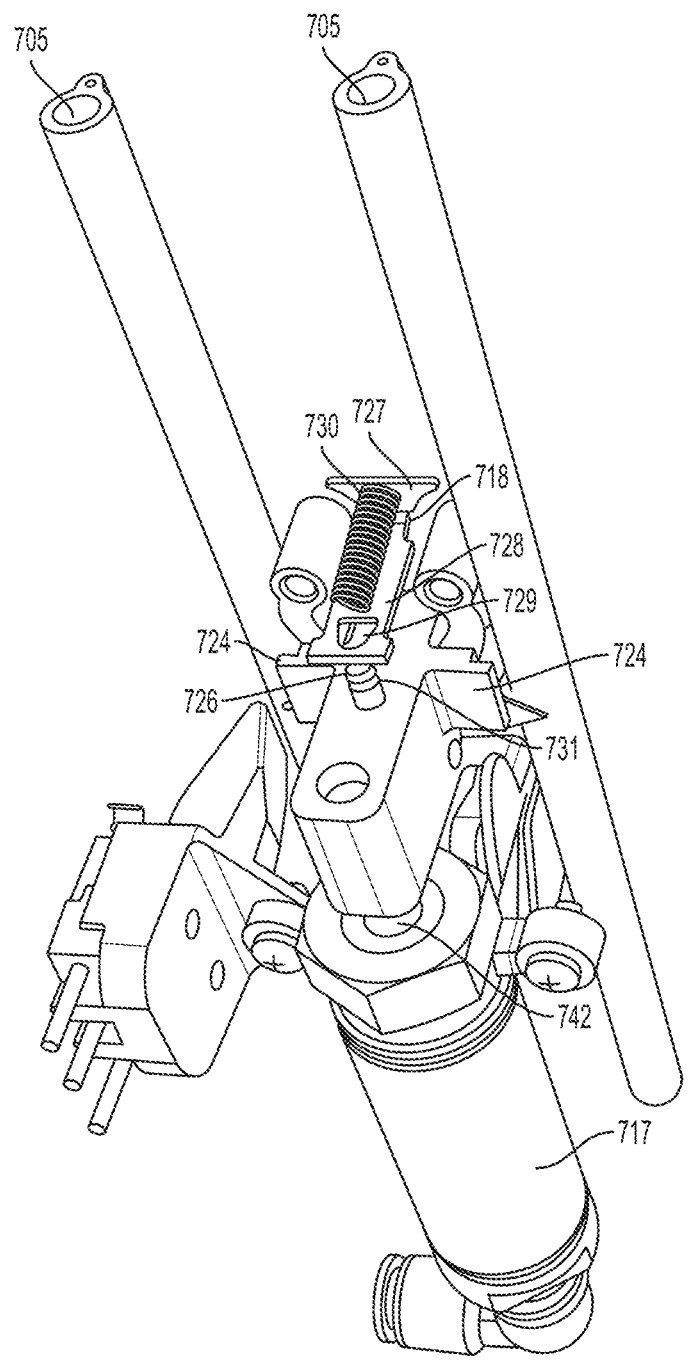
FIG. 56 is a rear/top perspective view of the occlusion assembly of FIG. 50 with an actuator arm in a fully retracted position.

FIG. 56 shows the back of the occlusion assembly 700 of FIG. 50 with the linear actuator 717 in a fully retracted position (i.e., in the occluding position) in accordance with an embodiment of the present disclosure. FIG. 56 shows the back side of the occlusion assembly 700 in the same configuration as shown for the front view of occlusion assembly 700 in FIG. 54. FIG. 56 shows several working parts of the occlusion assembly 700 of FIG. 50 to illustrate the operation of the actuator 717 and carriage 723 in accordance with an embodiment of the present disclosure. The carriage 723 moves with the extension or retraction of the piston arm 742 or with the actuation of the button 716. The carriage 723 includes guides 724 co-molded with or otherwise attached to the carriage 723. The guides 724 guide the carriage 723 as it moves via actuation of the piston arm 742 or with the actuation of the button 716. The guides 724 interface with tracks 725 of the frame 701 (see, e.g., FIG. 51).

In an optional embodiment, when door 706 is open, actuation of button 716 by a user or activation of actuator 717 by a controller causes carriage 723 and spreader 722 to move into a non-occluding position, and a retaining element or assembly allows the non-occluding position to be held without further force being applied either by the user or by the actuator 717. In an exemplary embodiment shown in FIG. 56, the carriage 723 may incorporate a latching pin 726 to cooperate with a slot or hole in a retention member 718. The retention member 718 includes a surface 727 positioned to be contacted by pins 738 located on the inside of door 706 when it is closed (see, e.g., FIGS. 51 and 52). Through holes 739 allow pins 738 to contact a portion of retention member 718 to displace it in a rearward direction. In the illustrated embodiment, pins 738 contact front plate 727 of retention member 718. Retention member 718 also includes a surface having a slot or hole 729 positioned to receive the head of a latching pin 726, which in the illustrated embodiment comprises a horizontal plate 728 defining a receiving portion 729. Retention member 718 is arranged to slide within grooves or guides of the frame 701 (not shown) in response to contact by the pins 738 when the door 706 is closed or opened (see, e.g. FIG. 51). A spring 730 mounted on the frame 701 may be biased to urge the retention member 718 forward to a stop feature (not shown) on the frame 701 so that opening the door 706 allows the retention member 718 to slide forward, re-aligning the receiving portion 729 in relation to the latching pin 726. When the door 706 is closed (see FIG. 50 or 51), the pins 738 on the door 706 press against the front plate 727 which compresses the spring 730 such that the receiving portion 729 of the horizontal plate 728 is positioned directly over the latching pin 726. Upon alignment of the receiving portion 729 with the latching pin 726, the area of the receiving portion 729 is large enough to allow the latching pin 726 to be released by the retention member 718, thereby allowing the carriage 723 to be subject to the spring force of the main spring 745 in the actuator 717. If pneumatic pressure is not then being applied to the actuator 717, the carriage 723 is then free to move into an occluding position. The retention member 718 in the disabled state (i.e., inoperative state) allows the latching pin 726 to move freely through the receiving portion 729 as the carriage 723 moves between the fully extended position and the fully retracted position.

Figure 57:
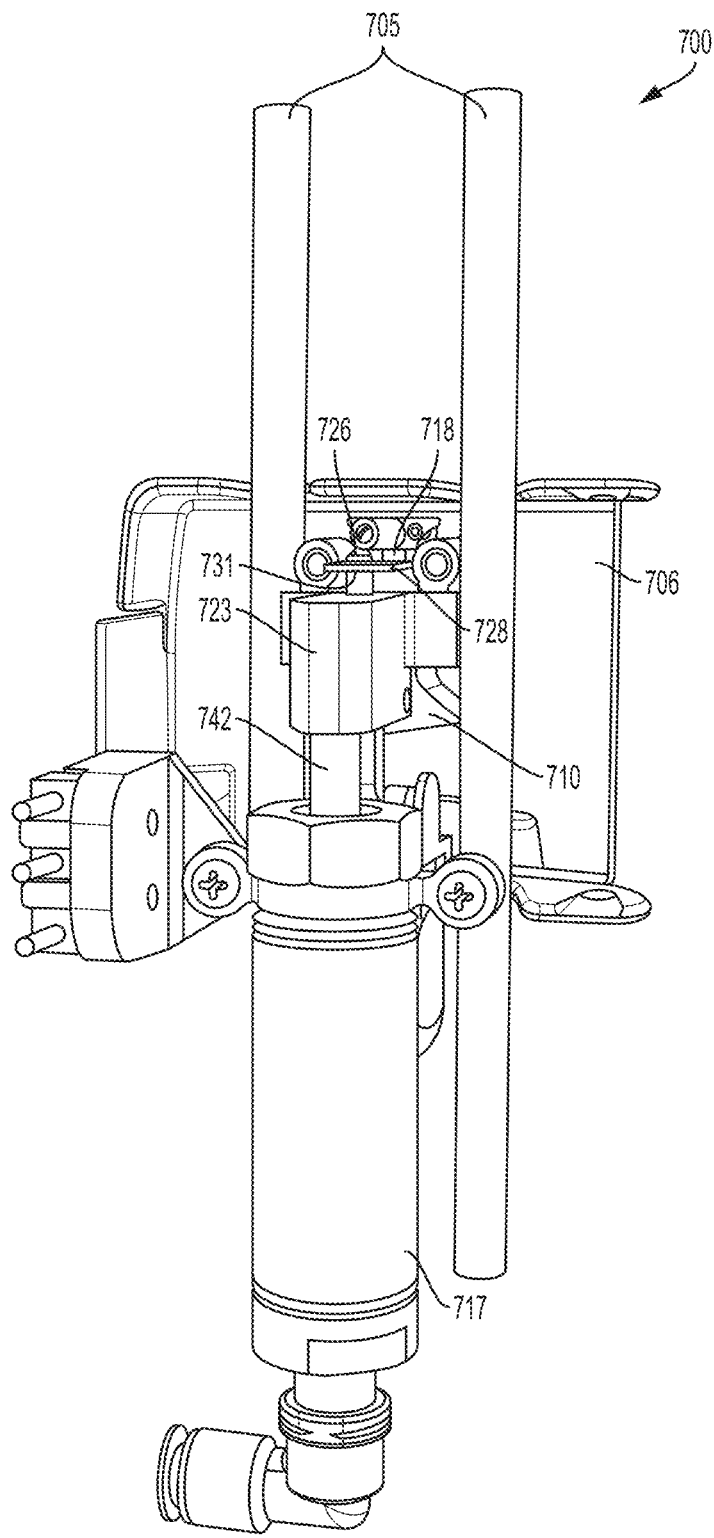
FIG. 57 is a rear perspective view of the occlusion assembly of FIG. 50 with an actuator arm in a fully extended position.

FIG. 57 is a rear view of the occlusion assembly 700 with the actuator 717 activated, and the piston arm 742 in an extended position to place the occluding arms 710, 711 in a non-occluding state. In this view, the head of the latching pin 726 is noted to be above the plane of the horizontal plate 728 of the retention member 718, and the recessed region 731 of the latching pin 726 is noted to be aligned with the receiving portion 729 of the retention member 718. In this illustration, door 706 is in a closed position, implying that the receiving portion 729 is in a sufficiently rearward position to prevent the latching pin 726 from being latched into the retention member 718.

When the door 706 is sufficiently opened, the pins 738 of the door 706 do not press against the front plate 727 and the spring 730 applies a force on the front plate 727 such that the receiving portion 729 of the retention member 718 is positioned to allow the latching pin 726 to engage an edge of the receiving portion 729 and latch to the retention member 718. The latching pin 726 moves into the receiving portion 729 pulling the front plate 727 rearward against the force of the spring 730 when the receiving portion 729 is positioned to latch to the latching pin 726. When the head of latching pin 726 moves sufficiently through the receiving portion 729, a recessed region 731 below the head of latching pin 726 becomes co-aligned with the horizontal plate 728 which moves as the edge of the receiving portion 729 moves into the recessed region 731 under the force of the spring 730 as applied to the front plate 727. When the pins 738 of the door 706 sufficiently engage the front plate 727, the receiving portion 729 is positioned to release the latching pin 726 from the latch 718. Thus, when the door 706 is open, the carriage 723 and spreader 722 can be held in a non-occluding position without the continuous application of force by the actuator 717 or by a user pressing against the button 716. This permits a user to load and unload tubing from occlusion assembly 700 without simultaneously having to apply force on the button 716. However, upon the closing of the door 706, the retention member 718 is no longer operative, and in the absence of continued application of force by either the actuator 717 or through the button 716, the carriage 723 and spreader 722 will move into a position to cause the occluding arms 710 and 711 to rotate to an occluding position.

FIGS. 58 and 59 show a side perspective view of several working parts of the occlusion assembly 700 of FIG. 50, with frame 701, blocks 702, 703, tube guide 704, door 706, occluding arm 711 and other parts removed for clarity. In FIG. 58, the piston arm 742 is fully extended in accordance with an embodiment of the present disclosure. FIG. 58 shows the latching pin 726 latched onto the retention member 718. That is, assuming that door 706 is in an open position, the horizontal plate 728 is positioned by the force of spring 730 to engage the recessed region 731 of the latching pin 726.

FIG. 59 shows a side, perspective view of the occlusion assembly 700 of FIG. 50 with the piston arm 742 in a fully retracted position, with certain elements removed as in FIG. 58 for clarity. In this example, the latching pin 726 is shown to be completely disengaged from the retention member 718; and in the absence of an activating force on the actuator 717 or a pressing force on the button 716, the piston arm 742, carriage 723 and spreader 722 are free to retract under the force of a main spring 745 (see FIG. 60) biased against the extension of piston arm 742. The spreader 722 then moves toward the occluding ends 713, 715 of the occluding arms 710, 711. In an embodiment, as shown in FIGS. 58 and 59, the button 716 pivots about a pivot 732 to raise a lever arm 733 when the button 716 is pressed. The lever arm 733 is pivotally connected to a connecting member 734 via a proximal pivot 735. The connecting member 734 in turn is pivotally connected to the carriage 723 via a distal pivot 736. When the button 716 is pressed or the piston arm 742 moves the carriage 723 toward the retention member 718, the connecting member 734 moves with the carriage 723, rotating the button 716 about the pivot 732 as shown in FIG. 58.

Figure 61:
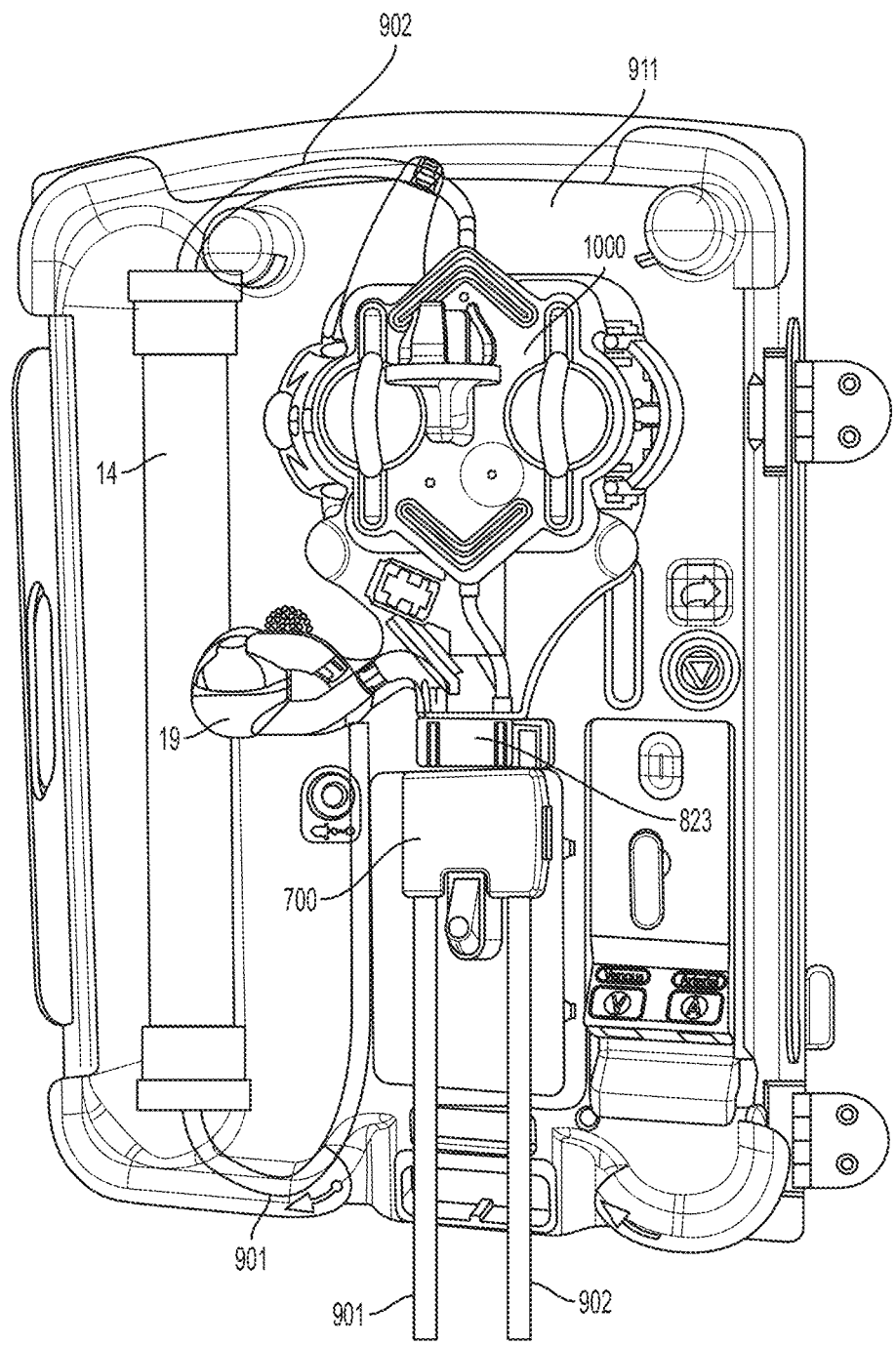
FIG. 61 shows the occlusion assembly of FIG. 50 mounted in a front panel assembly of a hemodialysis apparatus in accordance with an embodiment of the present disclosure.

FIG. 61 shows the occlusion assembly 700 of FIG. 50 used in a front-panel assembly 911 of a dialysis system in accordance with an embodiment of the present disclosure. The occlusion assembly 700 occludes flexible tubes 901, 902 through which blood flows to and from a patient. The right side tube 902 carries blood from a patient into a blood pump assembly 1000 (an arterial blood line) and the left side tube 901 carries blood from a dialyzer 14 back to the patient after passing through an air trap 19 (a venous blood line). The occlusion assembly 700 can occlude the flow of blood through both of these patient tubes 901, 902 simultaneously.

As discussed in detail above, the tubes 901, 902 are connected to a blood pump cassette or assembly 1000, which is a modular unit that may be mounted onto and dismounted from the front-panel 911. Both of the patient tubes 901, 902 may be provided as an assembly with the blood pump cassette 1000 and air trap 19, and may be loaded into the occlusion assembly 700 when the blood-pump cassette 1000 is mounted onto the front-panel 911. In this embodiment, the occlusion assembly 700 forms a permanent part of the front panel 911.

When the occlusion assembly 700 is in the non-occluding state, pumps located on blood pump cassette 1000 may be activated to pump blood from a patient through the right tube 902, up through the blood pumps and through a dialyzer 14. Blood processed by the dialyzer 14 then returns to the patient via tube 901 after first passing through an air trap 19 and an air-in-line detector 823.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The indefinite articles "a" and "an," as used herein in the specification and in the claims, unless clearly indicated to the contrary, should be understood to mean "at least one."

The invention claimed is:

1. A system for detecting replacement of blood by dialysate solution in a blood tubing set of a hemodialysis apparatus in which dialysate is pumped from a dialysate side to a blood side of a dialyzer, the system comprising:
    a first fluid line fluidly connecting a first catheter or needle in a blood vessel, fistula or graft to an inlet of a blood pump;
    a second fluid line fluidly connecting a second catheter or needle in the blood vessel, fistula or graft to an outlet of the blood pump;
    a first connector connecting the first fluid line to the first catheter or needle, and a second connector connecting the second fluid line to the second catheter or needle, the first connector having a first electrode in fluid communication with a fluid carrying lumen of said first connector, and the second connector having a second electrode in fluid communication with a fluid carrying lumen of said second connector;
    an electronic circuit having a first terminal electrically connected to the first electrode and a second terminal electrically connected to the second electrode, and configured to measure electrical impedance of fluid between the first connector and the second connector via a conductive path through the blood vessel, fistula or graft;
    a controller configured to receive a series of sampled electrical impedance values from the electronic circuit, and to process the electrical impedance values as a signal;
    wherein the controller is configured to:
        measure the signal or a filtered form of the signal as dialysate is pumped through the dialyzer to the blood tubing set;
        determine whether the signal or a filtered form of the signal has a first value equal to an expected value of the signal for blood in the first and second fluid lines, or has a second value equal to an expected value of the signal for dialysate solution in the first and second fluid lines;
        determine a point in time when the signal or a filtered form of the signal changes from the first value to the second value; and
        provide a first notification to a user if the controller detects a change from the first value to the second value, or provide a second notification to the user if the controller detects a change from the first value that is less than the second value within a pre-determined period of time.

2. The system of claim 1, wherein the controller is configured to associate the change from the first value to the second value with a change in hematocrit of blood in the first and second fluid lines.

3. The system of claim 2, wherein the controller is configured to detect an attenuation of the change of the hematocrit, and to declare an occlusion if the attenuation is greater than a pre-determined amount.

4. The system of claim 3, wherein the controller is configured to declare an occlusion if the pre-determined amount of attenuation corresponds to a percentage of the first value.

5. The system of claim 4, wherein the percentage is 99%.

6. The system of claim 4, wherein the percentage is within a range of 93-97%.

7. The system of claim 1, wherein the controller is configured to set the first value to correspond to the highest impedance value during the first 12 seconds of a rinseback process in which dialysate solution is pumped into the blood tubing set.

8. The system of claim 7, wherein the percentage is not less than 97% of the first value.

9. The system of claim 1, wherein the filtered form of the signal comprises a difference between the measured electrical impedance filtered using a first time constant and the measured electrical impedance filtered using a second smaller time constant.

10. The system of claim 9, wherein the controller is configured to adjust the filtered form of the signal to vary in proportion to a change in a value of the electrical impedance filtered using the first time constant.

11. The system of claim 1, wherein the filtered form of the signal comprises a ratio between the measured electrical impedance filtered using a first time constant and the measured electrical impedance using a second smaller time constant.

* * * * *